(12) United States Patent
Christianson et al.

(10) Patent No.: US 12,186,187 B2
(45) Date of Patent: Jan. 7, 2025

(54) TRANSCATHETER DELIVERABLE PROSTHETIC HEART VALVES AND METHODS OF DELIVERY

(71) Applicant: VDyne, Inc., Maple Grove, MN (US)

(72) Inventors: Mark Christianson, Plymouth, MN (US); Robert Vidlund, Forest Lake, MN (US); Neelakantan Saikrishnan, Plymouth, MN (US)

(73) Assignee: VDyne, Inc., Maple Grove, MN (US)

( * ) Notice: Subject to any disclaimer, the term of this patent is extended or adjusted under 35 U.S.C. 154(b) by 228 days.

(21) Appl. No.: 17/207,076

(22) Filed: Mar. 19, 2021

(65) Prior Publication Data

US 2021/0290385 A1    Sep. 23, 2021

Related U.S. Application Data

(63) Continuation of application No. PCT/US2019/051615, filed on Sep. 18, 2019, and a continuation-in-part of application No. 16/443,862, filed on Jun. 17, 2019, now Pat. No. 11,273,033, said application No. PCT/US2019/051615 is a continuation-in-part of application No. 16/163,577, filed on Oct. 18, 2018, now Pat. No. 11,071,627, said (Continued)

(51) Int. Cl.
*A61F 2/24*    (2006.01)
*A61F 2/95*    (2013.01)

(52) U.S. Cl.
CPC .......... *A61F 2/2427* (2013.01); *A61F 2/2409* (2013.01); *A61F 2/2412* (2013.01); *A61F 2/2418* (2013.01); *A61F 2/2433* (2013.01); *A61F 2/95* (2013.01); *A61F 2210/0014* (2013.01); *A61F 2220/0008* (2013.01); *A61F 2220/0016* (2013.01); *A61F 2220/0075* (2013.01); *A61F 2230/0006* (2013.01); *A61F 2230/001* (2013.01); *A61F 2230/0069* (2013.01); *A61F 2250/0039* (2013.01)

(58) Field of Classification Search
CPC .... A61F 2/2427; A61F 2/2409; A61F 2/2418; A61F 2/2433; A61F 2/2412; A61F 2/95; A61F 2220/0075
See application file for complete search history.

(56) References Cited

U.S. PATENT DOCUMENTS 3,744,060 A   7/1973  Bellhouse et al.
4,079,468 A   3/1978  Liotta et al.
(Continued)

FOREIGN PATENT DOCUMENTS

AU    2006203686 B2    11/2008
AU    2009219415 A1     9/2009
(Continued)

OTHER PUBLICATIONS

Office Action for U.S. Appl. No. 16/435,687, mailed Aug. 7, 2019, 19 pages.

(Continued)

*Primary Examiner* — Katherine M Rodjom
(74) *Attorney, Agent, or Firm* — COOLEY LLP

(57) ABSTRACT

Embodiments are described herein that relate to prosthetic heart valves, and devices and methods for use in the delivery and deployment of such valves.

7 Claims, 84 Drawing Sheets

Related U.S. Application Data application No. 16/443,862 is a continuation of application No. 16/155,890, filed on Oct. 10, 2018, now Pat. No. 10,321,995.

(60) Provisional application No. 62/777,070, filed on Dec. 8, 2018, provisional application No. 62/749,121, filed on Oct. 22, 2018, provisional application No. 62/737,343, filed on Sep. 27, 2018, provisional application No. 62/766,611, filed on Sep. 20, 2018.

(56) References Cited

U.S. PATENT DOCUMENTS

| | | |
|---|---|---|
| 5,397,351 A | 3/1995 | Pavcnik et al. |
| 5,509,428 A | 4/1996 | Dunlop |
| 5,554,185 A | 9/1996 | Block et al. |
| 5,800,531 A | 9/1998 | Cosgrove et al. |
| 5,906,642 A | 5/1999 | Caudillo et al. |
| 6,006,134 A | 12/1999 | Hill et al. |
| 6,197,013 B1 | 3/2001 | Reed et al. |
| 6,290,719 B1 | 9/2001 | Garberoglio |
| 6,312,464 B1 | 11/2001 | Navia |
| 6,449,507 B1 | 9/2002 | Hill et al. |
| 6,458,153 B1 | 10/2002 | Bailey et al. |
| 6,532,388 B1 | 3/2003 | Hill et al. |
| 6,582,467 B1 | 6/2003 | Teitelbaum et al. |
| 6,628,987 B1 | 9/2003 | Hill et al. |
| 6,669,724 B2 | 12/2003 | Park et al. |
| 6,718,208 B2 | 4/2004 | Hill et al. |
| 6,769,434 B2 | 8/2004 | Liddicoat et al. |
| 6,890,330 B2 | 5/2005 | Streeter et al. |
| 6,896,690 B1 | 5/2005 | Lambrecht et al. |
| 6,904,318 B2 | 6/2005 | Hill et al. |
| 6,929,653 B2 | 8/2005 | Strecter |
| 7,074,189 B1 | 7/2006 | Montegrande |
| 7,125,418 B2 | 10/2006 | Duran et al. |
| 7,175,660 B2 | 2/2007 | Cartledge et al. |
| 7,201,761 B2 | 4/2007 | Woolfson et al. |
| 7,225,019 B2 | 5/2007 | Jahns et al. |
| 7,269,457 B2 | 9/2007 | Shafer et al. |
| 7,331,991 B2 | 2/2008 | Kheradvar et al. |
| 7,361,189 B2 | 4/2008 | Case et al. |
| 7,374,571 B2 | 5/2008 | Pease et al. |
| 7,442,204 B2 | 10/2008 | Schwammenthal et al. |
| 7,449,027 B2 | 11/2008 | Hunt et al. |
| 7,621,948 B2 | 11/2009 | Herrmann et al. |
| 7,648,527 B2 | 1/2010 | Agnew |
| 7,717,952 B2 | 5/2010 | Case et al. |
| 7,749,245 B2 | 7/2010 | Cohn et al. |
| 7,753,949 B2 | 7/2010 | Lamphere et al. |
| 7,811,316 B2 | 10/2010 | Kalmann et al. |
| 7,828,840 B2 | 11/2010 | Biggs et al. |
| 7,846,199 B2 | 12/2010 | Paul, Jr. et al. |
| 8,303,648 B2 | 11/2012 | Grewe et al. |
| 8,366,768 B2 | 2/2013 | Zhang |
| 8,491,650 B2 | 7/2013 | Wiemeyer et al. |
| 8,568,474 B2 | 10/2013 | Yeung et al. |
| 8,628,571 B1 | 1/2014 | Hacohen et al. |
| 8,641,752 B1 | 2/2014 | Holm et al. |
| 8,696,743 B2 | 4/2014 | Holecek et al. |
| 8,728,153 B2 | 5/2014 | Bishop et al. |
| 8,758,395 B2 | 6/2014 | Kleshinski et al. |
| 8,846,390 B2 | 9/2014 | Dove et al. |
| 8,876,892 B2 | 11/2014 | Tran et al. |
| 8,900,295 B2 | 12/2014 | Migliazza et al. |
| 8,915,958 B2 | 12/2014 | Braido |
| 8,926,690 B2 | 1/2015 | Kovalsky |
| 8,926,692 B2 | 1/2015 | Dwork |
| 8,926,694 B2 | 1/2015 | Costello |
| 8,940,044 B2 | 1/2015 | Hammer et al. |
| 8,956,404 B2 | 2/2015 | Bortlein et al. |
| 8,986,370 B2 | 3/2015 | Annest et al. |
| 8,998,982 B2 | 4/2015 | Richter et al. |
| 9,011,524 B2 | 4/2015 | Eberhardt |
| 9,017,399 B2 | 4/2015 | Gross et al. |
| 9,050,188 B2 | 6/2015 | Schweich, Jr. et al. |
| 9,072,604 B1 | 7/2015 | Melnick et al. |
| 9,119,714 B2 | 9/2015 | Shandas et al. |
| 9,216,076 B2 | 12/2015 | Mitra et al. |
| 9,232,995 B2 | 1/2016 | Kovalsky et al. |
| 9,241,792 B2 | 1/2016 | Benichou et al. |
| 9,248,016 B2 | 2/2016 | Oba et al. |
| 9,259,215 B2 | 2/2016 | Chou et al. |
| 9,277,990 B2 | 3/2016 | Klima et al. |
| 9,289,282 B2 | 3/2016 | Olson et al. |
| 9,289,296 B2 | 3/2016 | Braido et al. |
| 9,295,547 B2 | 3/2016 | Costello et al. |
| 9,301,839 B2 | 4/2016 | Stante et al. |
| 9,308,086 B2 | 4/2016 | Ho |
| 9,339,367 B2 | 5/2016 | Carpenter et al. |
| 9,370,418 B2 | 6/2016 | Pintor et al. |
| 9,381,083 B2 | 7/2016 | Costello |
| 9,387,075 B2 | 7/2016 | Bortlein et al. |
| 9,393,111 B2 | 7/2016 | Ma et al. |
| 9,402,720 B2 | 8/2016 | Richter et al. |
| 9,414,915 B2 | 8/2016 | Lombardi et al. |
| 9,433,500 B2 | 9/2016 | Chau et al. |
| 9,440,054 B2 | 9/2016 | Bishop et al. |
| 9,456,899 B2 | 10/2016 | Yeung et al. |
| 9,468,525 B2 | 10/2016 | Kovalsky et al. |
| 9,474,604 B2 | 10/2016 | Centola et al. |
| 9,486,306 B2 | 11/2016 | Tegels et al. |
| 9,504,562 B2 | 11/2016 | Richter et al. |
| 9,510,941 B2 | 12/2016 | Bishop et al. |
| 9,526,613 B2 | 12/2016 | Gross et al. |
| 9,554,902 B2 | 1/2017 | Braido et al. |
| 9,579,196 B2 | 2/2017 | Morriss et al. |
| 9,579,200 B2 | 2/2017 | Lederman et al. |
| 9,597,181 B2 | 3/2017 | Christianson et al. |
| 9,610,159 B2 | 4/2017 | Christianson et al. |
| 9,615,925 B2 | 4/2017 | Subramanian et al. |
| 9,629,719 B2 | 4/2017 | Rothstein |
| 9,636,222 B2 | 5/2017 | Oslund |
| 9,649,191 B2 | 5/2017 | Savage et al. |
| 9,662,202 B2 | 5/2017 | Quill et al. |
| 9,662,203 B2 | 5/2017 | Sheahan et al. |
| 9,662,209 B2 | 5/2017 | Gross et al. |
| 9,675,454 B2 | 6/2017 | Vidlund et al. |
| 9,675,485 B2 | 6/2017 | Essinger et al. |
| 9,687,343 B2 | 6/2017 | Bortlein et al. |
| 9,707,076 B2 | 7/2017 | Stack et al. |
| 9,713,530 B2 | 7/2017 | Cabiri et al. |
| 9,750,607 B2 | 9/2017 | Ganesan et al. |
| 9,763,778 B2 | 9/2017 | Eidenschink et al. |
| 9,763,779 B2 | 9/2017 | Bortlein et al. |
| 9,788,946 B2 | 10/2017 | Bobo, Jr. et al. |
| 9,839,511 B2 | 12/2017 | Ma et al. |
| 9,849,011 B2 | 12/2017 | Zimmerman et al. |
| 9,855,384 B2 | 1/2018 | Cohen et al. |
| 9,861,464 B2 | 1/2018 | Azimpour et al. |
| 9,895,219 B2 | 2/2018 | Costello et al. |
| 9,901,330 B2 | 2/2018 | Akpinar |
| 9,918,838 B2 | 3/2018 | Ring |
| 9,943,409 B2 | 4/2018 | Kim et al. |
| 9,949,825 B2 | 4/2018 | Braido et al. |
| 9,968,444 B2 | 5/2018 | Millwee et al. |
| 9,968,445 B2 | 5/2018 | Kheradvar |
| 9,980,815 B2 | 5/2018 | Nitzan et al. |
| 9,987,121 B2 | 6/2018 | Blanzy |
| 10,010,411 B2 | 7/2018 | Peter |
| 10,010,412 B2 | 7/2018 | Taft et al. |
| 10,022,054 B2 | 7/2018 | Najafi et al. |
| 10,022,222 B2 | 7/2018 | Groothuis et al. |
| 10,022,223 B2 | 7/2018 | Bruchman |
| 10,028,821 B2 | 7/2018 | Centola et al. |
| 10,028,831 B2 | 7/2018 | Morin et al. |
| 10,034,667 B2 | 7/2018 | Morris et al. |
| 10,034,747 B2 | 7/2018 | Harewood |
| 10,039,638 B2 | 8/2018 | Bruchman et al. |
| 10,058,315 B2 | 8/2018 | Rafiee et al. |
| 10,058,411 B2 | 8/2018 | Fifer et al. |
| 10,058,421 B2 | 8/2018 | Eberhardt et al. |
| 10,058,426 B2 | 8/2018 | Barbarino |
| 10,064,405 B2 | 9/2018 | Dale et al. |

(56) References Cited

U.S. PATENT DOCUMENTS

| | | |
|---|---|---|
| 10,080,653 B2 | 9/2018 | Conklin et al. |
| 10,085,834 B2 | 10/2018 | Benson et al. |
| 10,085,835 B2 | 10/2018 | Thambar et al. |
| 10,105,224 B2 | 10/2018 | Buchbinder et al. |
| 10,117,741 B2 | 11/2018 | Schweich, Jr. et al. |
| 10,123,874 B2 | 11/2018 | Khairkhahan et al. |
| 10,130,331 B2 | 11/2018 | Stigall et al. |
| 10,130,467 B2 | 11/2018 | Braido et al. |
| 10,149,685 B2 | 12/2018 | Kizuka |
| 10,154,905 B2 | 12/2018 | Duffy |
| 10,179,043 B2 | 1/2019 | Cohen-Tzemach et al. |
| 10,182,908 B2 | 1/2019 | Tubishevitz et al. |
| 10,182,911 B2 | 1/2019 | Hillukka |
| 10,206,775 B2 | 2/2019 | Kovalsky et al. |
| 10,219,895 B2 | 3/2019 | Wagner et al. |
| 10,219,896 B2 | 3/2019 | Sandstrom et al. |
| 10,220,192 B2 | 3/2019 | Drasler et al. |
| 10,226,178 B2 | 3/2019 | Cohen et al. |
| 10,226,335 B2 | 3/2019 | Cartledge et al. |
| 10,245,142 B2 | 4/2019 | Bonhoeffer |
| 10,258,467 B2 | 4/2019 | Hou et al. |
| 10,265,173 B2 | 4/2019 | Griffin et al. |
| 10,321,987 B2 | 6/2019 | Wang et al. |
| 10,321,995 B1 | 6/2019 | Christianson et al. |
| 10,327,895 B2 | 6/2019 | Lozonschi et al. |
| 10,327,899 B2 | 6/2019 | Sandstrom et al. |
| 10,329,066 B2 | 6/2019 | Kruetzfeldt et al. |
| 10,350,047 B2 | 7/2019 | Rajpara et al. |
| 10,357,361 B2 | 7/2019 | Rafi et al. |
| 10,368,989 B2 | 8/2019 | Duffy et al. |
| 10,398,550 B2 | 9/2019 | Chalekian et al. |
| 10,426,611 B2 | 10/2019 | Hariton et al. |
| 10,433,957 B2 | 10/2019 | Khouengboua et al. |
| 10,433,960 B1 | 10/2019 | Sutherland et al. |
| 10,463,489 B2 | 11/2019 | Christianson et al. |
| 10,485,662 B2 | 11/2019 | Alkhatib |
| 10,485,976 B2 | 11/2019 | Streeter et al. |
| 10,517,718 B2 | 12/2019 | Richter et al. |
| 10,537,425 B2 | 1/2020 | Richter et al. |
| 10,595,994 B1 | 3/2020 | Christianson et al. |
| 10,631,983 B1 | 4/2020 | Christianson et al. |
| 10,653,522 B1 | 5/2020 | Vidlund et al. |
| 10,653,523 B2 | 5/2020 | Chambers et al. |
| 10,758,346 B1 | 9/2020 | Christianson et al. |
| 10,761,511 B2 | 9/2020 | Chen et al. |
| 10,779,937 B2 | 9/2020 | Vidlund et al. |
| 11,071,627 B2 | 7/2021 | Saikrishnan et al. |
| 11,076,956 B2 | 8/2021 | Christianson et al. |
| 11,109,969 B2 | 9/2021 | Vidlund et al. |
| 11,166,814 B2 | 11/2021 | Vidlund et al. |
| 11,173,027 B2 | 11/2021 | Christianson et al. |
| 11,179,239 B2 | 11/2021 | Vidlund et al. |
| 11,185,409 B2 | 11/2021 | Christianson et al. |
| 11,202,706 B2 | 12/2021 | Christianson et al. |
| 11,234,812 B2 | 2/2022 | Green et al. |
| 11,234,813 B2 | 2/2022 | Perrin |
| 11,253,359 B2 | 2/2022 | Vidlund et al. |
| 11,273,032 B2 | 3/2022 | Christianson et al. |
| 11,273,033 B2 | 3/2022 | Christianson et al. |
| 11,278,437 B2 | 3/2022 | Christianson et al. |
| 11,298,227 B2 | 4/2022 | Vidlund et al. |
| 11,331,186 B2 | 5/2022 | Christianson et al. |
| 11,337,807 B2 | 5/2022 | Christianson et al. |
| 11,344,412 B2 | 5/2022 | Vidlund et al. |
| 11,344,413 B2 | 5/2022 | Christianson et al. |
| 11,712,335 B2 | 8/2023 | Christianson et al. |
| 11,717,399 B2 | 8/2023 | Armer et al. |
| 11,786,366 B2 | 10/2023 | Vidlund et al. |
| 2002/0138138 A1 | 9/2002 | Yang |
| 2003/0040772 A1 | 2/2003 | Hyodoh et al. |
| 2003/0040808 A1 | 2/2003 | Stack et al. |
| 2003/0055495 A1 | 3/2003 | Pease et al. |
| 2003/0153901 A1 | 8/2003 | Herweck et al. |
| 2003/0166990 A1 | 9/2003 | Trauthen et al. |
| 2003/0171801 A1 | 9/2003 | Bates |
| 2004/0049207 A1 | 3/2004 | Goldfarb et al. |
| 2004/0088047 A1 | 5/2004 | Spence et al. |
| 2004/0093060 A1 | 5/2004 | Seguin et al. |
| 2004/0116996 A1 | 6/2004 | Freitag |
| 2004/0117009 A1 | 6/2004 | Cali et al. |
| 2004/0167619 A1 | 8/2004 | Case et al. |
| 2004/0199209 A1 | 10/2004 | Hill et al. |
| 2004/0225352 A1 | 11/2004 | Osborne et al. |
| 2005/0010246 A1 | 1/2005 | Streeter et al. |
| 2005/0075659 A1 | 4/2005 | Realyvasquez et al. |
| 2005/0075725 A1 | 4/2005 | Rowe |
| 2005/0107811 A1 | 5/2005 | Starksen et al. |
| 2005/0137686 A1 | 6/2005 | Salahieh et al. |
| 2005/0203614 A1 | 9/2005 | Forster et al. |
| 2005/0228472 A1 | 10/2005 | Case et al. |
| 2005/0228495 A1 | 10/2005 | Macoviak |
| 2006/0015167 A1 | 1/2006 | Armstrong et al. |
| 2006/0173524 A1 | 8/2006 | Salahieh et al. |
| 2006/0190075 A1 | 8/2006 | Jordan et al. |
| 2006/0195180 A1 | 8/2006 | Kheradvar et al. |
| 2006/0195183 A1 | 8/2006 | Navia et al. |
| 2006/0229708 A1 | 10/2006 | Powell et al. |
| 2006/0241745 A1 | 10/2006 | Solem |
| 2006/0271098 A1 | 11/2006 | Peacock, III |
| 2006/0276887 A1 | 12/2006 | Brady et al. |
| 2007/0016286 A1 | 1/2007 | Herrmann et al. |
| 2007/0027535 A1 | 2/2007 | Purdy et al. |
| 2007/0032850 A1 | 2/2007 | Ruiz et al. |
| 2007/0038295 A1 | 2/2007 | Case et al. |
| 2007/0073387 A1 | 3/2007 | Forster et al. |
| 2007/0100427 A1 | 5/2007 | Perouse |
| 2007/0162102 A1 | 7/2007 | Ryan et al. |
| 2007/0208417 A1 | 9/2007 | Agnew |
| 2007/0213805 A1 | 9/2007 | Schaeffer et al. |
| 2007/0233176 A1 | 10/2007 | Gilson et al. |
| 2007/0233228 A1 | 10/2007 | Eberhardt et al. |
| 2007/0239271 A1 | 10/2007 | Nguyen |
| 2007/0288087 A1 | 12/2007 | Fearnot et al. |
| 2008/0004686 A1 | 1/2008 | Hunt et al. |
| 2008/0020013 A1 | 1/2008 | Reyes et al. |
| 2008/0065204 A1 | 3/2008 | Macoviak et al. |
| 2008/0071287 A1 | 3/2008 | Goto |
| 2008/0132999 A1 | 6/2008 | Mericle et al. |
| 2008/0140181 A1 | 6/2008 | Reynolds et al. |
| 2008/0154355 A1 | 6/2008 | Benichou et al. |
| 2008/0183279 A1 | 7/2008 | Bailey et al. |
| 2008/0200977 A1 | 8/2008 | Paul et al. |
| 2008/0200980 A1 | 8/2008 | Robin et al. |
| 2008/0208332 A1 | 8/2008 | Lamphere et al. |
| 2008/0221672 A1 | 9/2008 | Lamphere et al. |
| 2008/0262592 A1 | 10/2008 | Jordan et al. |
| 2008/0262609 A1 | 10/2008 | Gross et al. |
| 2008/0275550 A1 | 11/2008 | Kheradvar et al. |
| 2009/0005863 A1 | 1/2009 | Goetz et al. |
| 2009/0048656 A1 | 2/2009 | Wen |
| 2009/0054976 A1 | 2/2009 | Tuval et al. |
| 2009/0094189 A1 | 4/2009 | Stephens |
| 2009/0132035 A1 | 5/2009 | Roth et al. |
| 2009/0164003 A1 | 6/2009 | Kheradvar |
| 2009/0192586 A1 | 7/2009 | Tabor et al. |
| 2009/0192601 A1 | 7/2009 | Rafiee et al. |
| 2009/0254174 A1 | 10/2009 | Case et al. |
| 2009/0264991 A1 | 10/2009 | Paul, Jr. et al. |
| 2009/0287290 A1 | 11/2009 | Macaulay et al. |
| 2010/0049294 A1 | 2/2010 | Zukowski et al. |
| 2010/0049313 A1 | 2/2010 | Alon et al. |
| 2010/0087918 A1 | 4/2010 | Vesely et al. |
| 2010/0121434 A1 | 5/2010 | Paul et al. |
| 2010/0160773 A1 | 6/2010 | Cohen et al. |
| 2010/0161043 A1 | 6/2010 | Maisano et al. |
| 2010/0168844 A1 | 7/2010 | Toomes et al. |
| 2010/0174363 A1 | 7/2010 | Castro |
| 2010/0179583 A1 | 7/2010 | Carpenter et al. |
| 2010/0179584 A1 | 7/2010 | Carpenter et al. |
| 2010/0179647 A1 | 7/2010 | Carpenter et al. |
| 2010/0185275 A1 | 7/2010 | Richter et al. |
| 2010/0280591 A1 | 11/2010 | Shin et al. |
| 2010/0298929 A1 | 11/2010 | Thornton et al. |
| 2010/0305685 A1 | 12/2010 | Millwee et al. |

(56) References Cited

U.S. PATENT DOCUMENTS

| | | |
|---|---|---|
| 2011/0004237 A1 | 1/2011 | Schneider et al. |
| 2011/0029071 A1 | 2/2011 | Zlotnick et al. |
| 2011/0029072 A1 | 2/2011 | Gabbay |
| 2011/0066233 A1 | 3/2011 | Thornton et al. |
| 2011/0071613 A1 | 3/2011 | Wood et al. |
| 2011/0098804 A1 | 4/2011 | Yeung et al. |
| 2011/0125145 A1 | 5/2011 | Mody et al. |
| 2011/0137397 A1 | 6/2011 | Chau et al. |
| 2011/0160836 A1 | 6/2011 | Behan |
| 2011/0172764 A1 | 7/2011 | Badhwar |
| 2011/0172784 A1 | 7/2011 | Richter et al. |
| 2011/0224785 A1 | 9/2011 | Hacohen et al. |
| 2011/0245911 A1 | 10/2011 | Quill et al. |
| 2011/0245917 A1 | 10/2011 | Savage et al. |
| 2011/0251675 A1 | 10/2011 | Dwork |
| 2011/0257721 A1 | 10/2011 | Tabor |
| 2011/0264191 A1 | 10/2011 | Rothstein |
| 2012/0022605 A1 | 1/2012 | Jahns et al. |
| 2012/0022633 A1 | 1/2012 | Olson et al. |
| 2012/0022639 A1 | 1/2012 | Hacohen et al. |
| 2012/0022640 A1 | 1/2012 | Gross et al. |
| 2012/0022644 A1 | 1/2012 | Reich et al. |
| 2012/0035701 A1 | 2/2012 | To |
| 2012/0035719 A1 | 2/2012 | Forster et al. |
| 2012/0065723 A1 | 3/2012 | Drasler et al. |
| 2012/0083874 A1 | 4/2012 | Dale et al. |
| 2012/0123531 A1 | 5/2012 | Tsukashima et al. |
| 2012/0137521 A1 | 6/2012 | Millwee et al. |
| 2012/0165928 A1 | 6/2012 | Nitzan et al. |
| 2012/0172981 A1 | 7/2012 | DuMontelle |
| 2012/0203336 A1 | 8/2012 | Annest |
| 2012/0209375 A1 | 8/2012 | Madrid et al. |
| 2012/0232574 A1 | 9/2012 | Kim et al. |
| 2012/0277853 A1 | 11/2012 | Rothstein |
| 2012/0310327 A1 | 12/2012 | McHugo |
| 2012/0310328 A1 | 12/2012 | Olson et al. |
| 2013/0035759 A1 | 2/2013 | Gross et al. |
| 2013/0046373 A1 | 2/2013 | Cartledge et al. |
| 2013/0055941 A1 | 3/2013 | Holecek et al. |
| 2013/0131714 A1 | 5/2013 | Wang et al. |
| 2013/0131792 A1 | 5/2013 | Miller et al. |
| 2013/0166017 A1 | 6/2013 | Cartledge et al. |
| 2013/0178931 A1 | 7/2013 | Fargahi |
| 2013/0184742 A1 | 7/2013 | Ganesan et al. |
| 2013/0190857 A1 | 7/2013 | Mitra et al. |
| 2013/0190861 A1 | 7/2013 | Chau et al. |
| 2013/0197621 A1 | 8/2013 | Ryan et al. |
| 2013/0226289 A1 | 8/2013 | Shaolian et al. |
| 2013/0238010 A1 | 9/2013 | Johnson et al. |
| 2013/0238089 A1 | 9/2013 | Lichtenstein et al. |
| 2013/0253570 A1 | 9/2013 | Bates |
| 2013/0274618 A1 | 10/2013 | Hou et al. |
| 2013/0274855 A1 | 10/2013 | Stante et al. |
| 2013/0282110 A1 | 10/2013 | Schweich, Jr. et al. |
| 2013/0297010 A1 | 11/2013 | Bishop et al. |
| 2013/0304197 A1 | 11/2013 | Buchbinder et al. |
| 2013/0304200 A1 | 11/2013 | McLean et al. |
| 2013/0331929 A1 | 12/2013 | Mitra et al. |
| 2013/0338764 A1 | 12/2013 | Thornton et al. |
| 2014/0000112 A1 | 1/2014 | Braido et al. |
| 2014/0005540 A1 | 1/2014 | Merhi |
| 2014/0005768 A1 | 1/2014 | Thomas et al. |
| 2014/0005778 A1 | 1/2014 | Buchbinder et al. |
| 2014/0012372 A1 | 1/2014 | Chau et al. |
| 2014/0018915 A1 | 1/2014 | Baidillah et al. |
| 2014/0025164 A1 | 1/2014 | Montorfano et al. |
| 2014/0031924 A1 | 1/2014 | Bruchman et al. |
| 2014/0039511 A1 | 2/2014 | Morris et al. |
| 2014/0039611 A1 | 2/2014 | Lane et al. |
| 2014/0052237 A1 | 2/2014 | Lane et al. |
| 2014/0067037 A1 | 3/2014 | Fargahi |
| 2014/0081383 A1 | 3/2014 | Eberhardt et al. |
| 2014/0088680 A1 | 3/2014 | Costello et al. |
| 2014/0107758 A1 | 4/2014 | Glazier |
| 2014/0110279 A1 | 4/2014 | Kruetzfeldt et al. |
| 2014/0114403 A1 | 4/2014 | Dale et al. |
| 2014/0121763 A1 | 5/2014 | Duffy et al. |
| 2014/0135895 A1 | 5/2014 | Andress et al. |
| 2014/0135908 A1 | 5/2014 | Glozman et al. |
| 2014/0142695 A1 | 5/2014 | Gross et al. |
| 2014/0172070 A1 | 6/2014 | Seguin |
| 2014/0172077 A1 | 6/2014 | Bruchman et al. |
| 2014/0172083 A1 | 6/2014 | Bruchman et al. |
| 2014/0180069 A1 | 6/2014 | Millett |
| 2014/0180070 A1 | 6/2014 | Millett et al. |
| 2014/0194704 A1 | 7/2014 | Millett et al. |
| 2014/0194983 A1 | 7/2014 | Kovalsky et al. |
| 2014/0207231 A1 | 7/2014 | Hacohen et al. |
| 2014/0214069 A1 | 7/2014 | Franklin |
| 2014/0214159 A1 | 7/2014 | Vidlund et al. |
| 2014/0222136 A1 | 8/2014 | Geist et al. |
| 2014/0222137 A1 | 8/2014 | Miller et al. |
| 2014/0222142 A1 | 8/2014 | Kovalsky et al. |
| 2014/0249566 A1 | 9/2014 | Quinn et al. |
| 2014/0249621 A1 | 9/2014 | Eidenschink |
| 2014/0257466 A1 | 9/2014 | Board et al. |
| 2014/0257467 A1 | 9/2014 | Lane et al. |
| 2014/0276616 A1 | 9/2014 | Smith et al. |
| 2014/0276971 A1 | 9/2014 | Kovach |
| 2014/0277342 A1 | 9/2014 | Roeder et al. |
| 2014/0277388 A1 | 9/2014 | Skemp |
| 2014/0277408 A1 | 9/2014 | Folan |
| 2014/0277563 A1 | 9/2014 | White |
| 2014/0288480 A1 | 9/2014 | Zimmerman et al. |
| 2014/0296962 A1 | 10/2014 | Cartledge et al. |
| 2014/0296969 A1 | 10/2014 | Tegels et al. |
| 2014/0296975 A1 | 10/2014 | Tegels et al. |
| 2014/0303718 A1 | 10/2014 | Tegels et al. |
| 2014/0303724 A1 | 10/2014 | Bluestein et al. |
| 2014/0309732 A1 | 10/2014 | Solem |
| 2014/0324161 A1 | 10/2014 | Tegels et al. |
| 2014/0324164 A1 | 10/2014 | Gross et al. |
| 2014/0350662 A1 | 11/2014 | Vaturi |
| 2014/0358224 A1 | 12/2014 | Tegels et al. |
| 2014/0371789 A1 | 12/2014 | Hariton et al. |
| 2014/0379076 A1 | 12/2014 | Vidlund et al. |
| 2015/0005808 A1 | 1/2015 | Chouinard et al. |
| 2015/0005874 A1 | 1/2015 | Vidlund et al. |
| 2015/0039081 A1 | 2/2015 | Costello |
| 2015/0045880 A1 | 2/2015 | Hacohen |
| 2015/0051687 A1 | 2/2015 | Dickerhoff et al. |
| 2015/0094802 A1 | 4/2015 | Buchbinder et al. |
| 2015/0112188 A1 | 4/2015 | Stigall et al. |
| 2015/0119982 A1 | 4/2015 | Quill et al. |
| 2015/0127093 A1 | 5/2015 | Hosmer et al. |
| 2015/0142103 A1 | 5/2015 | Vidlund |
| 2015/0157457 A1 | 6/2015 | Hacohen |
| 2015/0173897 A1 | 6/2015 | Raanani et al. |
| 2015/0173898 A1 | 6/2015 | Drasler et al. |
| 2015/0196390 A1 | 7/2015 | Ma et al. |
| 2015/0196391 A1 | 7/2015 | Dwork |
| 2015/0202044 A1 | 7/2015 | Chau et al. |
| 2015/0216661 A1 | 8/2015 | Hacohen et al. |
| 2015/0230919 A1 | 8/2015 | Chau et al. |
| 2015/0245934 A1 | 9/2015 | Lombardi et al. |
| 2015/0257878 A1 | 9/2015 | Lane et al. |
| 2015/0257880 A1 | 9/2015 | Bortlein et al. |
| 2015/0257882 A1 | 9/2015 | Bortlein et al. |
| 2015/0265400 A1 | 9/2015 | Eidenschink et al. |
| 2015/0272731 A1 | 10/2015 | Racchini et al. |
| 2015/0282922 A1 | 10/2015 | Hingston et al. |
| 2015/0282931 A1 | 10/2015 | Brunnett et al. |
| 2015/0289971 A1 | 10/2015 | Costello et al. |
| 2015/0289975 A1 | 10/2015 | Costello |
| 2015/0297241 A1 | 10/2015 | Yodfat et al. |
| 2015/0305867 A1 | 10/2015 | Liu et al. |
| 2015/0313701 A1 | 11/2015 | Krahbichler |
| 2015/0335424 A1 | 11/2015 | McLean et al. |
| 2015/0342717 A1 | 12/2015 | O'Donnell et al. |
| 2015/0351904 A1 | 12/2015 | Cooper et al. |
| 2015/0351906 A1 | 12/2015 | Hammer et al. |
| 2015/0351910 A1 | 12/2015 | Gilmore et al. |
| 2015/0359629 A1 | 12/2015 | Ganesan et al. |
| 2016/0008130 A1 | 1/2016 | Hasin |

(56) References Cited

U.S. PATENT DOCUMENTS

| | | |
|---|---|---|
| 2016/0008131 A1 | 1/2016 | Christianson et al. |
| 2016/0022417 A1 | 1/2016 | Karapetian et al. |
| 2016/0030165 A1 | 2/2016 | Mitra et al. |
| 2016/0030167 A1 | 2/2016 | Delaloye et al. |
| 2016/0038280 A1 | 2/2016 | Morriss et al. |
| 2016/0038283 A1 | 2/2016 | Divekar et al. |
| 2016/0045165 A1 | 2/2016 | Braido et al. |
| 2016/0045306 A1 | 2/2016 | Agrawal et al. |
| 2016/0045309 A1 | 2/2016 | Valdez et al. |
| 2016/0067031 A1 | 3/2016 | Kassab et al. |
| 2016/0081799 A1 | 3/2016 | Leo et al. |
| 2016/0095703 A1 | 4/2016 | Thomas et al. |
| 2016/0095704 A1 | 4/2016 | Whitman |
| 2016/0113764 A1 | 4/2016 | Sheahan et al. |
| 2016/0113766 A1 | 4/2016 | Ganesan et al. |
| 2016/0113768 A1 | 4/2016 | Ganesan et al. |
| 2016/0143721 A1 | 5/2016 | Rosenbluth et al. |
| 2016/0143730 A1 | 5/2016 | Kheradvar |
| 2016/0143735 A1 | 5/2016 | Subramanian et al. |
| 2016/0143739 A1 | 5/2016 | Horgan et al. |
| 2016/0158004 A1 | 6/2016 | Kumar et al. |
| 2016/0158007 A1 | 6/2016 | Centola et al. |
| 2016/0158008 A1 | 6/2016 | Miller et al. |
| 2016/0166382 A1 | 6/2016 | Nguyen |
| 2016/0184488 A1 | 6/2016 | Toyoda et al. |
| 2016/0194425 A1 | 7/2016 | Mitra et al. |
| 2016/0213470 A1 | 7/2016 | Ahlberg et al. |
| 2016/0213473 A1 | 7/2016 | Hacohen et al. |
| 2016/0220363 A1 | 8/2016 | Peter |
| 2016/0220367 A1 | 8/2016 | Barrett |
| 2016/0220372 A1 | 8/2016 | Medema et al. |
| 2016/0220734 A1 | 8/2016 | Dyamenahalli et al. |
| 2016/0228250 A1 | 8/2016 | Casley et al. |
| 2016/0235525 A1 | 8/2016 | Rothstein et al. |
| 2016/0235530 A1 | 8/2016 | Thomas et al. |
| 2016/0256269 A1 | 9/2016 | Cahalane et al. |
| 2016/0256270 A1 | 9/2016 | Folan et al. |
| 2016/0270911 A1 | 9/2016 | Ganesan et al. |
| 2016/0302921 A1 | 10/2016 | Gosal et al. |
| 2016/0303804 A1 | 10/2016 | Grbic et al. |
| 2016/0310274 A1 | 10/2016 | Gross et al. |
| 2016/0317301 A1 | 11/2016 | Quadri et al. |
| 2016/0324633 A1 | 11/2016 | Gross et al. |
| 2016/0324639 A1 | 11/2016 | Nguyen et al. |
| 2016/0331534 A1 | 11/2016 | Buchbinder et al. |
| 2016/0354201 A1 | 12/2016 | Keogh |
| 2016/0361169 A1 | 12/2016 | Gross et al. |
| 2016/0361184 A1 | 12/2016 | Tabor et al. |
| 2016/0367360 A1 | 12/2016 | Cartledge et al. |
| 2016/0367364 A1 | 12/2016 | Torrianni et al. |
| 2017/0000603 A1 | 1/2017 | Conklin et al. |
| 2017/0000604 A1 | 1/2017 | Conklin et al. |
| 2017/0020670 A1 | 1/2017 | Murray et al. |
| 2017/0035562 A1 | 2/2017 | Quadri et al. |
| 2017/0035568 A1 | 2/2017 | Lombardi et al. |
| 2017/0056163 A1 | 3/2017 | Tayeb et al. |
| 2017/0056166 A1 | 3/2017 | Ratz et al. |
| 2017/0056171 A1 | 3/2017 | Cooper et al. |
| 2017/0071733 A1 | 3/2017 | Ghione et al. |
| 2017/0071736 A1 | 3/2017 | Zhu et al. |
| 2017/0076014 A1 | 3/2017 | Bressloff |
| 2017/0079786 A1 | 3/2017 | Li et al. |
| 2017/0079795 A1 | 3/2017 | Morrissey |
| 2017/0100236 A1 | 4/2017 | Robertson et al. |
| 2017/0100246 A1 | 4/2017 | Rust et al. |
| 2017/0112620 A1 | 4/2017 | Curley et al. |
| 2017/0128208 A1 | 5/2017 | Christianson et al. |
| 2017/0143446 A1 | 5/2017 | Kölbel |
| 2017/0143488 A1 | 5/2017 | Lashinski |
| 2017/0143489 A1 | 5/2017 | Lashinski |
| 2017/0165065 A1 | 6/2017 | Rothstein et al. |
| 2017/0172737 A1 | 6/2017 | Kuetting et al. |
| 2017/0172738 A1 | 6/2017 | Kassas |
| 2017/0181851 A1 | 6/2017 | Annest |
| 2017/0181852 A1 | 6/2017 | Kassas |
| 2017/0189177 A1 | 7/2017 | Schweich, Jr. et al. |
| 2017/0196690 A1 | 7/2017 | Racchini et al. |
| 2017/0209266 A1 | 7/2017 | Lane et al. |
| 2017/0209268 A1 | 7/2017 | Cunningham et al. |
| 2017/0216023 A1 | 8/2017 | Lane et al. |
| 2017/0216026 A1 | 8/2017 | Quill et al. |
| 2017/0216030 A1 | 8/2017 | Jonsson |
| 2017/0224480 A1 | 8/2017 | Garde et al. |
| 2017/0224486 A1 | 8/2017 | Delaloye et al. |
| 2017/0231755 A1 | 8/2017 | Gloss et al. |
| 2017/0231760 A1 | 8/2017 | Lane et al. |
| 2017/0239047 A1 | 8/2017 | Quill et al. |
| 2017/0245993 A1 | 8/2017 | Gross et al. |
| 2017/0245994 A1 | 8/2017 | Khairkhahan et al. |
| 2017/0252163 A1 | 9/2017 | Kheradvar |
| 2017/0258584 A1 | 9/2017 | Chang et al. |
| 2017/0258585 A1 | 9/2017 | Marquez et al. |
| 2017/0273784 A1 | 9/2017 | Racchini et al. |
| 2017/0281337 A1 | 10/2017 | Campbell |
| 2017/0281341 A1 | 10/2017 | Lim et al. |
| 2017/0296340 A1 | 10/2017 | Gross et al. |
| 2017/0319333 A1 | 11/2017 | Tegels et al. |
| 2017/0325943 A1 | 11/2017 | Robin et al. |
| 2017/0325948 A1 | 11/2017 | Wallace et al. |
| 2017/0325976 A1 | 11/2017 | Nguyen et al. |
| 2017/0333184 A1 | 11/2017 | Ryan |
| 2017/0333240 A1 | 11/2017 | Stangenes et al. |
| 2017/0348099 A1 | 12/2017 | Mendelson et al. |
| 2017/0348100 A1 | 12/2017 | Lane et al. |
| 2017/0360557 A1 | 12/2017 | Kheradvar et al. |
| 2017/0360558 A1 | 12/2017 | Ma |
| 2017/0360561 A1 | 12/2017 | Bell et al. |
| 2018/0000586 A1 | 1/2018 | Ganesan et al. |
| 2018/0014932 A1 | 1/2018 | Hammer et al. |
| 2018/0021130 A1 | 1/2018 | Danino |
| 2018/0035971 A1 | 2/2018 | Brenner et al. |
| 2018/0042549 A1 | 2/2018 | Ho et al. |
| 2018/0042721 A1 | 2/2018 | Chambers |
| 2018/0042723 A1 | 2/2018 | Yellin et al. |
| 2018/0043133 A1 | 2/2018 | Wong |
| 2018/0049875 A1 | 2/2018 | Iflah et al. |
| 2018/0049876 A1 | 2/2018 | Miraki |
| 2018/0055628 A1 | 3/2018 | Patel et al. |
| 2018/0055633 A1 | 3/2018 | Costello et al. |
| 2018/0056045 A1 | 3/2018 | Donoghue et al. |
| 2018/0056046 A1 | 3/2018 | Kiersey et al. |
| 2018/0071088 A1 | 3/2018 | Badhwar et al. |
| 2018/0078367 A1 | 3/2018 | Saar et al. |
| 2018/0078368 A1 | 3/2018 | Vidlund et al. |
| 2018/0078370 A1 | 3/2018 | Kovalsky et al. |
| 2018/0085219 A1 | 3/2018 | Krivoruchko |
| 2018/0098837 A1 | 4/2018 | Shahriari |
| 2018/0098874 A1* | 4/2018 | Tuseth ............... A61M 60/148 |
| 2018/0099124 A1 | 4/2018 | McLoughlin et al. |
| 2018/0116793 A1 | 5/2018 | Salahieh et al. |
| 2018/0116843 A1 | 5/2018 | Schreck et al. |
| 2018/0125642 A1 | 5/2018 | White et al. |
| 2018/0125654 A1 | 5/2018 | Duffy |
| 2018/0126127 A1 | 5/2018 | Devereux et al. |
| 2018/0133000 A1 | 5/2018 | Scheinblum et al. |
| 2018/0133006 A1 | 5/2018 | Jones et al. |
| 2018/0133011 A1 | 5/2018 | Perouse |
| 2018/0140417 A1 | 5/2018 | Sciscio et al. |
| 2018/0147041 A1 | 5/2018 | Chouinard et al. |
| 2018/0147055 A1 | 5/2018 | Vidlund et al. |
| 2018/0153689 A1 | 6/2018 | Maimon et al. |
| 2018/0161158 A1 | 6/2018 | Kovalsky et al. |
| 2018/0161161 A1 | 6/2018 | Yellin et al. |
| 2018/0168793 A1 | 6/2018 | Lees et al. |
| 2018/0177580 A9 | 6/2018 | Shemesh et al. |
| 2018/0177594 A1 | 6/2018 | Patel et al. |
| 2018/0185153 A1 | 7/2018 | Bishop et al. |
| 2018/0193138 A1 | 7/2018 | Vidlund |
| 2018/0200049 A1 | 7/2018 | Chambers et al. |
| 2018/0206983 A1 | 7/2018 | Noe et al. |
| 2018/0214141 A1 | 8/2018 | Mendez |
| 2018/0221016 A1 | 8/2018 | Conklin et al. |
| 2018/0243071 A1 | 8/2018 | Eigler et al. |
| 2018/0243532 A1 | 8/2018 | Willard et al. |

(56) References Cited

U.S. PATENT DOCUMENTS

| | | |
|---|---|---|
| 2018/0256322 A1 | 9/2018 | Zhang et al. |
| 2018/0256327 A1 | 9/2018 | Perszyk et al. |
| 2018/0256329 A1 | 9/2018 | Chambers et al. |
| 2018/0263767 A1 | 9/2018 | Chau et al. |
| 2018/0263773 A1 | 9/2018 | Poppe et al. |
| 2018/0280174 A1 | 10/2018 | Dwork |
| 2018/0289474 A1 | 10/2018 | Rajagopal et al. |
| 2018/0289475 A1 | 10/2018 | Chung et al. |
| 2018/0289485 A1 | 10/2018 | Rajagopal et al. |
| 2018/0296325 A1 | 10/2018 | McLean |
| 2018/0296335 A1 | 10/2018 | Miyashiro |
| 2018/0296337 A1 | 10/2018 | Duhay et al. |
| 2018/0296341 A1 | 10/2018 | Noe et al. |
| 2018/0303488 A1 | 10/2018 | Hill |
| 2018/0303612 A1 | 10/2018 | Pasquino et al. |
| 2018/0311037 A1 | 11/2018 | Morriss et al. |
| 2018/0311474 A1 | 11/2018 | Tyler, II et al. |
| 2018/0318071 A1 | 11/2018 | Lozonschi et al. |
| 2018/0318073 A1 | 11/2018 | Tseng et al. |
| 2018/0318078 A1 | 11/2018 | Willard |
| 2018/0325665 A1 | 11/2018 | Gurovich et al. |
| 2018/0325671 A1 | 11/2018 | Abunassar et al. |
| 2018/0333259 A1 | 11/2018 | Dibie |
| 2018/0338832 A1 | 11/2018 | Ganesan et al. |
| 2018/0344456 A1 | 12/2018 | Barash et al. |
| 2018/0353293 A1 | 12/2018 | Colavito et al. |
| 2018/0353295 A1 | 12/2018 | Cooper et al. |
| 2018/0360439 A1 | 12/2018 | Niland et al. |
| 2018/0360599 A1 | 12/2018 | Drasler et al. |
| 2019/0000619 A1 | 1/2019 | Quijano et al. |
| 2019/0008636 A1 | 1/2019 | Francis et al. |
| 2019/0008640 A1 | 1/2019 | Cooper et al. |
| 2019/0015188 A1 | 1/2019 | Eigler et al. |
| 2019/0021834 A1 | 1/2019 | Nir et al. |
| 2019/0029819 A1 | 1/2019 | Huber |
| 2019/0029823 A1 | 1/2019 | Nguyen et al. |
| 2019/0038404 A1 | 2/2019 | Iamberger et al. |
| 2019/0038405 A1 | 2/2019 | Iamberger et al. |
| 2019/0053894 A1 | 2/2019 | Levi et al. |
| 2019/0053895 A1 | 2/2019 | Levi |
| 2019/0053897 A1 | 2/2019 | Levi et al. |
| 2019/0053898 A1 | 2/2019 | Maimon et al. |
| 2019/0053899 A1 | 2/2019 | Levi |
| 2019/0060051 A1 | 2/2019 | Scheeff et al. |
| 2019/0060057 A1 | 2/2019 | Cohen et al. |
| 2019/0060059 A1 | 2/2019 | Delgado et al. |
| 2019/0060069 A1 | 2/2019 | Maimon et al. |
| 2019/0060071 A1 | 2/2019 | Lane et al. |
| 2019/0069995 A1 | 3/2019 | Levi et al. |
| 2019/0070003 A1 | 3/2019 | Siegel et al. |
| 2019/0076233 A1 | 3/2019 | Fish |
| 2019/0076249 A1 | 3/2019 | Khairkhahan et al. |
| 2019/0083085 A1 | 3/2019 | Gilmore et al. |
| 2019/0091005 A1 | 3/2019 | Fifer et al. |
| 2019/0091015 A1 | 3/2019 | Dienno et al. |
| 2019/0091018 A1 | 3/2019 | Hariton et al. |
| 2019/0091022 A1 | 3/2019 | Yellin et al. |
| 2019/0099265 A1 | 4/2019 | Braido et al. |
| 2019/0099270 A1 | 4/2019 | Morrissey et al. |
| 2019/0105153 A1 | 4/2019 | Barash et al. |
| 2019/0117223 A1 | 4/2019 | Abunassar et al. |
| 2019/0117387 A1 | 4/2019 | Li et al. |
| 2019/0117391 A1 | 4/2019 | Humair |
| 2019/0117400 A1 | 4/2019 | Medema et al. |
| 2019/0117401 A1 | 4/2019 | Cortez, Jr. et al. |
| 2019/0125287 A1 | 5/2019 | Itou et al. |
| 2019/0125536 A1 | 5/2019 | Prabhu et al. |
| 2019/0133528 A1 | 5/2019 | Kassab et al. |
| 2019/0133756 A1 | 5/2019 | Zhang et al. |
| 2019/0133757 A1 | 5/2019 | Zhang et al. |
| 2019/0133765 A1 | 5/2019 | Yellin et al. |
| 2019/0142566 A1 | 5/2019 | Lansky et al. |
| 2019/0142582 A1 | 5/2019 | Drasler et al. |
| 2019/0150867 A1 | 5/2019 | Itou et al. |
| 2019/0151509 A1 | 5/2019 | Kheradvar et al. |
| 2019/0167423 A1 | 6/2019 | Hariton et al. |
| 2019/0167429 A1 | 6/2019 | Stearns et al. |
| 2019/0175338 A1 | 6/2019 | White et al. |
| 2019/0175339 A1 | 6/2019 | Vidlund |
| 2019/0175344 A1 | 6/2019 | Khairkhahan |
| 2019/0183639 A1 | 6/2019 | Moore |
| 2019/0183644 A1 | 6/2019 | Hacohen |
| 2019/0183648 A1 | 6/2019 | Trapp et al. |
| 2019/0192287 A1 | 6/2019 | Sandstrom et al. |
| 2019/0192296 A1 | 6/2019 | Schwartz et al. |
| 2019/0209317 A1 | 7/2019 | Zhang et al. |
| 2019/0209320 A1 | 7/2019 | Drasler et al. |
| 2019/0231523 A1 | 8/2019 | Lombardi et al. |
| 2019/0240020 A1 | 8/2019 | Rafiee et al. |
| 2019/0240022 A1 | 8/2019 | Rafiee et al. |
| 2019/0247050 A1 | 8/2019 | Goldsmith |
| 2019/0254815 A1 | 8/2019 | Bruchman et al. |
| 2019/0254816 A1 | 8/2019 | Anderson et al. |
| 2019/0262118 A1 | 8/2019 | Eigler et al. |
| 2019/0262129 A1 | 8/2019 | Cooper et al. |
| 2019/0269413 A1 | 9/2019 | Yodfat et al. |
| 2019/0269504 A1 | 9/2019 | Wang et al. |
| 2019/0269839 A1 | 9/2019 | Wilson et al. |
| 2019/0282360 A1 | 9/2019 | Colavito et al. |
| 2019/0290426 A1 | 9/2019 | Maimon et al. |
| 2019/0290427 A1 | 9/2019 | Mantanus et al. |
| 2019/0307563 A1 | 10/2019 | Sandstrom et al. |
| 2019/0307589 A1 | 10/2019 | Goldberg et al. |
| 2019/0321171 A1 | 10/2019 | Morriss et al. |
| 2019/0365538 A1 | 12/2019 | Chambers et al. |
| 2019/0388219 A1 | 12/2019 | Ane et al. |
| 2020/0008941 A1 | 1/2020 | Stappenbeck et al. |
| 2020/0093589 A1 | 3/2020 | Christianson et al. |
| 2020/0121452 A1 | 4/2020 | Saikrishnan et al. |
| 2020/0121458 A1 | 4/2020 | Vidlund et al. |
| 2020/0179146 A1 | 6/2020 | Christianson et al. |
| 2020/0188097 A1 | 6/2020 | Perrin et al. |
| 2020/0237506 A1 | 7/2020 | Christianson et al. |
| 2020/0289259 A1 | 9/2020 | Christianson et al. |
| 2020/0289263 A1 | 9/2020 | Christianson et al. |
| 2021/0000592 A1 | 1/2021 | Christianson et al. |
| 2021/0137677 A1 | 5/2021 | Christianson et al. |
| 2021/0154010 A1 | 5/2021 | Schneider et al. |
| 2021/0154011 A1 | 5/2021 | Christianson et al. |
| 2021/0186693 A1 | 6/2021 | Vidlund et al. |
| 2021/0220126 A1 | 7/2021 | Perrin |
| 2021/0220127 A1 | 7/2021 | Vidlund et al. |
| 2021/0220134 A1 | 7/2021 | Christianson et al. |
| 2021/0228349 A1 | 7/2021 | Vidlund et al. |
| 2021/0236280 A1 | 8/2021 | Christianson et al. |
| 2021/0244533 A1 | 8/2021 | Vidlund et al. |
| 2021/0244535 A1 | 8/2021 | Iyer et al. |
| 2021/0244536 A1 | 8/2021 | Christianson et al. |
| 2021/0290381 A1 | 9/2021 | Vidlund et al. |
| 2021/0315694 A1 | 10/2021 | Vidlund et al. |
| 2021/0330459 A1 | 10/2021 | Christianson et al. |
| 2021/0353412 A1 | 11/2021 | Christianson et al. |
| 2021/0401572 A1 | 12/2021 | Nasr et al. |
| 2022/0000614 A1 | 1/2022 | Vidlund et al. |
| 2022/0087815 A1 | 3/2022 | Bernshtein et al. |
| 2022/0096226 A1 | 3/2022 | Christianson et al. |
| 2022/0160504 A1 | 5/2022 | Vidlund et al. |
| 2022/0249228 A1 | 8/2022 | Vidlund et al. |
| 2022/0280292 A1 | 9/2022 | Vidlund et al. |
| 2022/0280296 A1 | 9/2022 | Christianson et al. |
| 2022/0296369 A1 | 9/2022 | Kheradvar et al. |
| 2022/0323212 A1 | 10/2022 | Vidlund et al. |
| 2022/0338978 A1 | 10/2022 | Yushtein |
| 2022/0370198 A1 | 11/2022 | Nir et al. |
| 2022/0378410 A1 | 12/2022 | Hacohen et al. |
| 2022/0387174 A1 | 12/2022 | Schwarcz et al. |
| 2022/0395370 A1 | 12/2022 | Vidlund et al. |
| 2022/0409369 A1 | 12/2022 | Christianson et al. |
| 2023/0157816 A1 | 5/2023 | Perrin |
| 2023/0172710 A1 | 6/2023 | Nir |
| 2023/0190463 A1 | 6/2023 | Nir |
| 2023/0200990 A1 | 6/2023 | Chen et al. |
| 2023/0263630 A1 | 8/2023 | Saar et al. |
| 2023/0338140 A1 | 10/2023 | Cartledge et al. |

(56) References Cited

U.S. PATENT DOCUMENTS

| | | | |
|---|---|---|---|
| 2024/0074855 A1 | 3/2024 | Atias et al. |
| 2024/0138983 A1 | 5/2024 | Ekvall et al. |
| 2024/0148496 A1 | 5/2024 | Christianson |
| 2024/0148497 A1 | 5/2024 | Bukin et al. |
| 2024/0225828 A1 | 7/2024 | Vidlund et al. |

FOREIGN PATENT DOCUMENTS

| | | | |
|---|---|---|---|
| AU | 2011238752 A1 | 10/2012 |
| AU | 2011240940 A1 | 10/2012 |
| AU | 2012272855 A1 | 1/2014 |
| AU | 2011236036 B2 | 6/2014 |
| AU | 2011248657 B2 | 12/2014 |
| AU | 2016228261 A1 | 4/2017 |
| AU | 2017210659 A1 | 8/2017 |
| AU | 2013245201 B2 | 10/2017 |
| AU | 2014360294 B2 | 10/2017 |
| AU | 2016249819 A1 | 11/2017 |
| AU | 2016371525 A1 | 5/2018 |
| AU | 2016366783 A1 | 6/2018 |
| AU | 2017214672 B2 | 10/2018 |
| AU | 2017285993 A1 | 1/2019 |
| AU | 2014201920 B2 | 2/2019 |
| AU | 2015411406 B2 | 2/2019 |
| AU | 2019202290 A1 | 4/2019 |
| AU | 2017388857 A1 | 8/2019 |
| BR | PI0909379 B1 | 9/2019 |
| CA | 2531528 A1 | 1/2005 |
| CA | 2609800 A1 | 1/2007 |
| CA | 2822636 A1 | 10/2008 |
| CA | 2398948 C | 8/2009 |
| CA | 2813419 A1 | 4/2012 |
| CA | 2856088 A1 | 5/2013 |
| CA | 2866315 A1 | 9/2013 |
| CA | 2922123 A1 | 4/2015 |
| CA | 2504258 C | 6/2015 |
| CA | 2677648 C | 10/2015 |
| CA | 2815331 C | 10/2015 |
| CA | 2986584 A1 | 11/2015 |
| CA | 2975294 A1 | 8/2016 |
| CA | 2995603 A1 | 2/2017 |
| CA | 2753853 C | 4/2017 |
| CA | 2702615 C | 6/2017 |
| CA | 2744395 C | 8/2017 |
| CA | 3020238 A1 | 11/2017 |
| CA | 3033666 A1 | 2/2018 |
| CA | 3031572 A1 | 3/2018 |
| CA | 3022641 A1 | 5/2018 |
| CA | 3044062 A1 | 6/2018 |
| CA | 3048893 A1 | 7/2018 |
| CA | 3049792 A1 | 7/2018 |
| CA | 3046693 A1 | 8/2018 |
| CA | 2778944 C | 8/2019 |
| CN | 2855366 Y | 1/2007 |
| CN | 100584292 C | 1/2010 |
| CN | 101677820 A | 3/2010 |
| CN | 101677851 A | 3/2010 |
| CN | 102858272 A | 1/2013 |
| CN | 102869320 A | 1/2013 |
| CN | 102892384 A | 1/2013 |
| CN | 103118630 A | 5/2013 |
| CN | 103189015 A | 7/2013 |
| CN | 103228231 A | 7/2013 |
| CN | 103298426 A | 9/2013 |
| CN | 103370035 A | 10/2013 |
| CN | 103391756 A | 11/2013 |
| CN | 102245120 B | 8/2014 |
| CN | 104220027 A | 12/2014 |
| CN | 102917668 B | 1/2015 |
| CN | 104394803 A | 3/2015 |
| CN | 104582637 A | 4/2015 |
| CN | 102905647 B | 7/2015 |
| CN | 103648570 B | 9/2015 |
| CN | 104884000 A | 9/2015 |
| CN | 104160076 B | 12/2015 |
| CN | 105380730 A | 3/2016 |
| CN | 105451687 A | 3/2016 |
| CN | 105520792 A | 4/2016 |
| CN | 105530893 A | 4/2016 |
| CN | 102458309 B | 5/2016 |
| CN | 103200900 B | 5/2016 |
| CN | 105555232 A | 5/2016 |
| CN | 105578992 A | 5/2016 |
| CN | 103338709 B | 6/2016 |
| CN | 105658178 A | 6/2016 |
| CN | 105792780 A | 7/2016 |
| CN | 103347467 B | 8/2016 |
| CN | 103648439 B | 8/2016 |
| CN | 103889472 B | 8/2016 |
| CN | 105899150 A | 8/2016 |
| CN | 103153232 B | 9/2016 |
| CN | 106061437 A | 10/2016 |
| CN | 106068109 A | 11/2016 |
| CN | 106073946 A | 11/2016 |
| CN | 106255475 A | 12/2016 |
| CN | 103917194 B | 2/2017 |
| CN | 106456324 A | 2/2017 |
| CN | 106456325 A | 2/2017 |
| CN | 105073068 B | 3/2017 |
| CN | 106470641 A | 3/2017 |
| CN | 105451684 B | 4/2017 |
| CN | 106573129 A | 4/2017 |
| CN | 103945792 B | 5/2017 |
| CN | 106659394 A | 5/2017 |
| CN | 106716098 A | 5/2017 |
| CN | 106794063 A | 5/2017 |
| CN | 106890035 A | 6/2017 |
| CN | 106943207 A | 7/2017 |
| CN | 106999054 A | 8/2017 |
| CN | 106999281 A | 8/2017 |
| CN | 104114127 B | 9/2017 |
| CN | 107115161 A | 9/2017 |
| CN | 107249482 A | 10/2017 |
| CN | 107260366 A | 10/2017 |
| CN | 104918582 B | 11/2017 |
| CN | 107374783 A | 11/2017 |
| CN | 107427364 A | 12/2017 |
| CN | 106255476 B | 1/2018 |
| CN | 107530157 A | 1/2018 |
| CN | 107530167 A | 1/2018 |
| CN | 107530177 A | 1/2018 |
| CN | 107613908 A | 1/2018 |
| CN | 104869948 B | 2/2018 |
| CN | 107714240 A | 2/2018 |
| CN | 107920897 A | 4/2018 |
| CN | 104853696 B | 6/2018 |
| CN | 108135696 A | 6/2018 |
| CN | 108430392 A | 8/2018 |
| CN | 108472142 A | 8/2018 |
| CN | 106726007 B | 11/2018 |
| CN | 109124829 A | 1/2019 |
| CN | 109199641 A | 1/2019 |
| CN | 109561962 A | 4/2019 |
| CN | 109567991 A | 4/2019 |
| CN | 109862835 A | 6/2019 |
| CN | 109906063 A | 6/2019 |
| CN | 109996581 A | 7/2019 |
| CN | 110013358 A | 7/2019 |
| CN | 110290764 A | 9/2019 |
| DE | 102014102648 A1 | 9/2015 |
| DE | 102014102650 A1 | 9/2015 |
| DE | 102014102718 A1 | 9/2015 |
| DE | 102014102722 A1 | 9/2015 |
| DE | 202017104793 U1 | 11/2018 |
| DE | 202016008737 U1 | 4/2019 |
| DK | 2549953 T3 | 2/2017 |
| DK | 2254514 T3 | 12/2018 |
| EA | 027348 B1 | 7/2017 |
| EP | 0902704 A4 | 3/1999 |
| EP | 1301225 A2 | 4/2003 |
| EP | 1684666 A2 | 8/2006 |
| EP | 1996246 A2 | 12/2008 |
| EP | 2211779 A1 | 8/2010 |
| EP | 2254513 A1 | 12/2010 |

(56) References Cited

FOREIGN PATENT DOCUMENTS

| | | |
|---|---|---|
| EP | 2263605 A1 | 12/2010 |
| EP | 2273947 A1 | 1/2011 |
| EP | 2296744 A1 | 3/2011 |
| EP | 2379008 A2 | 10/2011 |
| EP | 2400926 A2 | 1/2012 |
| EP | 2427145 A2 | 3/2012 |
| EP | 1582178 B1 | 9/2012 |
| EP | 2542186 A2 | 1/2013 |
| EP | 2558030 A1 | 2/2013 |
| EP | 2560579 A1 | 2/2013 |
| EP | 2575681 A1 | 4/2013 |
| EP | 2603172 A2 | 6/2013 |
| EP | 2637607 A1 | 9/2013 |
| EP | 2651337 A2 | 10/2013 |
| EP | 2658476 A1 | 11/2013 |
| EP | 2699201 A1 | 2/2014 |
| EP | 2405966 B1 | 4/2014 |
| EP | 2055263 B1 | 6/2014 |
| EP | 2741711 A2 | 6/2014 |
| EP | 2793763 A1 | 10/2014 |
| EP | 2822503 A2 | 1/2015 |
| EP | 2538879 B1 | 4/2015 |
| EP | 2444031 B1 | 7/2015 |
| EP | 1702247 B1 | 8/2015 |
| EP | 2772228 B1 | 11/2015 |
| EP | 2943160 A2 | 11/2015 |
| EP | 2470098 B1 | 12/2015 |
| EP | 1991168 B1 | 1/2016 |
| EP | 2254512 B1 | 1/2016 |
| EP | 2964152 A1 | 1/2016 |
| EP | 2967853 A1 | 1/2016 |
| EP | 2967860 A1 | 1/2016 |
| EP | 2994073 A1 | 3/2016 |
| EP | 3001978 A1 | 4/2016 |
| EP | 3003187 A1 | 4/2016 |
| EP | 3007649 A1 | 4/2016 |
| EP | 3010447 A1 | 4/2016 |
| EP | 3017792 A1 | 5/2016 |
| EP | 3019092 A1 | 5/2016 |
| EP | 2563236 B1 | 6/2016 |
| EP | 3027143 A1 | 6/2016 |
| EP | 3037064 A1 | 6/2016 |
| EP | 2211758 B1 | 7/2016 |
| EP | 3052053 A1 | 8/2016 |
| EP | 3060140 A1 | 8/2016 |
| EP | 3062745 A1 | 9/2016 |
| EP | 3071149 A1 | 9/2016 |
| EP | 2282700 B1 | 11/2016 |
| EP | 2967854 B1 | 11/2016 |
| EP | 1998713 B1 | 12/2016 |
| EP | 3099271 A1 | 12/2016 |
| EP | 3100701 A1 | 12/2016 |
| EP | 3141219 A1 | 3/2017 |
| EP | 3157469 A1 | 4/2017 |
| EP | 2538880 B1 | 5/2017 |
| EP | 2967852 B1 | 6/2017 |
| EP | 3174503 A1 | 6/2017 |
| EP | 3182931 A1 | 6/2017 |
| EP | 2830536 B1 | 8/2017 |
| EP | 2830537 B1 | 9/2017 |
| EP | 2720642 B1 | 10/2017 |
| EP | 3232941 A1 | 10/2017 |
| EP | 3256076 A1 | 12/2017 |
| EP | 3281608 A1 | 2/2018 |
| EP | 2608815 B1 | 3/2018 |
| EP | 3310302 A1 | 4/2018 |
| EP | 3311778 A1 | 4/2018 |
| EP | 3337412 A1 | 6/2018 |
| EP | 3340931 A1 | 7/2018 |
| EP | 3344188 A1 | 7/2018 |
| EP | 3344197 A1 | 7/2018 |
| EP | 3345573 A1 | 7/2018 |
| EP | 2822473 B1 | 8/2018 |
| EP | 3354208 A1 | 8/2018 |
| EP | 3370649 A1 | 9/2018 |
| EP | 3372198 A1 | 9/2018 |
| EP | 3372199 A1 | 9/2018 |
| EP | 3375411 A1 | 9/2018 |
| EP | 2928538 B1 | 11/2018 |
| EP | 3399947 A1 | 11/2018 |
| EP | 3400913 A1 | 11/2018 |
| EP | 3406224 A1 | 11/2018 |
| EP | 2555709 B1 | 12/2018 |
| EP | 3417813 A1 | 12/2018 |
| EP | 3426188 A1 | 1/2019 |
| EP | 3429507 A1 | 1/2019 |
| EP | 3431040 A1 | 1/2019 |
| EP | 3432825 A1 | 1/2019 |
| EP | 3432834 A1 | 1/2019 |
| EP | 3437669 A1 | 2/2019 |
| EP | 3448312 A1 | 3/2019 |
| EP | 3454787 A1 | 3/2019 |
| EP | 2663259 B1 | 5/2019 |
| EP | 3302364 B1 | 5/2019 |
| EP | 3478224 A1 | 5/2019 |
| EP | 3484411 A1 | 5/2019 |
| EP | 3487420 A1 | 5/2019 |
| EP | 2560580 B1 | 6/2019 |
| EP | 3508113 A1 | 7/2019 |
| EP | 3518748 A1 | 8/2019 |
| EP | 3522830 A1 | 8/2019 |
| EP | 3528749 A1 | 8/2019 |
| EP | 3288495 B1 | 9/2019 |
| EP | 3538024 A1 | 9/2019 |
| EP | 3538025 A1 | 9/2019 |
| EP | 3019123 B1 | 10/2019 |
| EP | 3552584 A1 | 10/2019 |
| EP | 3552655 A1 | 10/2019 |
| ES | 2369241 T3 | 11/2011 |
| ES | 2647777 T3 | 12/2017 |
| ES | 2664243 T3 | 4/2018 |
| ES | 2675726 T3 | 7/2018 |
| GB | 2539444 A | 12/2016 |
| JP | 2003530956 A | 10/2003 |
| JP | 2005521513 A | 7/2005 |
| JP | 2008506459 A | 3/2008 |
| JP | 2008512211 A | 4/2008 |
| JP | 2009148579 A | 7/2009 |
| JP | 2009525138 A | 7/2009 |
| JP | 2009527316 A | 7/2009 |
| JP | 2009254864 A | 11/2009 |
| JP | 4426182 B2 | 3/2010 |
| JP | 2010508093 A | 3/2010 |
| JP | 2010518947 A | 6/2010 |
| JP | 2010537680 A | 12/2010 |
| JP | 2011510797 A | 4/2011 |
| JP | 2013503009 A | 1/2013 |
| JP | 2013505082 A | 2/2013 |
| JP | 2013508027 A | 3/2013 |
| JP | 2013512765 A | 4/2013 |
| JP | 2013517011 A | 5/2013 |
| JP | 2013523261 A | 6/2013 |
| JP | 2013527010 A | 6/2013 |
| JP | 2013543399 A | 12/2013 |
| JP | 2014501563 A | 1/2014 |
| JP | 2014505537 A | 3/2014 |
| JP | 5527850 B2 | 6/2014 |
| JP | 2014518697 A | 8/2014 |
| JP | 2014522678 A | 9/2014 |
| JP | 2014528761 A | 10/2014 |
| JP | 2015503948 A | 2/2015 |
| JP | 2015510819 A | 4/2015 |
| JP | 2015517854 A | 6/2015 |
| JP | 5767764 B2 | 8/2015 |
| JP | 5803010 B2 | 11/2015 |
| JP | 2015531283 A | 11/2015 |
| JP | 2015534887 A | 12/2015 |
| JP | 2016503710 A | 2/2016 |
| JP | 2016506794 A | 3/2016 |
| JP | 2016508858 A | 3/2016 |
| JP | 2016517748 A | 6/2016 |
| JP | 2016520391 A | 7/2016 |
| JP | 2016526438 A | 9/2016 |
| JP | 2016530046 A | 9/2016 |

(56) References Cited

FOREIGN PATENT DOCUMENTS

| | | |
|---|---|---|
| JP | 2016533787 A | 11/2016 |
| JP | 2016540617 A | 12/2016 |
| JP | 2017000729 A | 1/2017 |
| JP | 2017504410 A | 2/2017 |
| JP | 2017515609 A | 6/2017 |
| JP | 2017516536 A | 6/2017 |
| JP | 2017516609 A | 6/2017 |
| JP | 2017131738 A | 8/2017 |
| JP | 2017159055 A | 9/2017 |
| JP | 2017529908 A | 10/2017 |
| JP | 2018501001 A | 1/2018 |
| JP | 2018501901 A | 1/2018 |
| JP | 2018506412 A | 3/2018 |
| JP | 6329570 B2 | 5/2018 |
| JP | 2018515306 A | 6/2018 |
| JP | 2018118136 A | 8/2018 |
| JP | 2018532556 A | 11/2018 |
| JP | 2018535074 A | 11/2018 |
| JP | 2019500952 A | 1/2019 |
| JP | 2019501696 A | 1/2019 |
| JP | 2019501712 A | 1/2019 |
| JP | 6466853 B2 | 2/2019 |
| JP | 6480343 B2 | 3/2019 |
| JP | 2019507664 A | 3/2019 |
| JP | 6506813 B2 | 4/2019 |
| JP | 6526043 B2 | 6/2019 |
| JP | 2019103821 A | 6/2019 |
| JP | 2019514490 A | 6/2019 |
| JP | 2019516527 A | 6/2019 |
| JP | 2019517346 A | 6/2019 |
| JP | 6568213 B2 | 8/2019 |
| JP | 2019134972 A | 8/2019 |
| JP | 2019523090 A | 8/2019 |
| JP | 2019155178 A | 9/2019 |
| JP | 2019526303 A | 9/2019 |
| KR | 20010013991 A | 2/2001 |
| KR | 20120101625 A | 9/2012 |
| KR | 101223313 B1 | 1/2013 |
| KR | 101354189 B1 | 1/2014 |
| KR | 20140139060 A | 12/2014 |
| KR | 20150097757 A | 8/2015 |
| KR | 20160024992 A | 3/2016 |
| RU | 177405 U1 | 2/2018 |
| WO | WO-0044308 A2 | 8/2000 |
| WO | WO-03072287 A1 | 9/2003 |
| WO | WO-2004093728 A2 | 11/2004 |
| WO | WO-2006029062 A1 | 3/2006 |
| WO | WO-2006066150 A2 | 6/2006 |
| WO | WO-2007047945 A2 | 4/2007 |
| WO | WO-2007054015 A1 | 5/2007 |
| WO | WO-2007095233 A2 | 8/2007 |
| WO | WO-2007129220 A2 | 11/2007 |
| WO | WO-2008013915 A2 | 1/2008 |
| WO | WO-2008055301 A1 | 5/2008 |
| WO | WO-2008091925 A2 | 7/2008 |
| WO | WO-2008103280 A2 | 8/2008 |
| WO | WO-2009081396 A2 | 7/2009 |
| WO | WO-2009094188 A2 | 7/2009 |
| WO | WO-2009094189 A1 | 7/2009 |
| WO | WO-2009094197 A1 | 7/2009 |
| WO | WO-2009094501 A1 | 7/2009 |
| WO | WO-2009100242 A2 | 8/2009 |
| WO | WO-2010029190 A1 | 3/2010 |
| WO | WO-2010079427 A1 | 7/2010 |
| WO | WO-2010119110 A1 | 10/2010 |
| WO | WO-2011112706 A2 | 9/2011 |
| WO | WO-2011137531 A1 | 11/2011 |
| WO | WO-2012009558 A2 | 1/2012 |
| WO | WO 2012/035279 | 3/2012 |
| WO | WO-2012063228 A1 | 5/2012 |
| WO | WO-2012063242 A1 | 5/2012 |
| WO | WO-2012112469 A2 | 8/2012 |
| WO | WO-2012145545 A1 | 10/2012 |
| WO | WO-2012161786 A1 | 11/2012 |
| WO | WO-2012175483 A1 | 12/2012 |
| WO | WO-2012178115 A2 | 12/2012 |
| WO | WO-2013021375 A2 | 2/2013 |
| WO | WO-2013085719 A1 | 6/2013 |
| WO | WO-2013103612 A1 | 7/2013 |
| WO | WO-2013116785 A1 | 8/2013 |
| WO | WO-2013128436 A1 | 9/2013 |
| WO | WO-2013148019 A1 | 10/2013 |
| WO | WO-2013166356 A2 | 11/2013 |
| WO | WO-2013177684 A1 | 12/2013 |
| WO | WO-2013184945 A1 | 12/2013 |
| WO | WO-2014011330 A1 | 1/2014 |
| WO | WO-2014064695 A2 | 5/2014 |
| WO | WO-2014121042 A1 | 8/2014 |
| WO | WO-2014133667 A1 | 9/2014 |
| WO | WO-2014137805 A1 | 9/2014 |
| WO | WO-2014140230 A1 | 9/2014 |
| WO | WO-2014162306 A2 | 10/2014 |
| WO | WO-2014164151 A1 | 10/2014 |
| WO | WO-2014168655 A1 | 10/2014 |
| WO | WO-2015004173 A1 | 1/2015 |
| WO | WO-2015014960 A1 | 2/2015 |
| WO | WO-2015017075 A1 | 2/2015 |
| WO | WO-2015055605 A1 | 4/2015 |
| WO | WO-2015057735 A1 | 4/2015 |
| WO | WO-2015058039 A1 | 4/2015 |
| WO | WO-2015061021 A1 | 4/2015 |
| WO | WO-2015117025 A1 | 8/2015 |
| WO | WO-2015120122 A2 | 8/2015 |
| WO | WO-2015123607 A2 | 8/2015 |
| WO | WO-2015127264 A1 | 8/2015 |
| WO | WO-2015142834 A1 | 9/2015 |
| WO | WO-2015153755 A2 | 10/2015 |
| WO | WO-2016011267 A1 | 1/2016 |
| WO | WO-2016025733 A1 | 2/2016 |
| WO | WO-2016083351 A1 | 6/2016 |
| WO | WO-2016097337 A1 | 6/2016 |
| WO | WO-2016100799 A1 | 6/2016 |
| WO | WO-2016118851 A1 | 7/2016 |
| WO | WO-2016130913 A1 | 8/2016 |
| WO | WO-2016148777 A1 | 9/2016 |
| WO | WO-2016149083 A1 | 9/2016 |
| WO | WO-2016150806 A1 | 9/2016 |
| WO | WO-2016189391 A2 | 12/2016 |
| WO | WO-2017040684 A1 | 3/2017 |
| WO | WO-2017096157 A1 | 6/2017 |
| WO | WO-2017114928 A1 | 7/2017 |
| WO | WO-2017120404 A1 | 7/2017 |
| WO | WO-2017121193 A1 | 7/2017 |
| WO | WO-2017121194 A1 | 7/2017 |
| WO | WO-2017121195 A1 | 7/2017 |
| WO | WO-2017123802 A1 | 7/2017 |
| WO | WO-2017136596 A1 | 8/2017 |
| WO | WO-2017151292 A1 | 9/2017 |
| WO | WO-2017155892 A1 | 9/2017 |
| WO | WO-2017156352 A1 | 9/2017 |
| WO | WO-2017161204 A1 | 9/2017 |
| WO | WO-2017165842 A1 | 9/2017 |
| WO | WO-2017196511 A1 | 11/2017 |
| WO | WO-2017201082 A1 | 11/2017 |
| WO | WO-2017202042 A1 | 11/2017 |
| WO | WO-2017210356 A1 | 12/2017 |
| WO | WO-2017218375 A1 | 12/2017 |
| WO | WO-2018008019 A2 | 1/2018 |
| WO | WO-2018026445 A1 | 2/2018 |
| WO | WO-2018026904 A1 | 2/2018 |
| WO | WO-2018035105 A1 | 2/2018 |
| WO | WO-2018040244 A1 | 3/2018 |
| WO | WO-2018042439 A1 | 3/2018 |
| WO | WO-2018045156 A2 | 3/2018 |
| WO | WO-2018071115 A1 | 4/2018 |
| WO | WO-2018077143 A1 | 5/2018 |
| WO | WO-2018077146 A1 | 5/2018 |
| WO | WO-2018080328 A1 | 5/2018 |
| WO | WO-2018083493 A1 | 5/2018 |
| WO | WO-2018090576 A1 | 5/2018 |
| WO | WO-2018098032 A1 | 5/2018 |
| WO | WO-2018106460 A1 | 6/2018 |
| WO | WO-2018119304 A1 | 6/2018 |
| WO | WO-2018136726 A1 | 7/2018 |

(56) References Cited

FOREIGN PATENT DOCUMENTS

| | | |
|---|---|---|
| WO | WO-2018138658 A1 | 8/2018 |
| WO | WO-2018145055 A1 | 8/2018 |
| WO | WO-2018156767 A1 | 8/2018 |
| WO | WO-2018156922 A1 | 8/2018 |
| WO | WO-2018158747 A1 | 9/2018 |
| WO | WO-2018160790 A1 | 9/2018 |
| WO | WO-2018165358 A1 | 9/2018 |
| WO | WO-2018170149 A1 | 9/2018 |
| WO | WO-2018175220 A1 | 9/2018 |
| WO | WO-2018175619 A1 | 9/2018 |
| WO | WO-2018178208 A1 | 10/2018 |
| WO | WO-2018178977 A1 | 10/2018 |
| WO | WO-2018183832 A1 | 10/2018 |
| WO | WO-2018184225 A1 | 10/2018 |
| WO | WO-2018184226 A1 | 10/2018 |
| WO | WO-2018187495 A1 | 10/2018 |
| WO | WO-2018187753 A1 | 10/2018 |
| WO | WO-2018191681 A1 | 10/2018 |
| WO | WO-2018200531 A1 | 11/2018 |
| WO | WO-2018200942 A2 | 11/2018 |
| WO | WO-2018201111 A2 | 11/2018 |
| WO | WO-2018201212 A1 | 11/2018 |
| WO | WO-2018204106 A1 | 11/2018 |
| WO | WO-2018209302 A1 | 11/2018 |
| WO | WO-2018213209 A1 | 11/2018 |
| WO | WO-2018217525 A1 | 11/2018 |
| WO | WO-2018222799 A1 | 12/2018 |
| WO | WO-2018226628 A1 | 12/2018 |
| WO | WO-2019003221 A1 | 1/2019 |
| WO | WO-2019006383 A2 | 1/2019 |
| WO | WO-2019010458 A1 | 1/2019 |
| WO | WO-2019014473 A1 | 1/2019 |
| WO | WO-2019018319 A1 | 1/2019 |
| WO | WO-2019023385 A1 | 1/2019 |
| WO | WO-2019026059 A1 | 2/2019 |
| WO | WO-2019032992 A2 | 2/2019 |
| WO | WO-2019037579 A1 | 2/2019 |
| WO | WO-2019040357 A1 | 2/2019 |
| WO | WO-2019042472 A1 | 3/2019 |
| WO | WO-2019046099 A1 | 3/2019 |
| WO | WO-2019046205 A1 | 3/2019 |
| WO | WO-2019051168 A2 | 3/2019 |
| WO | WO-2019051180 A2 | 3/2019 |
| WO | WO-2019051587 A1 | 3/2019 |
| WO | WO-2019055577 A1 | 3/2019 |
| WO | WO-2019058178 A1 | 3/2019 |
| WO | WO-2019067219 A1 | 4/2019 |
| WO | WO-2019081689 A1 | 5/2019 |
| WO | WO-2019081985 A2 | 5/2019 |
| WO | WO-2019086958 A1 | 5/2019 |
| WO | WO-2019089136 A1 | 5/2019 |
| WO | WO-2019089821 A1 | 5/2019 |
| WO | WO-2019093387 A1 | 5/2019 |
| WO | WO-2019095049 A1 | 5/2019 |
| WO | WO-2019096033 A1 | 5/2019 |
| WO | WO-2019099722 A2 | 5/2019 |
| WO | WO-2019116322 A1 | 6/2019 |
| WO | WO-2019119674 A1 | 6/2019 |
| WO | WO-2019126518 A1 | 6/2019 |
| WO | WO-2019131148 A1 | 7/2019 |
| WO | WO-2019136162 A1 | 7/2019 |
| WO | WO-2019140293 A1 | 7/2019 |
| WO | WO-2019143775 A1 | 7/2019 |
| WO | WO-2019144036 A1 | 7/2019 |
| WO | WO-2019147585 A1 | 8/2019 |
| WO | WO-2019165213 A1 | 8/2019 |
| WO | WO-2019173475 A1 | 9/2019 |
| WO | WO 2019/195860 | 10/2019 |
| WO | WO-2019190800 A1 | 10/2019 |
| WO | WO-2019191102 A1 | 10/2019 |
| WO | WO-2020061124 A1 | 3/2020 |
| WO | WO-2020061331 A2 | 3/2020 |
| WO | WO-2020131978 A1 | 6/2020 |
| WO | WO-2020154735 A1 | 7/2020 |
| WO | WO-2020181154 A2 | 9/2020 |
| WO | WO-2020186251 A1 | 9/2020 |
| WO | WO-2020227249 A1 | 11/2020 |
| WO | WO-2021035032 A1 | 2/2021 |
| WO | WO-2021040996 A1 | 3/2021 |
| WO | WO-2021146515 A1 | 7/2021 |
| WO | WO-2022010974 A1 | 1/2022 |
| WO | WO-2023164489 A2 | 8/2023 |
| WO | WO-2024081883 A1 | 4/2024 |

OTHER PUBLICATIONS

International Search Report and Written Opinion for International Application No. PCT/US2019/051615, mailed Mar. 2, 2020, 14 pages.
International Search Report and Written Opinion for International Application No. PCT/US2019/051957, mailed Apr. 30, 2020, 16 pages.
Office Action for U.S. Appl. No. 16/155,890, mailed Feb. 8, 2019, 13 pages.
Office Action for U.S. Appl. No. 16/448,108, mailed Jan. 21, 2020, 14 pages.
Office Action for U.S. Appl. No. 16/448,108, mailed Sep. 1, 2020, 14 pages.
Office Action for U.S. Appl. No. 16/455,417, mailed Sep. 23, 2019, 11 pages.
International Search Report and Written Opinion for International Application No. PCT/US2019/067010, mailed Mar. 10, 2020, 17 pages.
Office Action for U.S. Appl. No. 16/455,740, mailed Jul. 24, 2020, 7 pages.
International Search Report and Written Opinion for International Application No. PCT/US2020/015231, mailed Apr. 23, 2020, 10 pages.
Office Action for U.S. Appl. No. 17/167,983, mailed Apr. 13, 2021, 20 pages.
International Search Report and Written Opinion for International Application No. PCT/US2020/021300, mailed Oct. 7, 2020, 6 pages.
International Search Report and Written Opinion for International Application No. PCT/US2020/031390, mailed Aug. 3, 2020, 10 pages.
International Search Report and Written Opinion for International Application No. PCT/US2020/013240, mailed Jun. 3, 2020, 7 pages.
International Search Report and Written Opinion for International Application No. PCT/US2020/022828, mailed May 19, 2020, 12 pages.
Office Action for U.S. Appl. No. 16/442,504, mailed Jan. 14, 2020, 11 pages.
International Search Report and Written Opinion for International Application No. PCT/US2020/045195, mailed Jan. 8, 2021, 18 pages.
International Search Report and Written Opinion for International Application No. PCT/US2020/047162, mailed Dec. 30, 2020, 9 pages.
Office Action for U.S. Appl. No. 16/445,210, mailed Jan. 28, 2021, 7 pages.
Office Action for U.S. Appl. No. 16/448,108, mailed Mar. 8, 2021, 8 pages.
Office Action for U.S. Appl. No. 16/163,577, mailed Mar. 8, 2021, 10 pages.
Office Action for U.S. Appl. No. 17/154,227, mailed Mar. 29, 2021, 6 pages.
International Search Report and Written Opinion for International Application No. PCT/US2021/013570, mailed Apr. 1, 2021, 9 pages.
International Search Report and Written Opinion for International Application No. PCT/US2019/028822, mailed Oct. 24, 2019, 14 pages.
Office Action for U.S. Appl. No. 17/154,438, mailed May 3, 2021, 16 pages.
Office Action for U.S. Appl. No. 17/193,936, mailed May 27, 2021, 6 pages.

(56) References Cited

OTHER PUBLICATIONS

Extended European Search Report for European Application No. 19863898.3, mailed Apr. 29, 2022, 13 pages.
Extended European Search Report for European Application No. 19897707.6, mailed Sep. 6, 2022, 7 pages.
Extended European Search Report for European Application No. 20745513.0, mailed Sep. 20, 2022, 9 pages.
Extended European Search Report for European Application No. 20767325.2, mailed on Oct. 25, 2022, 5 pages.
Extended European Search Report for European Application No. 20769769.9, mailed Oct. 17, 2022, 6 pages.
Extended European Search Report for European Application No. 20801681.6, mailed Jan. 18, 2023, 13 pages.
Office Action for U.S. Appl. No. 16/443,862, mailed Nov. 12, 2021, 9 pages.
Office Action for U.S. Appl. No. 16/449,420, mailed Sep. 1, 2021, 16 pages.
Office Action for U.S. Appl. No. 16/711,415, mailed Jan. 18, 2022, 7 pages.
Office Action for U.S. Appl. No. 17/062,080, mailed Dec. 15, 2022, 14 pages.
Office Action for U.S. Appl. No. 17/154,227, mailed Jun. 18, 2021, 8 pages.
Office Action for U.S. Appl. No. 17/167,988, mailed Sep. 22, 2021, 19 pages.
Office Action for U.S. Appl. No. 17/221,547, mailed Aug. 4, 2021, 11 pages.
Office Action for U.S. Appl. No. 17/221,547, mailed Oct. 21, 2021, 9 pages.
Office Action for U.S. Appl. No. 17/222,182, mailed Sep. 2, 2021, 23 pages.
Office Action for U.S. Appl. No. 17/222,430, mailed Oct. 7, 2021, 17 pages.
Office Action for U.S. Appl. No. 17/236,219, mailed Aug. 4, 2021, 17 pages.
Office Action for U.S. Appl. No. 17/388,983, mailed Jan. 6, 2022, 11 pages.
International Search Report and Written Opinion for International Application No. PCT/US2023/076845 dated Mar. 4, 2024, 10 pages.
Non-Final Office Action for U.S. Appl. No. 17/526,691 dated Mar. 11, 2024, 9 pages.
Office Action and Search report for Chinese Application No. CN201980075586.9 dated Feb. 5, 2024, 15 pages.
Office Action for Canadian Application No. CA3152042 dated Feb. 20, 2024, 5 pages.
Office Action for Canadian Patent Application No. CA20203152632 dated Feb. 19, 2024, 4 pages.
Office Action for Canadian Patent Application No. CA3113429 dated Feb. 13, 2024, 4 pages.
Office Action for Japanese Application No. JP20210563105 mailed Feb. 26, 2024, 8 pages.
Office Action for Japanese Patent Application No. JP20210555207 dated Jan. 31, 2024, 6 pages.
Office Action for Japanese Patent Application No. JP2021547343 dated Jan. 31, 2024, 6 pages.
Extended European Search Report for European Application No. EP20856704 dated Aug. 22, 2023, 11 pages.
International Search Report and Written Opinion for PCT Application No. PCT/US2023/063044 dated Oct. 24, 2023, 13 pages.
Office Action for European Application No. 19863898.3 mailed Nov. 27, 2023, 4 pages.
Office Action for European Application No. 20769769.9 dated Sep. 8, 2023, 4 pages.
Office Action for European Application No. EP20200801681 dated Dec. 11, 2023, 7 pages.
Office Action for Japanese Application No. JP2021516666 dated Aug. 31, 2023, 19 pages.
Office Action for Japanese Application No. JP20210535023 dated Oct. 27, 2023, 17 pages.
Extended European Search Report for European Application No. EP20854535 dated Jun. 23, 2023, 8 pages.
Office Action for U.S. Appl. No. 17/666,086 dated Jul. 5, 2023, 16 pages.
Office Action for European Application No. 19863898.3 dated Mar. 24, 2023, 6 pages.
Invitation to Pay Additional Fees for International Application No. PCT/US2023/63044, mailed Jul. 31, 2023, 2 pages.
Office Action for Australian Application No. 2019342130 mailed May 22, 2024, 3 pages.
Office Action for Chinese Application No. 201980090378.6, with Search Report, mailed Mar. 12, 2024, 28 pages, English translation included.
Office Action for Chinese Application No. 202080074543.1, with Search Report, mailed Mar. 28, 2024, 18 pages, English translation included.
Office Action for Japanese Application No. 2021-516666 mailed Apr. 22, 2024, 6 pages, English translation included.
Office Action for Japanese Application No. 2021-535023 mailed Apr. 22, 2024, 4 pages, English translation included.
Office Action for Japanese Application No. 2021-547343 mailed May 13, 2024, 4 pages, English translation included.
Office Action for Japanese Application No. 2022-511360 mailed Apr. 18, 2024, 6 pages, English translation included.
Office Action for Japanese Application No. 2022-513172 mailed Apr. 18, 2024, 12 pages, English translation included.
Office Action for U.S. Appl. No. 17/707,493 mailed Mar. 29, 2024, 21 pages.
Office Action for U.S. Appl. No. 18/410,230, mailed Jun. 4, 2024, 11 pages.
Extended European Search Report for European Application No. 23215329.6, mailed on Jul. 5, 2024, 5 pages.
Office Action for U.S. Appl. No. 17/707,493 mailed Jul. 8, 2024, 9 pages.

* cited by examiner

FIG. 10
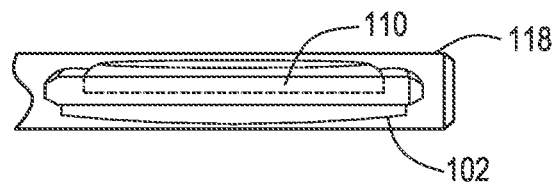
FIG. 11        FIG. 12
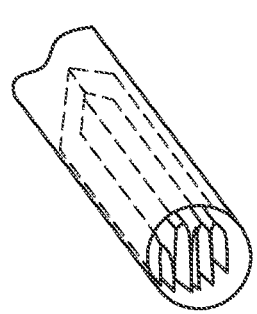 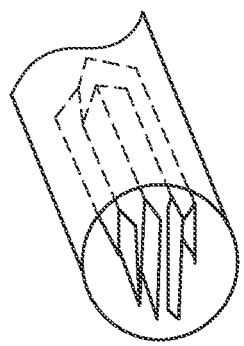
FIG. 13
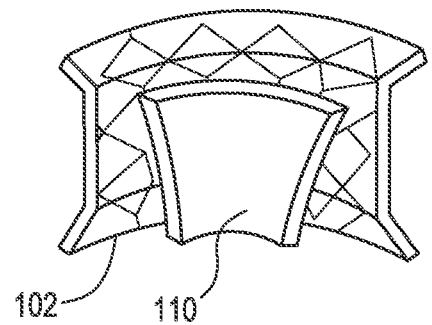

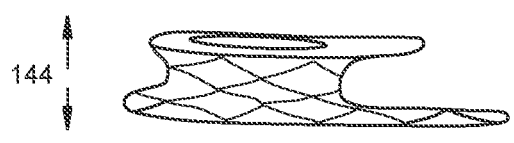
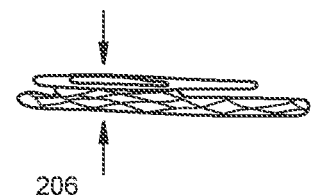
FIG. 56A
FIG. 56B
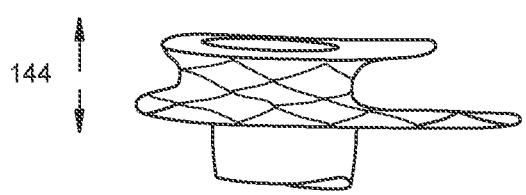
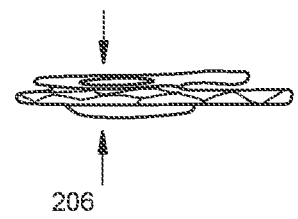
FIG. 57A
FIG. 57B FIG. 82A
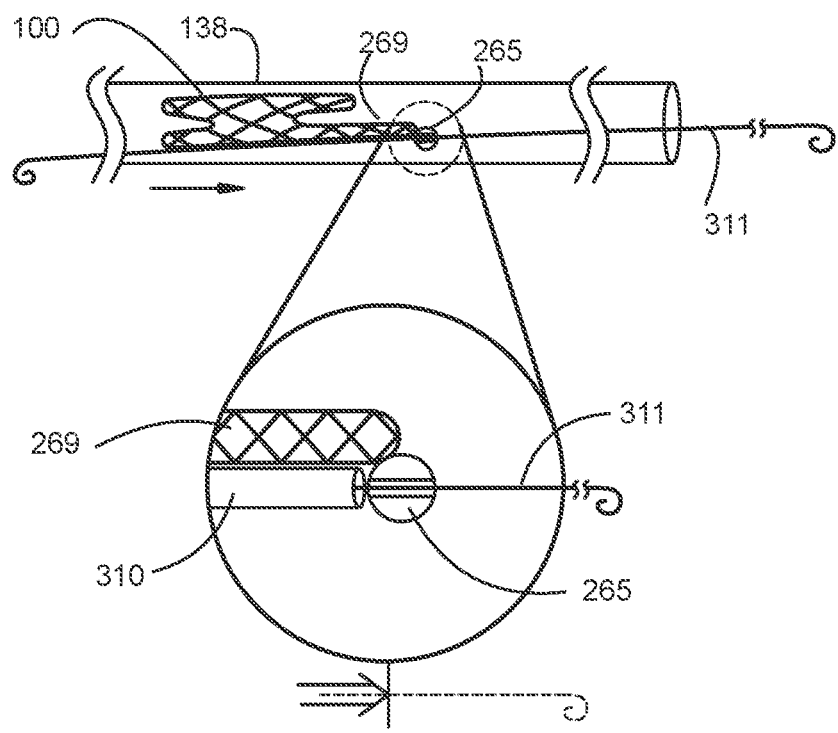
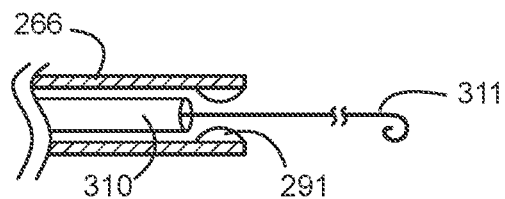
FIG. 82B
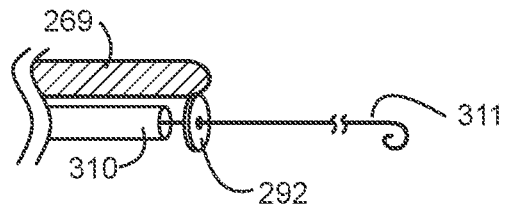
FIG. 82C
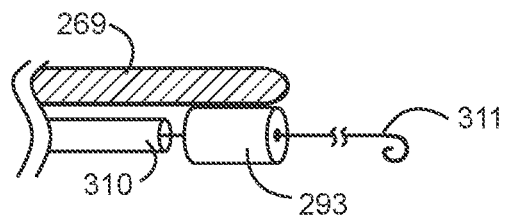
FIG. 82D

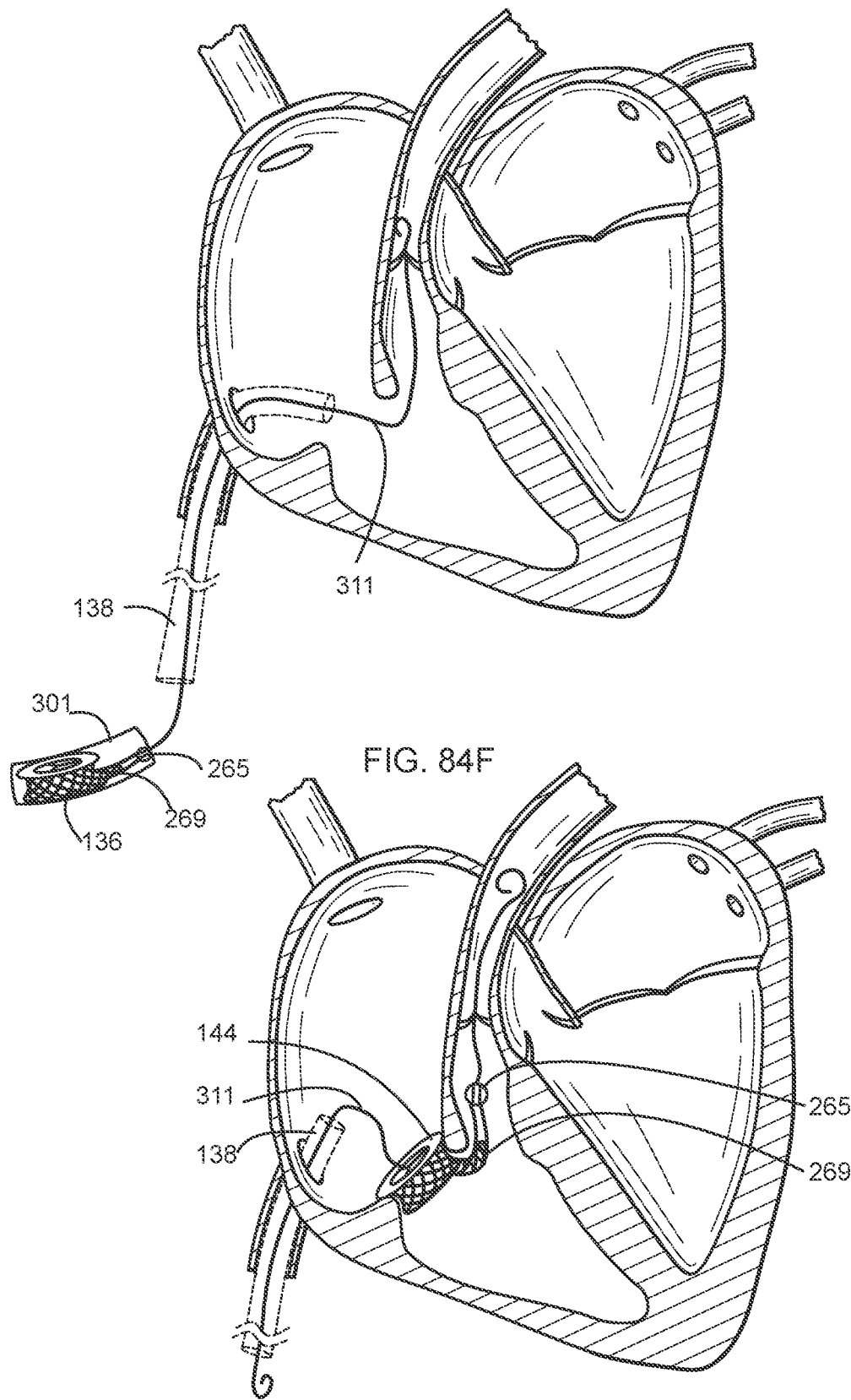

FIG. 93A
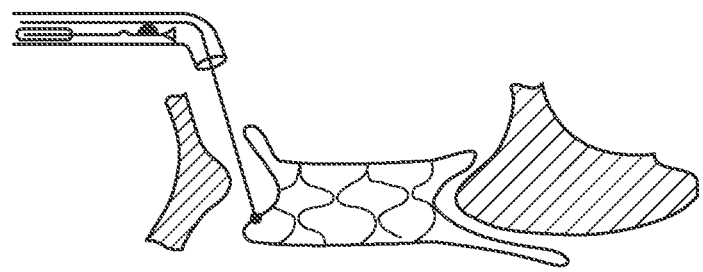
FIG. 93B
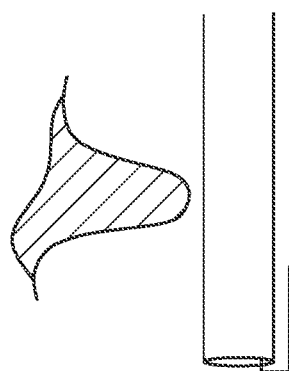 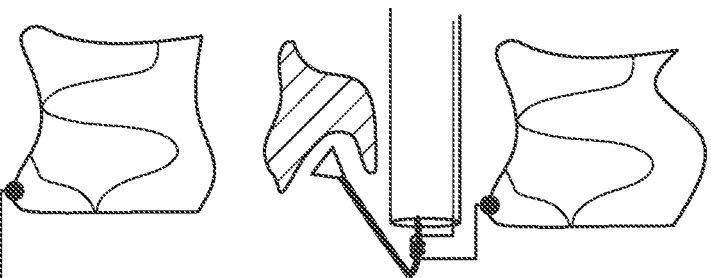
FIG. 93C
FIG. 93D
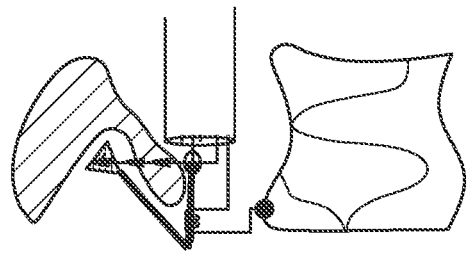
FIG. 93E
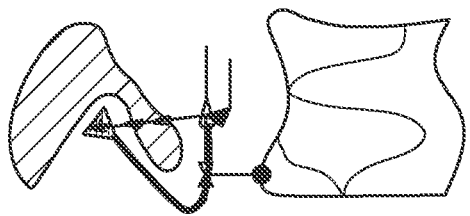

FIG. 95

Method for orthogonally loading
an implantable prosthetic valve
into a delivery catheter STEP 1: Providing a compressible prosthetic valve
where the valve has a tubular frame with
a flow control component mounted within the tubular frame
and
where the valve is configured to permit blood flow
in a first direction through an inflow end of the valve
and block blood flow in a second direction, opposite the first direction,
through an outflow end of the valve,
and
where the valve is compressible and expandable
and has a long-axis oriented at an intersecting angle
of between 45-135 degrees to the first direction,
where the long-axis parallels the
length-wise cylindrical axis of the delivery catheter
and
where the valve has
a height of about 5-60mm and
a diameter of about 25-80mm.

STEP 2: loading an implantable prosthetic valve
into a tapering fixture or funnel
attached to a delivery catheter, to a compressed configuration
for introduction into the body
using a delivery catheter
for implanting at a desired location in the body,

TRANSCATHETER DELIVERABLE PROSTHETIC HEART VALVES AND METHODS OF DELIVERY

CROSS-REFERENCE TO RELATED APPLICATIONS

This application is a continuation-in-part of U.S. application Ser. No. 16/443,862, entitled "Orthogonally Delivered Transcatheter Heart Valve Replacement," filed Jun. 17, 2019, which is a continuation of U.S. application Ser. No. 16/155,890, entitled "Orthogonally Delivered Transcatheter Heart Valve Replacement," filed Oct. 10, 2018 (now U.S. Pat. No. 10,321,995), which claims priority to and the benefit of U.S. Provisional Application Ser. No. 62/766,611, entitled "Side-Loading Transcatheter Heart Valve Replacement," filed Sep. 20, 2018, the disclosure of each of which is incorporated herein by reference in its entirety.

This application is also a continuation of International Patent Application Serial No. PCT/US2019/051615, entitled "Transcatheter Deliverable Prosthetic Heart Valves and Methods of Delivery," filed Sep. 18, 2019, which is a continuation-in-part of U.S. application Ser. No. 16/163,577, entitled "Orthogonally Delivered Transcatheter Heart Valve Frame for Valve in Valve Prostheses," filed Oct. 18, 2018, the disclosure of which is incorporated herein by reference in its entirety.

International Patent Application Serial No. PCT/US2019/051615 also claims priority to and the benefit of U.S. Provisional Application Ser. No. 62/766,611, entitled "Side-Loading Transcatheter Heart Valve Replacement," filed Sep. 20, 2018, U.S. Provisional Patent Application Ser. No. 62/737,343, entitled "Side-Loading Transcatheter Heart Valve Replacement," filed Sep. 27, 2018, U.S. Provisional Application Ser. No. 62/749,121, entitled "Guidewire Delivery of Tricuspid Valve," filed Oct. 22, 2018, and U.S. Provisional Application Ser. No. 62/777,070, entitled "Compression Capable Annular Frames for Orthogonal Delivery of Transcatheter Heart Valve Replacement," filed Dec. 8, 2018, the disclosure of each of which is incorporated herein by reference in its entirety.

BACKGROUND

Embodiments are described herein that relate to prosthetic heart valves, and devices and methods for use in the delivery and deployment of such valves.

Prosthetic heart valves can pose challenges for delivery and deployment within a heart, particularly for delivery by catheters through the patient's vasculature rather than through a surgical approach. Traditional valves have a central cylinder axis that is parallel to the lengthwise axis of the delivery catheter and are deployed from the end of the delivery catheter and expanded radially outward from the central annular axis, in a manner akin to pushing a closed spring-loaded umbrella out of a sleeve to make it spring open. Traditional valves can only be expanded as large as what the internal diameter of the delivery catheter will allow. Efforts to increase the expanded diameter of traditional valves have run into the problems of trying to compress too much material and structure into too little space.

A need exists for valves that can be delivered through small diameter delivery catheters, particularly to native valves such as tricuspid valves.

SUMMARY

Disclosed embodiments are directed to an orthogonally delivered transcatheter prosthetic valve comprising: (i) a tubular frame having a flow control component mounted within the tubular frame and configured to permit blood flow in a first direction through an inflow end of the valve and block blood flow in a second direction, opposite the first direction, through an outflow end of the valve, wherein the valve is compressible to a compressed configuration for introduction into the body using a delivery catheter, and expandable to an expanded configuration for implanting at a desired location in the body, wherein the valve is compressible and expandable along a long-axis substantially parallel to a cylindrical axis of the delivery catheter, and wherein the valve has a height of about 5-60 mm and a diameter of about 25-80 mm.

In another embodiment, there is provided an orthogonally delivered transcatheter prosthetic valve wherein the tubular frame forms a two-part framework, a first part comprises a flared atrial cuff joined to a second part that comprises cylindrical member, wherein the cuff is joined to the cylindrical member around the circumference of a top edge of the cylindrical member.

In another embodiment, there is provided an orthogonally delivered transcatheter prosthetic valve wherein said tubular frame is comprised of a braid, wire, or laser-cut wire frame, and said tubular frame is covered with a biocompatible material.

In another embodiment, there is provided an orthogonally delivered transcatheter prosthetic valve wherein the tubular frame has a side profile of a flat cone shape having a diameter R of 40-80 mm, a diameter r of 20-40 mm, and a height of 10-20 mm.

In another embodiment, there is provided an orthogonally delivered transcatheter prosthetic valve wherein the tubular frame has an inner surface and an outer surface, said inner surface covered with a biocompatible material comprising pericardial tissue, and said outer surface covered with a biocompatible material comprising a woven synthetic polyester material.

In another embodiment, there is provided an orthogonally delivered transcatheter prosthetic valve wherein the tubular frame has a side profile of an hourglass flat conical shape having a top diameter R1 of 40-80 mm, a bottom diameter R2 of 50-70 mm, an internal diameter r of 20-30 mm, and a height of 5-60 mm.

In another embodiment, there is provided an orthogonally delivered transcatheter prosthetic valve wherein the valve in an expanded configuration has a central tube axis that is substantially parallel to the first direction.

In another embodiment, there is provided an orthogonally delivered transcatheter prosthetic valve wherein the flow control component has an internal diameter of 20-30 mm and a height of 20-40 mm, and a plurality of leaflets of pericardial material joined to form a rounded cylinder at an inflow end and having a flat closable aperture at an outflow end.

In another embodiment, there is provided an orthogonally delivered transcatheter prosthetic valve wherein the flow control component is supported with one or more longitudinal supports integrated into or mounted upon the flow control component, the one or more longitudinal supports selected from rigid or semi-rigid ribs, rigid or semi-rigid battens, rigid or semi-rigid panels, and combination thereof.

In another embodiment, there is provided an orthogonally delivered transcatheter prosthetic valve comprising a tension arm extending from a distal side of the tubular frame, the tension arm comprised of wire loop or wire frame extending from about 10-40 mm away from the tubular frame.

In another embodiment, there is provided an orthogonally delivered transcatheter prosthetic valve comprising (i) an upper tension arm attached to a distal upper edge of the tubular frame, the upper tension arm comprised of wire loop or wire frame extending from about 2-20 mm away from the tubular frame, and (ii) a lower tension arm extending from a distal side of the tubular frame, the lower tension arm comprised of wire loop or wire frame extending from about 10-40 mm away from the tubular frame.

In another embodiment, there is provided an orthogonally delivered transcatheter prosthetic valve comprising at least one tissue anchor connected to the tubular frame for engaging annular tissue.

In another embodiment, there is provided a method for orthogonal delivery of implantable prosthetic valve to a desired location in the body, the method comprising the steps: (i) advancing a delivery catheter to the desired location in the body and delivering an expandable prosthetic valve to the desired location in the body by releasing the valve from the delivery catheter, wherein the valve comprises a tubular frame having a flow control component mounted within the tubular frame and configured to permit blood flow in a first direction through an inflow end of the valve and block blood flow in a second direction, opposite the first direction, through an outflow end of the valve, wherein the valve is compressible to a compressed configuration for introduction into the body using a delivery catheter, and expandable to an expanded configuration for implanting at a desired location in the body, wherein the valve is compressible and expandable along a long-axis substantially parallel to a cylindrical axis of the delivery catheter, wherein the valve has a height of about 5-60 mm and a diameter of about 25-80 mm.

In another embodiment, there is provided a method for orthogonal delivery of implantable prosthetic valve wherein releasing the valve from the delivery catheter comprises pulling the valve out of the delivery catheter using a rigid elongated pushing rod that is releasably connected to the distal side of the valve, wherein advancing the pushing rod away from the delivery catheter pulls the compressed valve out of the delivery catheter.

In another embodiment, there is provided a method for orthogonal delivery of implantable prosthetic valve comprising the additional step of anchoring one or more tissue anchors attached to the valve into annular tissue.

In another embodiment, there is provided a method for orthogonal delivery of implantable prosthetic valve comprising the additional step of positioning a tension arm of the heart valve prosthesis into the right ventricular outflow tract of the right ventricle.

In another embodiment, there is provided a method for orthogonal delivery of implantable prosthetic valve comprising the additional steps of positioning a lower tension arm of the heart valve prosthesis into the right ventricular outflow tract of the right ventricle., and positioning an upper tension arm into a supra-annular position, the upper tension arm connected to the lower tension arm, and the upper tension arm providing a supra-annular downward force in the direction of the ventricle and lower tension arm providing a sub-annular upward force in the direction of the atrium.

In another embodiment, there is provided a method for orthogonal delivery of implantable prosthetic valve comprising the additional step of rotating the heart valve prosthesis using a steerable catheter along an axis parallel to the plane of the valve annulus, wherein an upper tension arm mounted on the valve is conformationally pressure locked against supra-annular tissue, and wherein a lower tension arm mounted on the valve is conformationally pressure locked against sub-annular tissue.

In another embodiment, there is provided a method for orthogonally loading an implantable prosthetic valve into a delivery catheter, the method comprising the steps: (i) attaching a pulling wire to a sidewall of an implantable prosthetic valve and pulling the valve into a tapering fixture or funnel, wherein the valve comprises a tubular frame having a flow control component mounted within the tubular frame and configured to permit blood flow in a first direction through an inflow end of the valve and block blood flow in a second direction, opposite the first direction, through an outflow end of the valve, wherein pulling the valve into a tapering fixture or funnel compresses the valve to a compressed configuration for loading into a delivery catheter, wherein the valve is compressible and expandable along a long-axis substantially parallel to a cylindrical axis of the delivery catheter, wherein the valve has a height of about 5-60 mm and a diameter of about 25-80 mm.

Disclosed embodiments relate to delivery system for deployment of a prosthetic valve, having a hypotube sheathed guidewire assembly having an outer sheath and an inner guidewire shaft that pushes against a guidewire collar on a tension arm of a compressed transcatheter valve to deliver the valve and position the valve to the tricuspid valve or mitral valve location in the body.

Accordingly, disclosed embodiments are directed to a delivery system for deployment of a prosthetic valve, comprising: (i) a hypotube sheathed guidewire assembly having an outer sheath and an inner guidewire shaft; (ii) a transcatheter prosthetic valve having a tubular frame with a flow control component mounted within the tubular frame and configured to permit blood flow in a first direction through an inflow end of the valve and block blood flow in a second direction, opposite the first direction, through an outflow end of the valve, said tubular frame having a tension arm extending from a distal side of the tubular frame, the tension arm comprised of wire loop or wire frame, integrated frame section, or stent, extending from about 10-40 mm away from the tubular frame, said tension arm having a guidewire collar element attached the tension arm, wherein the guidewire collar element is sized and configured with a guidewire aperture to allow the inner guidewire shaft of the hypotube sheathed guidewire assembly to pass through the guide aperture, and to block passage of the outer sheath of the guidewire assembly through the guidewire aperture; (iii) a delivery catheter, the delivery catheter comprising an elongated tube with a central lumen, the lumen having a diameter from about 7 to 11 mm; wherein the valve is compressible to a compressed configuration for introduction into the body using the delivery catheter for implanting at a desired location in the body, wherein the valve has a height of about 5-60 mm and a diameter of about 25-80 mm.

In another embodiment, there is provided a delivery system wherein the compressed configuration of the valve is co-axial with the first direction.

In another embodiment, there is provided a delivery system wherein the valve is a balloon-inflated valve.

In another embodiment, there is provided a delivery system, wherein the valve is a self-expanding valve.

In another embodiment, there is provided a delivery system, wherein the compressed configuration of the valve is orthogonal to the axis of the first direction, wherein said compressed configuration having a long-axis oriented at an intersecting angle of between 45-135 degrees to the first direction, and expandable to an expanded configuration having a long-axis oriented at an intersecting angle of between 45-135 degrees to the first direction, wherein the long-axis of the compressed configuration of the valve is substantially parallel to a lengthwise cylindrical axis of the delivery catheter.

In another embodiment, there is provided a method for delivering a valve, comprising the steps: advancing a guidewire to a desired location within a body, said guidewire having an outer sheath and an inner shaft; advancing a delivery catheter over the guidewire to the desired location; mounting a valve capsule onto a proximal end of the guidewire, said valve capsule containing a compressed valve having a threaded guidewire collar, the guidewire extending through the threaded guidewire collar, the threaded guidewire collar having an aperture sized to permit the inner shaft to extend through the aperture and to block the outer sheath from extending through the aperture; loading the valve capsule into a proximal end of the delivery catheter; advancing the compressed valve from the valve capsule into and through a lumen of the delivery catheter to the desired location by advancing the outer sheath over the inner shaft, to deploy the valve at the desired location.

In another embodiment, there is provided a delivery method wherein the compressed configuration of the valve is co-axial with the first direction.

In another embodiment, there is provided a delivery method wherein the valve is a balloon-inflated valve.

In another embodiment, there is provided a delivery method wherein the valve is a self-expanding valve.

In another embodiment, there is provided a delivery method wherein the compressed configuration of the valve is orthogonal to the axis of the first direction, wherein said compressed configuration having a long-axis oriented at an intersecting angle of between 45-135 degrees to the first direction, and expandable to an expanded configuration having a long-axis oriented at an intersecting angle of between 45-135 degrees to the first direction, wherein the long-axis of the compressed configuration of the valve is substantially parallel to a lengthwise cylindrical axis of the delivery catheter.

In another embodiment, there is provided a delivery system for deployment of a prosthetic valve into a valve frame, comprising: (i) a hypotube sheathed guidewire assembly having an outer sheath and an inner guidewire shaft; (ii) a transcatheter prosthetic valve frame for a valve in frame prosthesis system, comprising: a tubular frame having a central lumen defined by an inner circumferential surface of the tubular frame, and a tension arm extending from a distal side of the tubular frame, the tension arm comprised of wire loop or wire frame, integrated frame section, or stent, extending from about 10-40 mm away from the tubular frame, said tension arm having a guidewire collar element attached the tension arm, wherein the guidewire collar element is sized and configured with a guidewire aperture to allow the inner guidewire shaft of the hypotube sheathed guidewire assembly to pass through the guide aperture, and to block passage of the outer sheath of the guidewire assembly through the guidewire aperture; (iii) a delivery catheter, the delivery catheter comprising an elongated tube with a central lumen, the lumen having a diameter from about 7 to 11 mm; wherein the tubular frame is compressible to a compressed configuration for introduction into the body using a delivery catheter for implanting at a desired location in the body, wherein the tubular frame has a height of about 5-60 mm and a diameter of about 25-80 mm.

In another embodiment, there is provided a a frame delivery system wherein the compressed configuration of the valve is co-axial with the first direction.

In another embodiment, there is provided a a frame delivery system wherein the valve is a balloon-inflated valve.

In another embodiment, there is provided a a frame delivery system wherein the valve is a self-expanding valve.

In another embodiment, there is provided a a frame delivery system wherein the compressed configuration of the valve is orthogonal to the axis of the first direction, wherein said compressed configuration having a long-axis oriented at an intersecting angle of between 45-135 degrees to the first direction, and expandable to an expanded configuration having a long-axis oriented at an intersecting angle of between 45-135 degrees to the first direction, wherein the long-axis of the compressed configuration of the valve is substantially parallel to a lengthwise cylindrical axis of the delivery catheter.

Disclosed embodiments are directed to methods and devices related to a transcatheter heart valve replacement, and in particular compression capable annular frames for a side (lengthwise) delivered transcatheter prosthetic heart valve having a annular support frame having compressible wire cells that facilitate rolling and folding the valve lengthwise, or orthogonal, to the central axis of the flow control component, allowing a very large diameter valve to be delivered and deployed from the inferior vena cava directly into the mitral or tricuspid valve, e.g. having a height of about 5-60 mm and a diameter of about 25-80 mm using a 24-36Fr delivery catheter, without requiring an oversized diameter catheter and without requiring delivery and deployment from a catheter at an acute angle of approach.

Method for Delivery of the Valve into a Patient

In another embodiment, there is provided a method for side delivery of implantable prosthetic heart valve to a desired location in the body, the method comprising the steps: advancing a delivery catheter to the desired location in the body and delivering an expandable prosthetic heart valve to the desired location in the body by releasing the valve from the delivery catheter, wherein advancing the delivery catheter includes (i) advancing to the tricuspid valve or pulmonary artery of the heart through the inferior vena cava via the femoral vein, (ii) advancing to the tricuspid valve or pulmonary artery of the heart through the superior vena cava via the jugular vein, (iii) advancing to the mitral valve of the heart through a trans-atrial approach, e.g. fossa ovalis or lower, via the IVC-femoral or the SVC jugular approach, wherein the valve comprises an annular support frame having a flow control component mounted within the annular support frame and configured to permit blood flow in a first direction through an inflow end of the valve and block blood flow in a second direction, opposite the first direction, through an outflow end of the valve, wherein the valve is compressible to a compressed configuration for introduction into the body using a delivery catheter for implanting at a desired location in the body, said compressed configuration having a long-axis oriented at an intersecting angle of between 45-135 degrees to the first direction, and expandable to an expanded configuration having a long-axis oriented at an intersecting angle of between 45-135 degrees to the first direction, wherein the long-axis of the compressed configuration of the valve is substantially parallel to a lengthwise cylindrical axis of the delivery catheter, wherein the valve has a height of about 5-60 mm and a diameter of about 25-80 mm.

In another embodiment, there is provided a method for side delivery, wherein releasing the valve from the delivery catheter is selected from the steps consisting of: (i) pulling the valve out of the delivery catheter using a rigid elongated pushing rod/draw wire that is releasably connected to the distal side of the valve, wherein advancing the pushing rod away from the delivery catheter pulls the compressed valve out of the delivery catheter, or (ii) pushing the valve out of the delivery catheter using a rigid elongated pushing rod that is releasably connected to the proximal side of the valve, wherein advancing the pushing rod out of from the delivery catheter pushes the compressed valve out of the delivery catheter.

In another embodiment, there is provided a method for side delivery, comprising the additional step of anchoring one or more tissue anchors attached to the valve into native tissue.

In another embodiment, there is provided a method for side delivery, comprising the additional step of positioning a tension arm of the heart valve prosthesis into the right ventricular outflow tract of the right ventricle.

In another embodiment, there is provided a method for side delivery, comprising the additional steps of positioning a lower tension arm of the heart valve prosthesis into the right ventricular outflow tract of the right ventricle., and positioning an upper tension arm into a supra-annular position, and the upper tension arm providing a supra-annular downward force in the direction of the ventricle and lower tension arm providing a sub-annular upward force in the direction of the atrium.

In another embodiment, there is provided a method for side delivery, comprising the additional step of rotating the heart valve prosthesis using a steerable catheter along an axis parallel to the plane of the valve annulus, wherein an upper tension arm mounted on the valve is conformationally pressure locked against supra-annular tissue, and wherein a lower tension arm mounted on the valve is conformationally pressure locked against sub-annular tissue.

Method for Loading the Valve into a Delivery Catheter

In another embodiment, there is provided a method for loading an implantable side-delivered prosthetic heart valve into a delivery catheter, the method comprising the steps: loading an implantable side-delivered prosthetic heart valve into a tapering fixture or funnel attached to a delivery catheter, wherein the valve comprises a annular support frame having a flow control component mounted within the annular support frame and configured to permit blood flow in a first direction through an inflow end of the valve and block blood flow in a second direction, opposite the first direction, through an outflow end of the valve, wherein said loading is perpendicular or substantially orthogonal to the first direction, wherein the valve is compressible to a compressed configuration for introduction into the body using a delivery catheter for implanting at a desired location in the body, said compressed configuration having a long-axis oriented at an intersecting angle of between 45-135 degrees to the first direction, and expandable to an expanded configuration having a long-axis oriented at an intersecting angle of between 45-135 degrees to the first direction, wherein the long-axis of the compressed configuration of the valve is substantially parallel to a lengthwise cylindrical axis of the delivery catheter, wherein the valve has a height of about 5-60 mm and a diameter of about 25-80 mm.

In another embodiment, there is provided a method for loading, wherein the step of loading includes attaching a loading accessory to a valve sidewall, to a valve cuff, to a valve tension arm, or a combination thereof, wherein the loading accessory is pushing rod or a pulling wire, and wherein the tapering fixture or funnel has a compression element on an inner surface of the tapering fixture or funnel to facilitate compression, iris-ing, or spiraling of the uncompressed valve.

Side Delivered Valve

Accordingly, disclosed embodiments are directed to a side delivered transcatheter prosthetic heart valve, comprising: a self-expanding annular support frame, said annular support frame having a central channel and an outer perimeter wall circumscribing a central vertical axis in an expanded configuration, said perimeter wall having a front wall portion and a back wall portion, the front wall portion and the back wall portion connected along a proximal side to a proximal fold area, and the front wall portion and the back wall portion connected along a distal side to a distal fold area, the front wall portion having a front upper collar portion and a front lower body portion, the back wall portion having a back upper collar portion and a back lower body portion, said annular support frame having a flow control component mounted within the annular support frame and configured to permit blood flow in a first direction through an inflow end of the valve and block blood flow in a second direction, opposite the first direction, through an outflow end of the valve, wherein the valve is compressible to a compressed configuration for introduction into the body using a delivery catheter for implanting at a desired location in the body, said compressed configuration is oriented along a horizontal axis at an intersecting angle of between 45-135 degrees to the central vertical axis, and expandable to an expanded configuration having a horizontal axis at an intersecting angle of between 45-135 degrees to the central vertical axis, wherein the horizontal axis of the compressed configuration of the valve is substantially parallel to a lengthwise cylindrical axis of the delivery catheter, wherein the valve has a height of about 5-60 mm and a diameter of about 25-80 mm.

In an embodiment, the valve has an outer annular support frame that has a diameter R of 40-80 mm and a height of 5-20 mm, and the inner flow control component has a diameter of 20-35 mm.

In another embodiment, the valve has a flow control component that has an internal diameter of 20-35 mm and a height of 5-30 mm, and from 2-4 leaflets of pericardial material are joined to form a rounded cylinder at an inflow end and having a closable aperture at an outflow end.

In another embodiment, there is provided a side delivered transcatheter heart valve, wherein the annular support frame is comprised of a plurality of compressible wire cells having a orientation and cell geometry substantially orthogonal to the central vertical axis to minimize wire cell strain when the annular support frame is configured in a vertical compressed configuration, a rolled compressed configuration, or a folded compressed configuration.

In another embodiment, there is provided a side delivered transcatheter heart valve, wherein the front lower body portion and the back lower body portion in an expanded configuration form a shape selected from a funnel, cylinder, flat cone, or circular hyperboloid.

In another embodiment, there is provided a side delivered transcatheter heart valve, wherein said annular support frame is comprised of a braided, wire, or laser-cut wire frame, and said annular support frame is covered with a biocompatible material.

In another embodiment, there is provided a side delivered transcatheter heart valve, wherein the annular support frame has a side profile of a flat cone shape having a diameter R of 40-80 mm, a diameter r of 20-60 mm, and a height of 5-60 mm In another embodiment, there is provided a side delivered transcatheter heart valve, wherein the annular support frame has an inner surface and an outer surface, said inner surface and said outer surface covered with a biocompatible material selected from the following consisting of: the inner surface covered with pericardial tissue, the outer surface covered with a woven synthetic polyester material, and both the inner surface covered with pericardial tissue and the outer surface covered with a woven synthetic polyester material.

In another embodiment, there is provided a side delivered transcatheter heart valve, wherein the annular support frame has a side profile of an hourglass shape having a top diameter R1 of 40-80 mm, a bottom diameter R2 of 50-70 mm, an internal diameter r of 20-60 mm, and a height of 5-60 mm.

In another embodiment, there is provided a side delivered transcatheter heart valve, wherein the valve in an expanded configuration has a central vertical axis that is substantially parallel to the first direction.

In another embodiment, there is provided a side delivered transcatheter heart valve, wherein the flow control component has an internal diameter of 20-60 mm and a height of 10-40 mm, and a plurality of leaflets of pericardial material joined to form a rounded cylinder at an inflow end and having a flat closable aperture at an outflow end.

In another embodiment, there is provided a side delivered transcatheter heart valve, wherein the flow control component is supported with one or more longitudinal supports integrated into or mounted upon the flow control component, the one or more longitudinal supports selected from rigid or semi-rigid posts, rigid or semi-rigid ribs, rigid or semi-rigid battons, rigid or semi-rigid panels, and combinations thereof.

In another embodiment, there is provided a side delivered transcatheter heart valve, comprising a tension arm extending from a distal side of the annular support frame as an RVOT tab, the tension arm comprised of wire loop or wire frame, integrated frame section, or stent, extending from about 10-40 mm away from the annular support frame.

In another embodiment, there is provided a side delivered transcatheter heart valve, comprising (i) an upper tension arm attached to a distal upper edge of the annular support frame, the upper tension arm comprised of wire loop or wire frame extending from about 2-20 mm away from the annular support frame, and (ii) a lower tension arm as an RVOT tab extending from a distal side of the annular support frame, the lower tension arm comprised of wire loop or wire frame, integrated frame section, or stent, extending from about 10-40 mm away from the annular support frame.

In another embodiment, there is provided a side delivered transcatheter heart valve, comprising at least one tissue anchor connected to the annular support frame for engaging native tissue.

In another embodiment, there is provided a side delivered transcatheter heart valve, wherein the front wall portion is a first flat panel and the back wall portion is a second flat panel, and wherein the proximal fold area and the distal fold area each comprise a sewn seam, a fabric panel, or a rigid hinge.

In another embodiment, there is provided a side delivered transcatheter heart valve, wherein the proximal fold area and the distal fold area, each comprise a flexible fabric span without any wire cells.

In another embodiment, there is provided a side delivered transcatheter heart valve, wherein the annular support frame is comprised of compressible wire cells selected from the group consisting of: braided-wire cells, laser-cut wire cells, photolithography produced wire cells, 3D printed wire cells, wire cells formed from intermittently connected single strand wires in a wave shape, a zig-zag shape, or spiral shape, and combinations thereof Process for Manufacturing In another embodiment, there is provided a process for manufacturing a side delivered transcatheter prosthetic heart valve frame, comprising: (i) using additive or subtractive metal or metal-alloy manufacturing to produce a self-expanding annular support frame, said annular support frame having a central channel and an outer perimeter wall circumscribing a central vertical axis in an expanded configuration, said perimeter wall having a front wall portion and a back wall portion, the front wall portion and the back wall portion connected along a proximal side to a proximal fold area, and the front wall portion and the back wall portion connected along a distal side to a distal fold area, the front wall portion having a front upper collar portion and a front lower body portion, the back wall portion having a back upper collar portion and a back lower body portion, wherein the valve is compressible to a compressed configuration for introduction into the body using a delivery catheter for implanting at a desired location in the body, said compressed configuration is oriented along a horizontal axis at an intersecting angle of between 45-135 degrees to the central vertical axis, and expandable to an expanded configuration having a horizontal axis at an intersecting angle of between 45-135 degrees to the central vertical axis, wherein the horizontal axis of the compressed configuration of the valve is substantially parallel to a lengthwise cylindrical axis of the delivery catheter, wherein the additive metal or metal-alloy manufacturing is 3D printing or direct metal laser sintering (powder melt), and wherein the subtractive metal or metal-alloy manufacturing is photolithography, laser sintering/cutting, CNC machining, electrical discharge machining, and wherein the valve frame has a height of about 5-60 mm and a diameter of about 25-80 mm.

In another embodiment, there is provided a process for manufacturing a side delivered transcatheter prosthetic heart valve frame, further comprising the steps of: (ii) mounting a flow control component within the valve frame, said flow control component configured to permit blood flow along the central vertical axis through an inflow end of the flow control component and block blood flow through an outflow end of the valve, (iii) covering an outer surface of the valve frame with a pericardium material or similar biocompatible material.

Method for Compressing the Valve

In another embodiment, there is provided a method for compressing an implantable prosthetic heart valve for lengthwise orthogonal release of the valve from a delivery catheter, comprising the steps: flattening, rolling or folding the implantable prosthetic heart valve into a compressed configuration wherein the long-axis of the compressed configuration of the valve is substantially parallel to a lengthwise cylindrical axis of the delivery catheter, wherein the implantable prosthetic heart valve comprises an annular support frame having a flow control component mounted within the annular support frame and configured to permit blood flow in a first direction through an inflow end of the valve and block blood flow in a second direction, opposite the first direction, through an outflow end of the valve, wherein the valve has a height of about 5-60 mm and a diameter of about 25-80 mm.

In another embodiment, there is provided a method of compressing, wherein the implantable prosthetic heart valve is rolled or folded into a compressed configuration using a step selected from the group consisting of: (i) unilaterally rolling into a compressed configuration from one side of the annular support frame; (ii) bilaterally rolling into a compressed configuration from two opposing sides of the annular support frame; (iii) flattening the annular support frame into two parallel panels that are substantially parallel to the long-axis, and then rolling the flattened annular support frame into a compressed configuration; and (iv) flattening the annular support frame along a vertical axis to reduce a vertical dimension of the valve from top to bottom.

Method for Improving Blood Flow Transition During Implantation

In another embodiment, there is provided a method for improving hemodynamic flow during implantation of a transcatheter prosthetic heart valve, comprising: advancing a delivery catheter to the desired location in the body and delivering the valve of claim 1 to the desired location in the body; partially releasing the valve from the delivery catheter to establish blood flow around the partially released valve and establish blood flow through the flow control component; completely releasing the valve from the delivery catheter while maintaining attachment to the valve with a positioning catheter or wire to transition to increased blood flow through the flow control component and decreasing blood flow around the valve; and deploying the valve into a final mounted position to transition to complete blood flow through the flow control component and minimal or no blood flow around the valve, and disconnecting and withdrawing the positioning catheter or wire from the valve.

In another embodiment, there is provided a method of improving hemodynamic flow, wherein the RVOT tab is in the RVOT during the transition from partial release of the valve to complete release of the valve.

In another embodiment, there is provided a side delivered transcatheter heart valve with wire cells compressible along a vertical axis, wherein the annular support frame forms a two part framework, a first part comprises a flared atrial cuff joined to a second part that comprises a trans-annular tubular or cylindrical segment, wherein the cuff is joined to the trans-annular tubular or cylindrical segment around the circumference of a top edge of the trans-annular tubular or cylindrical segment.

Example—Manufacturing Process. In an embodiment a process for manufacturing a side delivered transcatheter prosthetic heart valve frame includes: (i) using additive or subtractive metal or metal-alloy manufacturing to produce a self-expanding annular support frame, wherein the additive metal or metal-alloy manufacturing is 3D printing or direct metal laser sintering (powder melt), and wherein the subtractive metal or metal-alloy manufacturing is photolithography, laser sintering/cutting, CNC machining, electrical discharge machining.

In another embodiment, there is provided a process for manufacturing a side delivered transcatheter prosthetic heart valve frame, further comprising the steps of: (ii) mounting a flow control component within the valve frame, said flow control component configured to permit blood flow along the central vertical axis through an inflow end of the flow control component and block blood flow through an outflow end of the valve, (iii) covering an outer surface of the valve frame with a pericardium material or similar biocompatible material.

Accordingly, disclosed embodiments are directed to an orthogonally delivered transcatheter prosthetic valve frame for a valve in valve prosthesis system, comprising: a tubular frame having a central lumen defined by an inner circumferential surface of the tubular frame, said tubular frame having an outer circumferential surface for engaging native annular tissue, wherein the tubular frame is compressible to a compressed orthogonal configuration for sideways or lateral (orthogonal) introduction into the body using a delivery catheter for implanting at a desired location in the body, said compressed orthogonal configuration having a horizontal long-axis oriented at an intersecting angle roughly perpendicular, e.g. about 90 degrees, but ranging from 45-135 degrees, to a vertical axis of the central lumen, and expandable to an expanded configuration having a horizontal long-axis oriented at an intersecting angle roughly perpendicular, e.g. about 90 degrees, but ranging from of between 45-135 degrees to the vertical axis of the central lumen, wherein the horizontal long-axis of the compressed configuration of the tubular frame is substantially parallel to a lengthwise cylindrical axis of the delivery catheter, wherein the tubular frame has a height of about 5-60 mm and a diameter of about 25-80 mm.

In another embodiment, there is provided a valve frame wherein the tubular frame forms a two part framework, a first part comprises a flared atrial cuff joined to a second part that comprises a trans-annular tubular segment, wherein the cuff is joined to the trans-annular tubular segment around the circumference of a top edge of the trans-annular tubular segment.

In another embodiment, there is provided a valve frame wherein said tubular frame is comprised of a braided, wire, or laser-cut wire frame, and said tubular frame is covered with a biocompatible material.

In another embodiment, there is provided a valve frame wherein the tubular frame has a side profile of a flat cone shape having a diameter R of 40-80 mm, a diameter r of 20-60 mm, and a height of 5-60 mm.

In another embodiment, there is provided a valve frame wherein the tubular frame has the inner circumferential surface and an outer circumferential surface, said inner circumferential surface and said outer circumferential surface covered with a biocompatible material selected from the following consisting of: the inner surface covered with pericardial tissue, the outer circumferential surface covered with a woven synthetic polyester material, and both the inner surface covered with pericardial tissue and the outer circumferential surface covered with a woven synthetic polyester material.

In another embodiment, there is provided a valve frame wherein the tubular frame has a side profile of an hourglass shape having a top diameter R1 of 40-80 mm, a bottom diameter R2 of 50-70 mm, an internal diameter r of 20-60 mm, and a height of 5-60 mm.

In another embodiment, there is provided a valve frame wherein the valve in an expanded configuration has a central tube axis that is substantially parallel to the first direction.

In another embodiment, there is provided a valve frame additionally comprising a flow control component having an internal diameter of 20-60 mm and a height of 10-40 mm, and a plurality of leaflets of pericardial material joined to form a rounded cylinder at an inflow end and having a closable aperture at an outflow end.

In another embodiment, there is provided a valve frame wherein the flow control component is supported with one or more longitudinal supports integrated into or mounted upon the flow control component, the one or more longitudinal supports selected from rigid or semi-rigid posts, rigid or semi-rigid ribs, rigid or semi-rigid battons, rigid or semi-rigid panels, and combinations thereof.

In another embodiment, there is provided a valve frame having a tension arm extending from a distal side of the tubular frame, the tension arm comprised of wire loop or wire frame, integrated frame section, or stent, extending from about 10-40 mm away from the tubular frame.

In another embodiment, there is provided a valve frame having (i) an upper tension arm attached to a distal upper edge of the tubular frame, the upper tension arm comprised of wire loop or wire frame extending from about 2-20 mm away from the tubular frame, and (ii) a lower tension arm extending from a distal side of the tubular frame, the lower tension arm comprised of wire loop or wire frame, integrated frame section, or stent, extending from about 10-40 mm away from the tubular frame.

In another embodiment, there is provided a valve frame having at least one tissue anchor connected to the tubular frame for engaging native tissue.

In another embodiment, there is provided a method for orthogonal delivery of an implantable prosthetic valve frame to a desired location in the body for a valve prosthesis system, the method comprising the steps: (i) advancing a delivery catheter to the desired location in the body and delivering an expandable prosthetic valve frame to the desired location in the body by releasing the valve frame from the delivery catheter, wherein the valve frame comprises a tubular frame having a central lumen defined by an inner circumferential surface of the tubular frame, said tubular frame having an outer circumferential surface for engaging native annular tissue, wherein the tubular frame is compressible to a compressed orthogonal configuration for introduction into the body using a delivery catheter for implanting at a desired location in the body, said compressed orthogonal configuration having a horizontal long-axis oriented at an intersecting angle roughly perpendicular, e.g. 90 degrees, but ranging from between 45-135 degrees to a vertical axis of the central lumen, and expandable to an expanded configuration having a horizontal long-axis oriented at an intersecting angle roughly perpendicular, e.g. 90 degrees, but ranging from between 45-135 degrees to the vertical axis of the central lumen, wherein the horizontal long-axis of the compressed configuration of the tubular frame is substantially parallel to a lengthwise cylindrical axis of the delivery catheter, wherein the tubular frame has a height of about 5-60 mm and a diameter of about 25-80 mm; and (ii) advancing a second delivery catheter to the desired location in the body and delivering an expandable prosthetic valve to the central lumen of the valve frame, expanding the expandable prosthetic valve within the central lumen to mount the prosthetic valve within the valve frame, wherein the prosthetic valve is delivered and expanded parallel to the vertical axis of the central lumen, and releasing the prosthetic valve from the second delivery catheter.

In another embodiment, there is provided a delivery method wherein releasing the valve frame from the delivery catheter is selected from the steps consisting of: (i) pulling the valve frame out of the delivery catheter using a rigid elongated pushing rod that is releasably connected to the distal side of the valve frame, wherein advancing the pushing rod away from the delivery catheter pulls the compressed valve frame out of the delivery catheter, or (ii) pushing the valve frame out of the delivery catheter using a rigid elongated pushing rod that is releasably connected to the proximal side of the valve frame, wherein advancing the pushing rod out of from the delivery catheter pushes the compressed valve frame out of the delivery catheter.

In another embodiment, there is provided a delivery method comprising the additional step of anchoring one or more tissue anchors attached to the valve frame into native tissue.

In another embodiment, there is provided a delivery method comprising the additional step of positioning a tension arm of the valve frame into the right ventricular outflow tract of the right ventricle.

In another embodiment, there is provided a delivery method comprising the additional steps of positioning a lower tension arm of the valve frame into the right ventricular outflow tract of the right ventricle, and positioning an upper tension arm into a supra-annular position, and the upper tension arm providing a supra-annular downward force in the direction of the ventricle and lower tension arm providing a sub-annular upward force in the direction of the atrium.

In another embodiment, there is provided a delivery method comprising the additional step of rotating the valve frame using a steerable catheter along an axis parallel to the plane of the valve annulus, wherein an upper tension arm mounted on the valve frame is conformationally pressure locked against supra-annular tissue, and wherein a lower tension arm mounted on the valve frame is conformationally pressure locked against sub-annular tissue.

In another embodiment, there is provided a method for orthogonally loading an implantable prosthetic valve frame into a delivery catheter, the method comprising the step: loading an implantable prosthetic valve frame into a tapering fixture or funnel attached to a delivery catheter, wherein the valve frame comprises a tubular frame having a central lumen defined by an inner circumferential surface of the tubular frame, said tubular frame having an outer circumferential surface for engaging native annular tissue, wherein the tubular frame is compressible to a compressed orthogonal configuration for introduction into the body using a delivery catheter for implanting at a desired location in the body, said compressed orthogonal configuration having a horizontal long-axis oriented at an intersecting angle roughly perpendicular, e.g. 90 degrees, but ranging from between 45-135 degrees to a vertical axis of the central lumen, and expandable to an expanded configuration having a horizontal long-axis oriented at an intersecting angle roughly perpendicular, e.g. 90 degrees, but ranging from between 45-135 degrees to the vertical axis of the central lumen, wherein the horizontal long-axis of the compressed configuration of the tubular frame is substantially parallel to a lengthwise cylindrical axis of the delivery catheter, wherein the tubular frame has a height of about 5-60 mm and a diameter of about 25-80 mm.

In another embodiment, there is provided a loading method wherein the step of loading includes attaching a loading accessory to a valve sidewall, to a valve cuff, to a valve tension arm, or a combination thereof, wherein the loading accessory is pushing rod or a pulling wire, and wherein the tapering fixture or funnel has a compression element on an inner surface of the tapering fixture or funnel to facilitate compression, iris-ing, or spiraling of the uncompressed valve frame.

BRIEF DESCRIPTION OF THE FIGURES

FIG. 10 is an illustration of a plan view of an embodiment of the prosthetic valve shown in a compressed configuration within a delivery catheter.

FIG. 11 is an illustration of a cross-sectional view of one embodiment of a compressed valve within a delivery catheter.

FIG. 12 is an illustration of a cross-sectional view of another embodiment of a compressed valve within a delivery catheter.

FIG. 13 is an illustration of a cross-sectional view of one embodiment of the prosthetic valve.

FIG. 56A is an illustration of a side view of a vertically compressible valve with internal non-extending leaflets and compressible (wide) cells, in an expanded configuration.

FIG. 56B is an illustration of a side view of a vertically compressible valve with internal non-extending leaflets and compressible (wide) cells, in a compressed configuration.

FIG. 57A is an illustration of a side view of a vertically compressible valve with extended leaflets and compressible (wide) cells, in an expanded configuration.

FIG. 57B is an illustration of a side view of a vertically compressible valve with extended leaflets and compressible (wide) cells, in a compressed configuration where the wire frame is reduced in height and the extended leaflets are rolled up.

FIG. 70A is an illustration of a three-panel embodiment of an inner valve sleeve having three rigid support posts.

FIG. 70B is an illustration of a cut away plan view of a heart valve prosthesis according to an embodiment, and shows a three-panel, three-post embodiment of the inner panel valve sleeve mounted within the inner space defined by the tubular frame.

FIG. 71A is an illustration of one embodiment of a partial cut-away interior view of a tri-leaflet embodiment of a low profile, e.g. 8-20 mm, side-loaded prosthetic valve.

FIG. 71B is an illustration of another embodiment of a partial cut-away interior view of a tri-leaflet embodiment of a low profile, e.g. 8-20 mm, side-loaded prosthetic valve.

FIG. 71C is an illustration of a top view of a tri-leaflet embodiment of a low profile, e.g. 8-20 mm, side-loaded prosthetic valve.

FIG. 72 is a flowchart describing one set of method steps for delivery of a low profile, side-loaded prosthetic valve.

FIG. 73 is an illustration of a side view of human heart anatomy, with an inset showing the geometric relationship between the inferior vena cava (IVC), the three leaflet cusps of the tricuspid valve—anterior, posterior, septal—the right ventricular outflow tract (RVOT), and the pulmonary artery (PA).

FIG. 74 is an illustration of a side perspective view of a side delivered valve seated with the native tricuspid annulus with collar portion laying atrially above the tricuspid annulus and leaflets, lower body portion extending into and through the annulus to provide corrective hemodynamic flow from the flow control component, and RVOT footer tab and RVOT/PA extender wire.

FIG. 75A is an illustration of a plan view of a native right atrium of a human heart, and shows the superior vena cava (SVC), the inferior vena cava (IVC), the right atrium (RA), the tricuspid valve and annulus (TCV), the anterior leaflet (A), the posterior leaflet (P), the septal leaflet(S), the right ventricle (RV), and the right ventricular outflow tract (RVOT).

FIG. 75B is an illustration of a heart valve prosthesis having a braided/laser cut-frame according to an embodiment being delivered to tricuspid valve annulus.

FIG. 75C is an illustration of a heart valve prosthesis having a braided/laser cut-frame according to an embodiment being delivered to tricuspid valve annulus.

FIG. 75D is an illustration of a heart valve prosthesis having a braided/laser cut-frame according to an embodiment that has been delivered to tricuspid valve annulus.

Figure 76A:
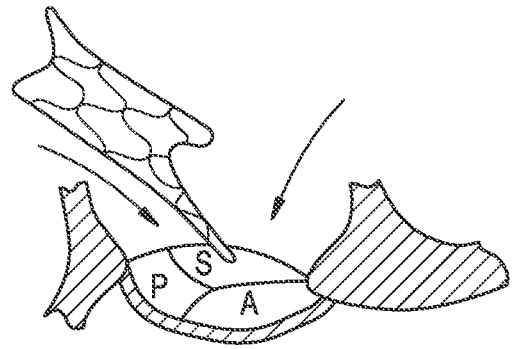

FIG. 76A is an illustration of a heart valve prosthesis according to an embodiment being delivered to tricuspid valve annulus and shows step 1 in a valve assessment process.

Figure 76B:
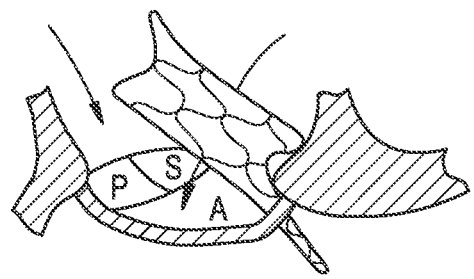

FIG. 76B is an illustration of a heart valve prosthesis according to an embodiment being delivered to tricuspid valve annulus, and shows Step 2 in a valve assessment process.

Figure 76C:
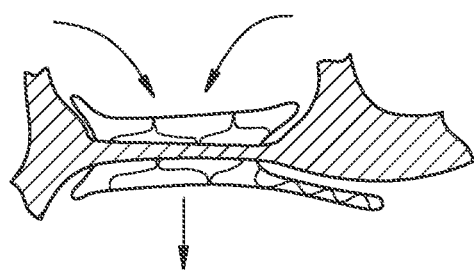

FIG. 76C is an illustration of a heart valve prosthesis according to an embodiment that has been delivered to tricuspid valve annulus, and shows Step 3 in a valve assessment process.

Figure 77A:
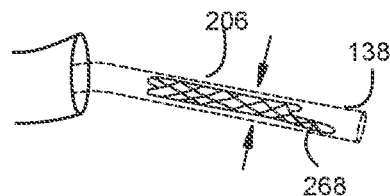

FIG. 77A is an illustration of a side perspective view of a valve that is vertically compressed without folding and loaded into a delivery catheter.

Figure 77B:
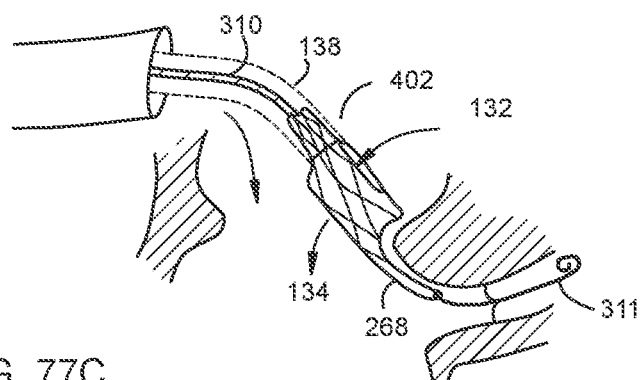

FIG. 77B is an illustration of a side perspective view of a partially expelled or released valve that allows a transition from native blood flow through the native tricuspid valve to a partial flow around the prosthetic valve and into the native annulus and a partial flow thru the prosthetic valve into the native annulus.

Figure 77C:
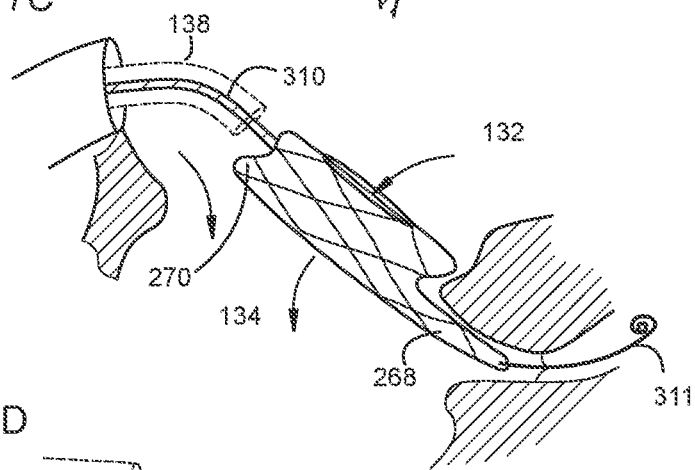

FIG. 77C is an illustration of a side perspective view of a fully expelled or released valve that is lodged against the distal surface of the annulus and held elevated at an angle above the native annulus prior to complete deployment, and that allows a further transition from native blood flow through the native tricuspid valve with a partial flow around the prosthetic valve and into the native annulus, and an increasing partial flow thru the prosthetic valve into the native annulus.

Figure 77D:
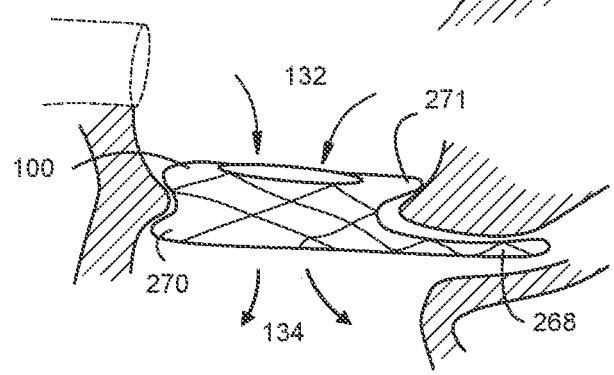

FIG. 77D is an illustration of a side perspective view of a fully expelled or released valve that is completely seated into the native annulus, and that allows a smooth transition from native blood flow to a full, complete flow thru the prosthetic valve into the native annulus.

Figure 78A:
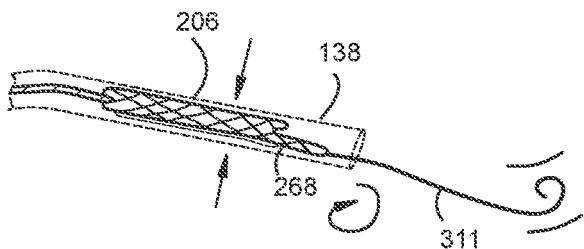

FIG. 78A is an illustration of a side perspective view of a valve that is vertically compressed without folding and loaded into a delivery catheter, and shows an extended inner leaflet component in a rolled configuration.

Figure 78B:
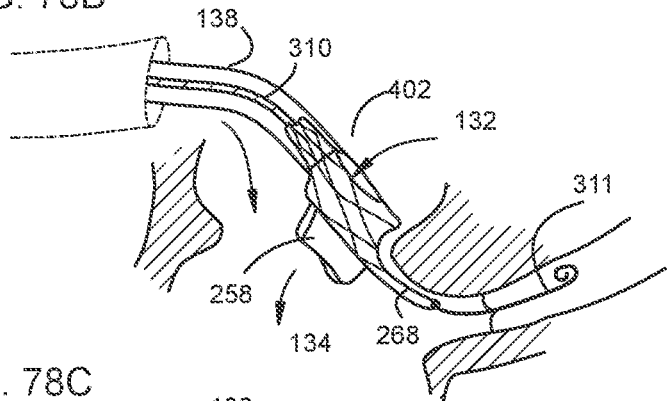

FIG. 78B is an illustration of a side perspective view of a partially expelled or released valve, with a partially unfurled extended inner leaflet component, and shows a transition from native blood flow through the native tricuspid valve to a partial flow around the prosthetic valve and into the native annulus and a partial flow thru the prosthetic valve into the native annulus.

Figure 78C:
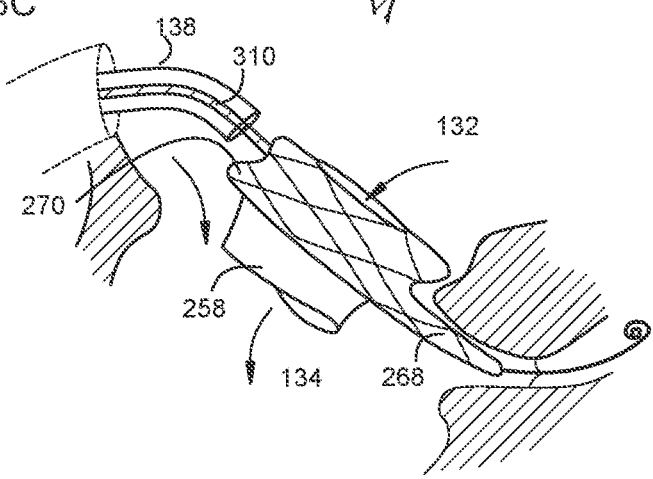

FIG. 78C is an illustration of a side perspective view of a fully expelled or released valve, with a fully unfurled extended inner leaflet component, where the valve is lodged against the distal surface of the annulus and held elevated at an angle above the native annulus prior to complete deployment, and that allows a further transition from native blood flow through the native tricuspid valve with a partial flow around the prosthetic valve and into the native annulus, and an increasing partial flow thru the prosthetic valve into the native annulus.

Figure 78D:
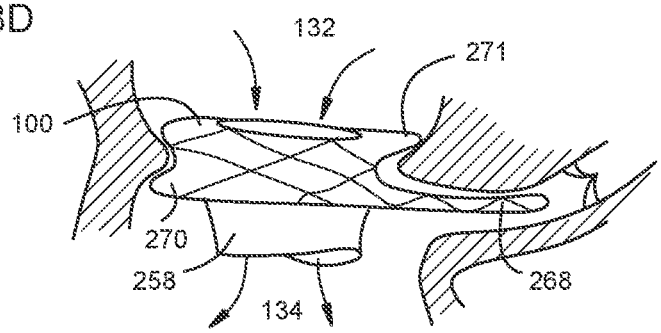

FIG. 78D is an illustration of a side perspective view of a fully expelled or released valve, with a fully unfurled extended inner leaflet component, and shows that is completely seated into the native annulus, and that allows a smooth transition from native blood flow to a full, complete flow thru the prosthetic valve into the native annulus.

Figure 79A:
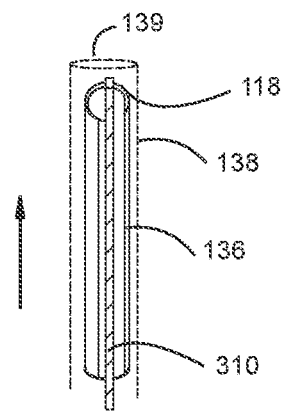

FIG. 79A is an illustration of a side view of a compressed valve within a delivery catheter.

Figure 79B:
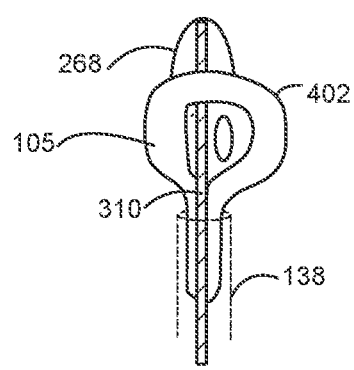

FIG. 79B is an illustration of a side view of a partially compressed valve that is partially released from the delivery catheter and shows how blood flow can being its transition.

Figure 79C:
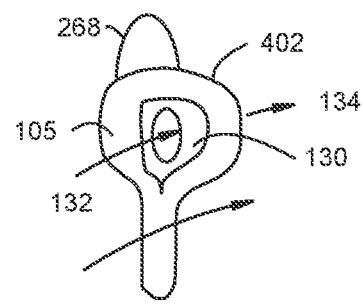

FIG. 79C is an illustration of a side view of a partially compressed valve showing blood flow through the valve and around the valve.

Figure 79D:
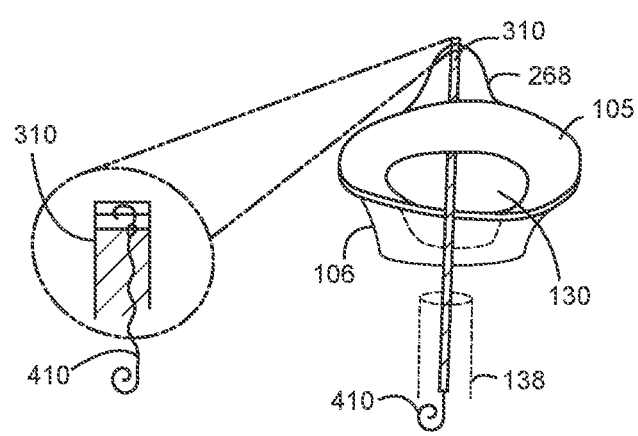

FIG. 79D is an illustration of a side view of an uncompressed valve orthogonally released (sideways) from the delivery catheter, and still attached to the distal pull wire/ deployment control wire or hypotube releasably attached to the RVOT tab.

Figure 79E:
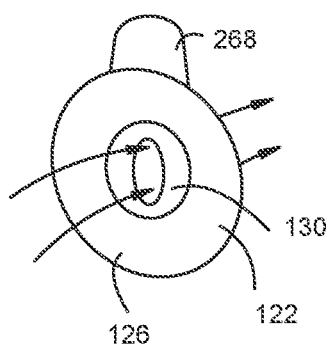

FIG. 79E is an illustration of a side view of an uncompressed valve showing transition to all blood flow through the valve and no flow around the valve.

Figure 80A:
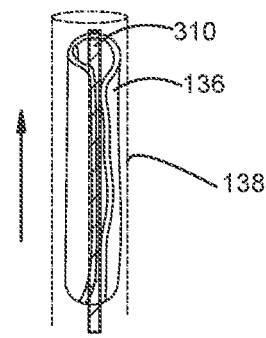

FIG. 80A is an illustration of a side view of a rolled valve within a delivery catheter and being advanced by a distal pull wire/draw-wire (or far-side push-pull wire) attached to the leading edge of the valve collar.

Figure 80B:
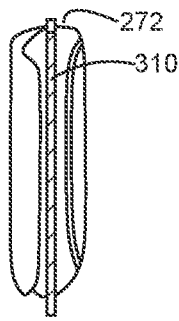

FIG. 80B is an illustration of a side view of a partially unrolled valve that has been deployed from the catheter.

Figure 80C:
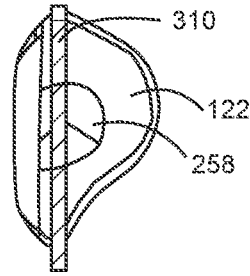

FIG. 80C is an illustration of a side view of a partially released unrolled valve that has been deployed from the catheter.

Figure 80D:
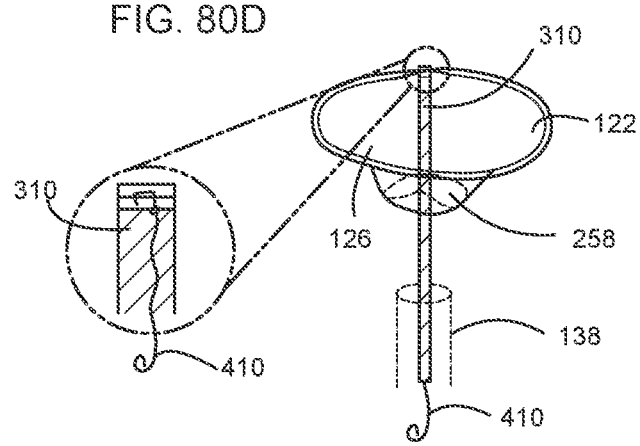

FIG. 80D is an illustration of a side view of a completely released unrolled valve where the wire attachment is used to position the valve within the native annulus.

Figure 81:
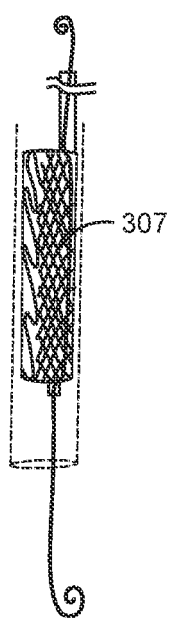

FIG. 81 is an illustration of a side view of a compressed valve within a delivery catheter, and shows draw/pulling wire attached to the forward end of the compressed valve to pull the valve out of the catheter.

FIG. 82A is an illustration of a side or plan transparent view of a delivery catheter loaded with an orthogonal valve having a tension arm with a guidewire collar element and a guidewire extending through the guidewire collar with a guidewire sheath pushing against the guidewire collar element. Inset shows a non-limiting example of a guidewire collar attached to a tension arm with guidewire through the aperture of the guidewire collar and hypotube sheath stopped by the larger circumference of the guidewire collar, permitting pushing on the tension arm to pull the valve out of the delivery catheter.

FIG. 82B is another non-limiting example of a guidewire collar attached to a tension arm with guidewire through the aperture of the guidewire collar and hypotube sheath stopped by the larger circumference of the guidewire collar, permitting pushing on the tension arm to pull the valve out of the delivery catheter.

FIG. 82C is another non-limiting example of a guidewire collar attached to a tension arm with guidewire through the aperture of the guidewire collar and hypotube sheath stopped by the larger circumference of the guidewire collar, permitting pushing on the tension arm to pull the valve out of the delivery catheter.

FIG. 82D is another non-limiting example of a guidewire collar attached to a tension arm with guidewire through the aperture of the guidewire collar and hypotube sheath stopped by the larger circumference of the guidewire collar, permitting pushing on the tension arm to pull the valve out of the delivery catheter.

Figure 83A:
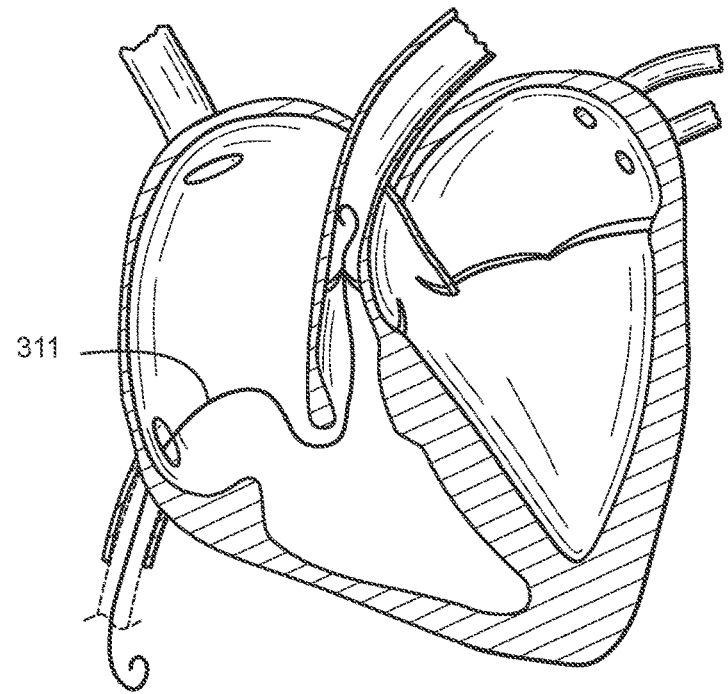

FIG. 83A is an illustration of step 1 of a 6-step process for delivery of an orthogonal prosthetic valve to the tricuspid annulus. FIG. 83A shows a 0.035 guidewire with hypotube sheath delivered to the right ventricular outflow tract (RVOT).

Figure 83B:
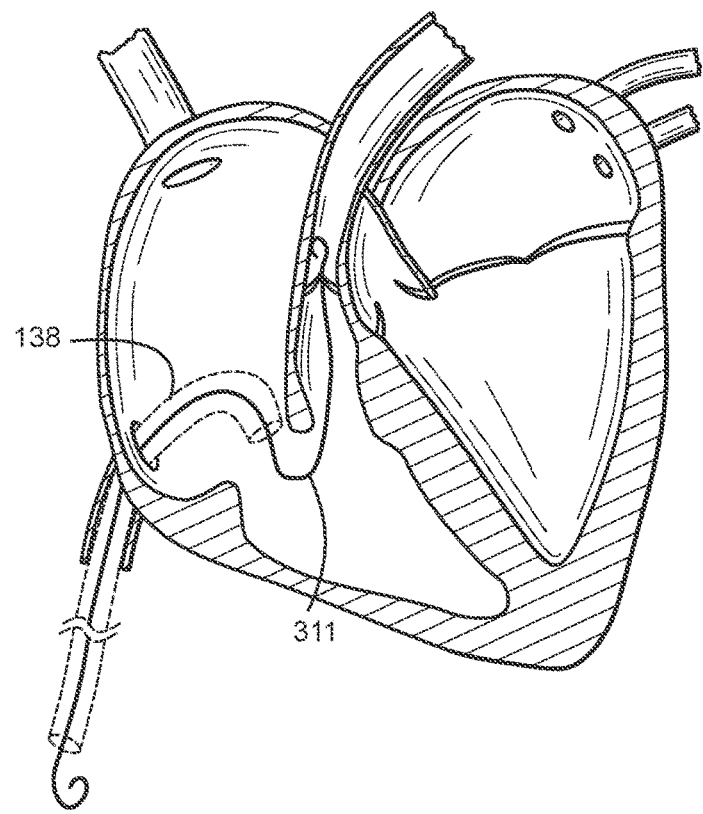

FIG. 83B is an illustration of step 2 of a 6-step process for delivery of an orthogonal prosthetic valve to the tricuspid annulus. FIG. 83B shows a 34 Fr delivery catheter being advanced over the guidewire to and through the native tricuspid annulus to the right ventricle.

Figure 83C:
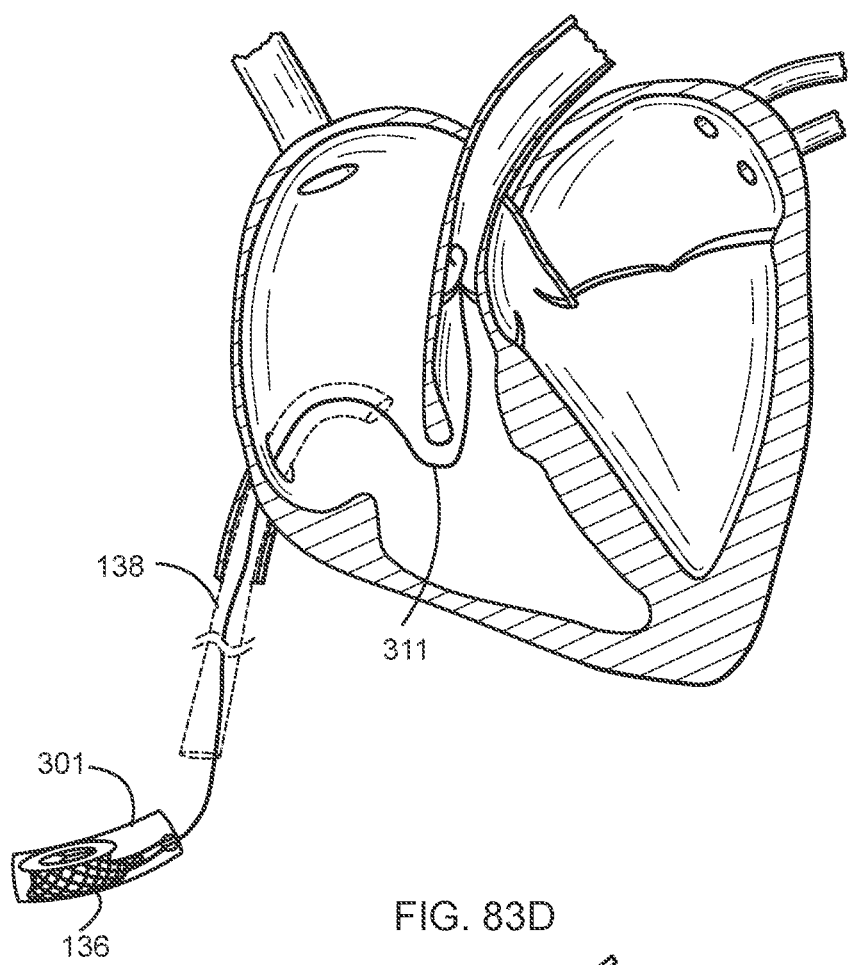

FIG. 83C is an illustration of step 3 of a 6-step process for delivery of an orthogonal prosthetic valve to the tricuspid annulus. FIG. 83C shows a capsule having a compressed valve therein where the capsule is loaded into the proximal end of the delivery catheter and the valve is withdrawn from the capsule into the delivery catheter, with sheathed guidewire threaded through the valve and providing a wire path to the RVOT, planned deployment location.

Figure 83D:
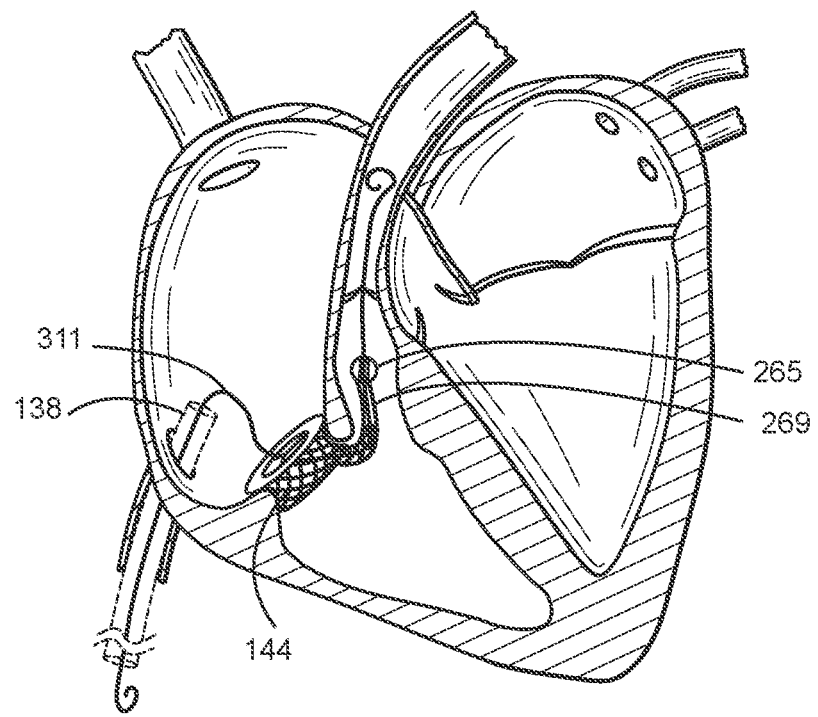

FIG. 83D is an illustration of step 4 of a 6-step process for delivery of an orthogonal prosthetic valve to the tricuspid annulus. FIG. 83D shows the valve advanced up the catheter and deployed into the native annulus by pushing on the outer sheath of the guidewire to pull the valve up the catheter and into position. Tension arm is used to position the valve.

Figure 83E:
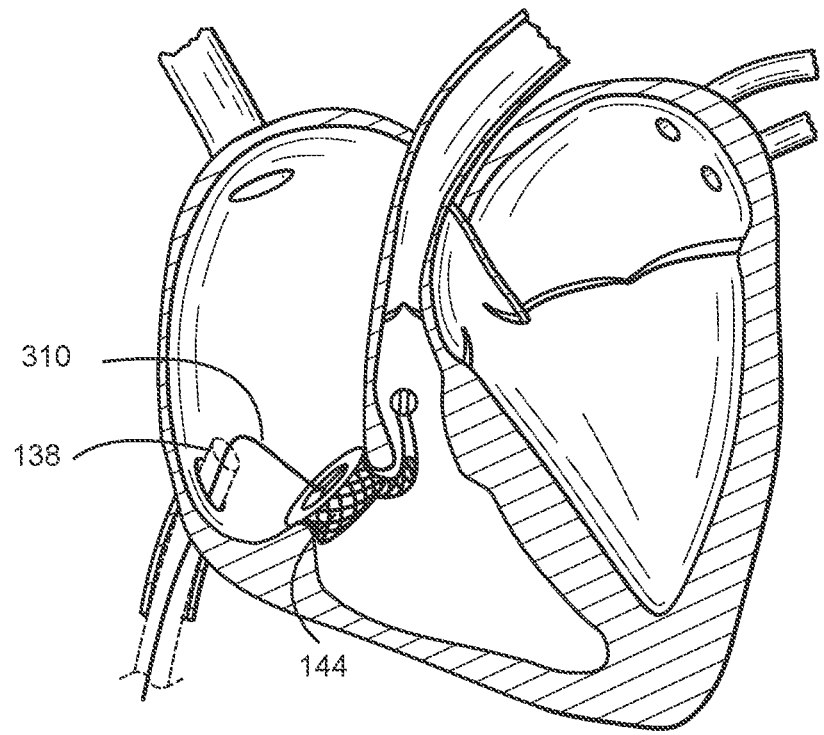

FIG. 83E is an illustration of step 5 of a 6-step process for delivery of an orthogonal prosthetic valve to the tricuspid annulus. FIG. 83E shows a catheter being used to push the proximal side of the valve into position within the annulus.

Figure 83F:
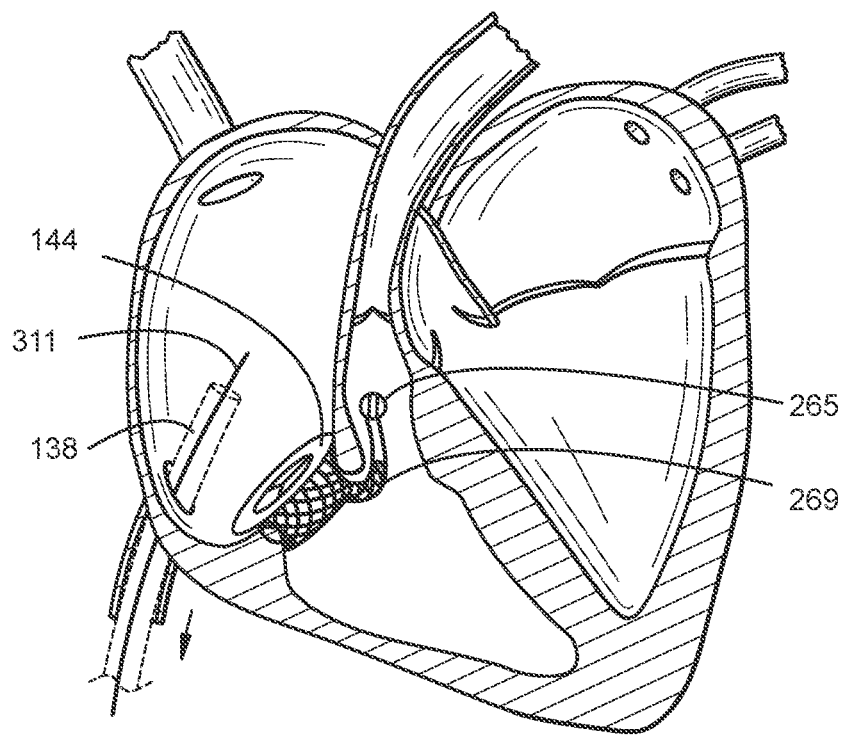

FIG. 83F is an illustration of step 6 of a 6-step process for delivery of an orthogonal prosthetic valve to the tricuspid annulus. FIG. 83F shows withdrawal of the delivery system and anchoring of the proximal side of the valve to the annular tissue.

Figure 84A:
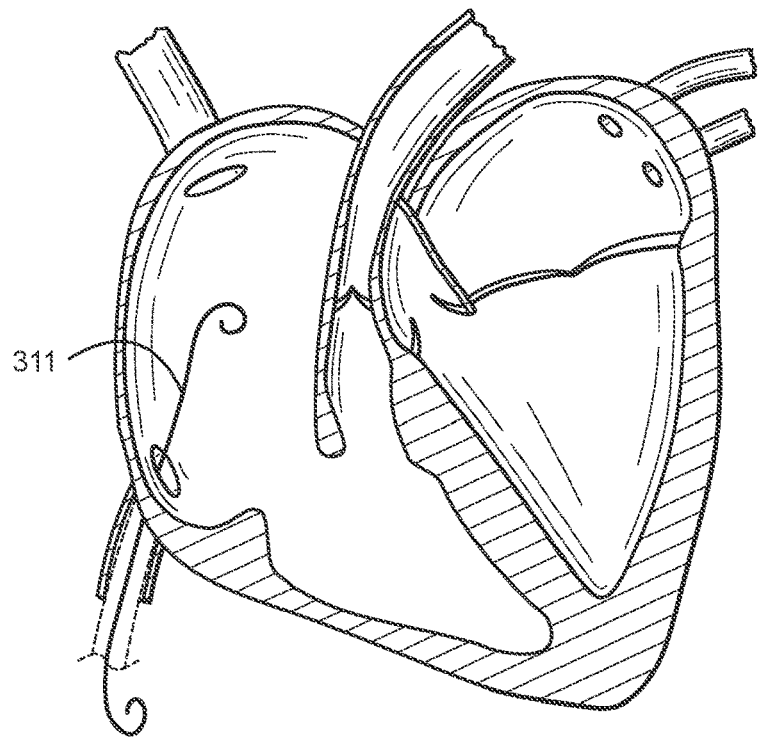

FIG. 84A is an illustration of step 1 of an 8-step process for delivery of an orthogonal prosthetic valve to the tricuspid annulus. FIG. 84A shows an 8 Fr guidewire advanced from the femoral through the inferior vena cava (IVC) to the right atrium.

Figure 84B:
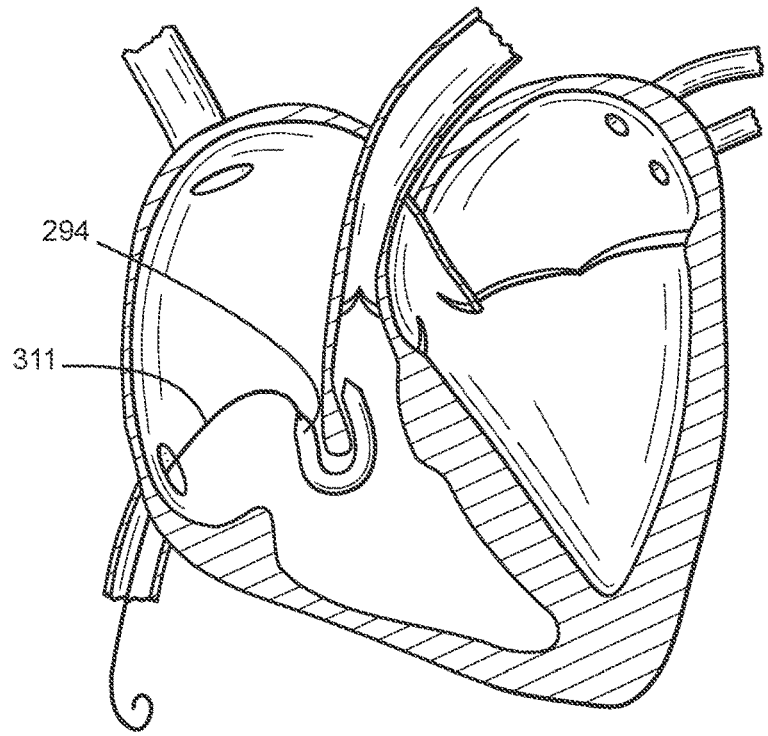

FIG. 84B is an illustration of step 2 of an 8-step process for delivery of an orthogonal prosthetic valve to the tricuspid annulus. FIG. 84B shows a balloon catheter advanced over the guidewire through the native annulus and into the RVOT to expand and push aside valve and leaflet tissue, chordae tendineae that might tangle transcatheter delivery of the valve.

Figure 84C:
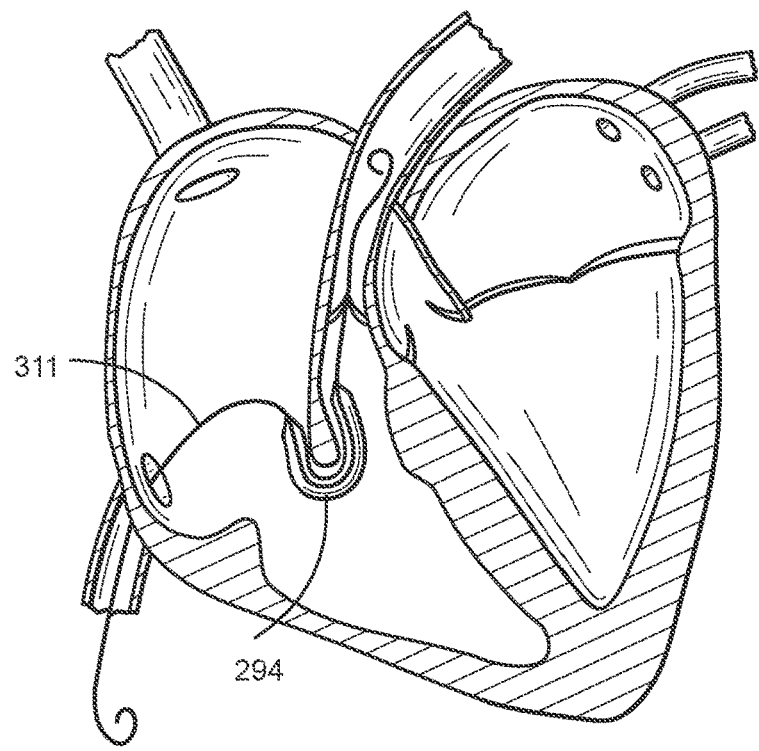

FIG. 84C is an illustration of step 3 of an 8-step process for delivery of an orthogonal prosthetic valve to the tricuspid annulus. FIG. 84C shows a 0.035 guidewire with hypotube sheath delivered to the right ventricular outflow tract (RVOT).

Figure 84D:
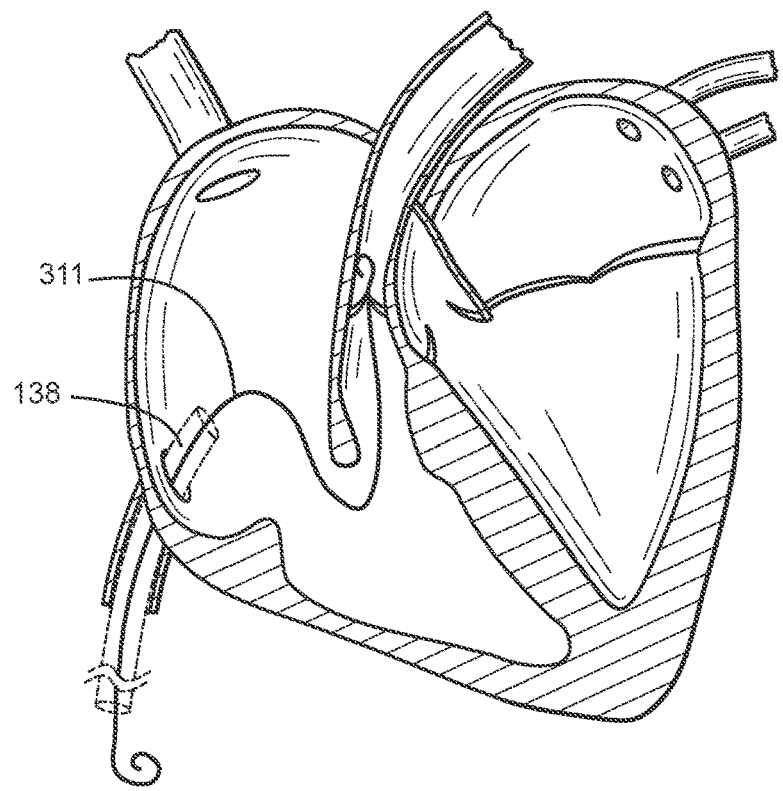

FIG. 84D is an illustration of step 4 of an 8-step process for delivery of an orthogonal prosthetic valve to the tricuspid annulus. FIG. 84D shows a 34 Fr delivery catheter being advanced over the guidewire to and through the native tricuspid annulus to the right ventricle.

FIG. 84E is an illustration of step 5 of an 8-step process for delivery of an orthogonal prosthetic valve to the tricuspid annulus. FIG. 84E shows a capsule having a compressed valve therein where the capsule is loaded into the proximal end of the delivery catheter and the valve is withdrawn from the capsule into the delivery catheter, with sheathed guidewire threaded through the valve and providing a wire path to the RVOT, planned deployment location.

FIG. 84F is an illustration of step 6 of an 8-step process for delivery of an orthogonal prosthetic valve to the tricuspid annulus. FIG. 84F shows the valve advanced up the catheter and deployed into the native annulus by pushing on the outer sheath of the guidewire to pull the valve up the catheter and into position. Tension arm is used to position the valve.

Figure 84G:
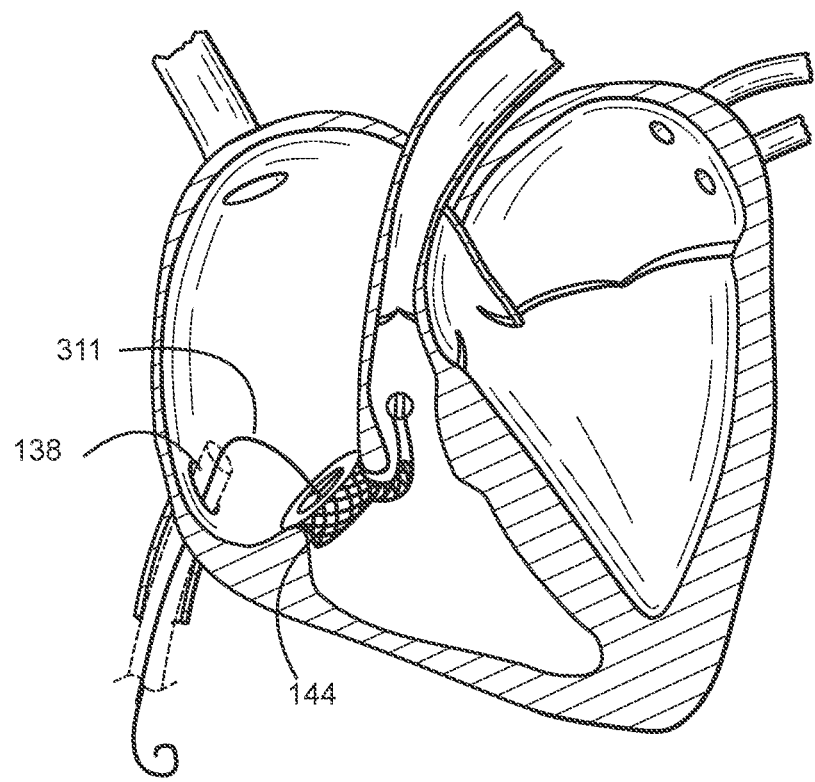

FIG. 84G is an illustration of step 7 of an 8-step process for delivery of an orthogonal prosthetic valve to the tricuspid annulus. FIG. 84G shows a catheter being used to push the proximal side of the valve into position within the annulus.

Figure 84H:
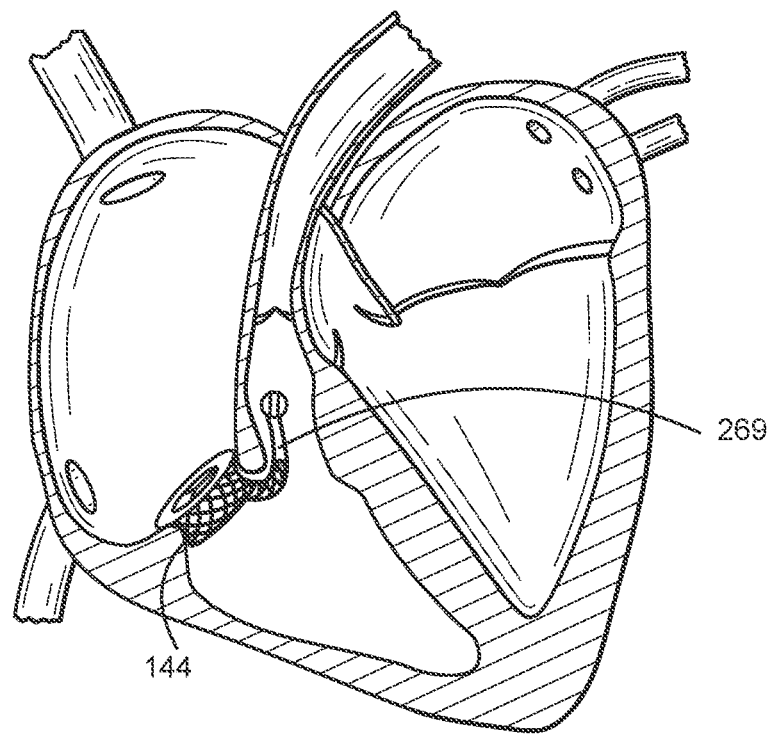

FIG. 84H is an illustration of step 8 of an 8-step process for delivery of an orthogonal prosthetic valve to the tricuspid annulus. FIG. 84H shows withdrawal of the delivery system and anchoring of the proximal side of the valve to the annular tissue.

Figure 85A:
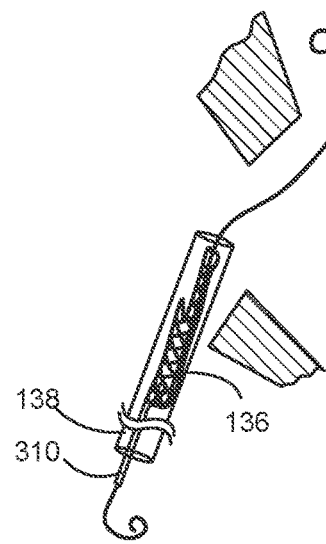

FIG. 85A is an illustration of step 1 of a 6-step process for delivery of an orthogonal prosthetic valve to the tricuspid annulus. FIG. 85A shows the valve advanced up the catheter and deployed into the native annulus.

Figure 85B:
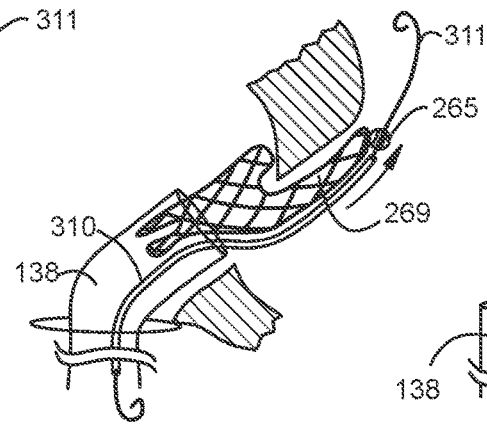

FIG. 85B is an illustration of step 2 of a 6-step process for delivery of an orthogonal prosthetic valve to the tricuspid annulus. FIG. 85B shows pushing on the outer sheath of the guidewire to pull the valve up the catheter and into position, partially expelling the valve with tension arm into the RVOT and the distal side of the valve lodged against the annular wall.

Figure 85C:
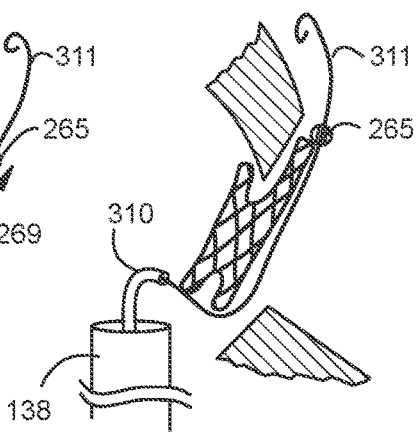

FIG. 85C is an illustration of step 3 of a 6-step process for delivery of an orthogonal prosthetic valve to the tricuspid annulus. FIG. 85C shows a catheter being used to push the proximal side of the valve into position within the annulus.

Figure 85D:
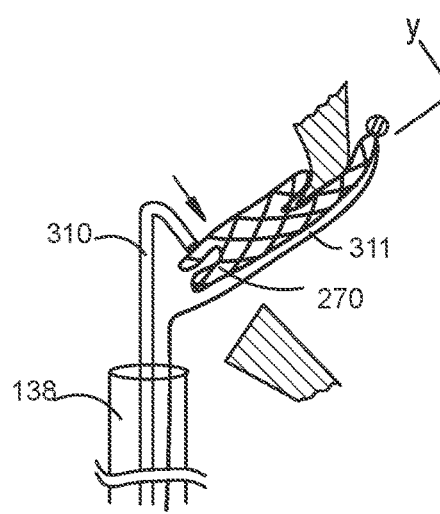

FIG. 85D is an illustration of step 4 of a 6-step process for delivery of an orthogonal prosthetic valve to the tricuspid annulus. FIG. 85D shows how tension arm is used to position the valve while catheter being used to push the proximal side of the valve into position within the annulus.

Figure 85E:
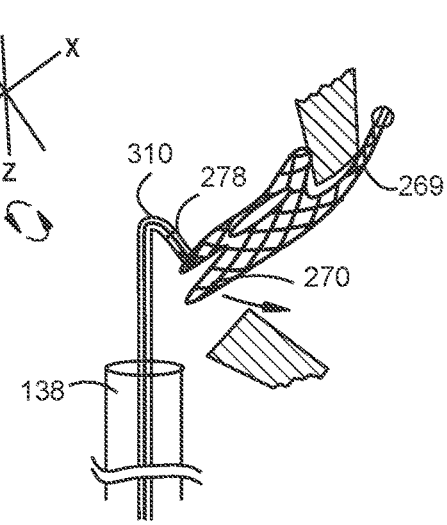

FIG. 85E is an illustration of step 5 of a 6-step process for delivery of an orthogonal prosthetic valve to the tricuspid annulus. FIG. 85E shows how catheter delivers a tissue anchor to secure the proximal side of the valve to the annular tissue.

Figure 85F:
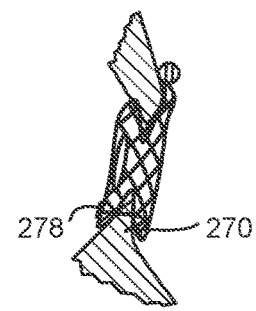

FIG. 85F is an illustration of step 6 of a 6-step process for delivery of an orthogonal prosthetic valve to the tricuspid annulus. FIG. 85F shows withdrawal of the delivery system and anchoring of the proximal side of the valve to the annular tissue.

Figure 86A:
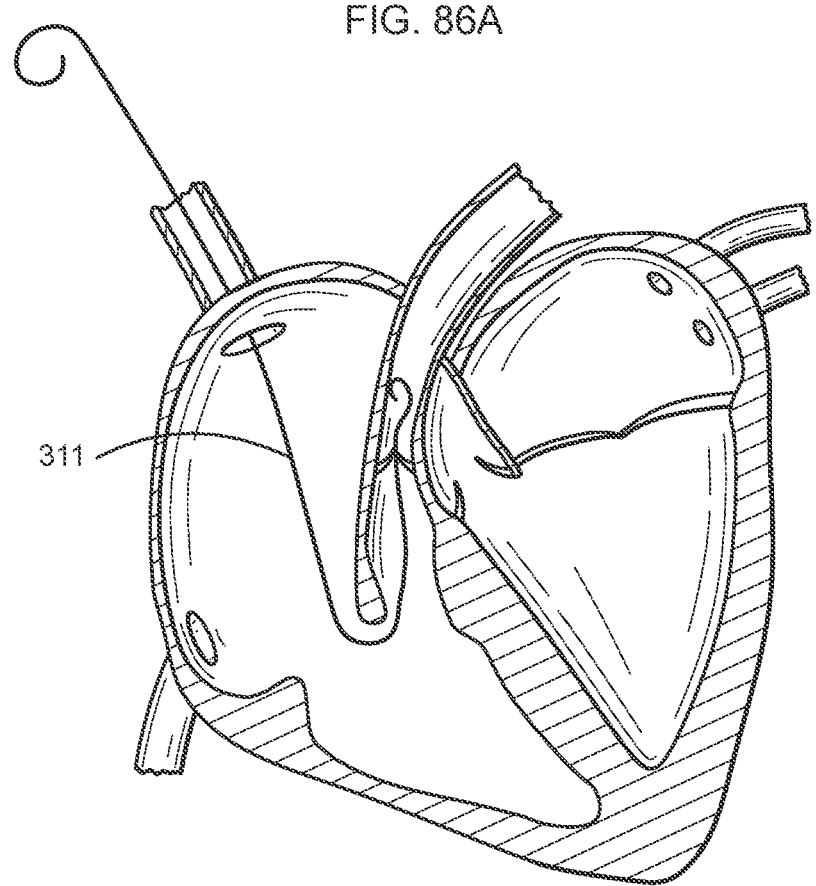

FIG. 86A is an illustration of step 1 of a 6-step process for delivery of a co-axial prosthetic valve to the tricuspid annulus. FIG. 86A shows a 0.035 guidewire with hypotube sheath delivered to the right ventricular outflow tract (RVOT) through the superior vena cava (SVC).

Figure 86B:
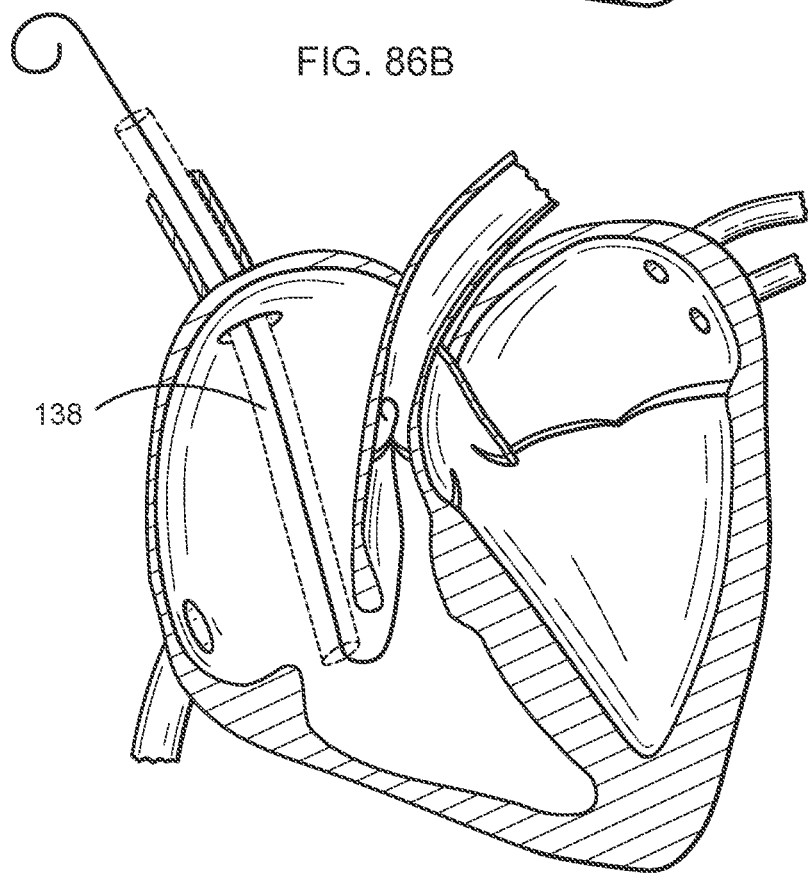

FIG. 86B is an illustration of step 2 of a 6-step process for delivery of a co-axial prosthetic valve to the tricuspid annulus. FIG. 86B shows a 34 Fr delivery catheter being advanced over the guidewire to and through the native tricuspid annulus to the right ventricle.

Figure 86C:
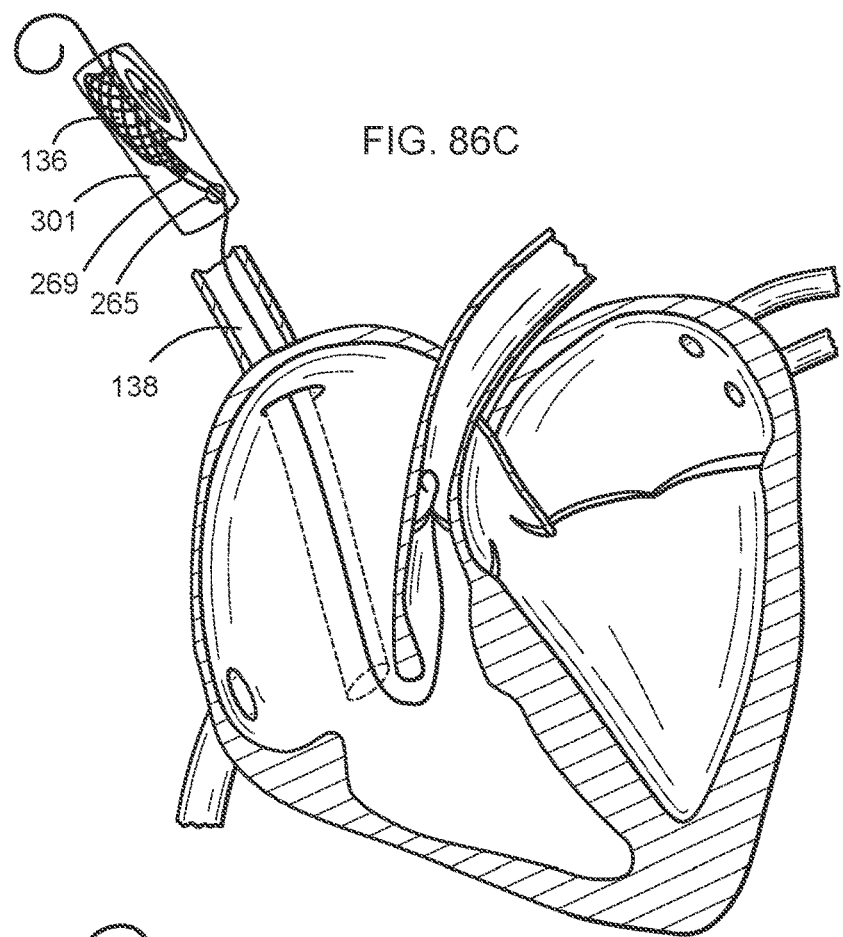

FIG. 86C is an illustration of step 3 of a 6-step process for delivery of a co-axial prosthetic valve to the tricuspid annulus. FIG. 86C shows a capsule having a compressed valve therein where the capsule is loaded into the proximal end of the delivery catheter and the valve is withdrawn from the capsule into the delivery catheter, with sheathed guidewire threaded through the valve and providing a wire path to the RVOT, planned deployment location.

Figure 86D:
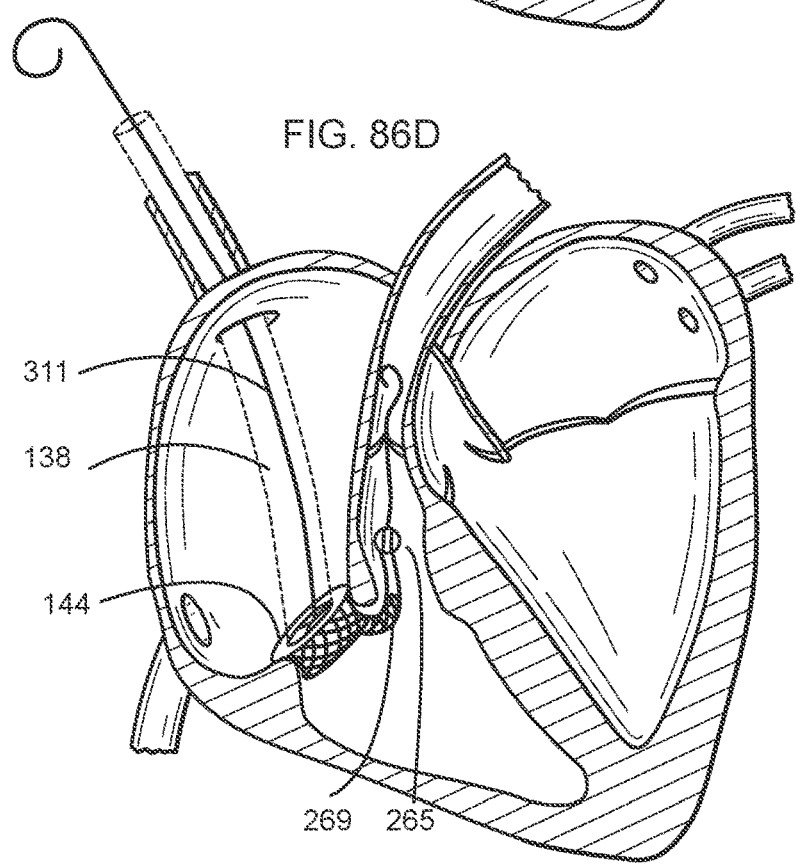

FIG. 86D is an illustration of step 4 of a 6-step process for delivery of a co-axial prosthetic valve to the tricuspid annulus. FIG. 86D shows the valve advanced up the catheter and deployed into the native annulus by pushing on the outer sheath of the guidewire to pull the valve up the catheter and into position. Tension arm is used to position the valve.

Figure 86E:
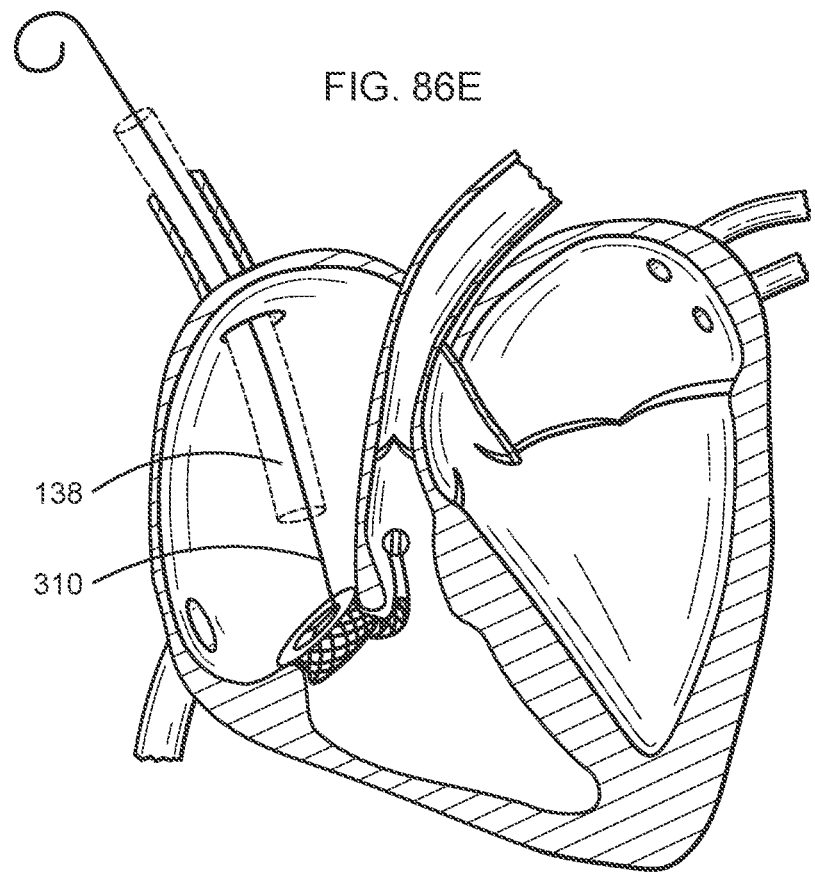

FIG. 86E is an illustration of step 5 of a 6-step process for delivery of a co-axial prosthetic valve to the tricuspid annulus. FIG. 86E shows a catheter being used to push the proximal side of the valve into position within the annulus.

Figure 86F:
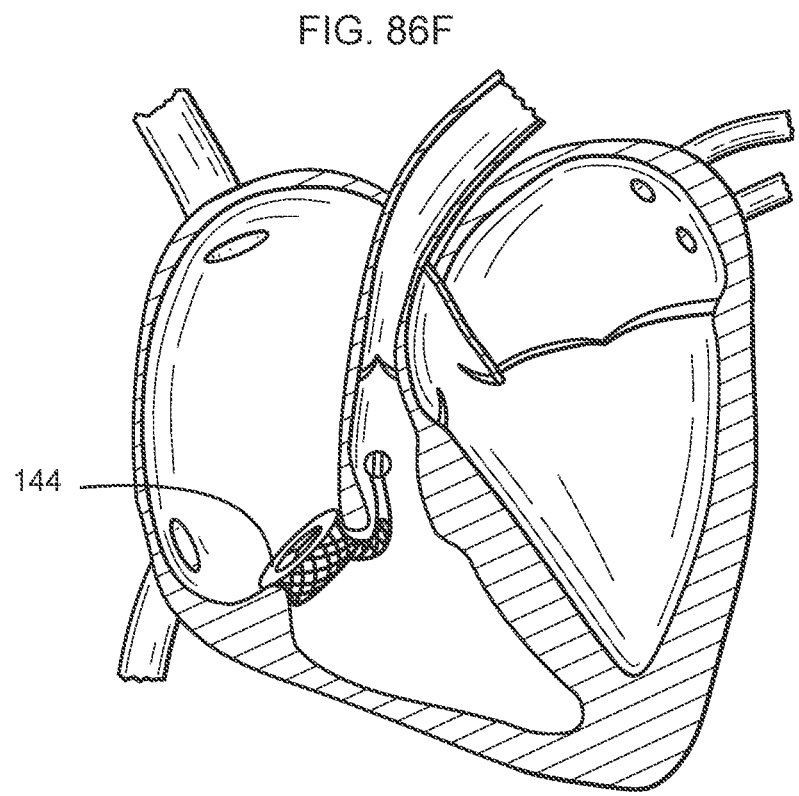

FIG. 86F is an illustration of step 6 of a 6-step process for delivery of a co-axial prosthetic valve to the tricuspid annulus. FIG. 86F shows withdrawal of the delivery system and anchoring of the proximal side of the valve to the annular tissue.

Figure 87A:
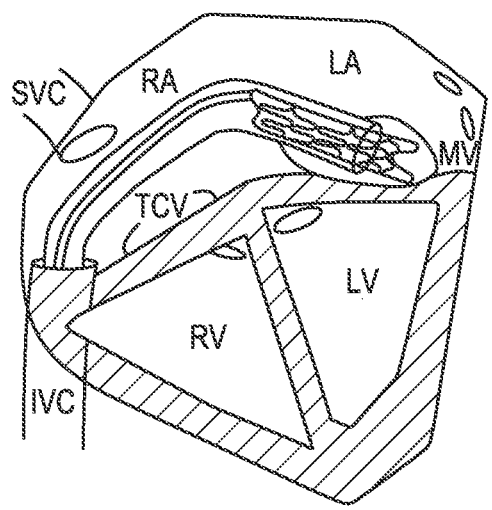

FIG. 87A is an illustration of the trans-septal (femoral-IVC) delivery of a low profile, e.g. 8-20 mm, side-loaded prosthetic mitral valve shown partially housed within the delivery catheter, and partially ejected for deployment into the native mitral annulus.

Figure 87B:
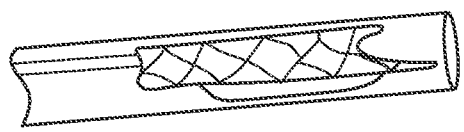

FIG. 87B is an illustration of a low profile, e.g. 8-20 mm, side-loaded prosthetic mitral valve shown housed within the delivery catheter.

Figure 87C:
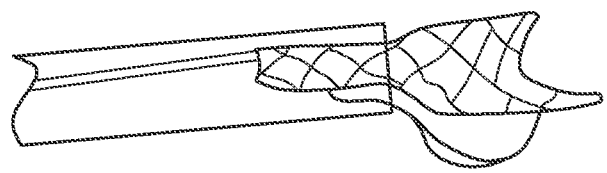

FIG. 87C is an illustration of a low profile, e.g. 8-20 mm, side-loaded prosthetic mitral valve shown partially housed within a delivery catheter and partially laterally ejected from the delivery catheter and positioned for deployment against the anterior side of the native mitral annulus.

Figure 87D:
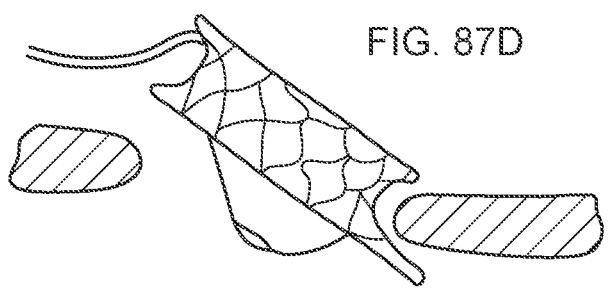

FIG. 87D is an illustration of a low profile, e.g. 8-20 mm, side-loaded prosthetic mitral valve shown ejected from the delivery catheter and positioned against the anterior side of the native mitral annulus.

Figure 87E:
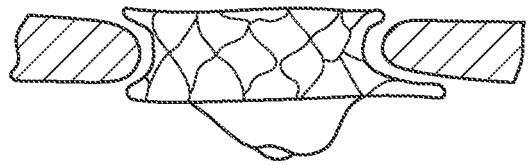

FIG. 87E is an illustration of a side or plan view of a low profile, e.g. 8-20 mm, side-loaded prosthetic valve shown deployed into the native mitral annulus.

Figure 88A:
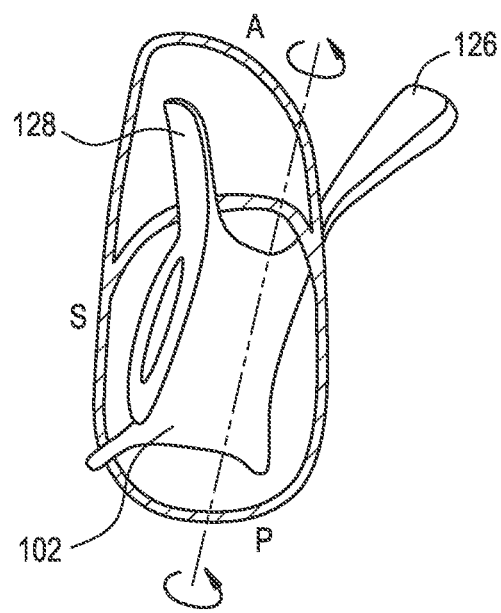

FIG. 88A is an illustration of a rotational lock embodiment where the prosthetic valve is delivered to the native annulus with an off-set sub-annular tension arm/tab positioned below the native annulus, and an off-set supra-annular tension arm/tab positioned above the native annulus, while the tubular frame is partially rolled off-set from the annular plane along a longitudinal axis.

Figure 88B:
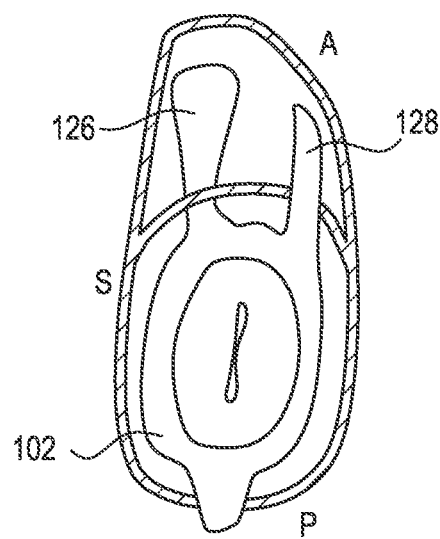

FIG. 88B is an illustration of a rotational lock embodiment where the prosthetic valve is delivered to the native annulus with an off-set sub-annular tension arm/tab positioned below the native annulus, and an off-set supra-annular tension arm/tab positioned above the native annulus, while the tubular frame is rolled into functional position parallel to the annular plane.

Figure 89A:
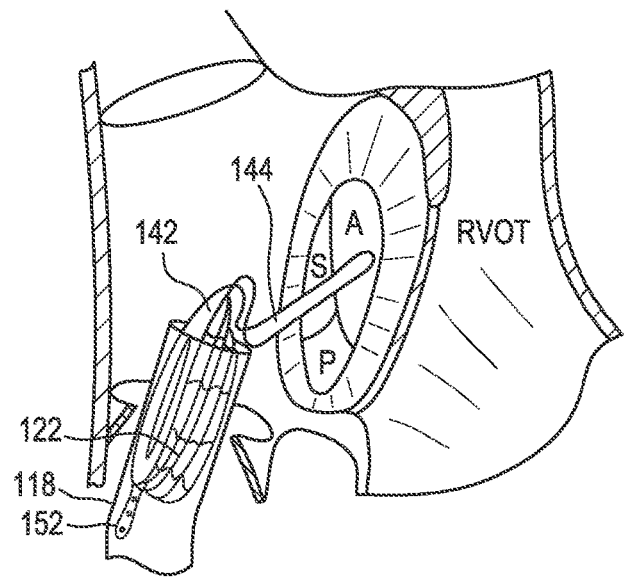

FIG. 89A is an illustration of a heart valve prosthesis having a wire-frame according to an embodiment being delivered to a tricuspid valve annulus.

Figure 89B:
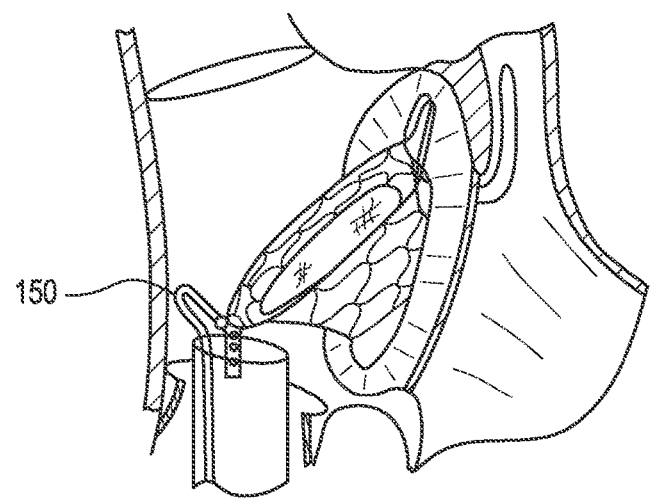

FIG. 89B is an illustration of a heart valve prosthesis having a wire-frame according to an embodiment being delivered to the tricuspid valve annulus.

Figure 89C:
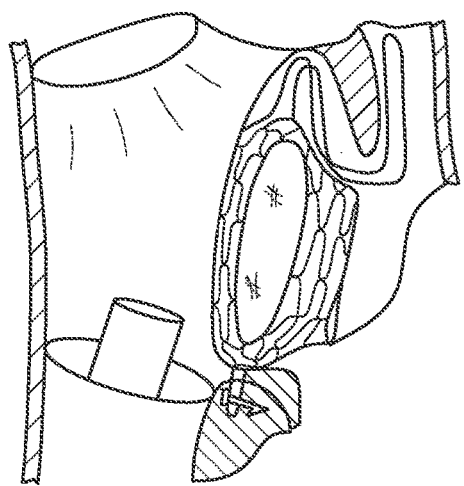

FIG. 89C is an illustration of a heart valve prosthesis having a wire-frame according to an embodiment that has been delivered to the tricuspid valve annulus.

Figure 90A:
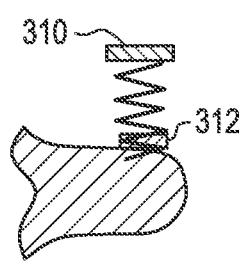
Figure 90B:
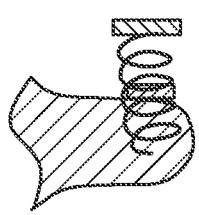
Figure 90C:
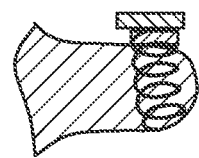

FIGS. 90A to 90C show a plan view of a tissue anchor having a floating radio-opaque marker. This figure shows the tissue anchor accessing the annular tissue with the radio-opaque marker at the distal end of the anchor and in contact with the atrial surface of the annular tissue. This figure shows the tissue anchor advancing into the annular tissue with the radio-opaque marker threaded onto the tissue anchor and maintaining position on the atrial surface of the annular tissue. This figure shows the tissue anchor completely advanced into the annular tissue such that the tissue anchor and the threaded floating marker are now adjacent, indicating the desired depth, tension, and/or plication of the tissue anchor with respect to the annular tissue.

Figure 91A:

FIG. 91A is an illustration of a plan view of a tissue anchor having a straight thread and a constant pitch.

Figure 91B:

FIG. 91B is an illustration of a plan view of a tissue anchor having a straight thread and a variable pitch.

Figure 91C:

FIG. 91C is an illustration of a plan view of a tissue anchor having a tapered thread and a constant pitch.

Figure 91D:

FIG. 91D is an illustration of a plan view of a tissue anchor having a sunken taper thread and a variable pitch.

Figure 92A:
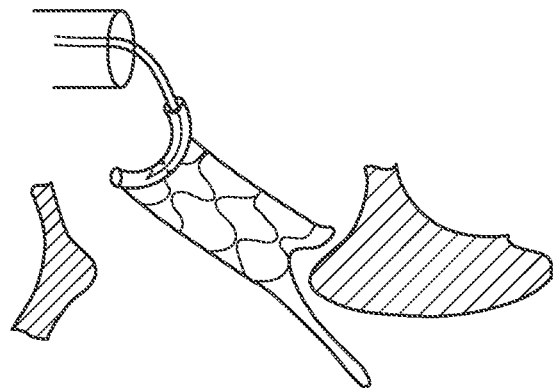

FIG. 92A is an illustration of Step 1 of a 4-step process for clipping a low profile valve to annular tissue, as shown here in a non-limiting example of clipping to a proximal or anterior side of the native annulus. FIG. 92A shows a low profile valve being inserted into the valve annulus and low profile valve having an integral anchor delivery conduit or channel with an anchor disposed in the lumen of the channel and an anchor delivery catheter attached to the anchor.

Figure 92B:
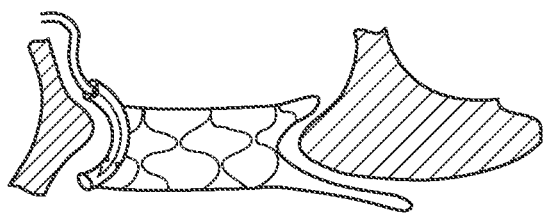

FIG. 92B is an illustration of Step 2 of a 4-step process for clipping a low profile valve to annular tissue, as shown here in a non-limiting example of clipping to a proximal or anterior side of the native annulus. FIG. 92B shows a low profile valve completely deployed within the valve annulus and an integral anchor delivery conduit or channel with an anchor disposed in the lumen of the channel and an anchor delivery catheter attached to the anchor.

Figure 92C:
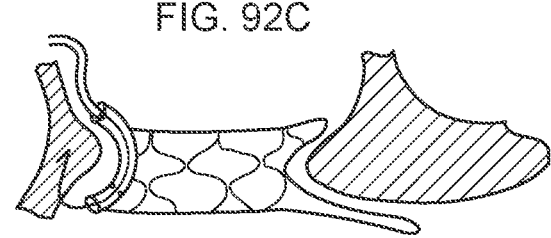

FIG. 92C is an illustration of Step 3 of a 4-step process for clipping a low profile valve to annular tissue, as shown here in a non-limiting example of clipping to a proximal or anterior side of the native annulus. FIG. 92C shows the anchor being pushed out of the lumen of the delivery conduit or channel and into the annular tissue.

Figure 92D:
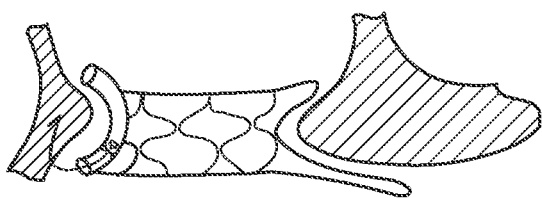

FIG. 92D is an illustration of Step 4 of a 4-step process for clipping a low profile valve to annular tissue, as shown here in a non-limiting example of clipping to a proximal or anterior side of the native annulus. FIG. 92D shows the anchor in a locked position after being pushed out of the lumen of the delivery conduit or channel and into the annular tissue, thus anchoring the proximal side of the low profile valve.

FIG. 93A is an illustration of Step 1 of a 5-step process for clipping a low profile valve to annular tissue, as shown here in a non-limiting example of clipping to a proximal or anterior side of the native annulus. FIG. 93A shows catheter delivery of an attachment wire with the clip housed within the lumen of the clip delivery catheter.

FIG. 93B is an illustration of Step 2 of a 5-step process for clipping a low profile valve to annular tissue, as shown here in a non-limiting example of clipping to a proximal or anterior side of the native annulus. FIG. 93B shows the clip delivery catheter inserted into an intra-annular space and shows an attachment wire and shows the clip housed within the lumen of the clip delivery catheter.

FIG. 93C is an illustration of Step 3 of a 5-step process for clipping a low profile valve to annular tissue, as shown here in a non-limiting example of clipping to a proximal or anterior side of the native annulus. FIG. 93C shows a receiver element ejected from the delivery catheter and positioned behind tissue to be captured.

FIG. 93D is an illustration of Step 4 of a 5-step process for clipping a low profile valve to annular tissue, as shown here in a non-limiting example of clipping to a proximal or anterior side of the native annulus. FIG. 93D shows an anchor element piercing the annular tissue and inserting into a receiver element.

FIG. 93E is an illustration of Step 5 of a 5-step process for clipping a low profile valve to annular tissue, as shown here in a non-limiting example of clipping to a proximal or anterior side of the native annulus. FIG. 93E shows that the clip delivery catheter is withdrawn and the anchor element and receiver element are connected to the annular tissue and connected by connector wire to the low profile valve.

Figure 94:
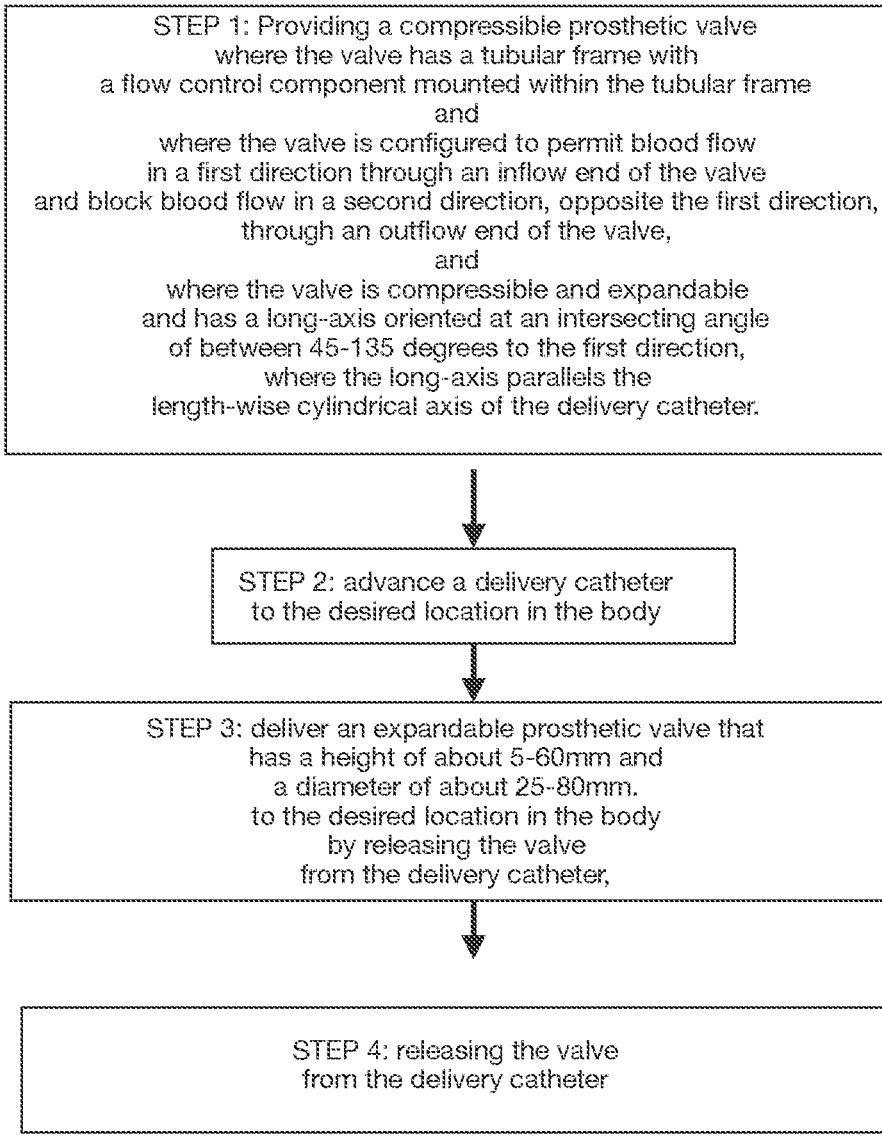

FIG. 94 is a flowchart showing an embodiment of a method for orthogonal delivery of implantable prosthetic valve to a desired location in the body.

FIG. 95 is a flowchart showing an embodiment of a method for orthogonal loading of an implantable prosthetic valve into a delivery catheter.

Figure 96A:
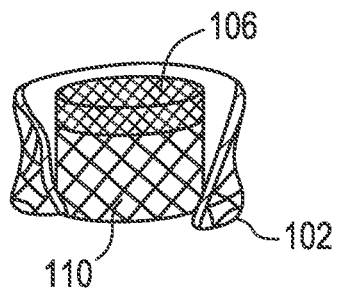

FIG. 96A is an illustration of an open cross-section view of a low profile, side-loaded prosthetic valve frame and shows a commercially available valve mounted within the lumen of the frame.

Figure 96B:
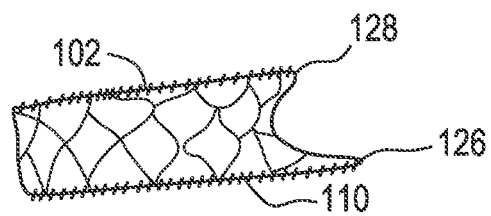

FIG. 96B is an illustration of a valve frame according to an embodiment having a braid or laser-cut construction for the tubular frame, with an extended tab or tension arm that extends away from the tubular frame.

Figure 96C:
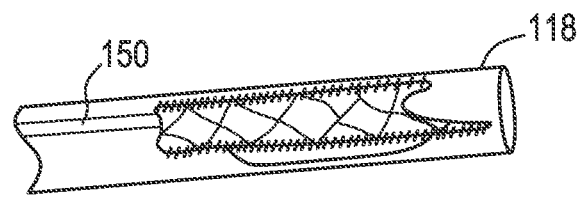

FIG. 96C is an illustration of a valve frame having a braid or laser-cut tubular frame and extended valve sleeve compressed within a delivery catheter.

Figure 96D:
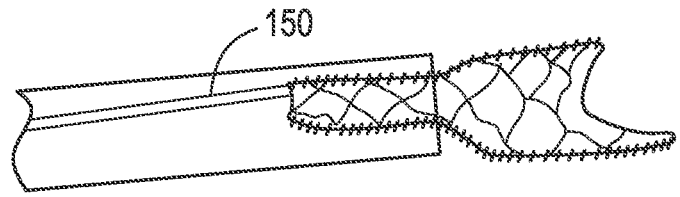

FIG. 96D is an illustration of a valve frame having a braid or laser-cut tubular frame and extended valve sleeve shown partially compressed within a delivery catheter, and partially ejected from the delivery catheter.

Figure 96E:
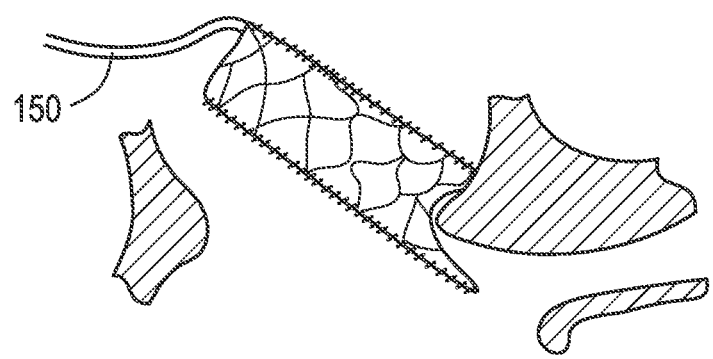

FIG. 96E is an illustration of a valve frame having a braid or laser-cut tubular frame and extended valve sleeve engaging the tissue on the anterior side of the native annulus with the curved distal sidewall of the tubular frame sealing around the native annulus.

Figure 96F:
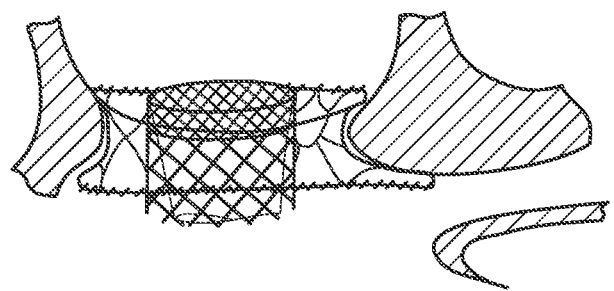

FIG. 96F is an illustration of a valve frame having a braid or laser-cut tubular frame and extended proximal tab or tension-arm engaging the tissue on the anterior side of the native annulus with the curved distal sidewall of the tubular frame sealing around the native annulus, and with the proximal sidewall tension-mounted into the posterior side of the native annulus, and a commercially available valve mounted within the lumen of the frame.

Figure 97A:
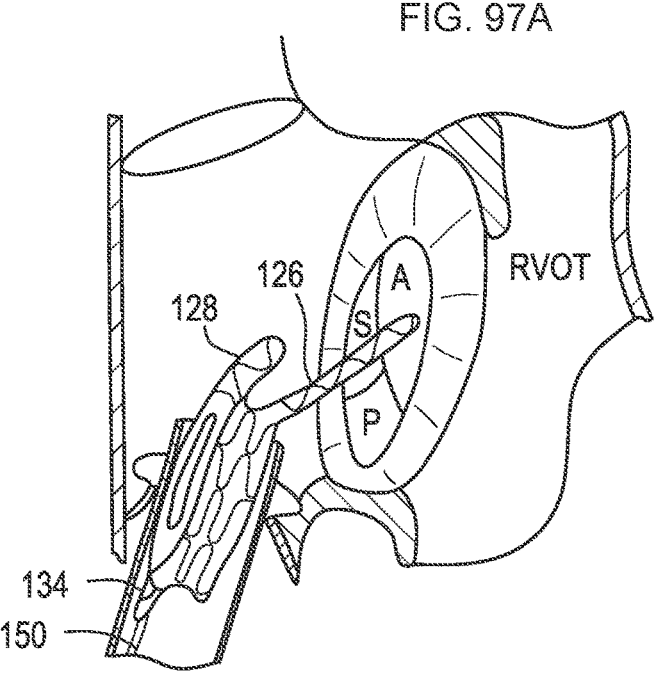

FIG. 97A is an illustration of a valve frame prosthesis having a braided/laser cut-frame according to an embodiment being delivered to tricuspid valve annulus.

Figure 97B:
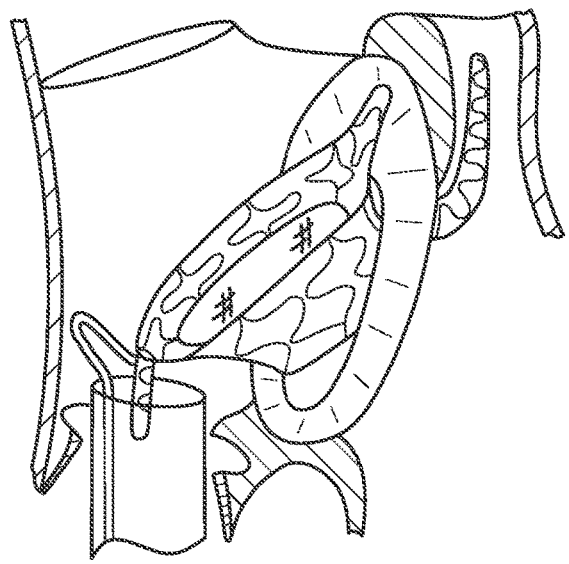

FIG. 97B is an illustration of a valve frame prosthesis having a braided/laser cut-frame according to an embodiment being delivered to tricuspid valve annulus.

Figure 97C:
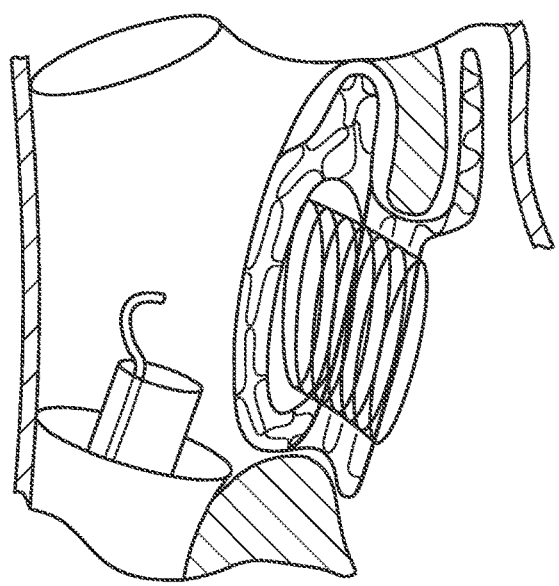

FIG. 97C is an illustration of a valve frame prosthesis having a braided/laser cut-frame according to an embodiment that has been delivered to tricuspid valve annulus. Independently deployed commercial valve is shown mounted within the aperture or lumen of the valve frame.

Figure 98A:
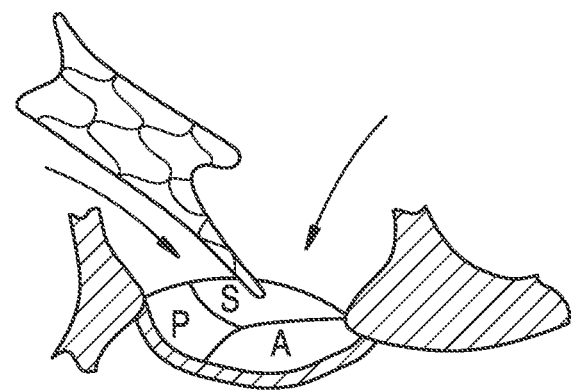

FIG. 98A is an illustration of a valve frame prosthesis according to an embodiment being delivered to tricuspid valve annulus and shows Step 1 in a valve assessment process.

Figure 98B:
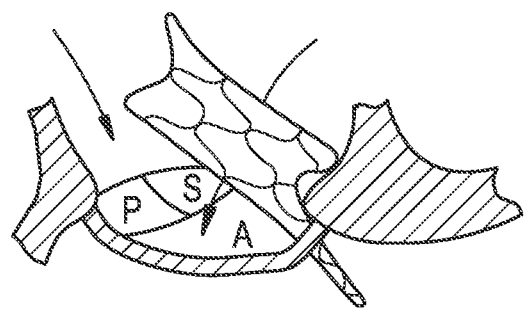

FIG. 98B is an illustration of a valve frame prosthesis according to an embodiment being delivered to tricuspid valve annulus, and shows Step 2 in a valve assessment process.

Figure 98C:
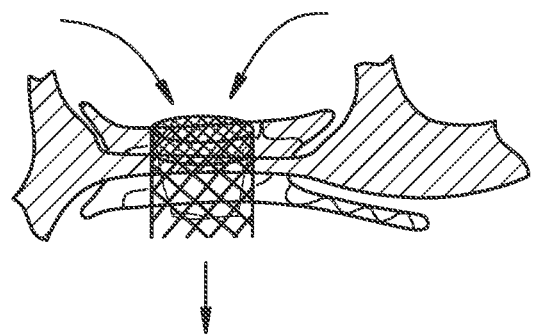

FIG. 98C is an illustration of a valve frame prosthesis according to an embodiment that has been delivered to tricuspid valve annulus, and shows Step 3 in a valve assessment process, with independently deployed commercial valve shown mounted within the aperture or lumen of the valve frame.

Figure 99A:
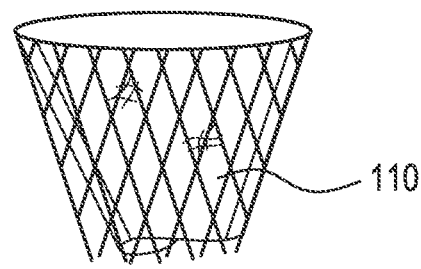

FIG. 99A is an illustration of an independently deployed balloon expandable commercial valve.

Figure 99B:
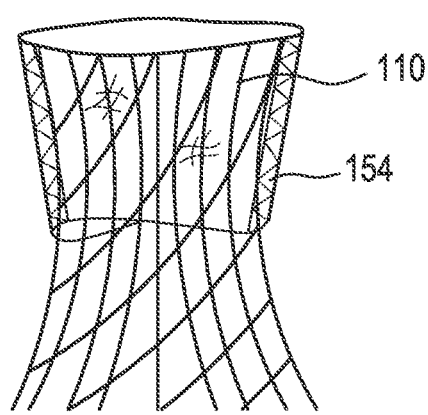

FIG. 99B is an illustration of a self-expanding independently deployed commercial valve.

Figure 99C:
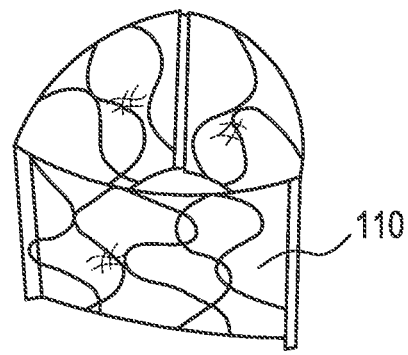

FIG. 99C is an illustration of a three-panel embodiment of a self-expanding independently deployed valve.

Figure 99D:
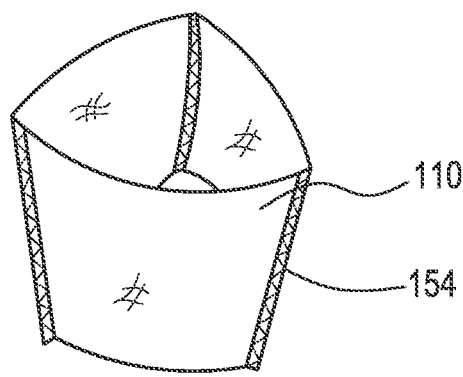

FIG. 99D is an illustration of a three-panel embodiment of an independently deployed valve having three rigid support posts.

Figure 100:
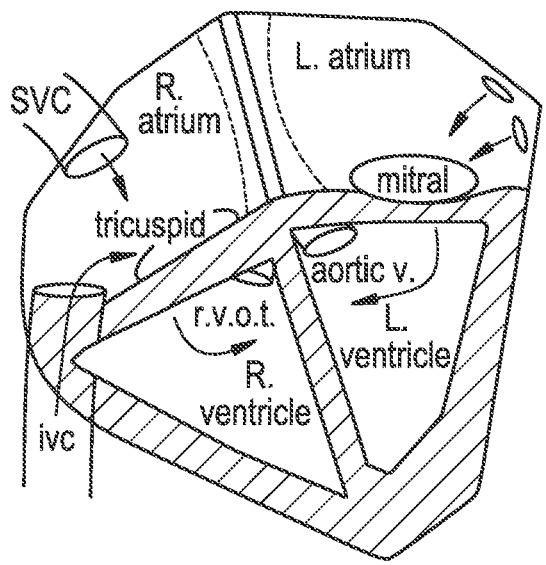

FIG. 100 is an illustration of the heart and shows an approximate location of the valves, the left and right atrium, the left and right ventricles, and the blood vessels that enter and exit the chambers of the heart.

Figure 101A:
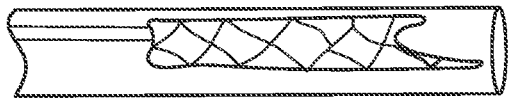

FIG. 101A is an illustration of a low profile, e.g. 8-20 mm, side-loaded valve frame shown housed within the delivery catheter.

Figure 101B:
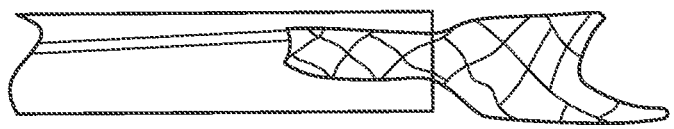

FIG. 101B is an illustration of a low profile, e.g. 8-20 mm, side-loaded valve frame shown partially housed within a delivery catheter and partially laterally ejected from the delivery catheter and positioned for deployment against the anterior side of the native annulus.

Figure 101C:
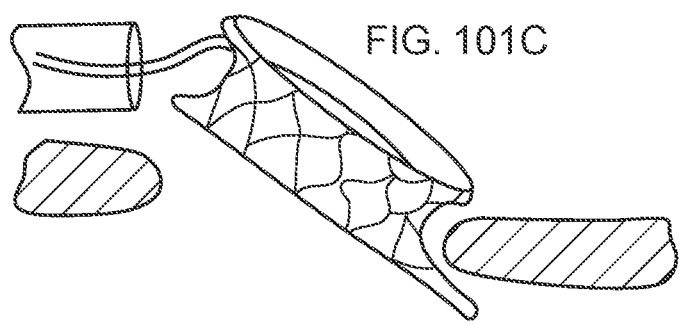

FIG. 101C is an illustration of a low profile, e.g. 8-20 mm, side-loaded valve frame shown ejected from the delivery catheter and positioned against the anterior side of the native annulus.

Figure 101D:
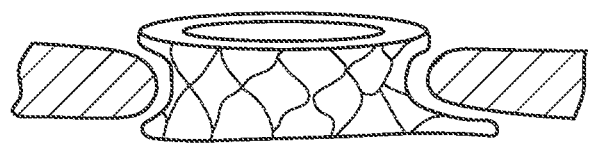

FIG. 101D is an illustration of a side or plan view of a low profile, e.g. 8-20 mm, side-loaded valve frame shown deployed into the native annulus of a heart valve.

Figure 101E:
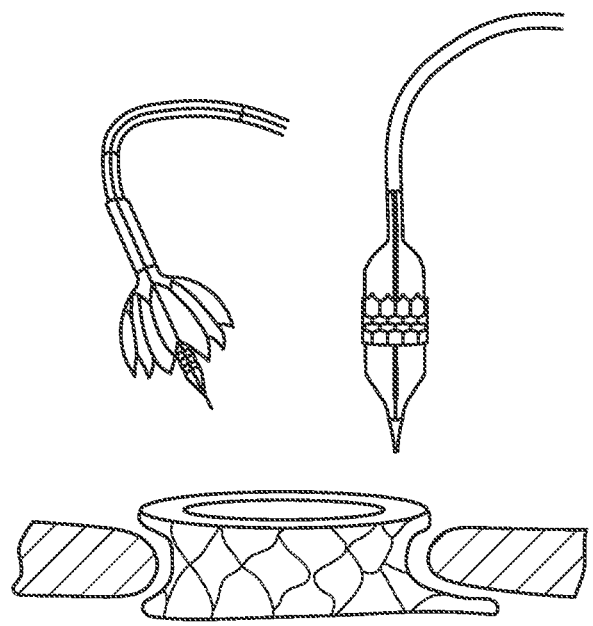

FIG. 101E is an illustration of a side view of two types of deliverable valves, the first is a self-expanding transcatheter valve, and the second is a commercially-approved transcatheter balloon-expandable prosthetic valve being vertically deployed into the central lumen of the already (laterally, horizontally, orthogonally) deployed valve frame.

Figure 101F:
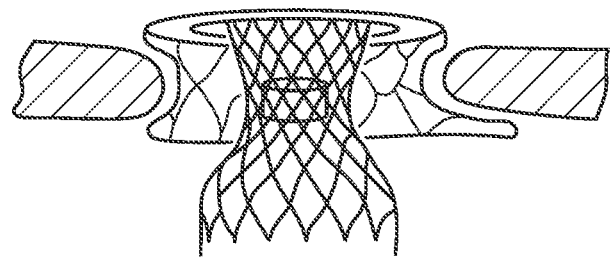

FIG. 101F is an illustration of a side view of a commercially-approved transcatheter self-expandable prosthetic valve mounted within the central lumen of the already (laterally, horizontally, orthogonally) deployed valve frame.

Figure 101G:
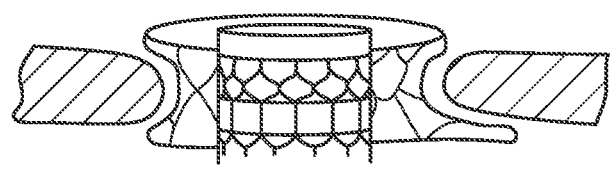

FIG. 101G is an illustration of a side view of a commercially-approved transcatheter balloon-expandable prosthetic valve mounted within the central lumen of the already (laterally, horizontally, orthogonally) deployed valve frame.

Figure 102A:
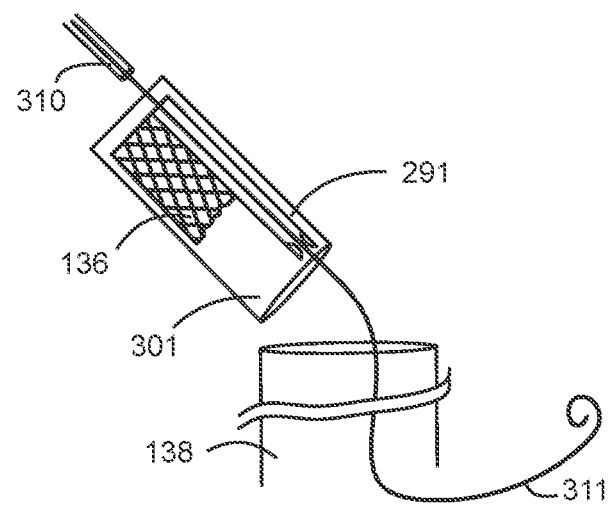

FIG. 102A is an illustration of step 1 of a 4-step process for delivery of a co-axial prosthetic valve to the tricuspid annulus. FIG. 102A shows a co-axial valve being loaded into the distal end of the delivery catheter, with the sheathed guidewire threaded through the tension arm and guidewire collar.

Figure 102B:
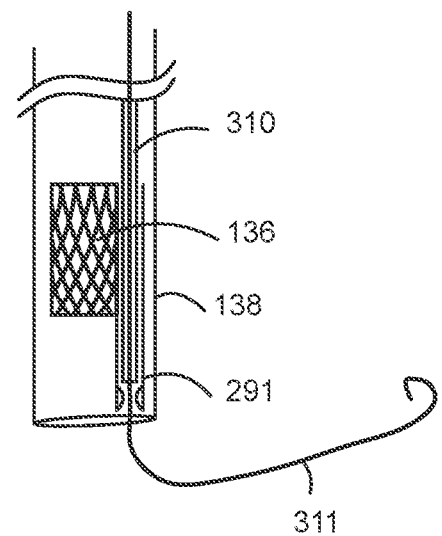

FIG. 102B is an illustration of step 2 of a 4-step process for delivery of a co-axial prosthetic valve to the tricuspid annulus. FIG. 102B shows a co-axial valve being delivered to the proximal end of the delivery catheter, with the sheathed guidewire threaded through the tension arm and guidewire collar.

Figure 102C:
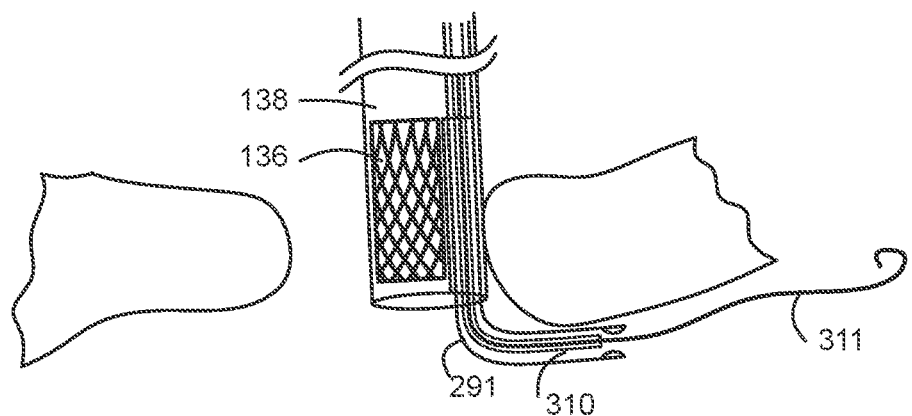

FIG. 102C is an illustration of step 3 of a 4-step process for delivery of a co-axial prosthetic valve to the tricuspid annulus. FIG. 102C shows a co-axial valve partially expelled from the delivery catheter, with the tension arm and guidewire collar being positioned into the RVOT.

Figure 102D:
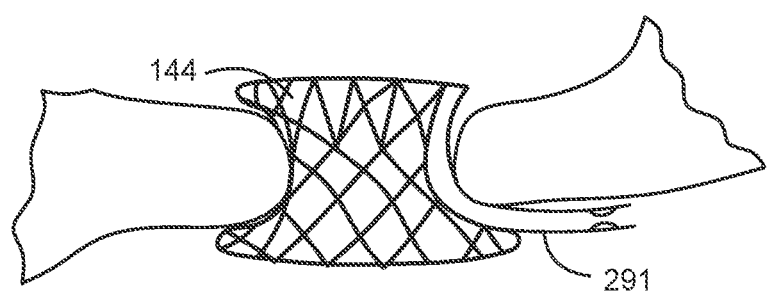

FIG. 102D is an illustration of step 4 of a 4-step process for delivery of a co-axial prosthetic valve to the tricuspid annulus. FIG. 102D shows that, once positioned, the self-expanding the valve can be completely expelled from the delivery catheter and deployed as a prosthetic valve.

Figure 103A:
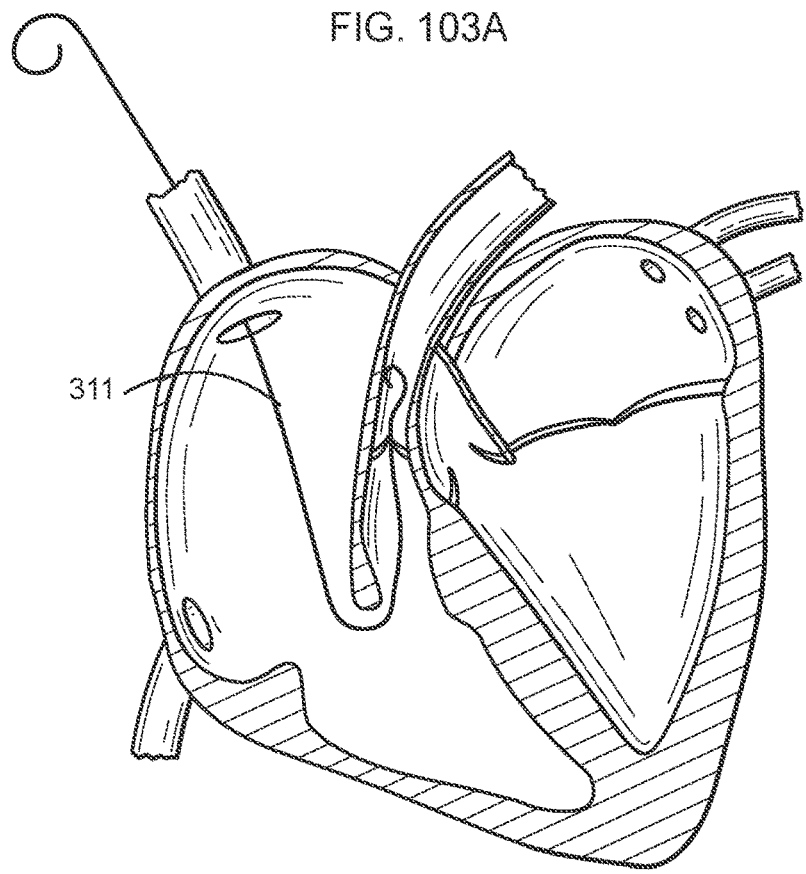

FIG. 103A is an illustration of step 1 of a 7-step process for delivery of a co-axial prosthetic valve to the tricuspid annulus. FIG. 103A shows a 0.035 guidewire with hypotube sheath delivered to the right ventricular outflow tract (RVOT) through the superior vena cava (SVC).

Figure 103B:
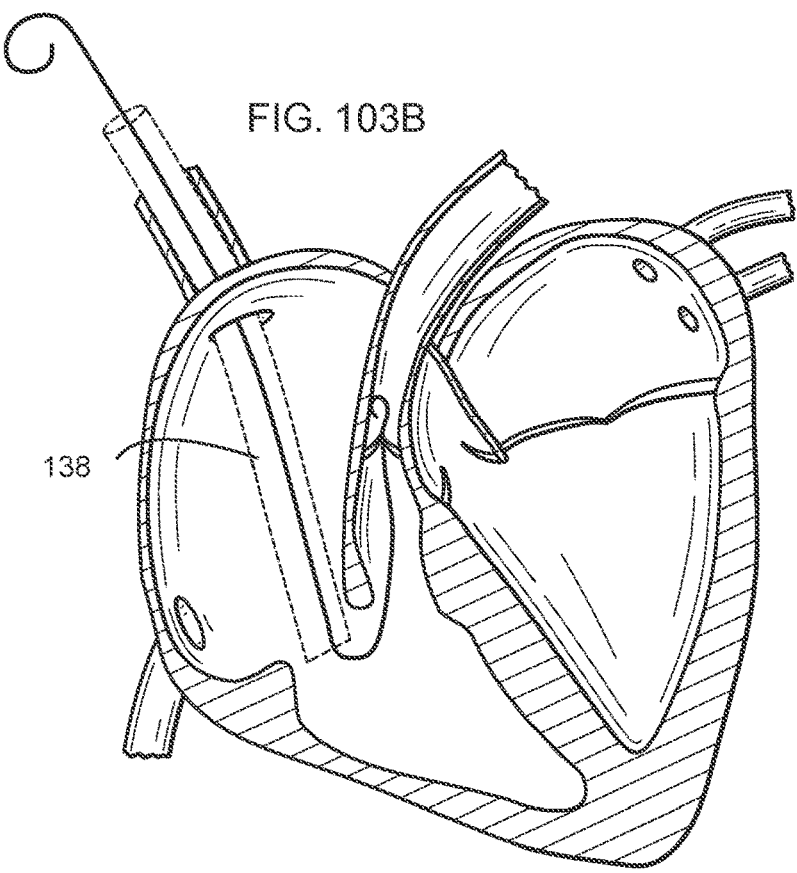

FIG. 103B is an illustration of step 2 of a 7-step process for delivery of a co-axial prosthetic valve to the tricuspid annulus. FIG. 103B shows a 34 Fr delivery catheter being advanced over the guidewire to and through the native tricuspid annulus to the right ventricle.

Figure 103C:
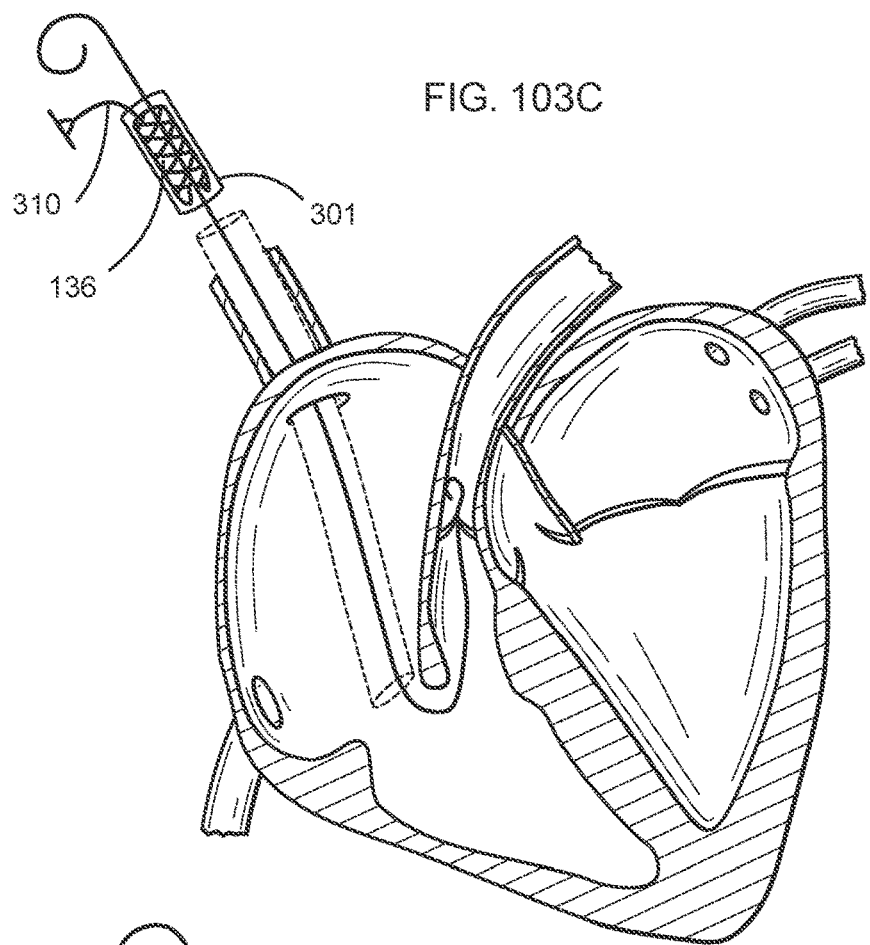

FIG. 103C is an illustration of step 3 of a 7-step process for delivery of a co-axial prosthetic valve to the tricuspid annulus. FIG. 103C shows a capsule having a compressed valve therein where the capsule is loaded into the proximal end of the delivery catheter and the valve is withdrawn from the capsule into the delivery catheter, with sheathed guidewire threaded through the valve and providing a wire path to the RVOT, planned deployment location.

Figure 103D:
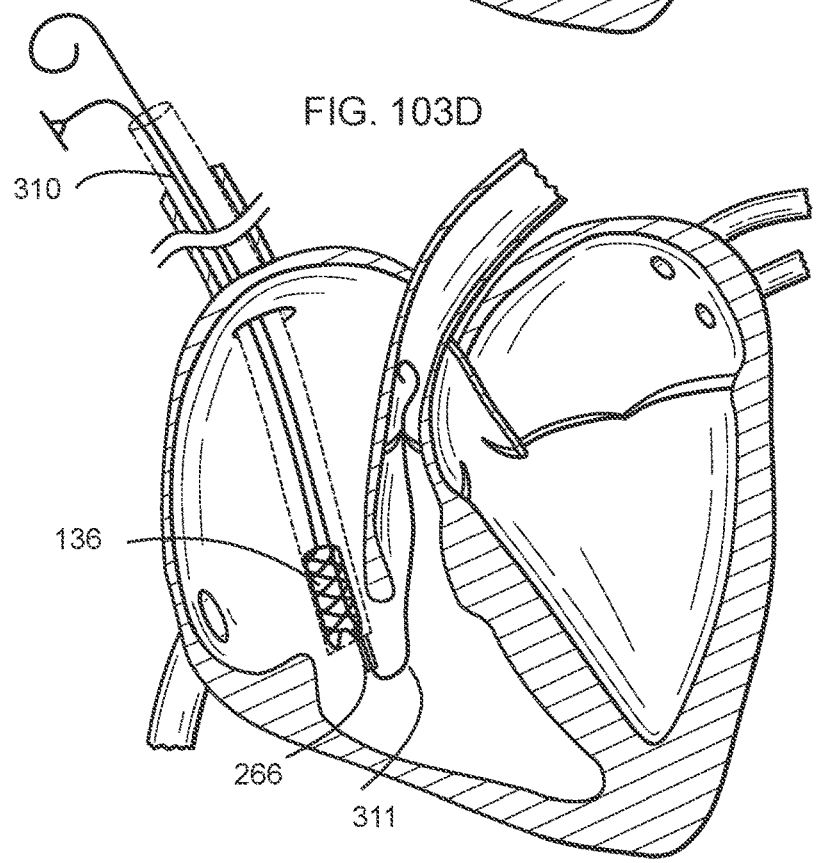

FIG. 103D is an illustration of step 4 of a 7-step process for delivery of a co-axial prosthetic valve to the tricuspid annulus. FIG. 103D shows the valve advanced up the catheter and deployed into the native annulus by pushing on the outer sheath of the guidewire to pull the valve up the catheter and into position. Tension arm is used to position the valve.

Figure 103E:
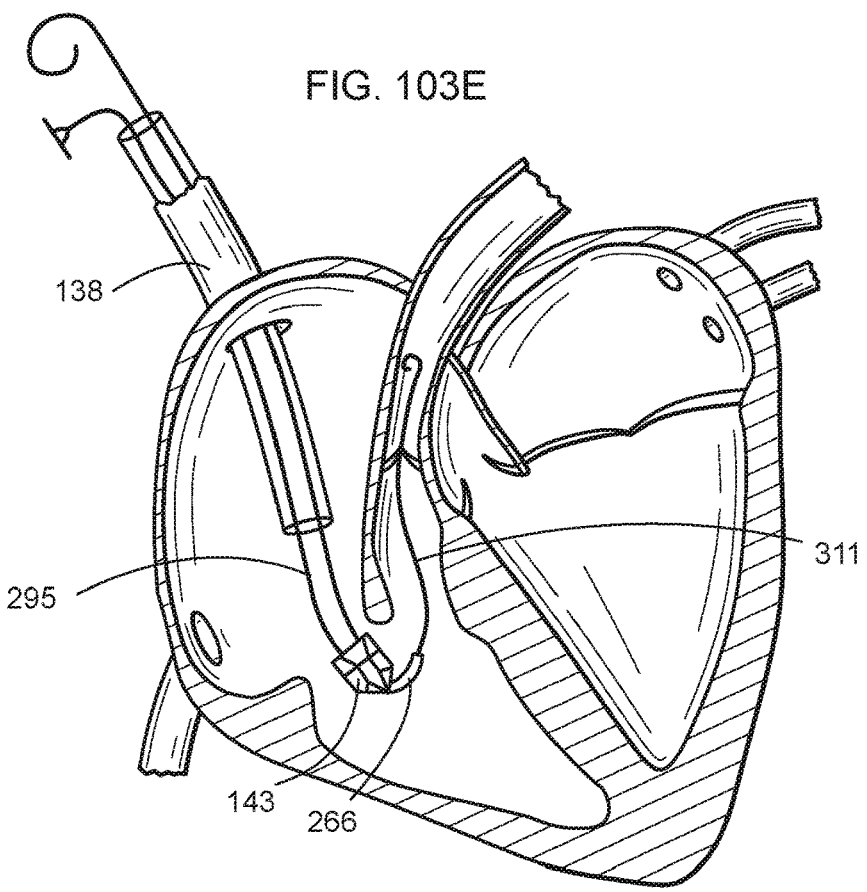

FIG. 103E is an illustration of step 5 of a 7-step process for delivery of a co-axial prosthetic valve to the tricuspid annulus. FIG. 103E shows a catheter being used to push the proximal side of the valve into position within the annulus.

Figure 103F:
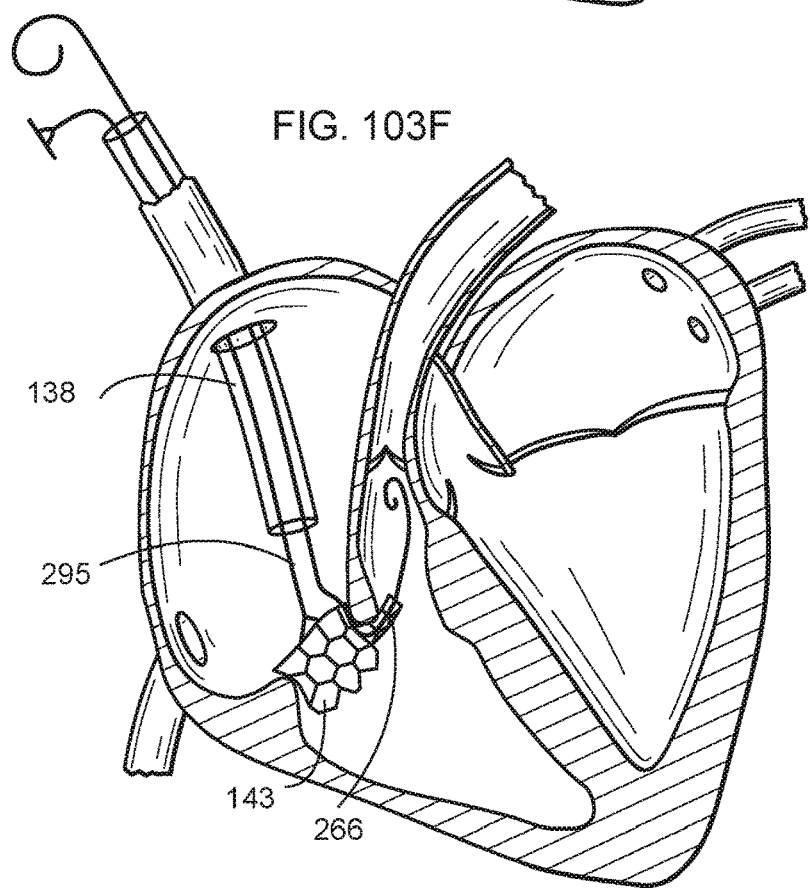

FIG. 103F is an illustration of step 6 of a 7-step process for delivery of a co-axial prosthetic valve to the tricuspid annulus. FIG. 103F shows balloon expansion of the co-axial valve in the native annulus and anchoring of the proximal side of the valve to the annular tissue.

Figure 103G:
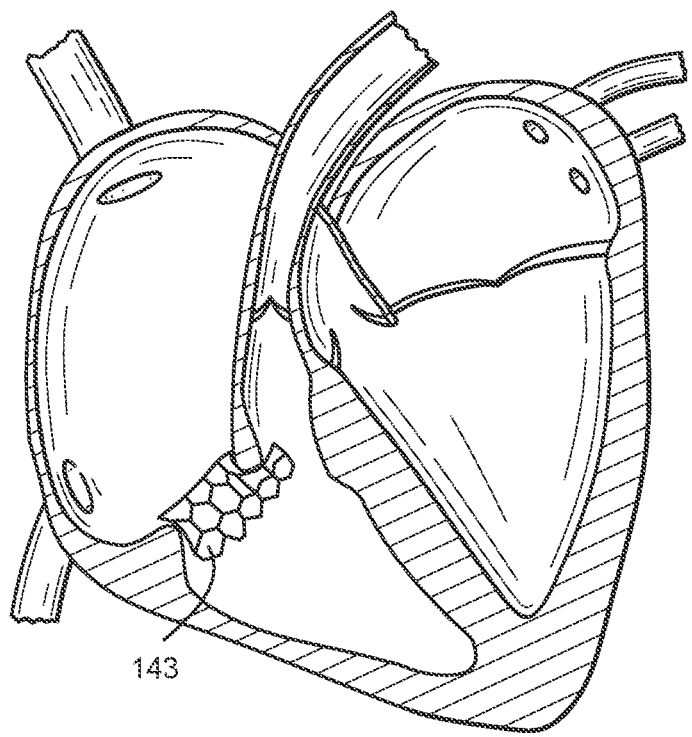

FIG. 103G is an illustration of step 7 of a 7-step process for delivery of a co-axial prosthetic valve to the tricuspid annulus. FIG. 103G shows withdrawal of the delivery system and anchoring of the proximal side of the valve to the annular tissue.

Figure 104A:
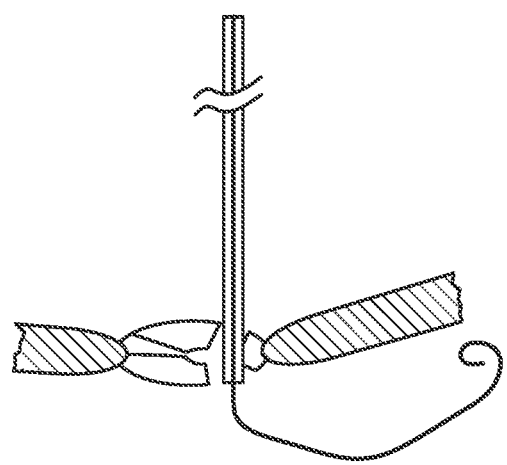

FIG. 104A is an illustration of step 1 of a 6-step process for delivery of a co-axial prosthetic valve to the tricuspid annulus. FIG. 104A shows the delivery catheter deployed to the native annulus.

Figure 104B:
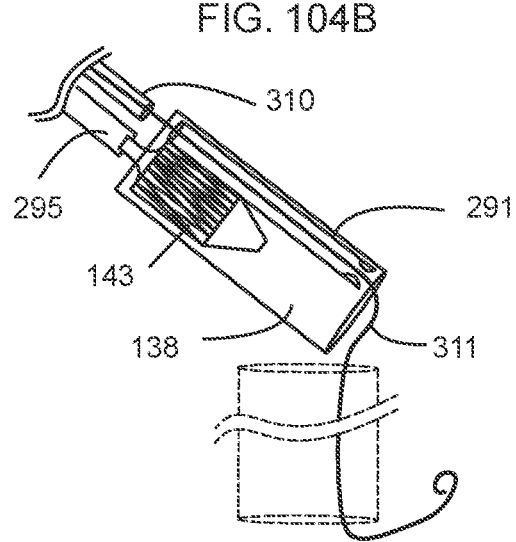

FIG. 104B is an illustration of step 2 of a 6-step process for delivery of a co-axial prosthetic valve to the tricuspid annulus. FIG. 104B shows a co-axial valve being loaded into the delivery catheter, with the sheathed guidewire threaded through the tension arm and guidewire collar.

Figure 104C:
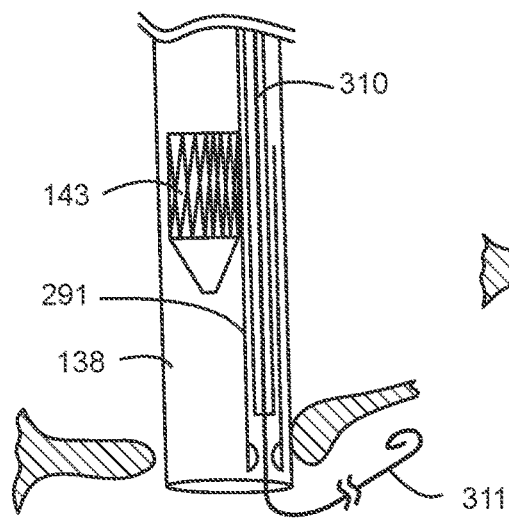

FIG. 104C is an illustration of step 3 of a 6-step process for delivery of a co-axial prosthetic valve to the tricuspid annulus. FIG. 104C shows a co-axial valve being delivered to the proximal end of the delivery catheter, with the sheathed guidewire threaded through the tension arm and guidewire collar.

Figure 104D:
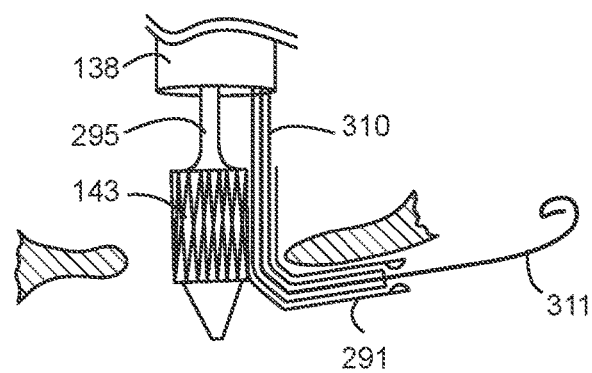

FIG. 104D is an illustration of step 4 of a 6-step process for delivery of a co-axial prosthetic valve to the tricuspid annulus. FIG. 104D shows a co-axial valve partially expelled from the delivery catheter, with the tension arm and guidewire collar being positioned into the RVOT.

Figure 104E:
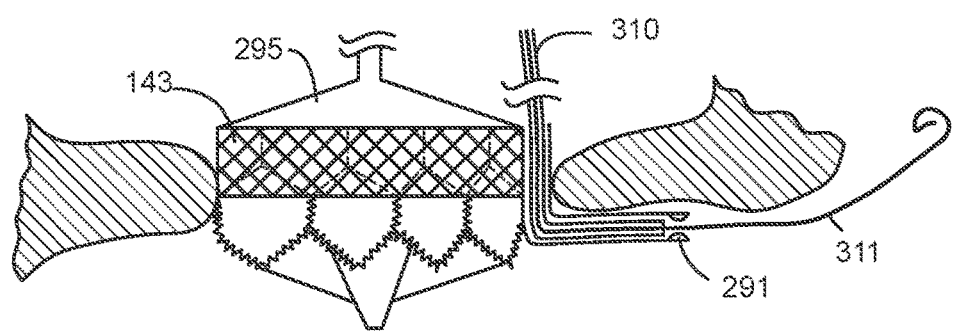

FIG. 104E is an illustration of step 5 of a 6-step process for delivery of a co-axial prosthetic valve to the tricuspid annulus. FIG. 104E shows that, once positioned, the balloon-expanding co-axial valve can be completely deployed into the inner circumference of the native annulus to function as a prosthetic valve.

Figure 104F:
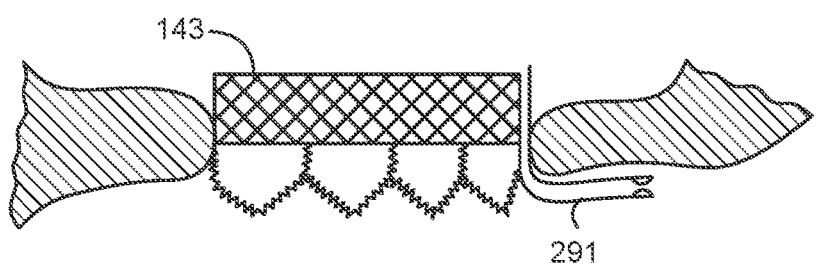

FIG. 104F is an illustration of step 6 of a 6-step process for delivery of a co-axial prosthetic valve to the tricuspid annulus. FIG. 104F shows the deployed valve.

DETAILED DESCRIPTION

Disclosed embodiments are directed to a transcatheter heart valve replacement that includes a low profile, orthogonally delivered, implantable prosthetic valve.

The term "valve prosthesis" or "prosthetic valve" can refer to a combination of a frame and a leaflet or flow control structure, and can encompass both complete replacement of an anatomical part, e.g. mechanical valve replaces a native valve, as well as medical devices that take the place of and/or assist, repair, or improve existing anatomical parts, e.g. native valve is left in place.

The disclosed valves include a member that can be seated within a native valve annulus and can be used as a mounting element for a leaflet structure, a flow control component, or a flexible reciprocating sleeve or sleeve-valve. It may or may not include such a leaflet structure or flow control component, depending on the embodiment. Such members can be referred to herein as an "annular support frame," "tubular frame," "wire frame," "flange," "collar," or similar terms.

The annular support frame can have a central axial lumen where a prosthetic valve or flow-control structure, such as a reciprocating compressible sleeve, is mounted across the diameter of the lumen. The annular support frame may have an outer circumferential surface for engaging native annular tissue that is also tensioned against the inner aspect of the native annulus and provides structural patency to a weakened native annular ring.

The annular support frame may optionally have a separate atrial collar attached to the upper (atrial) edge of the frame, for deploying on the atrial floor, that is used to direct blood from the atrium into the sleeve and to seal against blood leakage around the annular support frame. The annular support frame may also optionally have a separate ventricular collar attached to the lower (ventricular) edge of the frame, for deploying in the ventricle immediately below the native annulus that is used to prevent regurgitant leakage during systole, to prevent dislodging of the device during systole, to sandwich or compress the native annulus or adjacent tissue against the atrial collar, and optionally to attach to and support the sleeve/conduit.

The annular support frame may have a flow control component mounted within the annular support frame and configured to permit blood flow in a first direction through an inflow end of the valve and block blood flow in a second direction, opposite the first direction, through an outflow end of the valve.

The term "flow control component" can refer in a non-limiting sense to a leaflet structure having 2-, 3-, 4-leaflets of flexible biocompatible material such a treated or untreated pericardium that is sewn or joined to a annular support frame, to function as a prosthetic heart valve. Such a valve can be a heart valve, such as a tricuspid, mitral, aortic, or pulmonary, that is open to blood flowing during diastole from atrium to ventricle, and that closes from systolic ventricular pressure applied to the outer surface. Repeated opening and closing in sequence can be described as "reciprocating." The flow control component is contemplated to include a wide variety of (bio)prosthetic artificial heart valves, including ball valves (e.g. Starr-Edwards), bileaflet valves (St. Jude), tilting disc valves (e.g. Bjork-Shiley), stented pericardium heart-valve prosthesis' (bovine, porcine, ovine) (Edwards line of bioprostheses, St. Jude prosthetic valves), as well as homograft and autograft valves. Bioprosthetic pericardial valves can include bioprosthetic aortic valves, bioprosthetic mitral valves, bioprosthetic tricuspid valves, and bioprosthetic pulmonary valves.

In some embodiments, the flow control component and the annular support frame can be separate structures, and delivered separately. In such embodiments, the term "valve frame" or "prosthetic valve frame" or "valve-in-valve" can refer to a three-dimensional structural component, usually tubular, cylindrical, or oval or ring-shaped, and that can be seated within a native valve annulus and used as a mounting element for a commercially available valve such as a Sapien®, Sapien 3®, and Sapien XT® from Edwards Lifesciences, the Inspiris Resilia aortic valve from Edwards Lifesciences, the Masters HP 15 mm valve from Abbott, Lotus Edge valve from Boston Scientific, the Crown PRT leaflet structure from Livanova/Sorin, the Carbomedics family of valves from Sorin, or other flow control component, or a flexible reciprocating sleeve or sleeve-valve.

In some embodiments, the annular support frame used in the prosthetic heart valve may be deployed in the tricuspid annulus and may have a complex shape determined by the anatomical structures where the valve is being mounted. For example, in the tricuspid annulus, the circumference of the tricuspid valve may be a rounded ellipse, the septal wall is known to be substantially vertical, and the tricuspid is known to enlarge in disease states along the anterior-posterior line.

In some embodiments, the annular support frame used in the prosthetic heart valve may be deployed in the mitral annulus and may have a complex shape determined by the anatomical structures where the valve is being mounted. For example, in the mitral annulus, the circumference of the mitral valve may be a rounded ellipse, the septal wall is known to be substantially vertical, and the mitral is known to enlarge in disease states.

The annular support frame may be compressed for transcatheter delivery and may be expandable as a self-expandable shape-memory element or using a transcatheter expansion balloon. Some embodiments may have both an atrial collar and a ventricular collar, whereas other embodiments include prosthetic heart valves having either a single atrial collar, a single ventricular collar, or having no additional collar structure.

The term "expandable" as used herein may refer to a component of the heart valve capable of expanding from a first, delivery diameter to a second, implantation diameter. An expandable structure, therefore, does not mean one that might undergo slight expansion from a rise in temperature, or other such incidental cause. Conversely, "non-expandable" should not be interpreted to mean completely rigid or a dimensionally stable, as some slight expansion of conventional "non-expandable" heart valves, for example, may be observed.

The atrial collar can be shaped to conform to the native deployment location. In a mitral replacement, the atrial collar will be configured with varying portions to conform to the native valve. In one embodiment, the collar will have a distal and proximal upper collar portion. The distal collar portion can be larger than the proximal upper collar portion to account for annular or subannular geometries.

In some embodiments, the annular support frame can have a central channel and an outer perimeter wall circumscribing a central vertical axis in an expanded configuration. The perimeter wall can encompass both the collar and the lower body portions.

The perimeter wall can be further defined as having a front wall portion and a back wall portion, which are connected along a near side (to the inferior vena cava ("IVC")) or proximal side to a proximal fold area, and connected along a far or distal side to a distal fold area. This front wall portion can be further defined as having a front upper collar portion and a front lower body portion, and the back wall portion can be further defined as having a back upper collar portion and a back lower body portion.

The valves may be compressed and delivered in a sideways manner. The shape of the expanded valve can be that of a large diameter shortened cylinder with an extended collar or cuff. The valves can be compressed, in some embodiments, where the central axis of the valve is roughly perpendicular to (orthogonal to) the lengthwise axis of the delivery catheter. In some embodiments, the valves can be compressed vertically, similar to collapsing the height of a cylinder accordion-style from taller to shorter, and the valves are also compressed by folding a front panel against a back panel. In other embodiments, the valves can be compressed by rolling.

The terms "side-delivered", "side-delivery", "orthogonal", "orthogonally delivered" and so forth are used to describe that the valves are compressed and delivered at a roughly 90 degree angle compared to traditional transcatheter heart valves. Orthogonal delivery is a transverse delivery where a perimeter distal sidewall exits the delivery catheter first, followed by the central aperture, followed by the proximal sidewall.

Mathematically, the term orthogonal refers to an intersecting angle of 90 degrees between two lines or planes. As used herein, the term "substantially orthogonal" refers to an intersecting angle ranging from 75 to 105 degrees. The intersecting angle or orthogonal angle refers to both (i) the relationship between the lengthwise cylindrical axis of the delivery catheter and the long-axis of the compressed valve, where the long-axis is perpendicular to the central cylinder axis of traditional valves, and (ii) the relationship between the long-axis of the compressed or expanded valve and the axis defined by the blood flow through the prosthetic valve where the blood is flowing, e.g. from one part of the body or chamber of the heart to another downstream part of the body or chamber of the heart, such as from an atrium to a ventricle through a native annulus.

The annular support frame can be a ring, or cylindrical or conical tube, but may also have a side profile of a flat-cone shape, an inverted flat-cone shape (narrower at top, wider at bottom), a concave cylinder (walls bent in), a convex cylinder (walls bulging out), an angular hourglass, a curved, graduated hourglass, a ring or cylinder having a flared top, flared bottom, or both.

The annular support frame may have a height in the range of about 5-60 mm, may have an outer diameter dimension, R, in the range of about 30-80 mm, and may have an inner diameter dimension in the range of about 31-79 mm, accounting for the thickness of the wire material itself.

In some embodiments, the horizontal x-axis of the valve is orthogonal to (90 degrees), or substantially orthogonal to (75-105 degrees), or substantially oblique to (45-135 degrees) to the central vertical y-axis when in an expanded configuration.

In some embodiments, the horizontal x-axis of the compressed configuration of the valve is substantially parallel to a lengthwise cylindrical axis of the delivery catheter.

In some embodiments, the valve can have a compressed height (y-axis) and width (z-axis) of 6-15 mm, preferably 8-12 mm, and more preferably 9-10 mm, and an expanded deployed height of about 5-60 mm, preferably about 5-30 mm, and more preferably about 5-20 mm or even 8-12 mm or 8-10 mm. In some embodiments, the length of the valve, x-axis, does not require compression since it can extend along the length of the central cylindrical axis of the delivery catheter.

In some embodiments, the valve can have an expanded diameter length and width of 25-80 mm, preferably 40-80 mm, and in certain embodiments length and/or width may vary and include lengths of 25 mm, 30 mm, 35 mm, 40 mm, 45 mm, 50 mm, 55 mm, 60 mm, 65 mm, 70 mm, 75 mm, and 80 mm, in combination with widths that are the same or different as the length.

In some embodiments, the valve can be centric, or radially symmetrical. In other embodiments, the valve can be eccentric, or radially (y-axis) asymmetrical. In some eccentric embodiments, the outer frame may have a D-shape (viewed from the top) so the flat portion can be matched to the mitral annulus near the anterior leaflet.

In some embodiments, the inner frame holding the leaflet tissue is 25-29 mm in diameter, the outer frame is 50-70 mm in diameter, and the collar structure extends beyond the top edge of the outer frame by 10-30 mm to provide a seal on the atrial floor against perivalvular leaks (PVLs).

The annular support frame may be made from a variety of durable, biocompatible structural materials. Preferably, the frame is made from superelastic metal wire, such as a Nickel-Titanium alloy (e.g. Nitinol™) wire or other similarly functioning material. The material may be used for the frame/stent, for the collar, and/or for anchors. It is contemplated to use other shape memory alloys such as Cu—Zn—Al—Ni alloys, Cu—Al—Ni alloys, as well as polymer composites including composites containing carbon nanotubes, carbon fibers, metal fibers, glass fibers, and polymer fibers.

The frame design is preferably compressible and when released has the stated property that it returns to its original (uncompressed) shape. This requirement limits the potential material selections to metals and plastics that have shape memory properties. With regards to metals, Nitinol has been found to be especially useful since it can be processed to be austenitic, martensitic or super elastic. Martensitic and super elastic alloys can be processed to demonstrate the required compression features.

The frame may be constructed as a braid, wire, or laser cut wire frame. Such materials are available from any number of commercial manufacturers, such as Pulse Systems. One possible construction of the wire frame envisions the laser cutting of a thin, isodiametric Nitinol tube. The laser cuts form regular cutouts in the thin Nitinol tube. In one embodiment, the Nitinol tube expands to form a three-dimensional structure formed from diamond-shaped cells.

The structure may also have additional functional elements, e.g. loops, anchors, etc. for attaching accessory components such as biocompatible covers, tissue anchors, releasable deployment and retrieval control guides, knobs, attachments, rigging, and so forth. Secondarily the tube is placed on a mold of the desired shape, heated to the Martensitic temperature and quenched. The treatment of the wire frame in this manner will form a device that has shape memory properties and will readily revert to the memory shape at the calibrated temperature. Laser cut wire frames are preferably made from Nitinol, but also without limitation made from stainless steel, cobalt chromium, titanium, and other functionally equivalent metals and alloys.

Alternatively, a frame can be constructed utilizing simple braiding techniques. Using a Nitinol wire—for example, a 0.012" wire—and a simple braiding fixture, the wire can be wound on the braiding fixture in a simple over/under braiding pattern until an isodiametric tube is formed from a single wire. The two loose ends of the wire are coupled using a stainless steel or Nitinol coupling tube into which the loose ends are placed and crimped. Angular braids of approximately 60 degrees have been found to be particularly useful. Secondarily, the braided wire frame is placed on a shaping fixture and placed in a muffle furnace at a specified temperature to set the wire frame to the desired shape and to develop the martensitic or super elastic properties desired.

Since the frame is preferably made of superelastic metal or alloy such as Nitinol, the frame is compressible. Preferably, the frame is constructed of a plurality of compressible wire cells having an orientation and cell geometry substantially orthogonal to the central vertical axis to minimize wire cell strain when the annular support frame when configured in a vertical compressed configuration, a rolled compressed configuration, or a folded compressed configuration.

Accordingly, a prosthetic heart valve may start in a roughly tubular configuration, and be heat-shaped to provide an upper atrial cuff or flange for atrial sealing and a lower trans-annular tubular or cylindrical section having an hourglass cross-section for about 60-80% of the circumference to conform to the native annulus along the posterior and anterior annular segments while remaining substantially vertically flat along 20-40% of the annular circumference to conform to the septal annular segment.

The annular support frame is optionally internally or externally covered, partially or completely, with a biocompatible material such as pericardium. The annular or tubular frame may also be optionally externally covered, partially or completely, with a second biocompatible material such as polyester or Dacron®. Disclosed embodiments may use tissue, such as a biological tissue that is a chemically stabilized pericardial tissue of an animal, such as a cow (bovine pericardium), sheep (ovine pericardium), pig (porcine pericardium), or horse (equine pericardium). Preferably, the tissue is bovine pericardial tissue. Examples of suitable tissue include that used in the products Duraguard®, Peri-Guard®, and Vascu-Guard®, all products currently used in surgical procedures, and which are marketed as being harvested generally from cattle less than 30 months old. Other patents and publications disclose the surgical use of harvested, biocompatible animal thin tissues suitable herein as biocompatible "jackets" or sleeves for implantable stents, including for example, U.S. Pat. No. 5,554,185 to Block, U.S. Pat. No. 7,108,717 to Design & Performance-Cyprus Limited disclosing a covered stent assembly, U.S. Pat. No. 6,440,164 to Scimed Life Systems, Inc. disclosing a bioprosthetic valve for implantation, and U.S. Pat. No. 5,336,616 to LifeCell Corporation discloses acellular collagen-based tissue matrix for transplantation.

In some embodiments, components may be fabricated from a synthetic material such a polyurethane or polytetrafluoroethylene. Where a thin, durable synthetic material is contemplated, e.g. for a covering, synthetic polymer materials such expanded polytetrafluoroethylene or polyester may optionally be used. Other suitable materials may optionally include thermoplastic polycarbonate urethane, polyether urethane, segmented polyether urethane, silicone polyether urethane, silicone-polycarbonate urethane, and ultra-high molecular weight polyethylene. Additional biocompatible polymers may optionally include polyolefins, elastomers, polyethylene-glycols, polyethersulphones, polysulphones, polyvinylpyrrolidones, polyvinylchlorides, other fluoropolymers, silicone polyesters, siloxane polymers and/or oligomers, and/or polylactones, and block co-polymers using the same.

Polyamides (PA)—PA is an early engineering thermoplastic invented that consists of a "super polyester" fiber with molecular weight greater than 10,000. It is commonly called Nylon. Application of polyamides includes transparent tubings for cardiovascular applications, hemodialysis membranes, and also production of percutaneous transluminal coronary angioplasty (PTCA) catheters.

Polyolefin—Polyolefins include polyethylene and polypropylene are the two important polymers of polyolefins and have better biocompatibility and chemical resistance. In cardiovascular uses, both low-density polyethylene and high-density polyethylene are utilized in making tubing and housings. Polypropylene is used for making heart valve structures.

Polyesters—Polyesters includes polyethylene-terephthalate (PET), using the name Dacron. It is typically used as knitted or woven fabric for vascular grafts. Woven PET has smaller pores, which reduces blood leakage and better efficiency as vascular grafts compared with the knitted one. PET grafts are also available with a protein coating (collagen or albumin) for reducing blood loss and better biocompatibility. PET vascular grafts with endothelial cells have been searched as a means for improving patency rates. Moreover, polyesters are widely material for the manufacturing of bioabsorbable stents. Poly-L-lactic acids (PLLA), polyglycolic acid (PGA), and poly(D, L-lactide/glycolide) copolymer (PDLA) are some of the commonly used bioabsorbable polymers.

Polytetrafluoroethylene—Polytetrafluoroethylene (PTFE) is synthetic fluorocarbon polymer with the common commercial name of Teflon by DuPont Co. Common applications of PTFE in cardiovascular engineering include vascular grafts and heart valves. PTFE sutures are used in the repair of mitral valve for myxomatous disease and in surgery for prolapse of the anterior or posterior leaflets of mitral valves. PTFE is particularly used in implantable prosthetic heart valve rings. It has been successfully used as vascular grafts when the devices are implanted in high-flow, large-diameter arteries such as the aorta. Problem occurs when it is implanted below aortic bifurcations and another form of PTFE called elongated-PTFE (e-PTFE) was explored. Expanded PTFE is formed by compression of PTFE in the presence of career medium and finally extruding the mixture. Extrudate formed by this process is then heated to near its glass transition temperature and stretched to obtain microscopically porous PTFE known as e-PTFE. This form of PTFE was indicated for use in smaller arteries with lower flow rates promoting low thrombogenicity, lower rates of restenosis and hemostasis, less calcification, and biochemically inert properties.

Polyurethanes—Polyurethane has good physiochemical and mechanical properties and is highly biocompatible which allows unrestricted usage in blood contacting devices. It has high shear strength, elasticity, and transparency. Moreover, the surface of polyurethane has good resistance for microbes and the thrombosis formation by PU is almost similar to the versatile cardiovascular biomaterial like PTFE. Conventionally, segmented polyurethanes (SPUs) have been used for various cardiovascular applications such as valve structures, pacemaker leads and ventricular assisting device.

In some embodiments, frame components may include drug-eluting wire frames. Drug-eluting wire frames may consist of three parts: wire frame platform, coating, and drug. Some of the examples for polymer free coated frames are Amazon Pax (MINVASYS) using Amazonia CroCo (L605) cobalt chromium (Co—Cr) wire frame with Paclitaxel as an antiproliferative agent and abluminal coating have been utilized as the carrier of the drug. BioFreedom (Biosensors Inc.) using stainless steel as base with modified abluminal coating as carrier surface for the antiproliferative drug Biolimus A9. Optima (CID S.r.I.) using 316 L stainless steel wire frame as base for the drug Tacrolimus and utilizing integrated turbostratic carbofilm as the drug carrier. VESTA sync (MIV Therapeutics) using GenX stainless steel (316 L) as base utilizing microporous hydroxyapatite coating as carrier for the drug Sirolimus. YUKON choice (Translumina) used 316 L stainless steel as base for the drugs Sirolimus in combination with Probucol.

Biosorbable polymers may also be used herein as a carrier matrix for drugs. Cypher, Taxus, and Endeavour are the three basic type of bioabsorbable DES. Cypher (J&J, Cordis) uses a 316 L stainless steel coated with polyethylene vinyl acetate (PEVA) and poly-butyl methacrylate (PBMA) for carrying the drug Sirolimus. Taxus (Boston Scientific) utilizes 316 L stainless steel wire frames coated with translute Styrene Isoprene Butadiene (SIBS) copolymer for carrying Paclitaxel, which elutes over a period of about 90 days. Endeavour (Medtronic) uses a cobalt chrome driver wire frame for carrying zotarolimus with phosphorylcholine as drug carrier. BioMatrix employing S-Wire frame (316 L) stainless steel as base with polylactic acid surface for carrying the antiproliferative drug Biolimus. ELIXIR-DES program (Elixir Medical Corp) consisting both polyester and polylactide coated wire frames for carrying the drug novolimus with cobalt-chromium (Co—Cr) as base. JACTAX (Boston Scientific Corp.) utilized D-lactic polylactic acid (DLPLA) coated (316 L) stainless steel wire frames for carrying Paclitaxel. NEVO (Cordis Corporation, Johnson & Johnson) used cobalt chromium (Co—Cr) wire frame coated with polylactic-co-glycolic acid (PLGA) for carrying the drug Sirolimus.

The disclosed valve embodiments may be delivered by a transcatheter approach. The term "transcatheter" is used to define the process of accessing, controlling, and delivering a medical device or instrument within the lumen of a catheter that is deployed into a heart chamber, as well as an item that has been delivered or controlled by such as process. Transcatheter access is known to include via femoral artery and femoral vein, via brachial artery and vein, via carotid and jugular, via intercostal (rib) space, and via sub-xyphoid. Transcatheter can be synonymous with transluminal and is functionally related to the term "percutaneous" as it relates to delivery of heart valves.

In some embodiments, the transcatheter approach includes: (i) advancing to the tricuspid valve or pulmonary artery of the heart through the inferior vena cava via the femoral vein, (ii) advancing to the tricuspid valve or pulmonary artery of the heart through the superior vena cava via the jugular vein, (iii) advancing to the mitral valve of the heart through a trans-atrial approach, e.g. fossa ovalis or lower, via the IVC-femoral or the SVC jugular approach.

In some of the disclosed embodiments, the prosthetic valve is secured in part to native tissue by a tissue anchor. The term "tissue anchor" or "plication tissue anchor" or "secondary tissue anchor," or "dart" or "pin" refers to a fastening device that connects the upper atrial frame to the native annular tissue, usually at or near the periphery of the collar. The anchor may be positioned to avoid piercing tissue and just rely on the compressive force of the two plate-like collars on the captured tissue, or the anchor, itself or with an integrated securement wire, may pierce through native tissue to provide anchoring, or a combination of both. The anchor may have a specialized securement mechanism, such as a pointed tip with a groove and flanged shoulder that is inserted or popped into a mated aperture or an array of mated apertures that allow the anchor to attach, but prevent detachment when the aperture periphery locks into the groove near the flanged shoulder. The securement wire may be attached or anchored to the collar opposite the pin by any attachment or anchoring mechanisms, including a knot, a suture, a wire crimp, a wire lock having a cam mechanism, or combinations.

In some of the disclosed embodiments, the prosthetic valve can be seated within the native valvular annulus through the use of tines or barbs. The tines or barbs are located to provide attachment to adjacent tissue. Tines are forced into the annular tissue by mechanical means such as using a balloon catheter. In one non-limiting embodiment, the tines may optionally be semi-circular hooks that upon expansion of the wire frame body, pierce, rotate into, and hold annular tissue securely. Anchors are deployed by over-wire delivery of an anchor or anchors through a delivery catheter. The catheter may have multiple axial lumens for delivery of a variety of anchoring tools, including anchor setting tools, force application tools, hooks, snaring tools, cutting tools, radio frequency and radiological visualization tools and markers, and suture/thread manipulation tools. Once the anchor(s) are attached to the moderator band, tensioning tools may be used to adjust the length of tethers that connect to an implanted valve to adjust and secure the implant as necessary for proper functioning. It is also contemplated that anchors may be spring-loaded and may have tether-attachment or tether-capture mechanisms built into the tethering face of the anchor(s). Anchors may also have in-growth material, such as polyester fibers, to promote in-growth of the anchors into the myocardium. In one embodiment, where a prosthetic valve may or may not include a ventricular collar, the anchor or dart is not attached to a lower ventricular collar, but is attached directly into annular tissue or other tissue useful for anchoring.

Some disclosed embodiments include a support post. The term "support post" refers to a rigid or semi-rigid length of material such as Nitinol or PEEK, that may be mounted on a spoked frame and that runs axially, or down the center of, or within a sewn seam of, the flexible sleeve. The sleeve may be unattached to the support post, or the sleeve may be directly or indirectly attached to the support post.

The term "body channel" may be used to define a blood conduit or vessel within the body, and the particular application of the disclosed embodiments of prosthetic heart valves determines the body channel at issue. An aortic valve replacement, for example, would be implanted in, or adjacent to, the aortic annulus. Likewise, a tricuspid or mitral valve replacement would be implanted at the tricuspid or mitral annulus. Certain features are particularly advantageous for one implantation site or the other. However, unless the combination is structurally impossible, or excluded by claim language, any of the heart valve embodiments described herein could be implanted in any body channel.

As used herein, the term "lumen" can refer to the inside of a cylinder or tube. The term "bore" can refer to the inner diameter.

Figure 1:
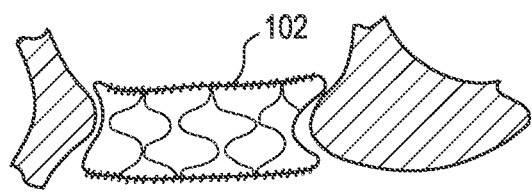
FIG. 1 is an illustration of a low profile, e.g. 8-20 mm, side-loaded prosthetic valve shown deployed into the native annulus.

FIG. 1 is an illustration of a low profile, e.g. 8-20 mm, side-loaded prosthetic valve shown deployed into the native annulus.

Figure 2:
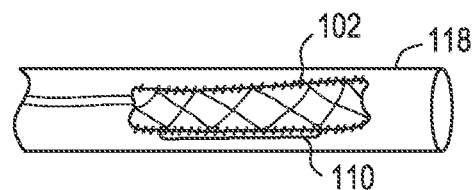
FIG. 2 is an illustration of a low profile, e.g. 8-20 mm, side-loaded prosthetic valve shown compressed or housed within the delivery catheter.

FIG. 2 is an illustration of a low profile, e.g. 8-20 mm, side-loaded prosthetic valve having frame 102 and sleeve 110 shown compressed or housed within the delivery catheter 118.

Figure 3:
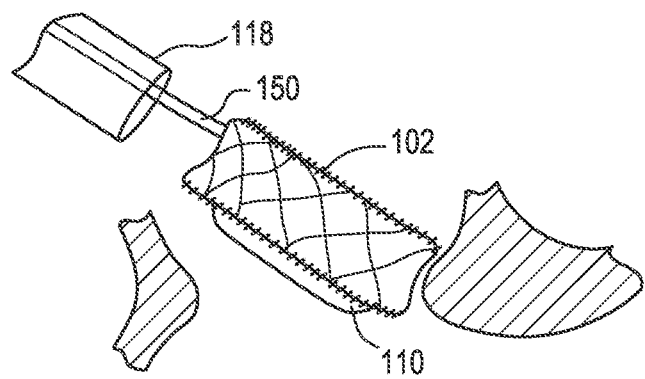
FIG. 3 is an illustration of a low profile, e.g. 8-20 mm, side-loaded prosthetic valve shown ejected from the delivery catheter and positioned against the anterior side of the native annulus.

FIG. 3 is an illustration of a low profile, e.g. 8-20 mm, side-loaded prosthetic valve shown ejected from the delivery catheter 118 and positioned against the anterior side of the native annulus. While the valve is held at this oblique angle by secondary catheter 150, valve function and patient condition are assessed, and if appropriate, the valve is completely deployed within the native annulus, and anchored using traditional anchoring elements.

Figure 4:
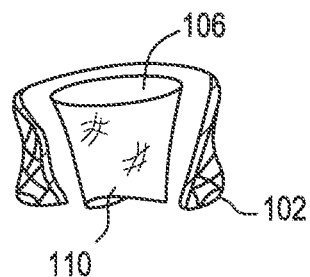
FIG. 4 is an illustration of an open cross-section view of a low profile, side-loaded prosthetic valve and shows the inner valve sleeve.

FIG. 4 is an illustration of an open cross-section view of a low profile, side-loaded prosthetic valve and shows the inner valve sleeve 110 and frame 102.

Figure 5:
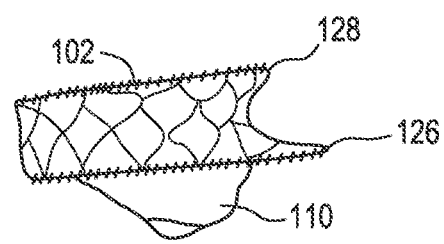
FIG. 5 is an illustration of a heart valve prosthesis according to an embodiment having a braid or laser-cut construction for the tubular frame, with a valve sleeve that extends beyond the bottom of the tubular frame.

FIG. 5 is an illustration of a low profile, side-loaded heart valve prosthesis according to an embodiment having a braid or laser-cut construction for the tubular frame 102, with a valve sleeve 110 that extends beyond the bottom of the tubular frame. FIG. 5 shows a longer lower tension arm 126 for extending sub-annularly towards the RVOT, and a shorter upper tension arm 128 for extending over the atrial floor.

Figure 6:
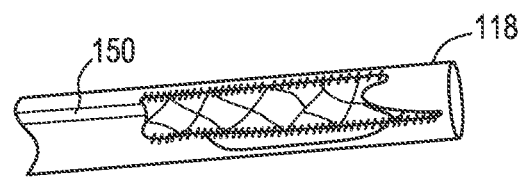
FIG. 6 is an illustration of a heart valve prosthesis having a braid or laser-cut tubular frame and extended valve sleeve compressed within a delivery catheter.

FIG. 6 is an illustration of a low profile, side-loaded heart valve prosthesis having a braid or laser-cut tubular frame and extended valve sleeve compressed within a delivery catheter 118. FIG. 6 shows the valve attached to a secondary steerable catheter 150 for ejecting, positioning, and anchoring the valve. The secondary catheter 150 can also be used to retrieve a failed deployment of a valve.

Figure 7:
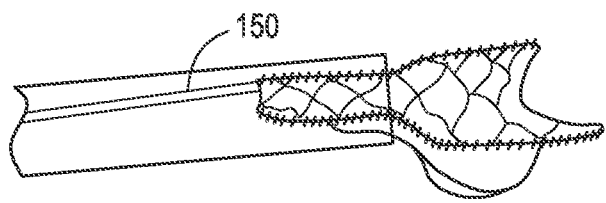
FIG. 7 is an illustration of a heart valve prosthesis having a braid or laser-cut tubular frame and extended valve sleeve shown partially compressed within a delivery catheter and partially ejected from the delivery catheter.

FIG. 7 is an illustration of a heart valve prosthesis having a braid or laser-cut tubular frame and extended valve sleeve shown partially compressed within a delivery catheter and partially ejected from the delivery catheter. FIG. 7 shows that while the valve is still compressed the lower tension arm can be manipulated through the leaflets and chordae tendineae to find a stable anterior-side lodgment for the distal side of the valve.

Figure 8:
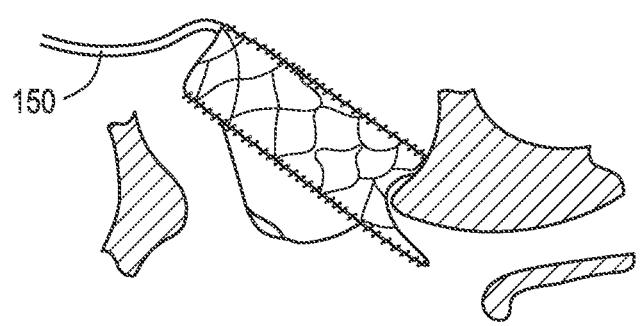
FIG. 8 is an illustration of a heart valve prosthesis having a braid or laser-cut tubular frame and extended valve sleeve engaging the tissue on the anterior side of the native annulus with the curved distal sidewall of the tubular frame sealing around the native annulus.

FIG. 8 is an illustration of a heart valve prosthesis having a braid or laser-cut tubular frame and extended valve sleeve engaging the tissue on the anterior side of the native annulus with the curved distal sidewall of the tubular frame sealing around the native annulus. FIG. 8 shows the valve held by the steerable secondary catheter at an oblique angle while valve function is assessed.

Figure 9:
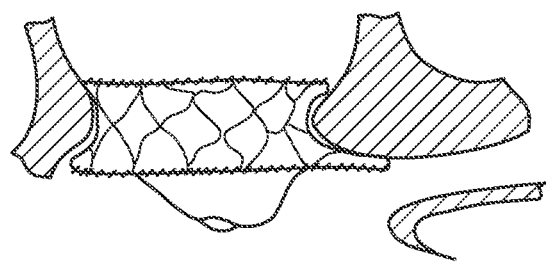
FIG. 9 is an illustration of a heart valve prosthesis having a braid or laser-cut tubular frame and extended valve sleeve engaging the tissue on the anterior side of the native annulus with the curved distal sidewall of the tubular frame sealing around the native annulus, and with the proximal sidewall tension-mounted into the posterior side of the native annulus.

FIG. 9 is an illustration of a heart valve prosthesis having a braid or laser-cut tubular frame and extended valve sleeve fully deployed into the tricuspid annulus. The distal side of the valve is shown engaging the tissue on the anterior side of the native annulus with the curved distal sidewall of the tubular frame sealing around the native annulus, and with the proximal sidewall tension-mounted into the posterior side of the native annulus.

FIG. 10 is an illustration of a plan view of an embodiment of a prosthetic valve shown in a compressed configuration within a delivery catheter. FIG. 10 shows the tubular frame wall rolled-over, outwardly, resulting in a 50% reduction in height of the catheter-housed valve. The low profile, side-loaded valves do not require the aggressive, strut-breaking, tissue-tearing, stitch-pulling forces that traditional transcatheter valves are engineered to mitigate.

FIG. 11 is an illustration of a cross-sectional view of an embodiment of a compressed valve within a delivery catheter 118. This cross-sectional end view shows one embodiment of a single-fold compression configuration where the tubular frame wall 102 and attached two-panel sleeve 110 are rolled-over, outwardly, five times, resulting in a 50% reduction in height, and providing the ability to fit within the inner diameter of a 1 cm (10 mm) delivery catheter.

FIG. 12 is an illustration of a cross-sectional view of another embodiment of a compressed valve within a delivery catheter. This cross-sectional end view shows another embodiment of a single-fold compression configuration where the tubular frame wall and attached two-panel sleeve are folded-over, outwardly, four times, resulting in a 50% reduction in height, and providing the ability to fit within the inner diameter of a 1 cm (10 mm) delivery catheter.

FIG. 13 is an illustration of a cross-sectional view of an embodiment of the prosthetic valve to further illustrate how the folding and rolling configurations can be effectuated due to the minimal material requirement of the low profile, side-loaded valve 102, 110.

Figure 14A:
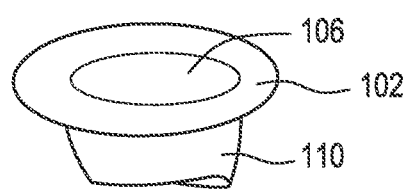
FIGS. 14A to 14C are an illustration of a sequence of a low profile valve being rolled into a configuration for placement within a delivery catheter.
Figure 14B:
Figure 14C:
Figure 15:
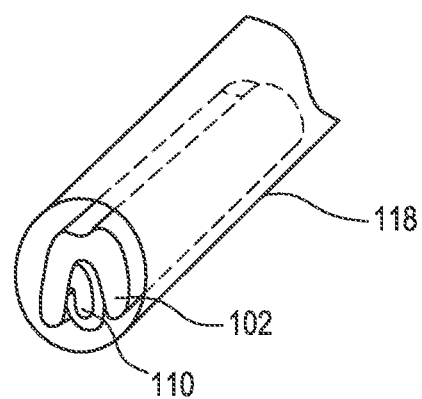
FIG. 15 is an illustration of an end view of a low profile valve that has been longitudinally rolled and loaded within a delivery catheter.

FIG. 14A, 14B, 14C is an illustration of a sequence of a low profile valve being rolled into a configuration for placement within a delivery catheter. Tubular frame 102 having aperture 106 supports sleeve 110.

Figure 51A:
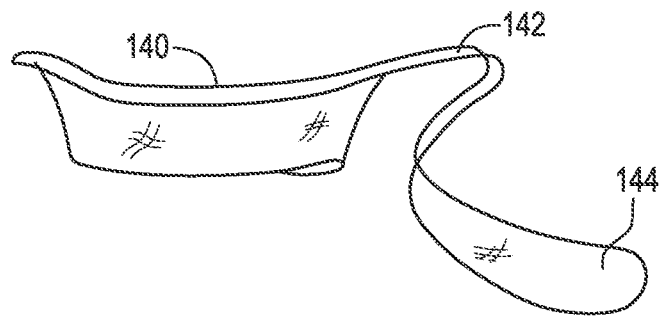
FIG. 51A is an illustration of a plan view of a low profile, e.g. 10 mm in height, wire loop embodiment of the heart valve prosthesis having an annulus support loop and an upper and lower tension arm formed as a unitary or integral part, and covered with a biocompatible material.
Figure 51B:
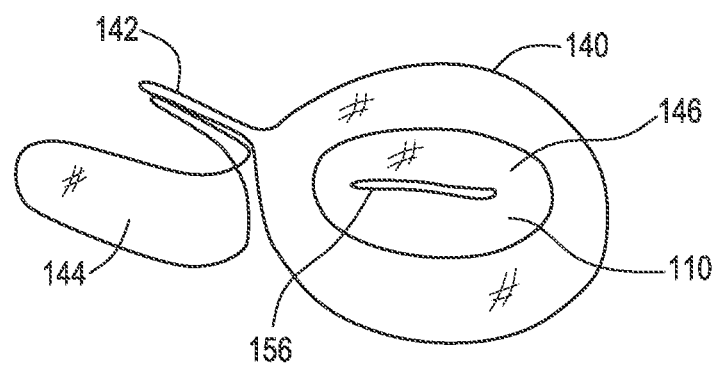
FIG. 51B is an illustration of a top view of a low profile, e.g. 10 mm in height, wire loop embodiment of the heart valve prosthesis having an annulus support loop, an upper and lower tension arm formed as a unitary or integral part, an inner two-panel conical valve sleeve, and covered with a biocompatible material.
Figure 51C:
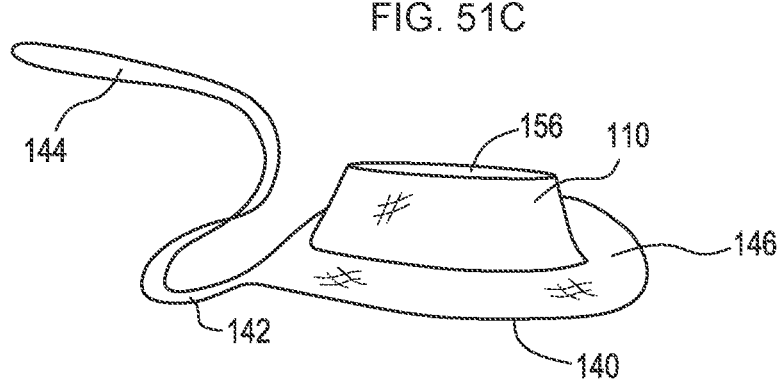
FIG. 51C is an illustration of a bottom view of a low profile, e.g. 10 mm in height, wire loop embodiment of the heart valve prosthesis having an annulus support loop, an upper and lower tension arm formed as a unitary or integral part, an inner two-panel conical valve sleeve, and covered with a biocompatible material.

FIG. 51C is an illustration of an end view of a low profile valve that has been longitudinally rolled and loaded within a delivery catheter 118, and shows frame 102 and sleeve 110.

Figure 16A:
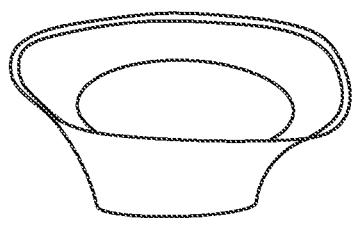
FIGS. 16A to 16D illustrate a four step process for orthogonally compressing a prosthetic valve to provide a long-axis that is co-planar or parallel with the lengthwise axis of a delivery catheter.
Figure 16B:
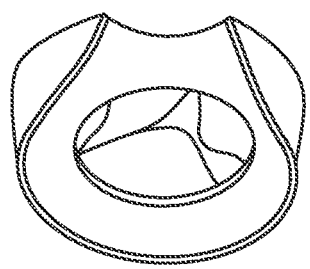
Figure 16C:
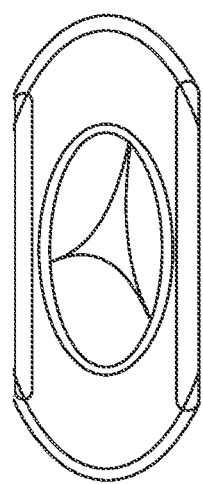
Figure 16D:

FIGS. 16A to 16D illustrate one embodiment showing a four step (a)-(d) process for orthogonally compressing a prosthetic valve to provide a long-axis that is co-planar or parallel with the lengthwise axis of a delivery catheter. These figures shows that a prosthetic valve having a tubular frame made of a cuff and a trans-annular tubular section, having a flow control component mounted within the tubular frame and configured to permit blood flow in a first direction through an inflow end of the valve and block blood flow in a second direction, opposite the first direction, through an outflow end of the valve, is compressible along a long-axis that is parallel to a lengthwise axis of a delivery catheter. These figures show that the valve is compressible to a compressed configuration for introduction into the body using a delivery catheter where said compressed configuration has a long-axis that is perpendicular to the blood flow direction axis, i.e. oriented at an intersecting (orthogonal) angle of between 45-135 degrees, e.g. 90 degrees, to the first (blood flow) direction, and where the long-axis of the compressed configuration of the valve is substantially parallel to a lengthwise cylindrical axis of the delivery catheter, wherein the valve has a height of about 5-60 mm and a diameter of about 25-80 mm. FIG. 16A shows an illustration of an uncompressed valve. FIG. 16B shows an illustration of an initial rolling or folding of the cuff. The folding or rolling can be inwards as shown here, or may be outwardly rolled, or may also be flattened together for rolling the entire valve up from bottom to top. FIG. 16C shows an illustration of a valve that has been rolled or folded, using multiple folds or rolls, along a long-axis into a tube-shape. FIG. 16D shows an illustration of a completely compressed valve, that has been folded or rolled, using a compression accessory, and which is then loaded into the delivery catheter. Such a compressed valve may be self-expanding when released from the delivery catheter using shape-memory alloys, or the valve may be balloon expanded in a secondary process once the valve is released from the delivery catheter.

Figure 17A:
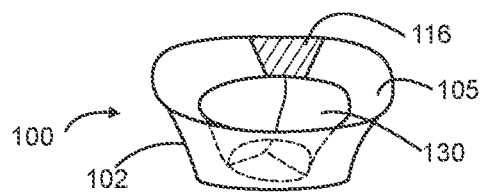
FIG. 17A is an illustration of a side perspective view of a side deliverable transcatheter heart valve with fold area according to an embodiment.

Referring now to the drawings, FIG. 17A is an illustration of a side perspective view of a side deliverable transcatheter heart valve 100 with fold area 116 according to an embodiment. FIG. 17A shows a distal fold area 116 in the collar portion 105 that permits compression of the valve without subjecting the annular frame 102 or inner flow control component 130 to damaging compression forces.

Figure 17B:
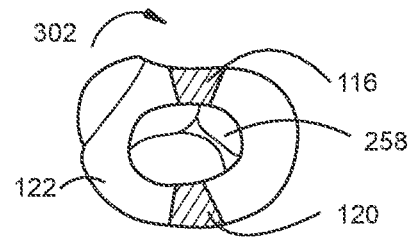
FIG. 17B is an illustration of a side perspective view of the valve showing one side of the valve commence a unilateral rolling process.

FIG. 17B is an illustration of a side perspective view of the valve showing an anterior side 122 of the valve commence a unilateral rolling process 302. FIG. 17B shows two fold areas, proximal (near) 120 and distal (far) 116. The fold areas 116, 120 may be devoid of wire cells or may consist of cells that are large or oriented to minimize the folding or rolling damage from the compression process. Leaflets 258 of the flow control component are visible from this angle.

Figure 17C:
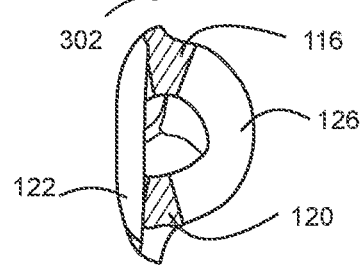
FIG. 17C is an illustration of a side perspective view of the valve showing a second rolling step of a unilateral rolling process.

FIG. 17C is an illustration of a side perspective view of the valve showing a second rolling step of a unilateral rolling process 302. Anterior collar 122 is rolled over to the central distal fold 116 and proximal fold 116 with posterior-septal collar 126 in an unrolled expanded configuration.

Figure 17D:
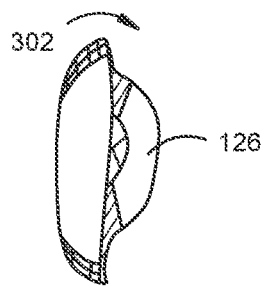
FIG. 17D is an illustration of a side perspective view of the valve showing a third rolling step of a unilateral rolling process.

FIG. 17D is an illustration of a side perspective view of the valve showing a third rolling step of a unilateral rolling process 302. The valve continues to be roll compressed towards the posterior-septal collar 126.

Figure 17E:
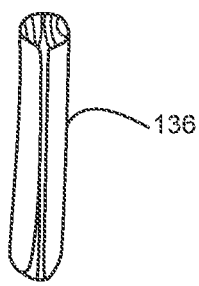
FIG. 17E is an illustration of a side perspective view of the valve showing a completion of the unilateral rolling process.

FIG. 17E is an illustration of a side perspective view of the valve showing a completion of the unilateral rolling process to achieve a roll-compressed configuration 136.

Figure 18A:
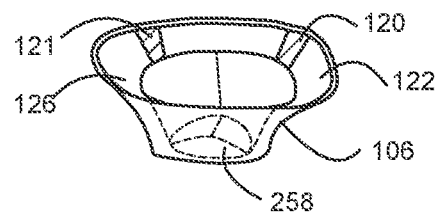
FIG. 18A is an illustration of a side perspective view of the valve showing two (2) sides of the valve commence a bilateral rolling process, with two of four (shown) fold areas.

FIG. 18A is an illustration of a side perspective view of the valve showing two (2) sides of the valve commence a bilateral rolling process 304, with two of four (shown) fold areas, distal fold 120 and second distal fold 121. Anterior collar 122 and posterior-septal collar 126 are shown with outer frame wall 106 and leaflets 258 in dashed line for reference.

Figure 18B:
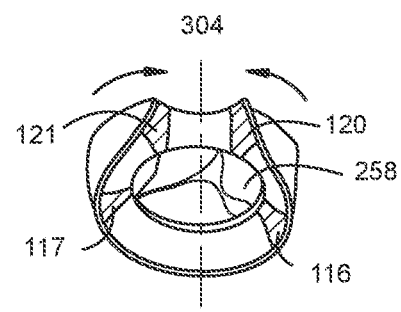
FIG. 18B is an illustration of a side perspective view of the valve showing a second rolling step of a bilateral rolling process.

FIG. 18B is an illustration of a side perspective view of the valve showing a second rolling step of a bilateral rolling process 304. The rim of the annular support frame is shown rolling inward towards the central axis 146. Distal fold 120 and second distal fold 121 are shown opposite from proximal fold area 116 and second proximal fold area 117. Flow control leaflets 258 are shown for reference.

Figure 18C:
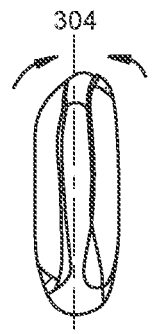
FIG. 18C is an illustration of a side perspective view of the valve showing a third rolling step of a bilateral rolling process.

FIG. 18C is an illustration of a side perspective view of the valve showing a third rolling step of a bilateral rolling process 304. Here, the rolled rim is further rolled inward towards the central axis.

Figure 18D:
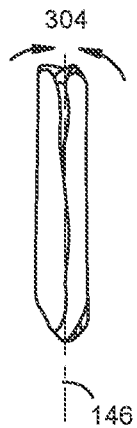
FIG. 18D is an illustration of a side perspective view of the valve showing a completion of the bilateral rolling compression process.

FIG. 18D is an illustration of a side perspective view of the valve showing a completion of the bilateral rolling compression process 304 shown rolled inward towards the central axis 146. FIG. 18D shows a roll-compressed valve as it would appear in a compressed configuration within a delivery catheter (not shown).

Figure 19A:
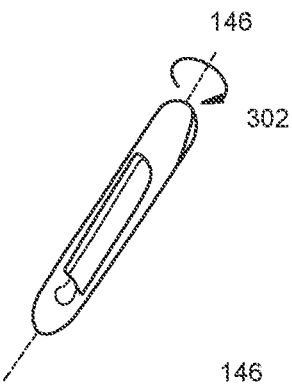
FIG. 19A is an illustration of a side perspective view of a compressed valve where compression used both rolling and folding.

FIG. 19A is an illustration of a side perspective view of a compressed valve where orthogonal compression uses both rolling and folding 302. The lower portion is rolled, and the upper collar portion is folded lengthwise around axis 146.

Figure 19B:
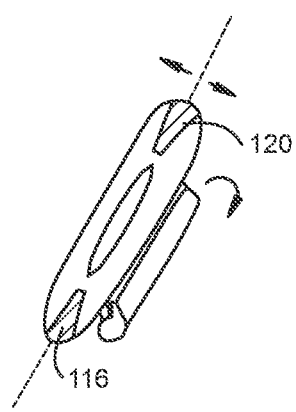
FIG. 19B is an illustration of a side perspective view of a partially uncompressed valve showing unrolling of the lower body portion and unfolding of the flattened upper collar portion.

FIG. 19B is an illustration of a side perspective view of a partially uncompressed valve showing unrolling of the lower body portion and unfolding of the flattened upper collar portion. FIG. 19B shows the fold areas 116, 120 in the collar portion.

Figure 19C:
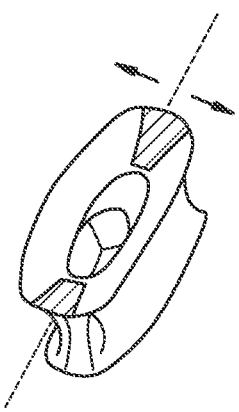
FIG. 19C is an illustration of a side perspective view of the valve showing an uncompressed valve showing an unrolled lower body portion and an unfolded upper collar portion.

FIG. 19C is an illustration of a side perspective view of the valve showing an uncompressed valve showing an unrolled lower body portion and an unfolded upper collar portion. Fold areas in the collar are wider as the valve assumes its expanded configuration.

Figure 19D:
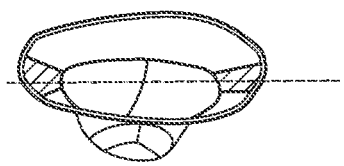
FIG. 19D is an illustration of a side perspective view of the uncompressed valve showing a different side/orientation.

FIG. 19D is an illustration of a side perspective view of the uncompressed valve showing a different side/orientation, which is 90 degrees from the prior views.

Figure 20:
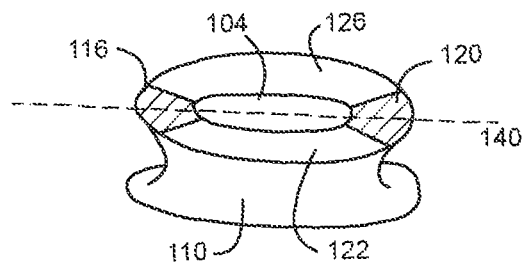
FIG. 20 is an illustration of a side perspective view of a valve having a circular hyperboloid (hourglass) shape.

FIG. 20 is an illustration of a side perspective view of a valve having a circular hyperboloid (hourglass) shape. Wire frame details are not shown since in practice the external surface would preferably be covered with Dacron polyester to facilitate in-growth. Distal fold area 120 and proximal fold area 116 are shown book-ending the anterior collar 122 and posterior-septal collar 126 along horizontal axis 140 with front anterior wall 110 and central channel 104 shown, according to an embodiment.

Figure 21:
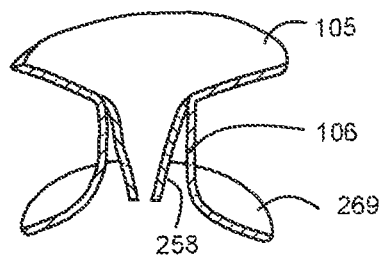
FIG. 21 is an illustration of a cut away view of a valve having a circular hyperboloid (hourglass) shape.

FIG. 21 is an illustration of a cut away view of a valve having a circular hyperboloid (hourglass) shape. FIG. 21 shows that inner leaflet 258 and inner frame of flow control component (not visible) are attached to the inner surface of the annular frame, with collar portion 105 attached to subannular anchor portion 269 via wall portion 106. Here, the flow control component is only attached at the top edge although other non-limiting attachments are contemplated, e.g. mid-wall, multiple attachment points, etc.

Figure 22:
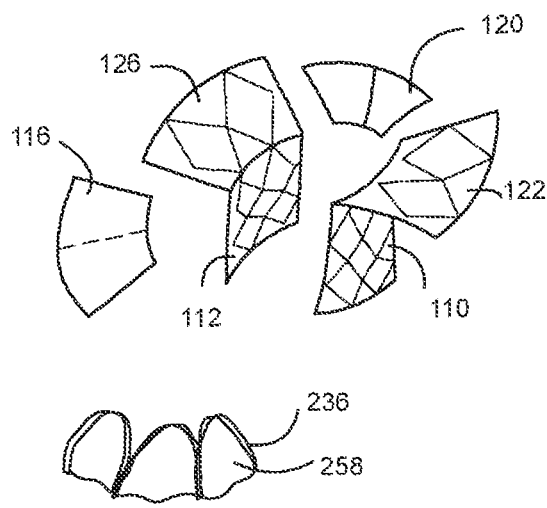
FIG. 22 is an illustration of an exploded view of a valve having a funnel collar and cylinder body shape.

FIG. 22 is an illustration of an exploded view of a valve having a funnel collar 122, 126 and cylinder body shape 110, 112. FIG. 22 shows one variation where the wire cell is used to create opposing panels, which are joined using fabric strain minimizing panels at distal 120 and proximal 116 fold areas. FIG. 22 also shows a three-leaflet 258 embodiment mounted on an inner U-shaped wire frame 236

Figure 23:
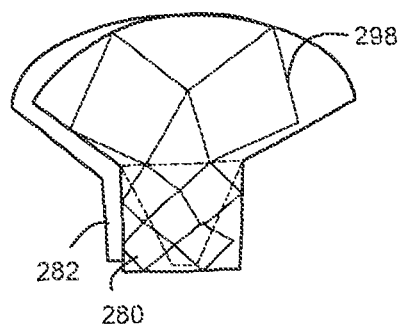
FIG. 23 is an illustration of a side view of a two-panel embodiment of the valve.

FIG. 23 is an illustration of a side view of a two (2) panel 280, 282 embodiment of the valve. FIG. 23 shows that diamond wire cell 298 for the collar portion may be one large diamond in height, while the lower body portion may be constructed using two smaller diamond wire cells in height. Dashed line illustrates where the inner flow control component is attached but not shown.

Figure 24:
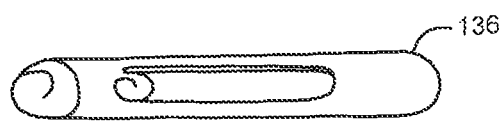
FIG. 24 is an illustration of a side view of a roll-compressed two-panel embodiment of the valve.

FIG. 24 is an illustration of a side view of a roll-compressed two-panel embodiment of the valve 136.

Figure 25:
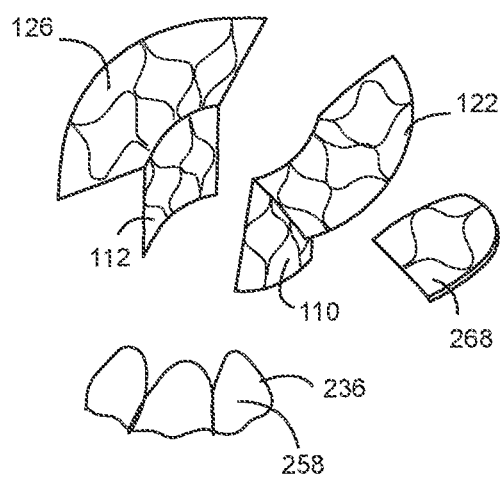
FIG. 25 is an illustration of an exploded view of a valve having a funnel collar, cylinder body shape, and RVOT tab.

FIG. 25 is an illustration of an exploded view of a valve having a funnel collar 122, 126 and cylinder body shape 110, 112. FIG. 25 shows one variation where the wire cell is used to create the entire opposing panels. FIG. 25 also shows a three-leaflet 258 embodiment mounted on an inner U-shaped wire frame 236.

Figure 26:
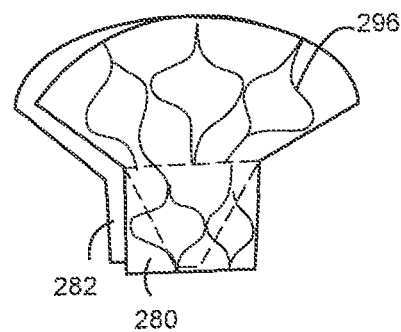
FIG. 26 is an illustration of a side view of a two-panel embodiment of the valve with a panel RVOT tab.

FIG. 26 is an illustration of a side view of a two-panel 280, 282 embodiment of the valve. FIG. 26 shows that wave wire cell 296 for the collar portion may be one large wave cell in height, while the lower body portion may be constructed using one or two smaller wave wire cells in height. Dashed line illustrates where the inner flow control component is attached but not shown.

Figure 27:
FIG. 27 is an illustration of a side view of a roll-compressed two-panel embodiment of the valve with RVOT tab.

FIG. 27 is an illustration of a side view of a roll-compressed two-panel embodiment of the valve 136.

Figure 28:
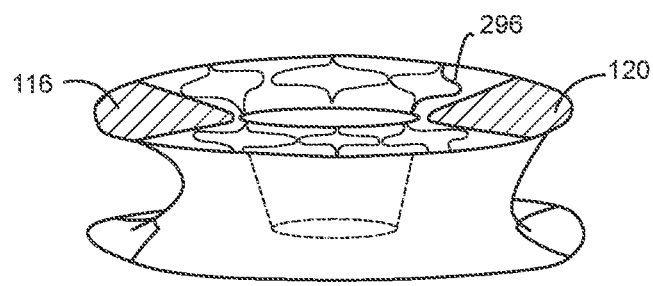
FIG. 28 is an illustration of a side perspective view of a valve with a folding gap in the wire frame.

FIG. 28 is an illustration of a side perspective view of a valve with a folding gap 116, 120 in the wave wire frame 296. Dashed line illustrates where the inner flow control component is attached but not shown.

Figure 29:
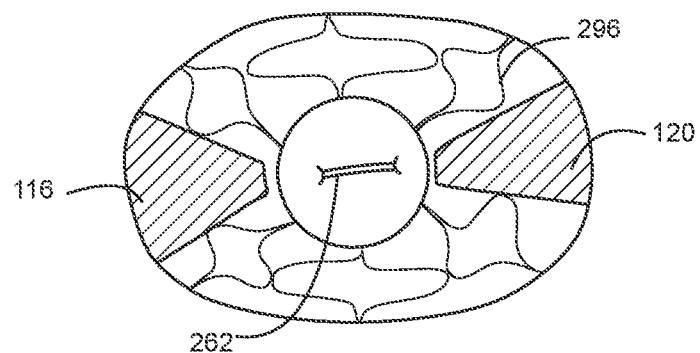
FIG. 29 is an illustration of a top view of a valve with a folding gap in the wire frame.

FIG. 29 is an illustration of a top view of a valve with a folding gap 116, 120 in the wave wire frame 296. Central flow control component opening is shown as a horizontal linear gap 262.

Figure 30:
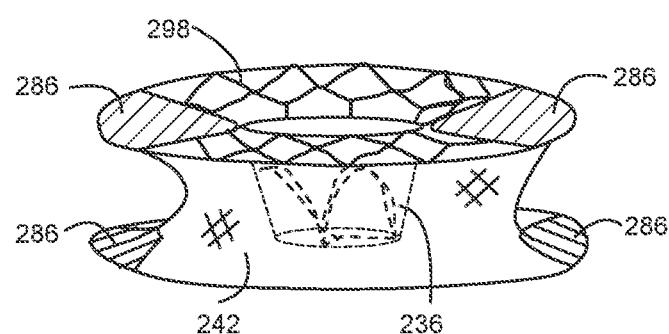
FIG. 30 is an illustration of a side perspective view of a valve with a folding gap in a generic annular support wire frame.

FIG. 30 is an illustration of a side perspective view of a valve with a folding gap 286 in a generic annular support wire frame 298. Dashed line illustrates where the inner flow control component 236 is attached but not shown. Wire frame details are not shown since in practice the external surface would preferably be covered with Dacron polyester 242 to facilitate in-growth.

Figure 31:
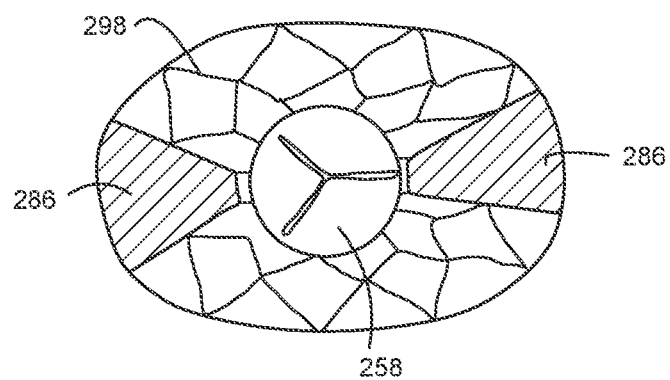
FIG. 31 is an illustration of a top view of a valve with a folding gap in the generic annular support wire frame.

FIG. 31 is an illustration of a top view of a valve with a folding gap 286 in the generic annular support wire frame 298. Central flow control component 258 opening is shown as a three-leaflet structure.

Figure 32A:
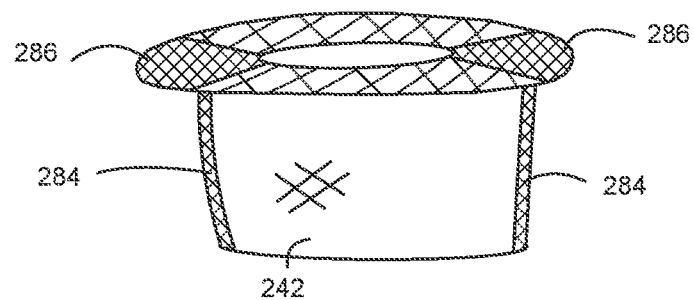
FIG. 32A is an illustration of a side perspective view of a valve with a folding gap in the wire frame where the gap is covered with a fabric mesh spanning the gap, and fabric folding panels on the proximal and distal sides of the lower body portion.

FIG. 32A is an illustration of a side perspective view of a valve with a folding gap 286 in the wire frame where the gap is covered with a fabric mesh spanning the gap. Fabric folding panels 284 are illustrated on the proximal and distal sides of the lower body portion. Polyester cover 242 for the body portion of outer frame is also shown.

Figure 32B:
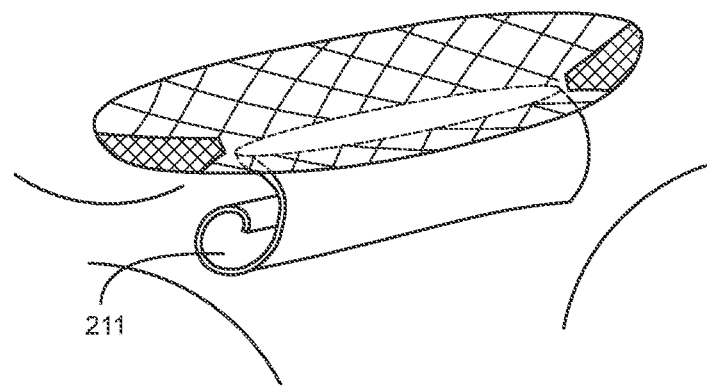
FIG. 32B is an illustration of a side view of a partially rolled valve frame/sheet.

FIG. 32B is an illustration of a side view of a partially rolled lower body portion 211 of valve frame/sheet. FIG. 32B shows that the lower body portion 211 is unfurled towards the septal leaflet. Native anterior and posterior native leaflets are shown in foreground.

Figure 33A:
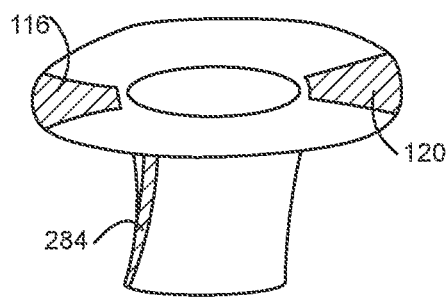
FIG. 33A is an illustration of a side perspective view of valve having a flat collar and cylinder body.

FIG. 33A is an illustration of a side perspective view of valve having a flat collar and cylinder body. FIG. 33A shows fold areas 116, 120 in the collar and in the lower body portion 284.

Figure 33B:
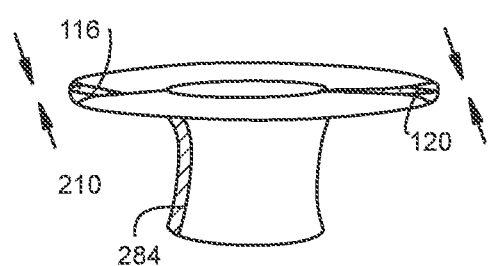
FIG. 33B is an illustration of a side perspective view of the flattened, partially compressed valve.

FIG. 33B is an illustration of a side perspective view of the flattened, partially compressed valve 210. FIG. 33B shows the two sides of the collar slide inward, compressing the fold areas 116, 120, to collapse the central axial opening, while flattening the lower body portion along seam 284.

Figure 33C:
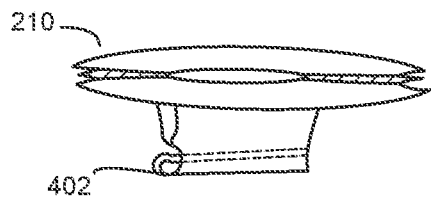
FIG. 33C is an illustration of a side perspective view of the flattened, partially compressed valve with the lower body portion being compressed by rolling.

FIG. 33C is an illustration of a side perspective view of the flattened, partially compressed valve 210 with the lower body portion being compressed by rolling 402.

Figure 33D:
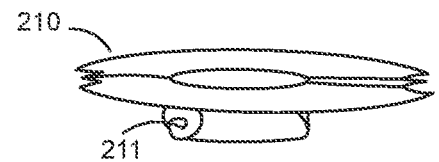
FIG. 33D is an illustration of a side perspective view of the flattened, partially compressed valve with the lower body portion being completely compressed by rolling up to the collar portion.

FIG. 33D is an illustration of a side perspective view of the flattened, partially compressed valve 210 with the lower body portion being completely compressed 211 by rolling up to the collar portion.

Figure 33E:
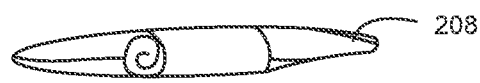
FIG. 33E is an illustration of a side perspective view of the flattened, compressed valve with the lower body portion compressed by rolling and folded onto the flattened upper collar.

FIG. 33E is an illustration of a side perspective view of the flattened, compressed valve 208 with the lower body portion compressed by rolling and folded onto the flattened upper collar.

Figure 34A:
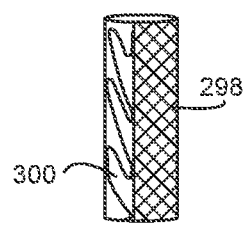
FIG. 34A is an illustration of a side perspective view of a composite laser-cut workpiece prior to expansion into the valve frame.

FIG. 34A is an illustration of a side perspective view of a composite laser-cut workpiece prior to expansion into the valve frame. FIG. 34A shows that a wire loop 300 in combination with a wire mesh or wire braid 298 can be combined in a single wire frame.

Figure 34B:
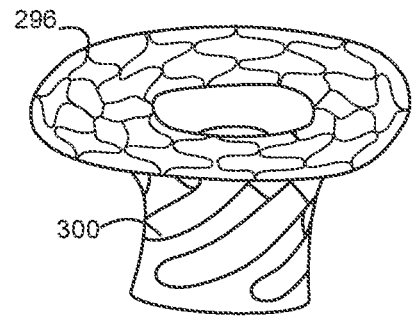
FIG. 34B is an illustration of a side perspective view of the composite laser-cut workpiece after expansion into a valve wireframe.

FIG. 34B is an illustration of a side perspective view of the composite laser-cut workpiece after expansion into a valve wireframe. FIG. 34B shows collar having a braid or laser wire cell 296, and lower having a wire loop 300.

Figure 35A:
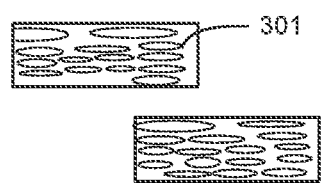
FIG. 35A is an illustration of a side perspective view of a laser-cut cell workpiece prior to expansion into the valve frame panels.

FIG. 35A is an illustration of a side perspective view of a laser-cut orthogonal cell workpiece prior to expansion into the valve frame panels. FIG. 35A illustrates asymmetric irregular rounded wire cells 301.

Figure 35B:
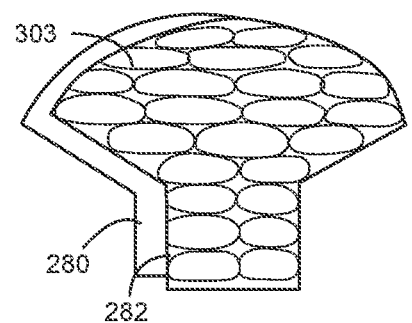
FIG. 35B is an illustration of a side perspective view of the laser-cut workpiece after expansion into the valve wireframe panels.

FIG. 35B is an illustration of a side perspective view of the laser-cut orthogonal workpiece after expansion into the valve wireframe panels 280, 282, prior to assembly. FIG. 35B shows rounded, horizontally oriented wire cells 303 for minimizing wire strain during folding, rolling and compression.

Figure 36A:
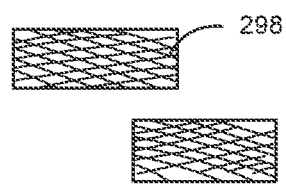
FIG. 36A is an illustration of a side perspective view of a laser-cut cell workpiece prior to expansion into the valve frame panels.

FIG. 36A is an illustration of a side perspective view of a laser-cut orthogonal cell workpiece with zig-zag/diamond shape cells 298 prior to expansion into the valve frame panels.

Figure 36B:
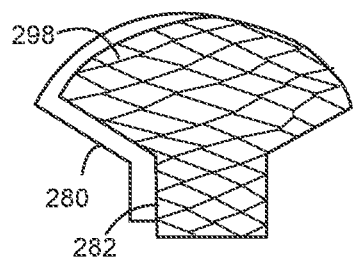
FIG. 36B is an illustration of a side perspective view of the laser-cut workpiece after expansion into the valve wireframe panels.

FIG. 36B is an illustration of a side perspective view of the laser-cut orthogonal workpiece with zig-zag/diamond shape cells 298 after expansion into the valve wireframe panels 280, 282, prior to assembly. FIG. 36B illustrates diamond-shaped, horizontally oriented wire cells 298 for minimizing wire strain during folding, rolling and compression.

Figure 37A:
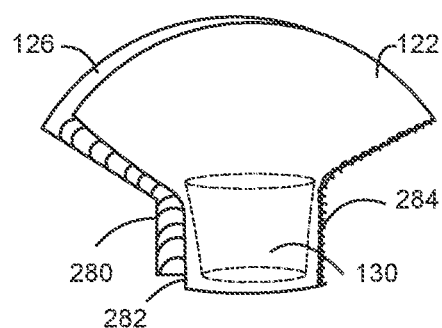
FIG. 37A is an illustration of a side perspective view of valve wireframe panels that are stitched along the side edges to form a three-dimensional valve having an arc-shape collar and a cylinder body with an internal flow control component mounted within the body portion.

FIG. 37A is an illustration of a side perspective view of valve wireframe panels 280, 282 that are stitched along the side edges 284 to form a three-dimensional valve having an arc-shape collar 122, 126 and a cylinder body with an internal flow control component 130 mounted within the body portion.

Figure 37B:
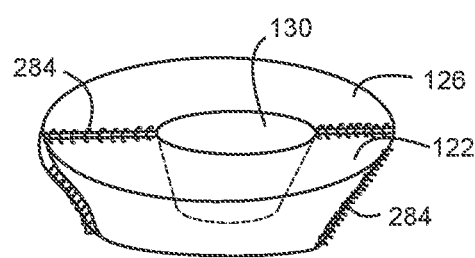
FIG. 37B is an illustration of a top perspective view of valve wireframe panels that are stitched along the side edges to form a three-dimensional valve having an arc-shape collar and a cylinder body with an internal flow control component mounted within the body portion.

FIG. 37B is an illustration of a top perspective view of valve wireframe panels that are stitched along the side edges 284 to form a three-dimensional valve having an arc-shape collar 122, 126 and a cylinder body with an internal flow control component 130 mounted within the body portion. Dashed line illustrates where the inner flow control component is attached but not shown.

Figure 37C:
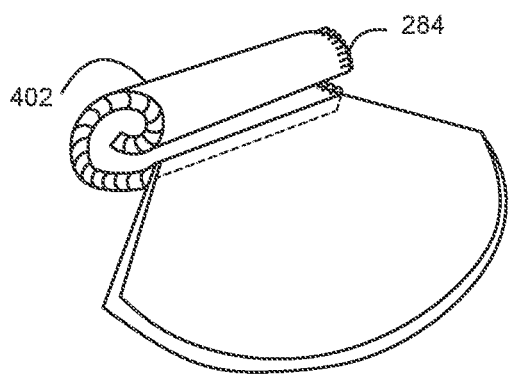
FIG. 37C is an illustration of a side perspective view of the two-panel embodiment being compressed by rolling.

FIG. 37C is an illustration of a side perspective view of the two-panel embodiment being compressed by rolling 402. FIG. 37C shows two panels, sewn along the joining (stitched, joined) edges 284.

Figure 37D:
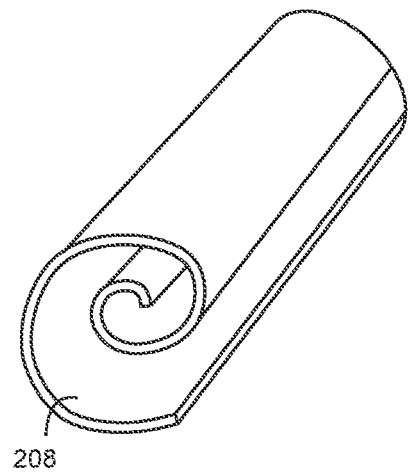
FIG. 37D is an illustration of a side perspective view of a two-panel embodiment rolled at least 1 turn, and up to 1.5 turns, or at least 360 degrees, and up to at least 540 degrees.

FIG. 37D is an illustration of a side perspective view of a two-panel embodiment rolled 208 at least 1 turn, and up to 1.5 turns, or at least 360 degrees, and up to at least 540 degrees.

Figure 38A:
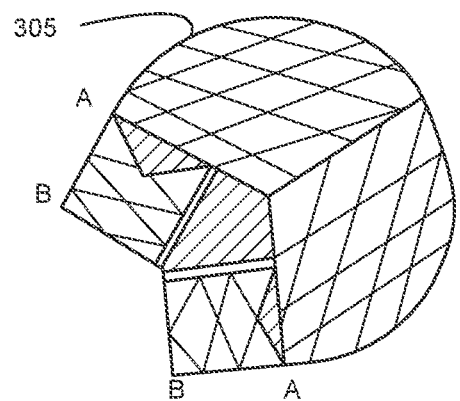
FIG. 38A is an illustration of a top view of a single sheet of metal or metal alloy with compressible cells cut or formed into a first and second collar panel and a first and second body portion.

FIG. 38A is an illustration of a top view of a single sheet 305 of metal or metal alloy with compressible cells cut or formed into a first and second collar panel and a first and second body portion. FIG. 38A shows a cut and fold design. FIG. 38A shows where the collar can be folded so that the two points A on the collar are brought together, and the lower portion can be folded so that the two points B on the lower portion are brought together to form a three-dimensional valve structure with partial folding to minimize the requirement for extensive sewing.

Figure 38B:
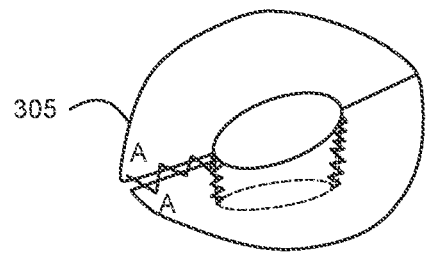
FIG. 38B is an illustration of a top perspective view of the single sheet valve frame after folding, assembly, and attachment along the open seams.

FIG. 38B is an illustration of a top perspective view of the single sheet valve frame 305 after folding, assembly, and attachment along the open seams.

Figure 38C:
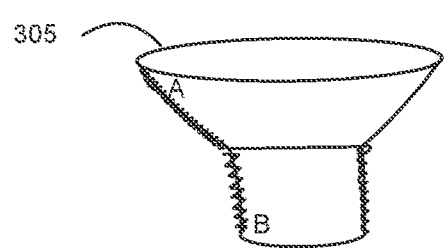
FIG. 38C is an illustration of a side perspective view of the single sheet valve frame after folding, assembly, and attachment along the open seams.

FIG. 38C is an illustration of a side perspective view of the single sheet valve frame 305 after folding, assembly, and attachment along the open seams.

Figure 39:
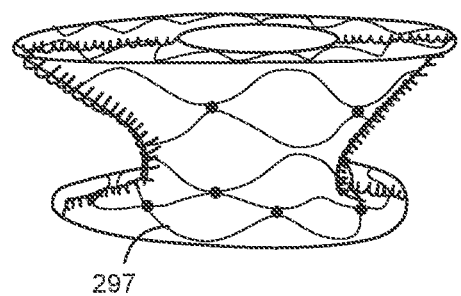
FIG. 39 is an illustration of a side perspective view of a valve formed from a series of wave-shaped wires connected at connection points, with an upper collar portion, and an hourglass shape for the body portion.

FIG. 39 is an illustration of a side perspective view of a valve formed from a series of horizontal wave-shaped wires 297 connected at connection points, with an upper collar portion, and an hourglass shape for the body portion.

Figure 40:
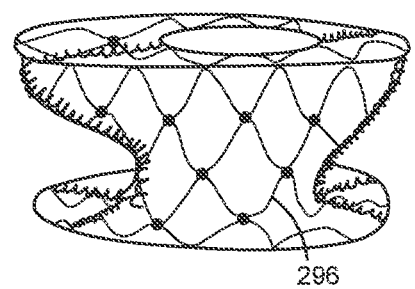
FIG. 40 is an illustration of a side perspective view of a valve formed from a series of zigzag-shaped wires connected at connection points, with an upper collar portion, and an hourglass shape for the body portion.

FIG. 40 is an illustration of a side perspective view of a valve formed from a series of (vertical) zigzag-shaped wires 296 connected at connection points, with an upper collar portion, and an hourglass shape for the body portion. Sewing features are shown along the joining edges.

Figure 41A:
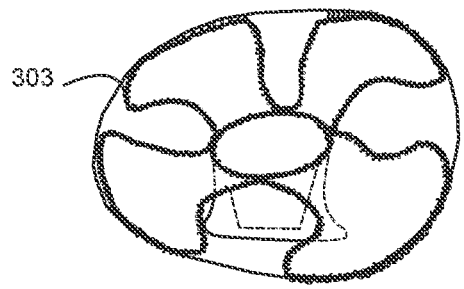
FIG. 41A is an illustration of a top perspective view of a valve upper collar portion formed from a series of fan-shaped wires connected circumferentially to the top peripheral edge of the lower body portion.

FIG. 41A is an illustration of a top perspective view of a valve upper collar portion formed from a series of fan-shaped asymmetric, irregular rounded cells/wires 303 connected circumferentially to the top peripheral edge of the lower body portion.

Figure 41B:
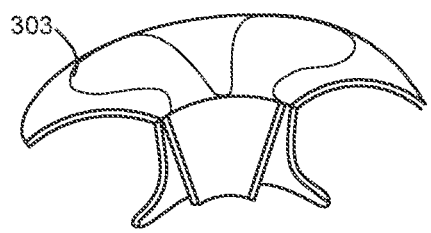
FIG. 41B is an illustration of a cut away view of a valve upper collar portion formed from a series of fan-shaped wires connected circumferentially to the top peripheral edge of the lower body portion, and shows half of the flow control component mounted with the lower body portion.

FIG. 41B is an illustration of a cut away view of a valve upper collar portion formed from a series of fan-shaped asymmetric, irregular rounded cells/wires 303 connected circumferentially to the top peripheral edge of the lower body portion, and shows half of the flow control component mounted with the lower body portion.

Figure 41E:
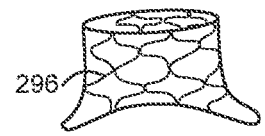
FIG. 41E is an illustration of a side perspective view of a lower body portion having a braided wire cell construction.
Figure 41C:
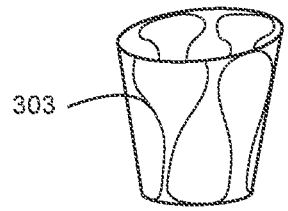
FIG. 41C is an illustration of a side perspective view of an upper cuff or collar in a partially expanded configuration, showing how the elongated fan-shape wires permit elongation and radial compression.

FIG. 41C is an illustration of a side perspective view of an upper cuff or collar in a partially expanded configuration, showing how the elongated fan-shape asymmetric, irregular rounded cells/wires 303 permit elongation and radial compression.

Figure 41F:
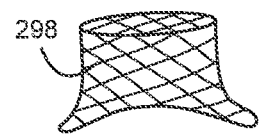
FIG. 41F is an illustration of a side perspective view of a lower body portion having a laser-cut wire cell construction.
Figure 41D:
FIG. 41D is an illustration of a side perspective view of a two-panel embodiment of a flow control component.

FIG. 41D is an illustration of a side perspective view of a two-panel embodiment of a flow control component.

FIG. 41E is an illustration of a side perspective view of a lower body portion having a braided wire cell construction 296.

FIG. 41F is an illustration of a side perspective view of a lower body portion having a diamond laser-cut wire cell construction 298.

Figure 41G:
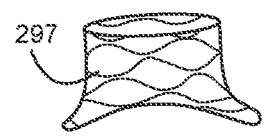
FIG. 41G is an illustration of a side perspective view of a lower body portion having a connected-wave wire cell construction.

FIG. 41G is an illustration of a side perspective view of a lower body portion having a connected-wave wire cell construction 297.

Figure 42:
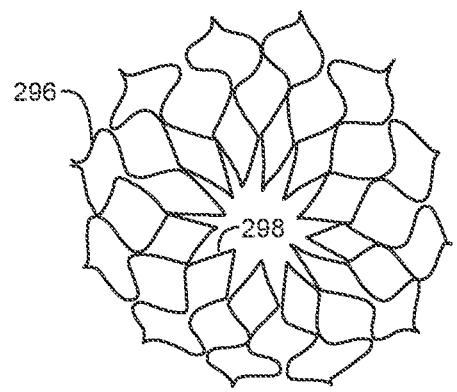
FIG. 42 is an illustration of a top view of flat wire frame of metal or metal alloy having compressible wire cells configured in a strain minimizing orientation to facilitate loading and delivery of a prosthetic tricuspid valve.

FIG. 42 is an illustration of a top view of flat wire frame of metal or metal alloy having compressible wire cells configured in a strain minimizing orientation to facilitate orthogonal loading and delivery of a prosthetic tricuspid valve. FIG. 42 shows outer wave cells 296 used for a collar portion with inner diamond cells 298 used for a body portion of the outer frame.

Figure 43:
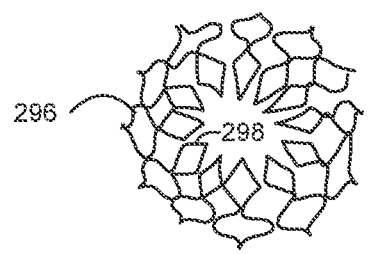
FIG. 43 is an illustration of a top view of smaller sized flat wire frame of metal or metal alloy having compressible wire cells configured in a strain minimizing orientation to facilitate loading and delivery of a prosthetic tricuspid valve.

FIG. 43 is an illustration of a top view of smaller sized flat wire frame of metal or metal alloy having compressible wire cells configured in a strain minimizing orientation to facilitate orthogonal loading and delivery of a prosthetic tricuspid valve. FIG. 43 shows outer wave cells 296 used for a collar portion with inner diamond cells 298 used for a body portion of the outer frame.

Figure 44:
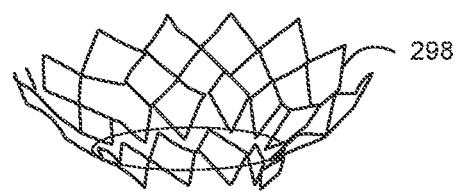
FIG. 44 is an illustration of a side perspective view of a wire frame in a funnel configuration (heat set) showing compressible wire cells configured in a strain minimizing orientation to facilitate loading and delivery of a prosthetic tricuspid valve.

FIG. 44 is an illustration of a side perspective view of a wire frame in a funnel configuration (heat set) showing compressible wire cells configured in a strain minimizing orientation to facilitate orthogonal loading and delivery of a prosthetic tricuspid valve. FIG. 44 shows outer diamond cells 298 used for a collar portion with inner diamond cells 298 used for a body portion of the outer frame.

Figure 45:
FIG. 45 is an illustration of a side perspective view of a wire frame in a funnel configuration (heat set) showing compressible wire cells configured in a strain minimizing orientation to facilitate loading and delivery of a prosthetic tricuspid valve.

FIG. 45 is an illustration of a side perspective view of an wire frame in a funnel configuration (heat set) showing compressible wire cells configured in a strain minimizing orientation to facilitate orthogonal loading and delivery of a prosthetic tricuspid valve. FIG. 45 shows outer diamond cells 298 used for a collar portion with inner diamond cells 298 used for a body portion of the outer frame.

Figure 46:
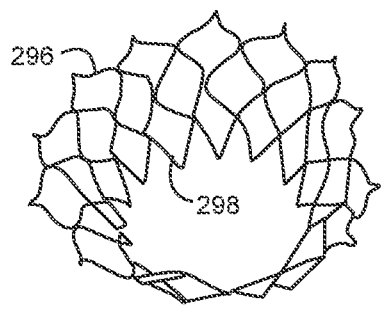
FIG. 46 is an illustration of a top view down the central axis of a wire frame in a funnel configuration (heat set) showing compressible wire cells configured in a strain minimizing orientation to facilitate loading and delivery of a prosthetic tricuspid valve.

FIG. 46 is an illustration of a top view down the central axis of a wire frame in a funnel configuration (heat set) showing compressible wire cells configured in a strain minimizing orientation to facilitate orthogonal loading and delivery of a prosthetic tricuspid valve. FIG. 46 shows outer wave cells 296 used for a collar portion with inner diamond cells 298 used for a body portion of the outer frame.

Figure 47A:
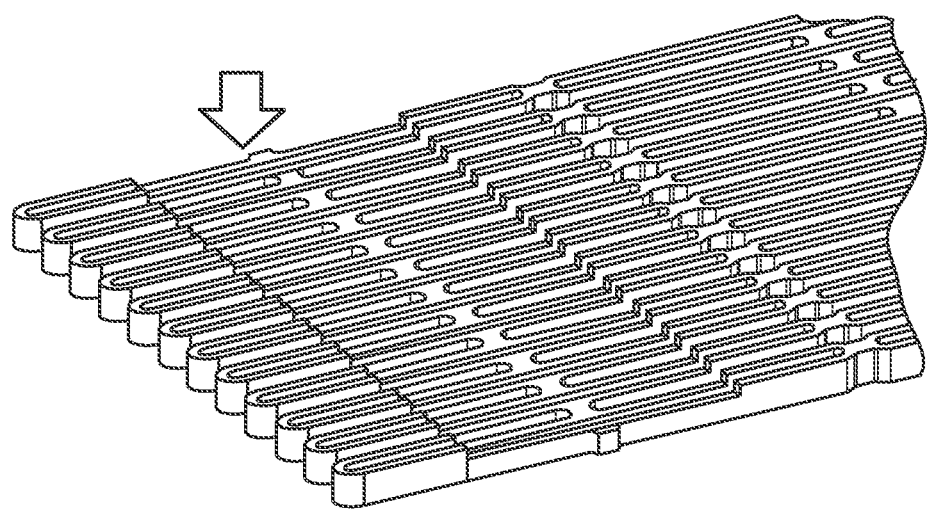
FIG. 47A is an illustration of a side perspective view of a metal alloy sheet that has been etched partially on a single side using photolithography and resistive masks.

FIG. 47A is an illustration of a side perspective view of a metal alloy sheet that has been etched partially on a single side using photolithography and resistive masks.

Figure 47B:
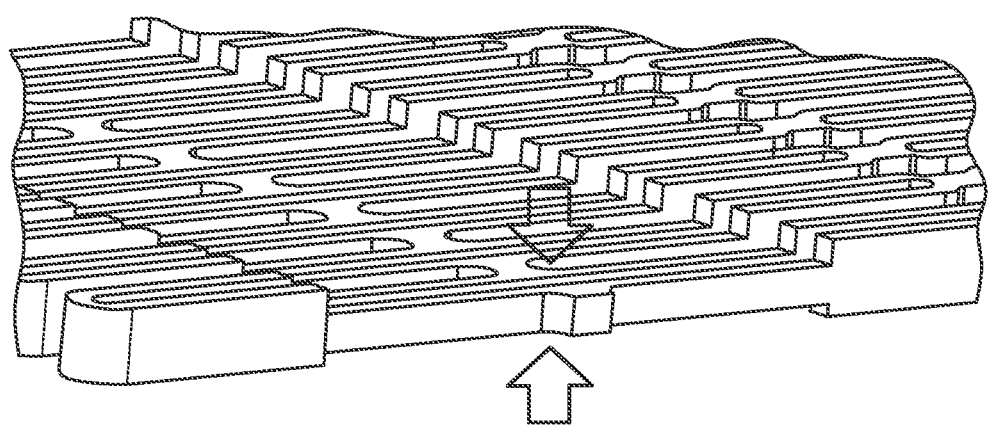
FIG. 47B is an illustration of a side perspective view of a metal alloy sheet that has been etched partially in a two-sided configuration using photolithography and resistive masks.

FIG. 47B is an illustration of a side perspective view of a metal alloy sheet that has been etched partially in a two-sided configuration using photolithography and resistive masks.

Figure 48:
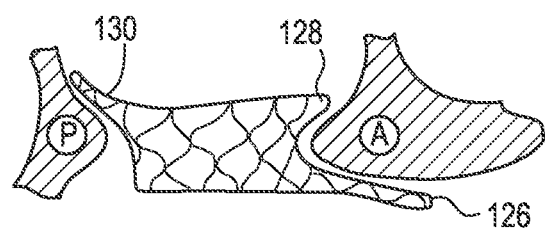
FIG. 48 is an illustration of a plan view of a heart valve prosthesis according to an embodiment with a valve frame having a distal upper and lower tension arm mounted on, and anchored to, the anterior leaflet side of the native annulus, and having a mechanical anchor element, e.g. proximal sealing cuff, for anchoring on the posterior and septal side of the native annulus.

FIG. 48 is an illustration of a plan view of an embodiment of a heart valve prosthesis with a valve frame 102 having a distal upper tension arm 128 and lower tension arm 126 mounted on, and anchored to, the anterior leaflet side of the native annulus, and having a mechanical anchor element, e.g. proximal sealing cuff, 130 for anchoring on the posterior and septal side of the native annulus. The sealing cuff 130 may be a short tab on the posterior side of the valve or may be a semi-circular or circular collar or cuff that engages the atrial floor to seal the annulus from perivalvular leaks.

Figure 49:
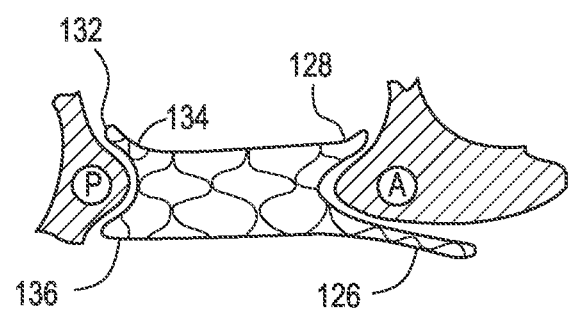
FIG. 49 is an illustration of a plan view of a heart valve prosthesis according to an embodiment with a valve frame having a distal upper and lower tension arm mounted on, and anchored to, the anterior leaflet side of the native annulus, and having a mechanical anchor element, e.g. hourglass annular seal, for anchoring on the posterior and/or septal side of the native annulus.

FIG. 49 is an illustration of a plan view of another embodiment of a heart valve prosthesis according to an embodiment with a valve frame having a distal upper and lower tension arm mounted on, and anchored to, the anterior leaflet side of the native annulus, and having a mechanical anchor element, e.g. hourglass annular seal, 132 for anchoring on the posterior and/or septal side of the native annulus. The hourglass, or concave, sealing cuff 132 may be only a short segment on the posterior side of the valve or may be a semi-circular or circular combined upper and lower collar or cuff that engages the atrial floor and the ventricular ceiling to seal the annulus from perivalvular leaks. This embodiment may also include embodiments having a partial collar. This embodiment may be used in conjunction with other anchoring elements described herein.

Figure 50:
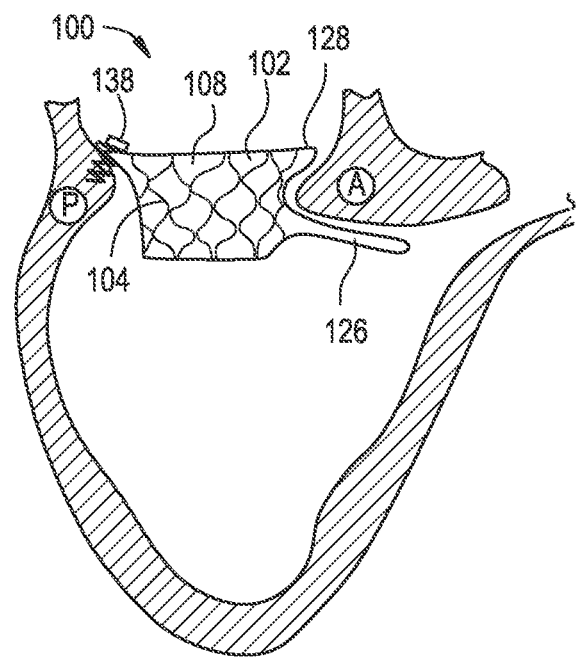
FIG. 50 is an illustration of a plan view of a heart valve prosthesis according to an embodiment with a valve frame having a distal upper and lower tension arm mounted on, and anchored to, the anterior leaflet side of the native annulus, and having a mechanical anchor element, e.g. surgical tissue screw, anchored on a posterior or septal side of the native annulus.

FIG. 50 is an illustration of a plan view of a heart valve prosthesis 100 according to an embodiment with a valve frame 102 having upper tension arm 128 and lower tension arm 126 mounted on and anchoring to the annulus. FIG. 50 shows lower tension arm/tab 126 extending into the Right Ventricular Outflow Tract (RVOT). The lateral, or side-loaded, delivery of the valve 100 through the inferior vena cava provides for direct access to the valve annulus without the need to deliver a compressed valve around a right angle turn, as is required for IVC delivery of axially, or vertically loaded, traditional transcatheter valves. FIG. 50 shows one embodiment where a screw or other anchor device 138 is used in conjunction with the tension-mounting method described herein where upper and lower tension arms on the anterior leaflet side anchor the valve in place, and a secondary anchor element completes the securement of the valve in the annular site.

FIG. 50 shows polyester mesh covering 108 a valve tubular frame 102 encircling a collapsible flow control sleeve 110. FIG. 50 also shows the frame 102 having Nitinol wire frame in diamond shapes with a biocompatible covering. In one embodiment, the frame may have a pericardial material on top and a polyester material, e.g. surgical Dacron®, underneath to be in contact with the native annulus and promote ingrowth.

FIG. 51A is an illustration of a plan view of a low profile, e.g. 10 mm in height, wire loop embodiment of the heart valve prosthesis having an annulus support loop 140 and an upper and lower tension arm 142, 144 formed as a unitary or integral part, and covered with a biocompatible material. This embodiment shows how a low profile, side-loaded valve can have a very large diameter, 40-80 mm, with requiring an excessively large delivery catheter, as would be required by a large diameter valve that is delivered using the traditional, vertical or axial, orientation.

FIG. 51B is an illustration of a top view of a low profile, e.g. 10 mm in height, wire loop embodiment of the heart valve prosthesis having an annulus support loop 140, an upper and lower tension arm 142, 144 formed as a unitary or integral part, an inner two-panel conical valve sleeve 110, and covered with a biocompatible material. FIG. 51B shows the inner two-panel sleeve and the reciprocating collapsible aperture at the lower end for delivering blood to the ventricle.

FIG. 51C is an illustration of a bottom view of a low profile, e.g. 10 mm in height, wire loop embodiment of the heart valve prosthesis having an annulus support loop, an upper and lower tension arm formed as a unitary or integral part, an inner two-panel conical valve sleeve, and covered with a biocompatible material. FIG. 51C shows a plan view of the inner two-panel sleeve 110 and the collapsible terminal aperture 156 at the ventricular side.

Figure 51D:
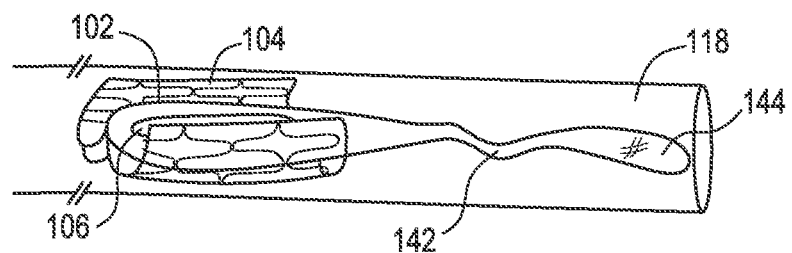
FIG. 51D is an illustration of a compressed and elongated wire loop embodiment of the heart valve prosthesis disposed within a delivery catheter and having an annulus support loop and an upper and lower tension arm formed as a unitary or integral part.

FIG. 51D is an illustration of a compressed and elongated wire loop embodiment of the heart valve prosthesis disposed within a delivery catheter 118 and having a ring shaped tubular frame 102 with braid/laser-cut 104 and an upper and lower tension arm 142, 144 formed as a unitary or integral part. FIG. 51D illustrates how a large diameter valve, using side loading, can be delivered.

Figure 51E:
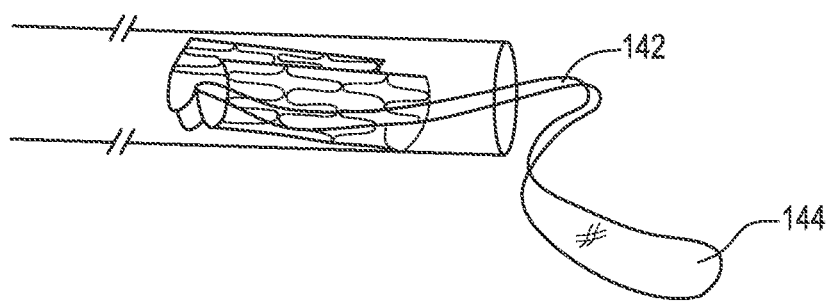
FIG. 51E is an illustration of a compressed and elongated wire loop embodiment of the heart valve prosthesis partially ejected, and partially disposed within, a delivery catheter and having an annulus support loop and an upper and lower tension arm formed as a unitary or integral part.

FIG. 51E is an illustration of a compressed and elongated wire loop embodiment of the heart valve prosthesis partially ejected, and partially disposed within, a delivery catheter and having an annulus support loop and an upper and lower tension arm formed as a unitary or integral part. FIG. 51E shows how a valve can be partially delivered for positioning in the annulus. The lower tension arm 144 can be used to navigate through the tricuspid leaflets and chordae tendineae while the valve body, the tubular frame, 102 is still within the steerable IVC delivery catheter 118.

Figure 52A:
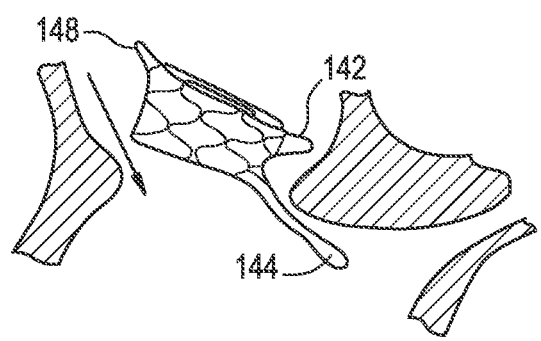
FIG. 52A is an illustration of a plan view of a heart valve prosthesis partially mounted within the valve annulus.

FIG. 52A is an illustration of a plan view of a heart valve prosthesis partially mounted within the valve annulus. By using the side-loaded valve of the disclosed embodiments, the distal side of the prosthesis 142, 144 can be mounted against the anterior aspect of the native annulus, and valve function can be assessed. By allowing two pathways for blood flow, the first through the native valve near the posterior leaflet, and the second through the central aperture of the prosthetic valve, a practitioner can determine if the heart is decompensating or if valve function is less than optimal.

Figure 52B:
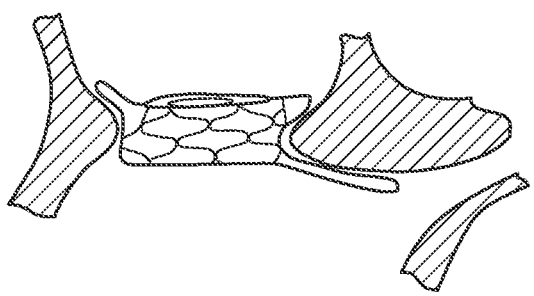
FIG. 52B is an illustration of a plan view of a heart valve prosthesis completely seated within the valve annulus.

FIG. 52B is an illustration of a plan view of a heart valve prosthesis completely seated within the valve annulus. FIG. 52B shows that the valve can be secured in place once the valve function assessment shows that the deployment is successful. Importantly, since the valve is a low profile valve, and fits easily within a standard, e.g. 8-12 mm, delivery catheter without requiring the forceful loading of typical transcatheter valves, the side-loading valve can be easily retrieved using the same delivery catheter that is used to deploy the valve.

Figure 53A:
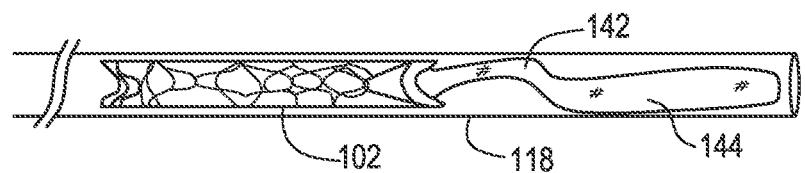
FIG. 53A is an illustration of a wire-frame embodiment of a heart valve prosthesis according to an embodiment in a compressed, intra-catheter phase.

FIG. 53A is an illustration of a heart valve prosthesis according to an embodiment in a compressed, intra-catheter phase. The lower and upper tension arms 144, 142 are elongated to the right and the prosthetic valve 102 is shown laterally compressed in the delivery catheter 118. The lateral compression is a function of the use of minimal structural materials, e.g. a minimal inner valve sleeve 110, and the relatively short height of the outer cylindrical frame 102. This lateral delivery provides for very large, e.g. up to 80 mm or more, valve prosthesis to be delivered. The lateral delivery also avoids the need to perform a 90-degree right turn when delivering a valve using the IVC femoral route. This sharp delivery angle has also limited the size and make up of prior valve prostheses, but is not a problem for the inventive valve herein.

Figure 53B:
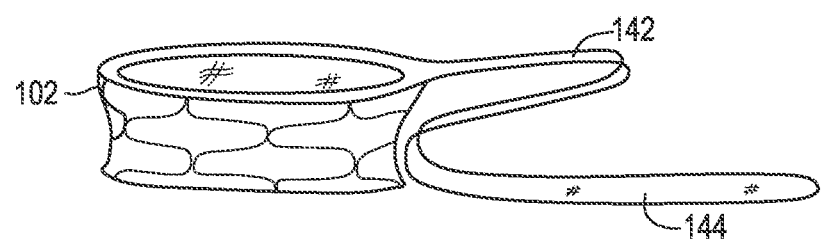
FIG. 53B is an illustration of a profile, or plan, view of a wire-frame embodiment of the heart valve prosthesis according to an embodiment in an un-compressed, post-catheter-ejection phase.

FIG. 53B is an illustration of a profile, or plan, view of a wire-frame embodiment of the heart valve prosthesis according to an embodiment in an un-compressed, post-catheter-ejection phase. FIG. 53B shows an embodiment where the upper wire-frame tension arm 142 is attached to the tubular frame 102, but the lower tension arm 144 is shaped in an S-shape and connects only to the upper tension arm 142.

Figure 53C:
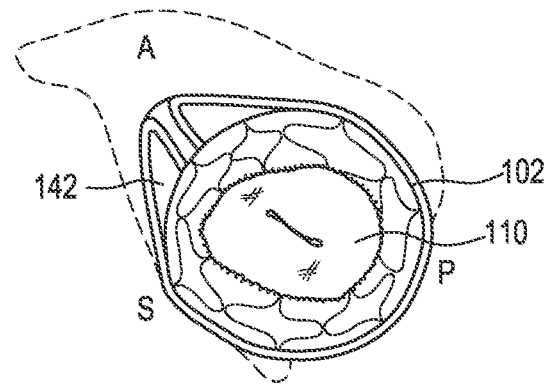
FIG. 53C is an illustration of a top view of a heart valve prosthesis according to an embodiment having covered wire loops for the upper tension arm(s).

FIG. 53C is an illustration of a top view of a heart valve prosthesis according to an embodiment having covered wire loop for the upper tension arm(s). FIG. 53C shows the tubular frame 102 having an inner sleeve 110 sewn into the central aperture 106, with the two (2) panels extending downward (into the page) in a ventricular direction. FIG. 53C shows the upper tension arms 142 oriented towards the anterior leaflet side of the atrial floor, shown in dashed outline.

Figure 53D:
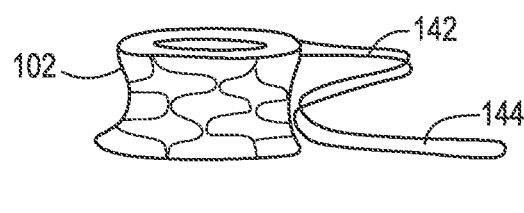
FIG. 53D is an illustration of a plan view of a heart valve prosthesis according to an embodiment having a wire loop construction for the upper and lower tension arms.

FIG. 53D is an illustration of a plan view of a heart valve prosthesis according to an embodiment having a wire loop construction for the upper 142 and lower 144 tension arms.

Figure 53E:
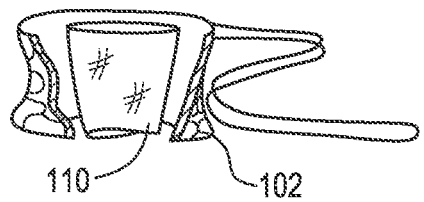
FIG. 53E is an illustration of a cut away plan view of a heart valve prosthesis according to an embodiment, and shows the inner panel valve sleeve mounted within the inner space defined by the tubular frame.

FIG. 53E is an illustration of a cut away plan view of a heart valve prosthesis according to an embodiment, and shows the inner panel valve sleeve 110 mounted within the inner space defined by the tubular frame. FIG. 53E shows an elongated two-panel valve sleeve 110 that extends into the sub-annular leaflet space. The tubular frame 102 shown in FIG. 53E is about 10 mm in height and the valve sleeve 110 extends about 10 mm below the bottom of the tubular frame, resulting in a valve 20 mm in total height.

Figure 53F:
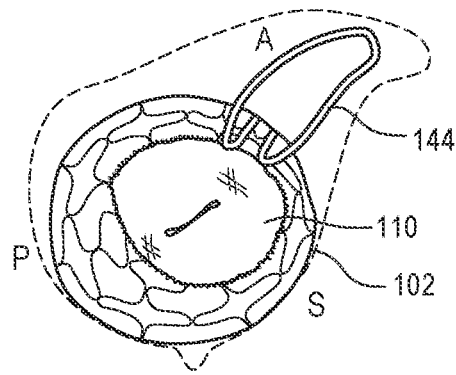
FIG. 53F is an illustration of a bottom view of a heart valve prosthesis according to an embodiment having covered wire loops for the lower tension arm.

FIG. 53F is an illustration of a bottom view of a heart valve prosthesis according to an embodiment having a covered wire loop for the lower tension arm 144. FIG. 53F shows the tubular frame 102 having an inner sleeve 110 sewn into the central aperture, with the two (2) panels extending upward (out of the page) in a ventricular direction. FIG. 53F shows the lower tension arm 144 oriented towards the anterior leaflet side of the ventricular ceiling, shown in dashed outline.

Figure 54A:
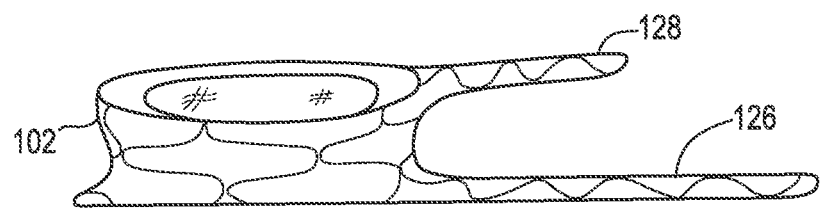
FIG. 54A is an illustration of a profile, or plan, view of a braided or laser-cut frame embodiment of the heart valve prosthesis according to an embodiment in an un-compressed, post-catheter-ejection phase.

FIG. 54A is an illustration of a profile, or plan, view of a braid or laser-cut frame embodiment of the heart valve prosthesis according to an embodiment in an un-compressed, post-catheter-ejection phase. FIG. 54A shows an embodiment where the upper braid or laser-cut tension arm 128 is attached to the upper edge of the tubular frame 102, and the lower tension arm 126 is attached to the lower edge of the tubular frame 102.

Figure 54B:
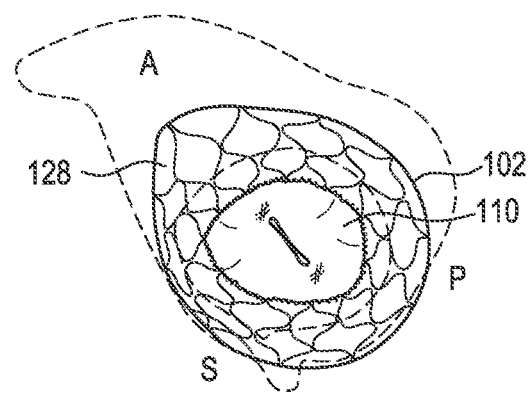
FIG. 54B is an illustration of a top view of a heart valve prosthesis according to an embodiment having braid or laser-cut wire frame for the upper tension arm(s).

FIG. 54B is an illustration of a top view of a heart valve prosthesis according to an embodiment having covered braid or laser-cut frame 102 for the upper tension arm 128. FIG. 54B shows the tubular frame 102 having an inner sleeve 110 sewn into the central aperture, with the two (2) panels extending downward (into the page) in a ventricular direction. FIG. 54B shows the upper tension arm 128 oriented towards the anterior leaflet side of the atrial floor, shown in dashed outline.

Figure 54C:
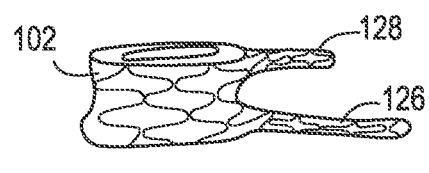
FIG. 54C is an illustration of a plan view of a heart valve prosthesis according to an embodiment having braid or laser-cut wire frame construction for the upper and lower tension arms.

FIG. 54C is an illustration of a plan view of a heart valve prosthesis according to an embodiment having a braid or laser-cut frame construction 102 for the upper and lower tension arms 128, 126.

Figure 54D:
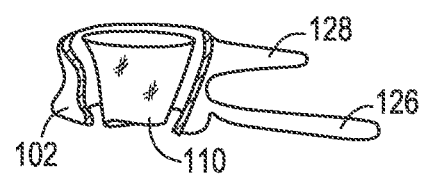
FIG. 54D is an illustration of a cut away plan view of a braid or laser-cut embodiment of the heart valve prosthesis according to an embodiment, and shows the inner panel valve sleeve mounted within the inner space defined by the tubular frame.

FIG. 54D is an illustration of a cut away plan view of a heart valve prosthesis according to an embodiment, and shows the inner panel valve sleeve 110 mounted within the inner space defined by the tubular frame 102.

Figure 54E:
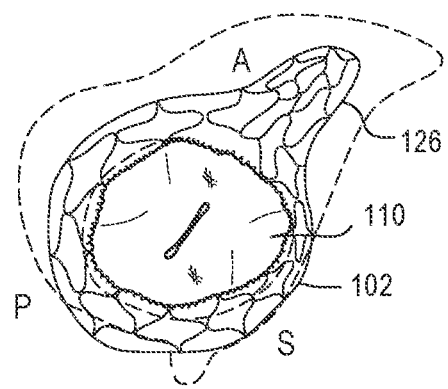
FIG. 54E is an illustration of a bottom view of a heart valve prosthesis according to an embodiment having braid or laser-cut wire frame for the lower tension arm.

FIG. 54E is an illustration of a bottom view of a heart valve prosthesis according to an embodiment having a covered braid or laser-cut frame for the lower tension arm. FIG. 54E shows the tubular frame 102 having an inner sleeve 110 sewn into the central aperture, with the two (2) panels extending upward (out of the page) in a ventricular direction. FIG. 54E shows the lower tension arm 126 oriented towards the anterior leaflet side of the ventricular ceiling, shown in dashed outline.

Figure 55A:
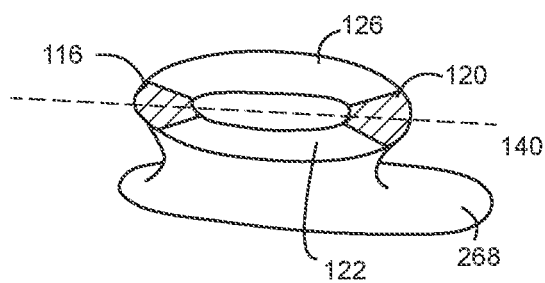
FIG. 55A is an illustration of a side perspective view of a valve having a circular hyperboloid (hourglass) shape and an RVOT tab.

FIG. 55A is an illustration of a side perspective view of a valve having a circular hyperboloid (hourglass) shape with an extended RVOT tab 268. Wire frame details are not shown since in practice the external surface would preferably be covered with Dacron polyester to facilitate in-growth. Distal fold area 120 and proximal fold area 116 are shown book-ending the anterior collar 122 and posterior-septal collar 126 along horizontal axis 140 with front anterior wall 110 and central channel 104 shown, according to an embodiment.

Figure 55B:
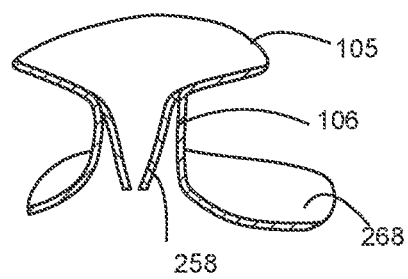
FIG. 55B is an illustration of a cut away view of a valve having a circular hyperboloid (hourglass) shape and RVOT tab.

FIG. 55B is an illustration of a cut away view of a valve having a circular hyperboloid (hourglass) shape and RVOT tab 268. FIG. 55B shows that inner leaflet 258 and flow control component inner frame (not visible) are attached to the inner surface of the annular frame, with collar portion 105 attached to subannular anchor portion 268 via wall portion 106. Here, it is only attached at the top edge although other non-limiting attachments are contemplated, e.g. mid-wall, multiple attachment points, etc.

FIG. 56A is an illustration of a side view of a vertically compressible valve 144 with internal non-extending leaflets and compressible orthogonal (wide) cells, in an expanded configuration 144.

FIG. 56B is an illustration of a side view of a vertically compressible valve with internal non-extending leaflets and compressible orthogonal (wide) cells, in a compressed configuration 206.

FIG. 57A is an illustration of a side view of a vertically compressible valve with extended leaflets and compressible orthogonal (wide) cells, in an expanded configuration 144.

FIG. 57B is an illustration of a side view of a vertically compressible valve with extended leaflets and compressible orthogonal (wide) cells, in a compressed configuration 206 where the wire frame is reduced in height and the extended leaflets are rolled up.

Figure 58A:
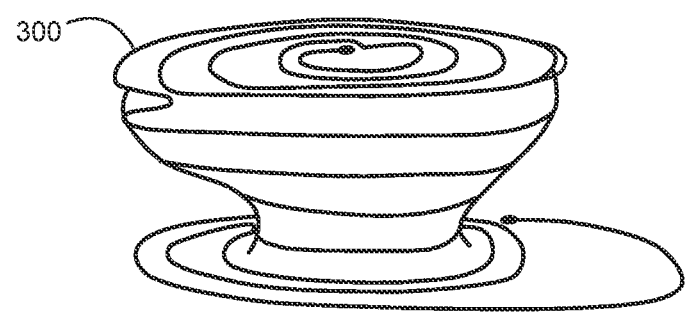
FIG. 58A is an illustration of a side perspective view of a valve formed from a single continuous wire, with an upper collar portion, an hourglass shape for the body portion, and an RVOT tab extending away from the lower edge of the body portion.

FIG. 58A is an illustration of a side perspective view of a valve formed from a single continuous wire 300, with an upper collar portion, an hourglass shape for the body portion, and an RVOT tab extending away from the lower edge of the body portion.

Figure 58B:
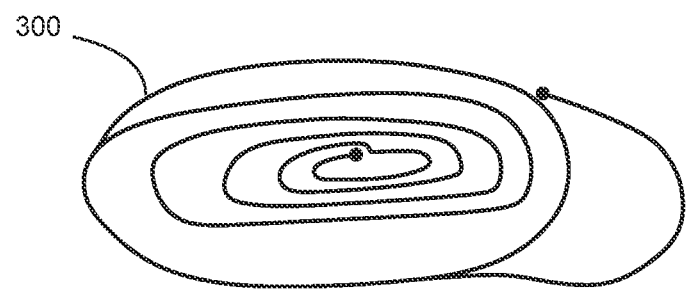
FIG. 58B is an illustration of a top view of a valve formed from a single continuous wire, with an upper collar portion, an hourglass shape for the body portion (not shown), and an RVOT tab extending away from the lower edge of the body portion.

FIG. 58B is an illustration of a top view of a valve formed from a single continuous wire 300, with an upper collar portion, an hourglass shape for the body portion (not shown), and an RVOT tab extending away from the lower edge of the body portion.

Figure 59:
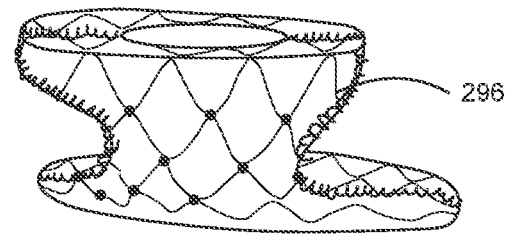
FIG. 59 is an illustration of a side perspective view of a valve formed from a series of wave-shaped wires connected at connection points, with an upper collar portion, an hourglass shape for the body portion, and an RVOT tab extending away from the lower edge of the body portion.

FIG. 59 is an illustration of a side perspective view of a valve formed from a series of wave-shaped wires 296 connected at connection points, with an upper collar portion, an hourglass shape for the body portion, and an RVOT tab extending away from the lower edge of the body portion.

Figure 60:
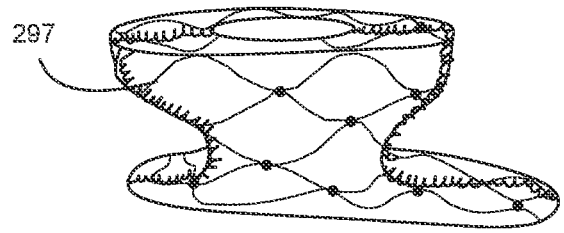
FIG. 60 is an illustration of a side perspective view of a valve formed from a series of zigzag-shaped wires connected at connection points, with an upper collar portion, an hourglass shape for the body portion, and an RVOT tab extending away from the lower edge of the body portion.

FIG. 60 is an illustration of a side perspective view of a valve formed from a series of horizontal wave-shaped wires 297 connected at connection points, with an upper collar portion, an hourglass shape for the body portion, and an RVOT tab extending away from the lower edge of the body portion. Sewing features are shown along the joining edges.

Figure 61:
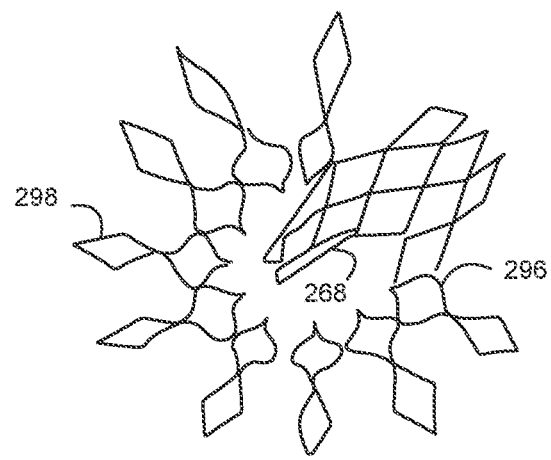
FIG. 61 is an illustration of a top view of flat wire frame having an RVOT tab of metal or metal alloy having compressible wire cells configured in a strain minimizing orientation to facilitate orthogonal loading and delivery of a prosthetic tricuspid valve.

FIG. 61 is an illustration of a top view of flat wire frame having an RVOT tab of metal or metal alloy having compressible wire cells configured in a strain minimizing orientation to facilitate orthogonal loading and delivery of a prosthetic tricuspid valve. FIG. 61 shows outer diamond cells 298 used for a collar portion with inner wave cells 296 used for a body portion of the outer frame, and diamond cells 298 used for the subannular tab 268.

Figure 62:
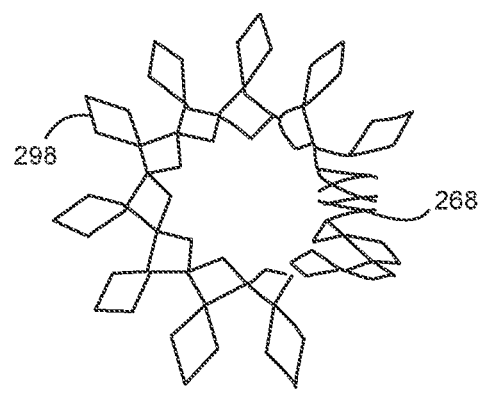
FIG. 62 is an illustration of a top view of a wire frame with RVOT tab in a funnel configuration (heat set) showing compressible wire cells configured in a strain minimizing orientation to facilitate orthogonal loading and delivery of a prosthetic tricuspid valve.

FIG. 62 is an illustration of a top view of a wire frame with RVOT tab in a funnel configuration (heat set) showing compressible wire cells configured in a strain minimizing orientation to facilitate orthogonal loading and delivery of a prosthetic tricuspid valve. FIG. 62 shows outer diamond cells 298 used for a collar portion with inner diamond cells 298 used for a body portion of the outer frame, and diamond cells used for the subannular tab 268.

Figure 63:
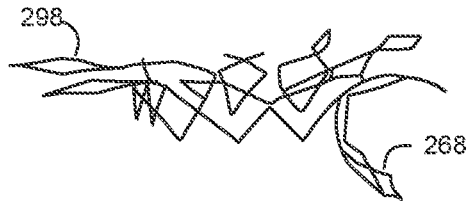
FIG. 63 is an illustration of a side view of a wire frame with RVOT tab in a funnel configuration (heat set) showing compressible wire cells configured in a strain minimizing orientation to facilitate orthogonal loading and delivery of a prosthetic tricuspid valve.

FIG. 63 is an illustration of a side view of a wire frame with RVOT tab in a funnel configuration (heat set) showing compressible wire cells configured in a strain minimizing orientation to facilitate orthogonal loading and delivery of a prosthetic tricuspid valve. FIG. 63 shows outer diamond cells 298 used for a collar portion with inner diamond cells 298 used for a body portion of the outer frame, and diamond cells 298 used for the subannular tab 268.

Figure 64:
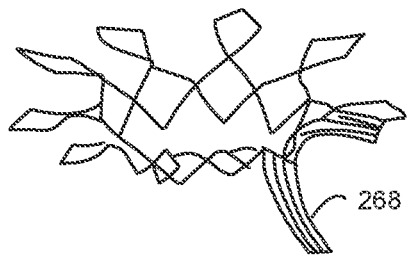
FIG. 64 is an illustration of a side perspective view of a wire frame with RVOT tab in a funnel configuration (heat set) showing compressible wire cells configured in a strain minimizing orientation to facilitate orthogonal loading and delivery of a prosthetic tricuspid valve.

FIG. 64 is an illustration of a side perspective view of a wire frame with RVOT tab in a funnel configuration (heat set) showing compressible wire cells configured in a strain minimizing orientation to facilitate orthogonal loading and delivery of a prosthetic tricuspid valve. FIG. 64 shows outer diamond cells 298 used for a collar portion with inner diamond cells 298 used for a body portion of the outer frame, and irregular shaped cells used for the subannular tab 268.

Figure 65A:
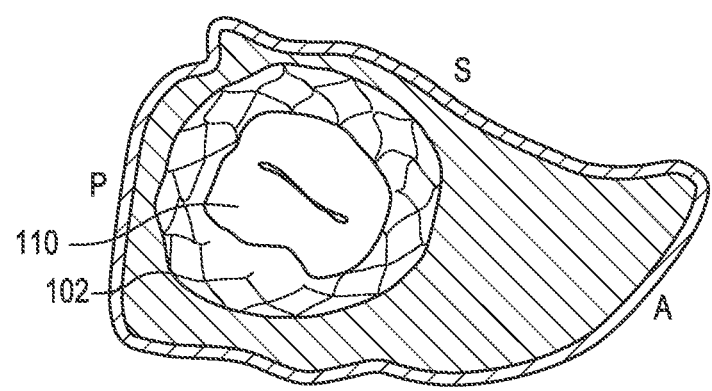
FIG. 65A is an illustration of a top view of a heart valve prosthesis according to an embodiment having braid or laser-cut wire frame and shown mounted within a cross-sectional view of the atrial floor at the annulus.

FIG. 65A is an illustration of a top view of a heart valve prosthesis according to an embodiment having braid or laser-cut wire frame 102 and shown mounted within a cross-sectional view of the atrial floor at the annulus.

Figure 65B:
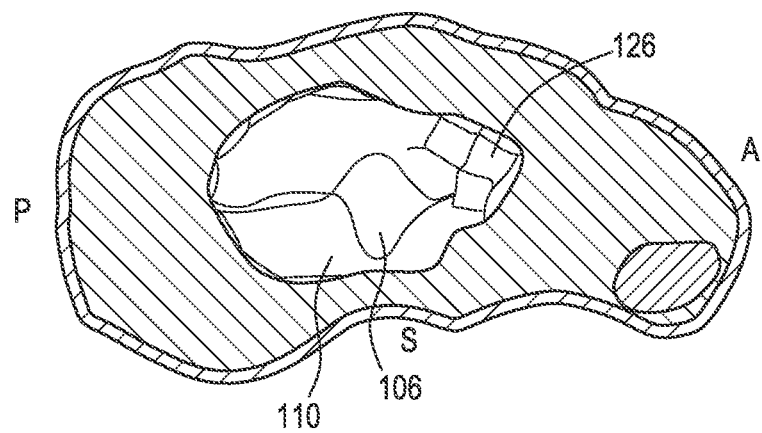
FIG. 65B is an illustration of a bottom view of a heart valve prosthesis according to an embodiment having braid or laser-cut wire frame for a lower tension arm and shown mounted within a cross-sectional view of the ventricular ceiling at the annulus.
Figure 66:
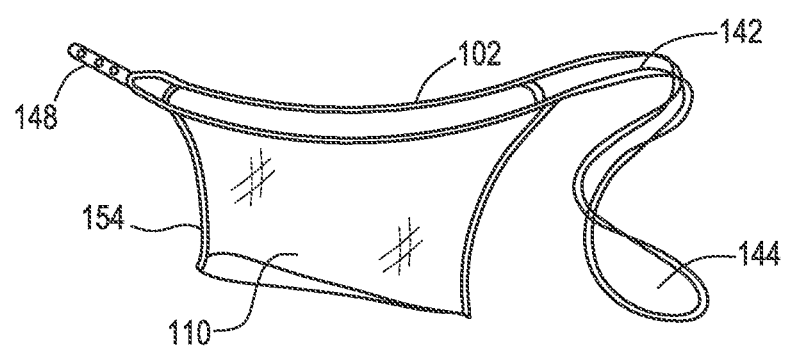
FIG. 66 is an illustration of a heart valve prosthesis according to an embodiment having a wire loop construction for the tubular frame, with two vertical support posts extending down the edge on opposing sides of the valve sleeve. During compression into the delivery catheter, the posts are engineered to fold horizontally during compression, and to elastically unfold during ejection to deploy the valve sleeve.

FIG. 65B is an illustration of a bottom view of a heart valve prosthesis according to an embodiment having braid or laser-cut wire frame 102 for a lower tension arm 126 and shown mounted within a cross-sectional view of the ventricular ceiling at the annulus. FIG. 65B shows the two-panel valve sleeve 110 in an open position 106, e.g. atrial systole and ventricular diastole. FIG. 66 shows the RVOT as a darkened circle.

FIG. 66 is an illustration of a heart valve prosthesis according to an embodiment having a wire loop construction for the tubular frame 102, with two vertical support posts 154 extending down the edge on opposing sides of the sleeve 110. During compression into the delivery catheter 118 (not shown), the posts 154 are engineered to fold horizontally during compression, and to elastically unfold during ejection to deploy the valve sleeve 110.

Figure 67:
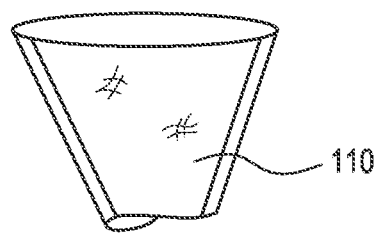
FIG. 67 is an illustration of a two-panel embodiment of an inner valve sleeve.

FIG. 67 is an illustration of a two-panel embodiment of an inner valve sleeve 110.

Figure 68A:
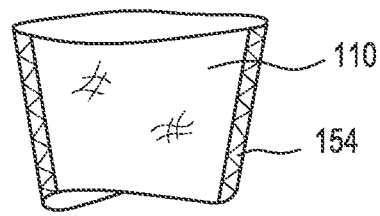
FIG. 68A is an illustration of one embodiment of an inner valve sleeve having two rigid support posts.

FIG. 68A is an illustration of one embodiment of an inner valve sleeve 110 having two rigid support posts 154.

Figure 68B:
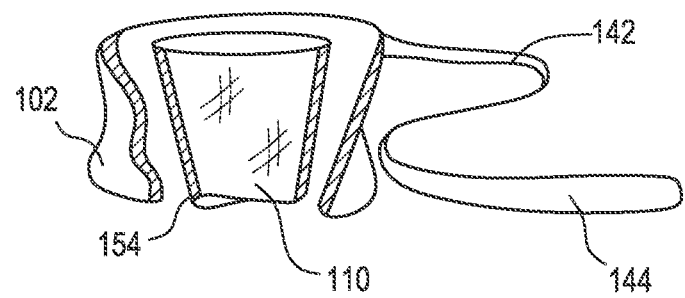
FIG. 68B is an illustration of a cut away plan view of a heart valve prosthesis according to an embodiment, and shows a two-post embodiment of the inner panel valve sleeve mounted within the inner space defined by the tubular frame.

FIG. 68B is an illustration of a cut away plan view of a heart valve prosthesis according to an embodiment, and shows a two-post embodiment 154 of the inner panel valve sleeve 110 mounted within the inner space defined by the tubular frame 102.

Figure 69:
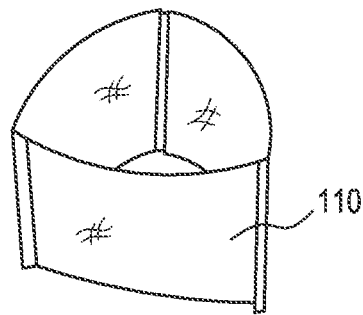
FIG. 69 is an illustration of a three-panel embodiment of an inner valve sleeve.

FIG. 69 is an illustration of a three-panel embodiment of an inner valve sleeve 110.

Figure 70A:
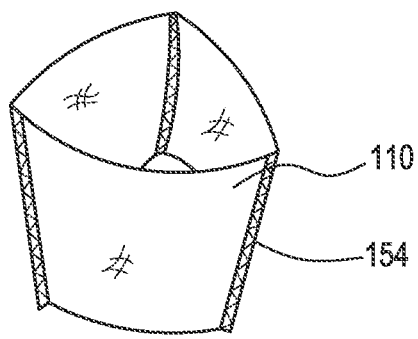

FIG. 70A is an illustration of a three-panel embodiment of an inner valve sleeve 110 having three rigid support posts 154.

Figure 70B:
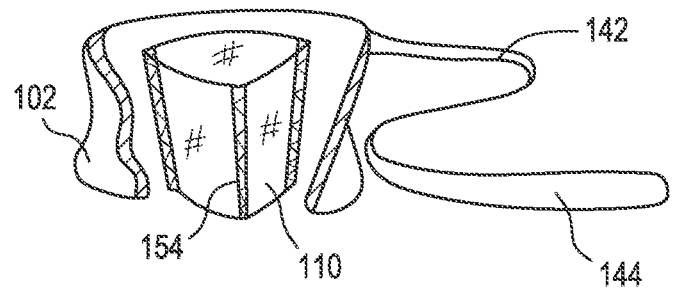

FIG. 70B is an illustration of a cut away plan view of a heart valve prosthesis according to an embodiment, and shows a three-panel, three-post embodiment of the inner panel valve sleeve mounted within the inner space defined by the tubular frame.

Figure 71A:
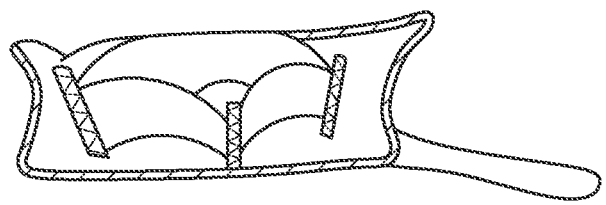

FIG. 71A is an illustration of one embodiment of a partial cut-away interior view of a tri-leaflet embodiment of a low profile, e.g. 8-20 mm, side-loaded prosthetic valve.

Figure 71B:
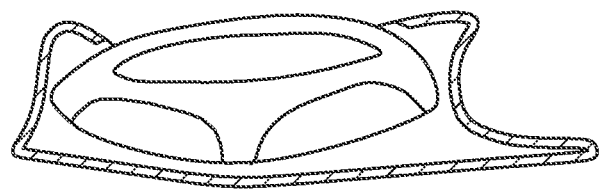

FIG. 71B is an illustration of another embodiment of a partial cut-away interior view of a tri-leaflet embodiment of a low profile, e.g. 8-20 mm, side-loaded prosthetic valve.

Figure 71C:
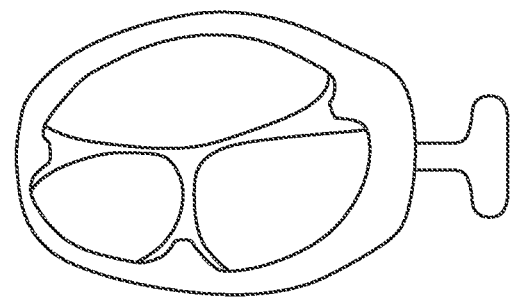

FIG. 71C is an illustration of a top view of a tri-leaflet embodiment of a low profile, e.g. 8-20 mm, side-loaded prosthetic valve.

Figure 72:
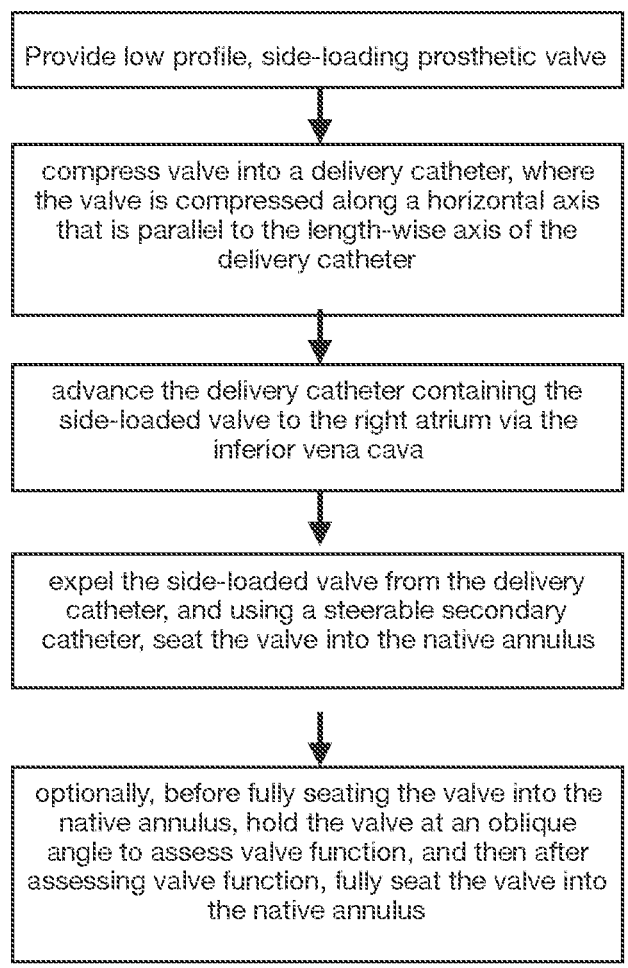

FIG. 72 is a flowchart describing one set of method steps for delivery of a low profile, side-loaded prosthetic valve.

Figure 73:
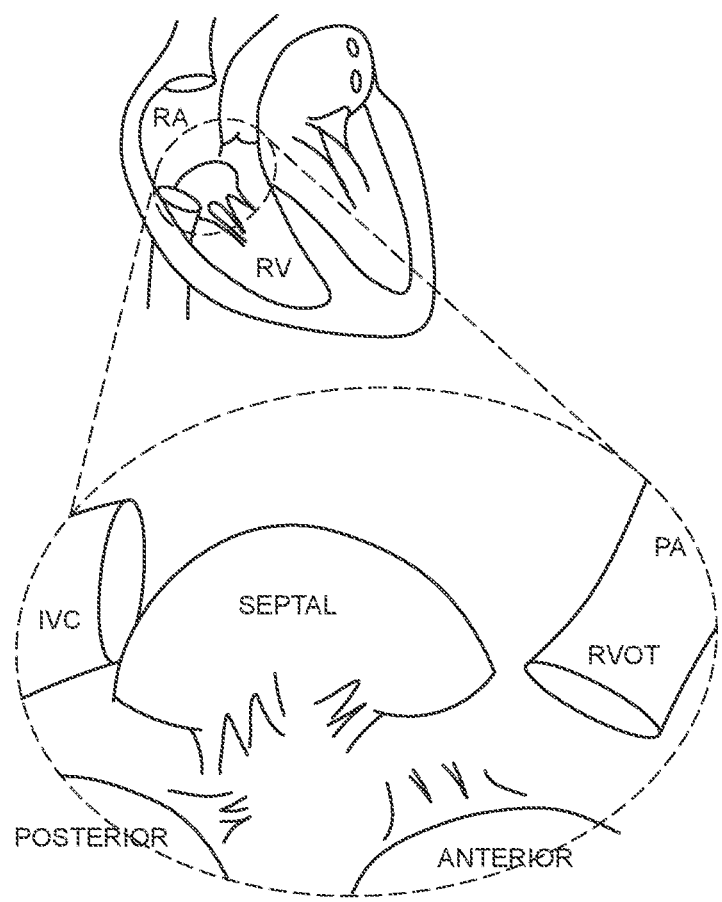

FIG. 73 is an illustration of a side view of human heart anatomy, with an inset showing the geometric relationship between the inferior vena cava (IVC), the three leaflet cusps of the tricuspid valve—anterior, posterior, septal—the right ventricular outflow tract (RVOT), and the pulmonary artery (PA).

Figure 74:
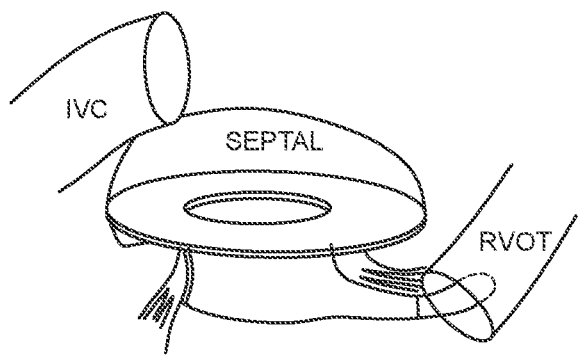

FIG. 74 is an illustration of a side perspective view of a side delivered valve seated with the native tricuspid annulus with collar portion laying atrially above the tricuspid annulus and leaflets, lower body portion extending into and through the annulus to provide corrective hemodynamic flow from the flow control component, and RVOT footer tab and RVOT/PA extender wire.

Figure 75A:
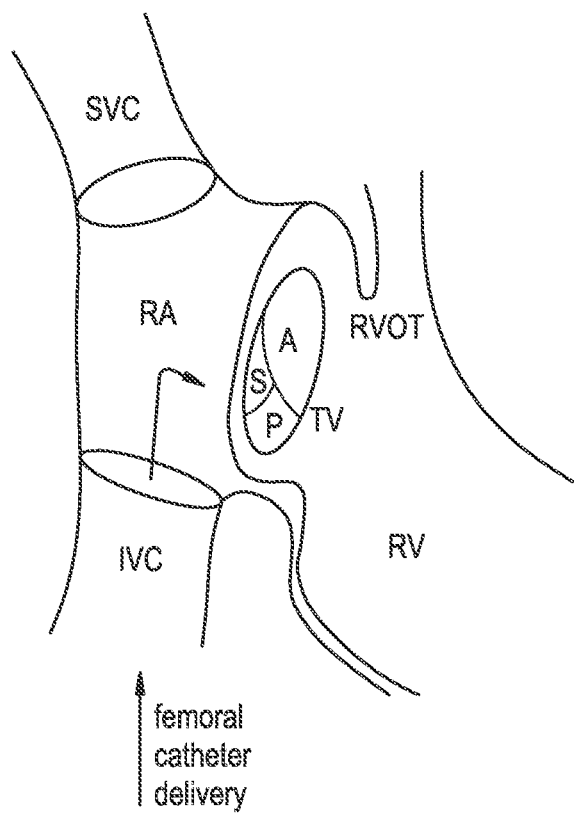

FIG. 75A is an illustration of a plan view of a native right atrium of a human heart, and shows the superior vena cava (SVC), the inferior vena cava (IVC), the right atrium (RA), the tricuspid valve and annulus (TCV), the anterior leaflet (A), the posterior leaflet (P), the septal leaflet (S), the right ventricle (RV), and the right ventricular outflow tract (RVOT).

Figure 75B:
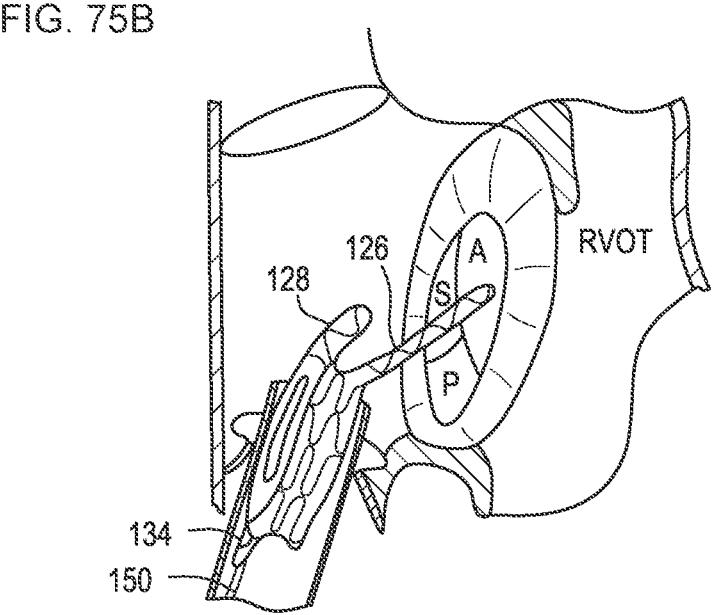

FIG. 75B is an illustration of a heart valve prosthesis according to an embodiment being delivered to tricuspid valve annulus. FIG. 75B shows braided/laser cut-frame lower tension arm 126 ejected from the delivery catheter 118 and being directed through the annulus and towards the right ventricular outflow tract.

Figure 75C:
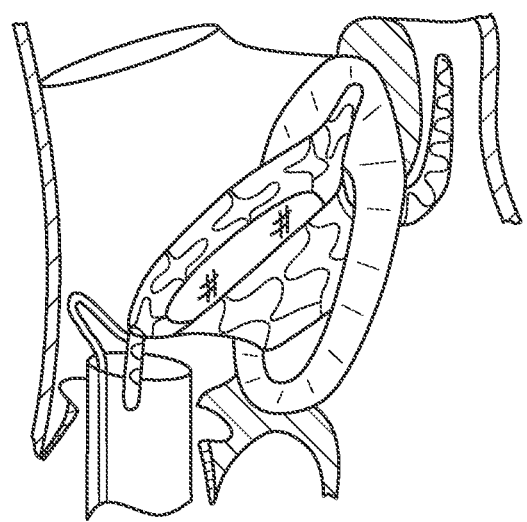

FIG. 75C is an illustration of a heart valve prosthesis according to an embodiment being delivered to tricuspid valve annulus. FIG. 75C shows braided/laser cut-frame lower tension arm 126 and upper tension arm 128 ejected from the delivery catheter 118, the lower tension arm directed through the annulus and into the right ventricular outflow tract, and the upper tension arm staying in a supra-annular position, and causing a passive, structural anchoring of the distal side of the valve about the annulus.

Figure 75D:
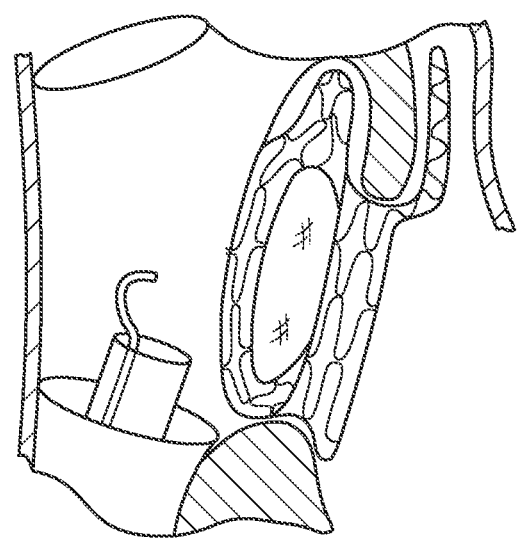

FIG. 75D is an illustration of a heart valve prosthesis according to an embodiment being delivered to tricuspid valve annulus. FIG. 75D shows the entire braided/laser cut-frame valve 102 ejected from the delivery catheter 118, the lower tension arm directed through the annulus and into the right ventricular outflow tract, and the upper tension arm staying in a supra-annular position, and causing a passive, structural anchoring of the distal side of the valve about the annulus, and at least one tissue anchor anchoring the proximal side of the prosthesis into the annulus tissue.

FIG. 76A is an illustration of a heart valve prosthesis according to an embodiment being delivered to tricuspid valve annulus and shows step 1 in a valve assessment process. FIG. 76A shows braided/laser cut-frame lower tension arm ejected from the delivery catheter and being directed through the annulus and towards the right ventricular outflow tract.

FIG. 76B is an illustration of a heart valve prosthesis according to an embodiment being delivered to tricuspid valve annulus, and shows Step 2 in a valve assessment process. FIG. 76B shows braided/laser cut-frame lower tension arm and upper tension arm ejected from the delivery catheter, the lower tension arm directed through the annulus and into the right ventricular outflow tract, and the upper tension arm staying in a supra-annular position, and causing a passive, structural anchoring of the distal side of the valve about the annulus. FIG. 76B shows that a steerable anchoring catheter can hold the valve at an oblique angle in a pre-attachment position, so that the valve can be assessed, and once valve function and patient conditions are correct, the steerable anchoring catheter can push the proximal side of the valve from its oblique angle, down into the annulus. The steerable anchoring catheter can then install one or more anchoring elements.

FIG. 76C is an illustration of a heart valve prosthesis according to an embodiment that has been delivered to tricuspid valve annulus, and shows Step 3 in a valve assessment process. FIG. 76C shows the entire braided/laser cut-frame valve ejected from the delivery catheter, the lower tension arm directed through the annulus and into the right ventricular outflow tract, and the upper tension arm staying in a supra-annular position, and causing a passive, structural anchoring of the distal side of the valve about the annulus, and at least one tissue anchor anchoring the proximal side of the prosthesis into the annulus tissue.

FIG. 77A is an illustration of a side perspective view of a valve that is vertically compressed 206 without folding and loaded into a delivery catheter 138. By using horizontal rather than tradition vertical diamond shaped cells, the frame can be compressed from top to bottom. This allows for orthogonal delivery of a much larger diameter valve than can be delivered using tradition axial compression. Additionally, the orthogonal delivery provides access from the IVC to the tricuspid annulus using a subannular distal-side anchoring tab 268. Normally, a traditional axial valve would need to make a 90-120 degree right turn before expelling the transcatheter valve. By providing a valve that can be directly expelled into the distal side of the tricuspid annulus, the sharp right turn is avoided due to the inventive design.

FIG. 77B is an illustration of a side perspective view of a partially expelled or released valve 402 from a delivery catheter 138 that allows a transition from native blood flow through the native tricuspid valve to a partial flow around the prosthetic valve and into the native annulus and a partial flow thru an inflow end 132 and out of an outflow end 134 of the prosthetic valve into the native annulus. Guide wire 311 is shown pig-tailed into the pulmonary artery.

The rigid pull rod/wire 310 in some embodiments is engineered to ride over the guide wire, thus allowing the valve to be delivered exactly where intended. The distal subannular tab 268 can be directed into the right ventricular outflow tract (RVOT) and provides anchoring to the valve while it is being positioned and assessed.

FIG. 77C is an illustration of a side perspective view of a fully expelled or released valve from a delivery catheter 138 that is lodged using the distal tab 268 against the distal surface of the annulus and held using the rigid pusher 310 elevated at an angle above the native annulus prior to complete deployment. This allows a further transition from native blood flow through the native tricuspid valve with a partial flow around the prosthetic valve and into the native annulus, and an increasing partial flow thru an inflow end 132 and out of an outflow end 134 of the prosthetic valve into the native annulus. FIG. 77C also shows guide wire 311 and proximal side subannular anchoring tab (proximal tab) 270.

FIG. 77D is an illustration of a side perspective view of a fully expelled or released valve 100 that is completely seated into the native annulus, and that allows a smooth transition from native blood flow to a full, complete flow thru the prosthetic valve into the native annulus. The valve is anchored using subannular distal tab 268 and subannular proximal tab 270, and supra-annular (atrial) upper tension arm 271. Corrected replacement flow is shown by flow thru an inflow end 132 and out of an outflow end 134 of the prosthetic valve into the native annulus.

FIG. 78A is an illustration of a side perspective view of a valve that is vertically compressed 206 without folding and loaded into a delivery catheter 138, and shows an extended inner leaflet component in a rolled configuration. Guide wire 311 and RVOT tab 268 are shown extended into the pulmonary artery and allowing the valve to be precisely delivered.

FIG. 78B is an illustration of a side perspective view of a partially expelled or released valve 402 from a delivery catheter 138, with a partially unfurled extended inner leaflet component 258. FIG. 78B shows a transition from native blood flow through the native tricuspid valve to a partial flow around the prosthetic valve and into the native annulus and a partial flow 132, 134 thru the prosthetic valve into the native annulus. The valve has a distal mid-wall arch above the RVOT tab 268 for engaging the native annulus.

FIG. 78C is an illustration of a side perspective view of a fully expelled or released valve, with a fully unfurled extended inner leaflet component 258, where the valve is lodged using the distal tab 268 against the distal surface of the annulus and held using the rigid pusher 310 elevated at an angle above the native annulus prior to complete deployment. This allows a further transition from native blood flow through the native tricuspid valve with a partial flow around the prosthetic valve and into the native annulus, and an increasing partial flow thru an inflow end 132 and out of an outflow end 134 of the prosthetic valve into the native annulus. FIG. 78C shows distal mid-wall arch engaging the distal native annulus and shows proximal mid-wall arch raised above the native annulus in preparation for a smooth transition to prosthetic flow when the valve is seated in the native annulus.

FIG. 78D is an illustration of a side perspective view of a fully expelled or released valve 100 that is completely seated into the native annulus, and that allows a smooth transition from native blood flow to a full, complete flow thru the prosthetic valve into the native annulus. The valve is anchored using subannular distal tab 268 and subannular proximal tab 270, and supra-annular (atrial) upper tension arm 271. Corrected replacement flow through leaflets 258 is shown by flow thru an inflow end 132 and out of an outflow end 134 of the prosthetic valve into the native annulus.

FIG. 79A is an illustration of a side view of a compressed valve within a delivery catheter 138. FIG. 79A shows how a central tube or wire 310 can be distally attached to the distal edge or RVOT tab 118 and by pushing on the rigid tube or wire 310, the compressed valve 136 can be pulled from the end closest to the catheter 138 deployment end 139. This pulling action avoids pushing the valve out of the delivery catheter 138, causing additional radial expansion and radial forces that can damage the valve when it is compressed within the delivery catheter 138.

FIG. 79B is an illustration of a side view of a partially compressed valve 402 that is partially released from the delivery catheter 138 and shows how blood flow can begin its transition. The gradual, smooth transition from native flow to flow through the prosthesis by pulling on the rigid pusher 310 attached to the distal subannular anchoring tab 268 avoids the sphincter effect where the heart is cut off from the flow, resulting in a dry pump action, and causing heart failure. When the valve is partially open exposing only a part of the collar 105, on a small fraction of right atrial blood flow is going through the prosthetic valve, but the washing effect provides for a smooth transition to a larger volume going through the prosthesis.

FIG. 79C is an illustration of a side view of a partially compressed valve 402, that is partially released from the delivery catheter 138 and shows how blood flow can begin its transition. The gradual, smooth transition from native flow to flow through the prosthesis from an inflow end 132 to an outflow end 134 by pulling from the distal subannular anchoring tab 268 avoids the sphincter effect where the heart is cut off from the flow, resulting in a dry pump action, and causing heart failure. When the valve is partially open exposing only a part of the collar 105, on a small fraction of right atrial blood flow is initially going through the prosthetic valve, with an increasing amount transitioning from flow around the valve to flow going through the valve, with the washing effect providing for a smooth transition to a larger volume going through the prosthesis.

FIG. 79D is an illustration of a side view of an expanded uncompressed valve orthogonally released from the delivery catheter 138, and still releasably attached to the distal pull wire/deployment control wire or hypotube 310 via the distal tab/RVOT tab 268. Collar 105 and frame body 106 are fully expanded permitting functioning of the flow control component 130. FIG. 79D shows that the valve can be positioned or re-positioned using the rigid pull wire 310. Since the blood flow is not blocked, this allows the interventionalist the opportunity and time to ensure correct orientation of the valve, especially where the distal tab (mitral)/RVOT tab (tricuspid) embodiment is used to assist in anchoring. Once proper orientation is achieved, the valve can be slowly seated into the native tricuspid annulus, providing a smooth blood flow transition from the native flow to the prosthetic flow. FIG. 79D also shows release mechanism 410 for releasing the rigid pull device 310 from the valve body by pulling on a trigger wire that is attached to a release hook, lock, bead, or other mechanism.

FIG. 79E is an illustration of a side view of an uncompressed valve showing transition to all blood flow through the flow control component 130 of the valve and no flow around the valve during to atrial sealing of the anterior collar 122 and posterior-septal collar 126.

FIG. 80A is an illustration of a side view of a rolled valve 136 within a delivery catheter 138 and being advanced by a distal rigid pull wire/draw-wire 310 (or far-side push-pull wire) attached to the leading edge of the valve collar.

FIG. 80B is an illustration of a side view of a partially unrolled valve that has been deployed from the catheter by action of the pushing rod 310 on the distal upper edge 272.

FIG. 80C is an illustration of a side view of a partially released unrolled valve that has been deployed from the catheter, and shows pushing rod 310 maintaining connection to the valve while anterior collar portion 122 is unrolled and leaflets 258 are uncovered.

FIG. 80D is an illustration of a side view of a completely released unrolled valve where the rigid pull device 310 is used to position the valve within the native annulus and obtain a good perivalvular seal with anterior collar 122 and posterior-septal collar 126 to transition to blood flow through the prosthetic leaflets 258. FIG. 80D also shows release mechanism 410 for releasing the rigid pull device 310 from the valve body by pulling on a trigger wire that is attached to a release hook, lock, bead, or other mechanism.

FIG. 81 is an illustration of a side view of a compressed combination construction valve 307 within a delivery catheter, and shows draw/pulling wire attached to the forward end of the compressed valve to pull the valve out of the catheter.

FIG. 82A is an illustration of a side or plan transparent view of a delivery catheter 138 loaded with a side-delivered (orthogonal) valve 100 having a tension arm 269 with a guidewire collar element 265 and a guidewire 311 extending through the guidewire collar 265 with a guidewire sheath 310 pushing against the guidewire collar element 265. Inset shows a non-limiting example of a guidewire collar 265 attached to a tension arm 269 with guidewire 311 through the aperture of the guidewire collar 265 and hypotube sheath 310 stopped by the larger circumference of the guidewire collar 265, permitting pushing on the tension arm 269 to pull the valve 100 out of the delivery catheter 138.

FIG. 82B is another non-limiting example of a guidewire collar 291 attached to a tension arm 269 with guidewire 311 through the aperture of the guidewire collar 291 and hypotube sheath 310 stopped by the larger circumference of the guidewire collar 291, permitting pushing on the tension arm 269 to pull the valve out of the delivery catheter 138.

FIG. 82C is another non-limiting example of a guidewire collar 292 attached to a tension arm 269 with guidewire 311 through the aperture of the guidewire collar 292 and hypotube sheath 310 stopped, as it slides over the guidewire—the guidewire is in the lumen of the hypotube sheath—by the larger circumference of the guidewire collar 292, permitting pushing on the tension arm 269 to pull the valve out of the delivery catheter 138.

FIG. 82D is another non-limiting example of a guidewire collar 293 attached to a tension arm 269 with guidewire 311 through the aperture of the guidewire collar 293 and hypotube sheath 310 stopped by the larger circumference of the guidewire collar 293, permitting pushing on the tension arm 269 to pull the valve out of the delivery catheter 138.

FIG. 83A is an illustration of step 1 of a 6-step process for delivery of an orthogonal prosthetic valve to the tricuspid annulus. FIG. 83A shows a 0.035 guidewire 311 with hypotube sheath delivered to the right ventricular outflow tract (RVOT).

FIG. 83B is an illustration of step 2 of a 6-step process for delivery of an orthogonal prosthetic valve to the tricuspid annulus. FIG. 83B shows a 24-34 Fr delivery catheter 138 being advanced over the guidewire 311 to and through the native tricuspid annulus to the right ventricle.

FIG. 83C is an illustration of step 3 of a 6-step process for delivery of an orthogonal prosthetic valve to the tricuspid annulus. FIG. 83C shows a capsule/compression catheter 301 having a compressed valve 136 therein where the capsule 301 is loaded into the proximal end of the delivery catheter 138 and the valve is withdrawn from the capsule 301 into the delivery catheter 138, with sheathed guidewire 311 threaded through the valve and providing a wire path to the RVOT, planned deployment location.

FIG. 83D is an illustration of step 4 of a 6-step process for delivery of an orthogonal prosthetic valve to the tricuspid annulus. FIG. 83D shows the valve advanced up and out of the catheter 138 and deployed into the native annulus by pushing on the outer sheath 310 of the guidewire 311 to pull the valve 144 up the catheter and into position. Tension arm 269 is used to position the expanded valve 144.

FIG. 83E is an illustration of step 5 of a 6-step process for delivery of an orthogonal prosthetic valve to the tricuspid annulus. FIG. 83E shows a pushing catheter 310, or steerable catheter, being used to push the proximal side of the valve 144 into position within the annulus.

FIG. 83F is an illustration of step 6 of a 6-step process for delivery of an orthogonal prosthetic valve to the tricuspid annulus. FIG. 83F shows withdrawal of the delivery system and anchoring of the proximal side of the valve to the annular tissue. FIG. 83F shows expanded valve 144 with atrial sealing collar facing the atrium, valve body deployed within the native annulus and extending from atrium to ventricle, anchoring tension arm 269 is shown extending subannularly into the RVOT area, and guidewire collar/ball 265 is shown at a distal end of the tension arm. Guide wire 311 and delivery catheter 138 are being withdrawn.

FIG. 84A is an illustration of step 1 of an 8-step process for delivery of an orthogonal prosthetic valve to the tricuspid annulus. FIG. 84A shows an 8 Fr guidewire 311 advanced from the femoral through the inferior vena cava (IVC) to the right atrium.

FIG. 84B is an illustration of step 2 of an 8-step process for delivery of an orthogonal prosthetic valve to the tricuspid annulus. FIG. 84B shows a balloon catheter 294 advanced over the guidewire 311 through the native annulus and into the RVOT to expand and push aside valve and leaflet tissue, chordae tendineae that might tangle transcatheter delivery of the valve.

FIG. 84C is an illustration of step 3 of an 8-step process for delivery of an orthogonal prosthetic valve to the tricuspid annulus. FIG. 84C shows a 0.035 guidewire 311 with hypotube sheath delivered to the right ventricular outflow tract (RVOT).

FIG. 84D is an illustration of step 4 of an 8-step process for delivery of an orthogonal prosthetic valve to the tricuspid annulus. FIG. 84D shows a 24-34 Fr delivery catheter 138 being advanced over the guidewire 311 to and through the native tricuspid annulus to the right ventricle.

FIG. 84E is an illustration of step 5 of an 8-step process for delivery of an orthogonal prosthetic valve 136 (compressed configuration) to the tricuspid annulus. FIG. 84E shows a capsule 301 having a compressed valve 136 therein where the capsule 301 or compression catheter is loaded into the proximal end of the delivery catheter 138 and the compressed valve 136 is advanced through the delivery catheter 138, with sheathed guidewire 311 threaded through the valve and providing a wire path to the RVOT, planned deployment location.

FIG. 84F is an illustration of step 6 of an 8-step process for delivery of an orthogonal prosthetic valve to the tricuspid annulus. FIG. 84F shows the expanded valve 144 advanced up the catheter, expelled, and deployed into the native annulus by pushing on the outer sheath (310) of the guidewire 311 to pull the valve, pulling from the guidewire collar at the distal end of the tension arm 269, up the catheter 138 and into position. Tension arm 269 is used to position the valve.

FIG. 84G is an illustration of step 7 of an 8-step process for delivery of an orthogonal prosthetic valve to the tricuspid annulus. FIG. 84G shows a hypotube sheath/guidewire 311, or steerable catheter, being used to push the proximal side of (114) nearest the IVC or access point, of the valve 144 into position within the annulus.

FIG. 84H is an illustration of step 8 of an 8-step process for delivery of an orthogonal prosthetic valve to the tricuspid annulus. FIG. 84H shows withdrawal of the delivery system and anchoring of the proximal side of the valve 144 to the annular tissue and anchoring the distal side of the valve using the distal subannular anchoring tension arm 269.

FIG. 85A is an illustration of step 1 of a 6-step process for delivery of an orthogonal prosthetic valve to the tricuspid annulus. FIG. 85A shows the compressed side-deliverable valve 136 advanced up the catheter 138 using pushing sheath or rod 310 and deployed into the native annulus by following the track of the guidewire 311, which is disposed in the lumen of the pushing sheath 310.

FIG. 85B is an illustration of step 2 of a 6-step process for delivery of an orthogonal prosthetic valve to the tricuspid annulus. FIG. 85B shows pushing on the outer sheath 310 of the guidewire 311 tracking along with the guidewire 311 threaded through the guidewire collar 265 to pull the valve up the catheter 138 and into position, partially expelling the valve with tension arm 269 into the RVOT and the distal side of the valve lodged against the annular wall.

FIG. 85C is an illustration of step 3 of a 6-step process for delivery of an orthogonal prosthetic valve to the tricuspid annulus. FIG. 85C shows a pushing catheter 310 extending from the delivery catheter 138 being used to push the proximal side of the valve into position within the annulus.

FIG. 85D is an illustration of step 4 of a 6-step process for delivery of an orthogonal prosthetic valve to the tricuspid annulus. FIG. 85D shows how tension arm 269 is used to position the valve while pushing catheter 310 being used to push the proximal side of the valve into position within the annulus to allow the proximal subannular anchoring tab (proximal tab) 270 to engage and secure the valve against the native tissue.

FIG. 85E is an illustration of step 5 of a 6-step process for delivery of an orthogonal prosthetic valve to the tricuspid annulus. FIG. 85E shows how pushing catheter 310 delivers a tissue anchor 278 to secure the proximal side of the valve to the annular tissue.

FIG. 85F is an illustration of step 6 of a 6-step process for delivery of an orthogonal prosthetic valve to the tricuspid annulus. FIG. 85F shows withdrawal of the delivery system and anchoring of the proximal side of the valve to the annular tissue.

FIG. 86A is an illustration of step 1 of a 6-step process for delivery of a co-axial prosthetic valve to the tricuspid annulus. FIG. 86A shows a 0.035 guidewire 311 with hypotube sheath delivered to the right ventricular outflow tract (RVOT) through the superior vena cava (SVC).

FIG. 86B is an illustration of step 2 of a 6-step process for delivery of a co-axial prosthetic valve to the tricuspid annulus. FIG. 86B shows a 24-34 Fr delivery catheter 138 being advanced over the guidewire to and through the native tricuspid annulus to the right ventricle.

FIG. 86C is an illustration of step 3 of a 6-step process for delivery of a co-axial prosthetic valve to the tricuspid annulus. FIG. 86C shows a capsule 301 having a compressed valve 136 therein where the capsule 301 is loaded into the proximal end of the delivery catheter 138 and the valve is either withdrawn from the capsule 301 into the delivery catheter 138 for further advancement or capsule 301 is used to advance within the delivery catheter 138, with sheathed guidewire 311 threaded through the valve and providing a wire path to the RVOT, planned deployment location.

FIG. 86D is an illustration of step 4 of a 6-step process for delivery of a co-axial prosthetic valve to the tricuspid annulus. FIG. 86D shows the expanded valve 144 advanced up and expelled out of the catheter 138 and deployed into the native annulus by pushing on the outer sheath (310) of the guidewire 311 to pull the valve by the ball 265 up the catheter 138 and into position. Tension arm 269 is used as a ball 265 mount, to position the valve during deployment, and to provide subannular anchoring on the distal side.

FIG. 86E is an illustration of step 5 of a 6-step process for delivery of a co-axial prosthetic valve to the tricuspid annulus. FIG. 86E shows a pushing catheter 310 extending from the delivery catheter 138 being used to push the proximal side of the valve into position within the annulus.

FIG. 86F is an illustration of step 6 of a 6-step process for delivery of a co-axial prosthetic valve to the tricuspid annulus. FIG. 86F shows withdrawal of the delivery system and anchoring of the proximal side of the expanded valve 144 to the annular tissue FIG. 87A is an illustration of the trans-septal (femoral-IVC) delivery of a low profile, e.g. 8-20 mm, side-loaded prosthetic mitral valve shown partially housed within the delivery catheter, and partially ejected for deployment into the native mitral annulus.

FIG. 87B is an illustration of a low profile, e.g. 8-20 mm, side-loaded prosthetic mitral valve shown housed within the delivery catheter FIG. 87C is an illustration of a low profile, e.g. 8-20 mm, side-loaded prosthetic mitral valve shown partially housed within a delivery catheter and partially laterally ejected from the delivery catheter and positioned for deployment against the anterior side of the native mitral annulus.

FIG. 87D is an illustration of a low profile, e.g. 8-20 mm, side-loaded prosthetic mitral valve shown ejected from the delivery catheter and positioned against the anterior side of the native mitral annulus.

FIG. 87E is an illustration of a side or plan view of a low profile, e.g. 8-20 mm, side-loaded prosthetic valve shown deployed into the native mitral annulus.

FIG. 88A is an illustration of a rotational lock embodiment where the prosthetic valve is delivered to the native annulus with an off-set sub-annular tension arm/tab 126 positioned below the native annulus, and an off-set supra-annular tension arm/tab 128 positioned above the native annulus, while the tubular frame 102 is partially rolled off-set from the annular plane along a longitudinal axis.

FIG. 88B is an illustration of a rotational lock embodiment where the prosthetic valve is delivered to the native annulus with an off-set sub-annular tension arm/tab 126 positioned below the native annulus, and an off-set supra-annular tension arm/tab 128 positioned above the native annulus, while the tubular frame 102 is rolled into functional position parallel to the annular plane. Once the valve is rolled into position, and the tension arms are locked against the sub-annular and supra-annular tissues, the valve can also be further anchored using traditional anchoring elements as disclosed herein.

FIG. 89A is an illustration of a heart valve prosthesis according to an embodiment being delivered to tricuspid valve annulus. FIG. 89A shows wire-frame lower tension arm 144 ejected from the delivery catheter 118 and being directed through the annulus and towards the right ventricular outflow tract. FIG. 89A shows an embodiment of an accordion-compressed low profile valve 122 and shows the lower tension arm directed towards the anterior leaflet for placement into the RVOT.

FIG. 89B is an illustration of a heart valve prosthesis according to an embodiment being delivered to tricuspid valve annulus. FIG. 89B shows wire-frame lower tension arm 144 and upper tension arm 142 ejected from the delivery catheter 118, the lower tension arm directed through the annulus and into the right ventricular outflow tract, and the upper tension arm staying in a supra-annular position, and causing a passive, structural anchoring of the distal side of the valve about the annulus. FIG. 89B also shows steerable anchoring catheter 150 attached to a proximal anchoring tab 152. While the valve is held in a pre-seating position, the valve can be assessed, and once valve function and patient conditions are correct, the steerable anchoring catheter can push the proximal side of the valve from its oblique angle, down into the annulus. The steerable anchoring catheter can then install one or more anchoring elements 152.

FIG. 89C is an illustration of a heart valve prosthesis according to an embodiment being delivered to tricuspid valve annulus. FIG. 89C shows the entire valve ejected from the delivery catheter, the wire-frame lower tension arm directed through the annulus and into the right ventricular outflow tract, and the upper wire-frame tension arm staying in a supra-annular position, and causing a passive, structural anchoring of the distal side of the valve about the annulus, and at least one tissue anchor anchoring the proximal side of the prosthesis into the annulus tissue.

FIGS. 90A-90C show a plan view of a tissue anchor having a floating radio-opaque marker. This figure shows the tissue anchor accessing the annular tissue with the radio-opaque marker at the distal end of the anchor and in contact with the atrial surface of the annular tissue. This figure shows the tissue anchor advancing into the annular tissue with the radio-opaque marker threaded onto the tissue anchor and maintaining position on the atrial surface of the annular tissue. This figure shows the tissue anchor completely advanced into the annular tissue such that the tissue anchor and the threaded floating marker are now adjacent, indicating the desired depth, tension, and/or plication of the tissue anchor with respect to the annular tissue FIG. 91A is an illustration of a plan view of a tissue anchor having a straight thread and a constant pitch.

FIG. 91B is an illustration of a plan view of a tissue anchor having a straight thread and a variable pitch.

FIG. 91C is an illustration of a plan view of a tissue anchor having a tapered thread and a constant pitch.

FIG. 91D is an illustration of a plan view of a tissue anchor having a sunken taper thread and a variable pitch.

FIG. 92A is an illustration of Step 1 of a 4-step process for clipping a low profile valve to annular tissue, as shown here in a non-limiting example of clipping to a proximal or anterior side of the native annulus. FIG. 92A shows a low profile valve being inserted into the valve annulus and low profile valve having an integral anchor delivery conduit or channel with an anchor disposed in the lumen of the channel and an anchor delivery catheter attached to the anchor.

FIG. 92B is an illustration of Step 2 of a 4-step process for clipping a low profile valve to annular tissue, as shown here in a non-limiting example of clipping to a proximal or anterior side of the native annulus. FIG. 92B shows a low profile valve completely deployed within the valve annulus and an integral anchor delivery conduit or channel with an anchor disposed in the lumen of the channel and an anchor delivery catheter attached to the anchor.

FIG. 92C is an illustration of Step 3 of a 4-step process for clipping a low profile valve to annular tissue, as shown here in a non-limiting example of clipping to a proximal or anterior side of the native annulus. FIG. 92C shows the anchor being pushed out of the lumen of the delivery conduit or channel and into the annular tissue.

FIG. 92D is an illustration of Step 4 of a 4-step process for clipping a low profile valve to annular tissue, as shown here in a non-limiting example of clipping to a proximal or anterior side of the native annulus. FIG. 92D shows the anchor in a locked position after being pushed out of the lumen of the delivery conduit or channel and into the annular tissue, thus anchoring the proximal side of the low profile valve.

FIG. 93A is an illustration of Step 1 of a 5-step process for clipping a low profile valve to annular tissue, as shown here in a non-limiting example of clipping to a proximal or anterior side of the native annulus. FIG. 93A shows catheter delivery of an attachment wire with the clip housed within the lumen of the clip delivery catheter.

FIG. 93B is an illustration of Step 2 of a 5-step process for clipping a low profile valve to annular tissue, as shown here in a non-limiting example of clipping to a proximal or anterior side of the native annulus. FIG. 93B shows the clip delivery catheter inserted into an intra-annular space and shows an attachment wire and shows the clip housed within the lumen of the clip delivery catheter.

FIG. 93C is an illustration of Step 3 of a 5-step process for clipping a low profile valve to annular tissue, as shown here in a non-limiting example of clipping to a proximal or anterior side of the native annulus. FIG. 93C shows a receiver element ejected from the delivery catheter and positioned behind tissue to be captured.

FIG. 93D is an illustration of Step 4 of a 5-step process for clipping a low profile valve to annular tissue, as shown here in a non-limiting example of clipping to a proximal or anterior side of the native annulus. FIG. 93D shows an anchor element piercing the annular tissue and inserting into a receiver element.

FIG. 93E is an illustration of Step 5 of a 5-step process for clipping a low profile valve to annular tissue, as shown here in a non-limiting example of clipping to a proximal or anterior side of the native annulus. FIG. 93E shows that the clip delivery catheter is withdrawn and the anchor element and receiver element are connected to the annular tissue and connected by connector wire to the low profile valve.

FIG. 94 is a flowchart showing an embodiment of a method for orthogonal delivery of implantable prosthetic valve to a desired location in the body, the method comprising the steps: advancing a delivery catheter to the desired location in the body and delivering an expandable prosthetic valve to the desired location in the body by releasing the valve from the delivery catheter, wherein the valve comprises a tubular frame having a flow control component mounted within the tubular frame and configured to permit blood flow in a first direction through an inflow end of the valve and block blood flow in a second direction, opposite the first direction, through an outflow end of the valve, wherein the valve is compressible to a compressed configuration for introduction into the body using a delivery catheter for implanting at a desired location in the body, said compressed configuration having a long-axis oriented at an intersecting angle of between 45-135 degrees to the first direction, and expandable to an expanded configuration having a long-axis oriented at an intersecting angle of between 45-135 degrees to the first direction, wherein the long-axis of the compressed configuration of the valve is substantially parallel to a lengthwise cylindrical axis of the delivery catheter, wherein the valve has a height of about 5-60 mm and a diameter of about 25-80 mm.

FIG. 95 is a flowchart showing an embodiment of a method for orthogonally loading an implantable prosthetic valve into a delivery catheter, the method comprising the steps: loading an implantable prosthetic valve into a tapering fixture or funnel attached to a delivery catheter, wherein the valve comprises a tubular frame having a flow control component mounted within the tubular frame and configured to permit blood flow in a first direction through an inflow end of the valve and block blood flow in a second direction, opposite the first direction, through an outflow end of the valve, wherein said loading is perpendicular or substantially orthogonal to the first direction, wherein the valve is compressible to a compressed configuration for introduction into the body using a delivery catheter for implanting at a desired location in the body, said compressed configuration having a long-axis oriented at an intersecting angle of between 45-135 degrees to the first direction, and expandable to an expanded configuration having a long-axis oriented at an intersecting angle of between 45-135 degrees to the first direction, wherein the long-axis of the compressed configuration of the valve is substantially parallel to a lengthwise cylindrical axis of the delivery catheter, wherein the valve has a height of about 5-60 mm and a diameter of about 25-80 mm.

FIG. 96A is an illustration of an open cross-section view of a low profile, side-loaded prosthetic valve frame and shows an example of a commercially available valve 110 mounted within the inner surface of frame 102.

FIG. 96B is an illustration of a low profile, side-loaded valve frame according to an embodiment having a braid or laser-cut construction for the tubular frame 102. FIG. 96B shows a longer lower tension arm 126 for extending sub-annularly towards the RVOT, and a shorter upper tension arm 128 for extending over the atrial floor. FIG. 96B shows an elongated two-panel valve sleeve 110 that extends into the sub-annular leaflet space. The tubular frame 102 shown in FIG. 96B is about 10 mm in height and the valve sleeve 110 extends about 10 mm below the bottom of the tubular frame, resulting in a valve 20 mm in total height.

FIG. 96C is an illustration of a low profile, side-loaded valve frame prosthesis having a braid or laser-cut tubular frame and extended valve sleeve compressed within a delivery catheter 118. FIG. 96C shows the valve attached to a secondary steerable catheter 150 for ejecting, positioning, and anchoring the valve frame. The secondary catheter 150 can also be used to retrieve a failed deployment of a valve frame.

FIG. 96D is an illustration of a valve frame having a braid or laser-cut tubular frame shown partially compressed within a delivery catheter, and partially ejected from the delivery catheter. FIG. 96D shows that while the valve frame is still compressed the lower tension arm can be manipulated through the leaflets and chordae tendineae to find a stable anterior-side lodgment for the distal side of the valve frame.

FIG. 96E is an illustration of a valve frame having a braid or laser-cut tubular frame engaging the tissue on the anterior side of the native annulus with the curved distal sidewall of the tubular frame sealing around the native annulus. FIG. 96E shows the valve frame held by the steerable secondary catheter at an oblique angle while valve frame function is assessed.

FIG. 96F is an illustration of a heart valve frame prosthesis having a braid or laser-cut tubular frame fully deployed into the tricuspid annulus. The distal side of the valve is shown engaging the tissue on the anterior side of the native annulus with the curved distal sidewall of the tubular frame sealing around the native annulus, and with the proximal sidewall tension-mounted into the posterior side of the native annulus.

FIG. 97A is an illustration of a valve frame according to an embodiment being delivered to tricuspid valve annulus. FIG. 97A shows braided/laser cut-frame lower tension arm 126 ejected from the delivery catheter 118 and being directed through the annulus and towards the right ventricular outflow tract.

FIG. 97B is an illustration of a valve frame according to an embodiment being delivered to tricuspid valve annulus. FIG. 97B shows braided/laser cut-frame lower tension arm 126 and upper tension arm 128 ejected from the delivery catheter 118, the lower tension arm directed through the annulus and into the right ventricular outflow tract, and the upper tension arm staying in a supra-annular position, and causing a passive, structural anchoring of the distal side of the valve frame about the annulus.

FIG. 97C is an illustration of a valve frame prosthesis according to an embodiment being delivered to tricuspid valve annulus. FIG. 97C shows the entire braided/laser cut-frame 102 ejected from the delivery catheter 118, the lower tension arm directed through the annulus and into the right ventricular outflow tract, and the upper tension arm staying in a supra-annular position, and causing a passive, structural anchoring of the distal side of the valve frame about the annulus, and at least one tissue anchor anchoring the proximal side of the prosthesis into the annulus tissue. FIG. 97C shows how a commercial valve can be secondarily deployed into the opening of the frame.

FIG. 98A is an illustration of a valve frame according to an embodiment being delivered to tricuspid valve annulus and shows step 1 in a valve assessment process. FIG. 98A shows braided/laser cut-frame lower tension arm ejected from the delivery catheter and being directed through the annulus and towards the right ventricular outflow tract.

FIG. 98B is an illustration of a valve frame prosthesis according to an embodiment being delivered to tricuspid valve annulus, and shows Step 2 in a valve frame assessment process. FIG. 98B shows braided/laser cut-frame lower tension arm and upper tension arm ejected from the delivery catheter, the lower tension arm directed through the annulus and into the right ventricular outflow tract, and the upper tension arm staying in a supra-annular position, and causing a passive, structural anchoring of the distal side of the valve frame about the annulus. FIG. 98B shows that a steerable anchoring catheter can hold the valve frame at an oblique angle in a pre-attachment position, so that the valve frame can be assessed, and once valve frame function and patient conditions are correct, the steerable anchoring catheter can push the proximal side of the valve frame from its oblique angle, down into the annulus. The steerable anchoring catheter can then install one or more anchoring elements.

FIG. 98C is an illustration of a valve frame prosthesis according to an embodiment that has been delivered to tricuspid valve annulus, and shows Step 3 in a valve frame assessment process. FIG. 98C shows the entire braided/laser cut-frame valve frame ejected from the delivery catheter, the lower tension arm directed through the annulus and into the right ventricular outflow tract, and the upper tension arm staying in a supra-annular position, and causing a passive, structural anchoring of the distal side of the valve about the annulus, and at least one tissue anchor anchoring the proximal side of the prosthesis into the annulus tissue. FIG. 98C shows how a commercial valve can be secondarily deployed into the opening of the frame.

FIG. 99A is an illustration of a commercial valve that can be mounted within the disclosed frame.

FIG. 99B is an illustration of a commercial valve that can be mounted within the frame 110 having two rigid support posts 154.

FIG. 99C is an illustration of a commercial valve that can be mounted within the frame, having a three-panel embodiment.

FIG. 99D is an illustration of a commercial valve that can be mounted within the frame, having a three-panel embodiment and having three rigid support posts 154.

FIG. 100 is an illustration of the heart and shows an approximate location of the valves, the left and right atrium, the left and right ventricles, and the blood vessels that enter and exit the chambers of the heart.

FIG. 101A is an illustration of a low profile, e.g. 8-20 mm, side-loaded valve frame shown housed within the delivery catheter.

FIG. 101B is an illustration of a low profile, e.g. 8-20 mm, side-loaded valve frame shown partially housed within a delivery catheter and partially laterally ejected from the delivery catheter and positioned for deployment against the anterior side of the native annulus.

FIG. 101C is an illustration of a low profile, e.g. 8-20 mm, side-loaded valve frame shown ejected from the delivery catheter and positioned against the anterior side of the native annulus.

FIG. 101D is an illustration of a side or plan view of a low profile, e.g. 8-20 mm, side-loaded valve frame shown deployed into the native annulus of a heart valve.

FIG. 101E is an illustration of a side view of two types of deliverable valves, the first is a self-expanding transcatheter valve, and the second is a commercially-approved transcatheter balloon-expandable prosthetic valve being vertically deployed into the central lumen of the already (laterally, horizontally, orthogonally) deployed valve frame.

FIG. 101F is an illustration of a side view of a commercially approved transcatheter self-expandable prosthetic valve mounted within the central lumen of the already (laterally, horizontally, orthogonally) deployed valve frame.

FIG. 101G is an illustration of a side view of a commercially approved transcatheter balloon-expandable prosthetic valve mounted within the central lumen of the already (laterally, horizontally, orthogonally) deployed valve frame.

FIG. 102A is an illustration of step 1 of a 4-step process for delivery of a co-axial prosthetic valve to the tricuspid annulus. FIG. 102A shows a co-axial compressed valve 136 being loaded using a compression capsule or compression catheter 301 into the distal end of the delivery catheter 138, with the sheathed 310 guidewire 311 threaded through the tension arm 269 and guidewire collar 291.

FIG. 102B is an illustration of step 2 of a 4-step process for delivery of a co-axial prosthetic valve to the tricuspid annulus. FIG. 102B shows a co-axial compressed valve 136 being delivered to the distal end of the delivery catheter 138, with the hypotube 310 sheathed guidewire 311 threaded through the tension arm 269 and channel-type guidewire collar 291.

FIG. 102C is an illustration of step 3 of a 4-step process for delivery of a co-axial prosthetic valve to the tricuspid annulus. FIG. 102C shows a co-axial compressed valve 136 partially expelled from the delivery catheter 138, with the tension arm 269 and channel-type guidewire collar 291 being positioned into the RVOT.

FIG. 102D is an illustration of step 4 of a 4-step process for delivery of a co-axial prosthetic valve to the tricuspid annulus. FIG. 102D shows that, once positioned, the self-expanding valve 144 can be completely expelled from the delivery catheter and deployed as a prosthetic valve.

FIG. 103A is an illustration of step 1 of a 7-step process for delivery of a co-axial prosthetic balloon-expandable valve to the tricuspid annulus. FIG. 103A shows a 0.035 guidewire 31 with hypotube sheath 310 delivered to the right ventricular outflow tract (RVOT) through the superior vena cava (SVC).

FIG. 103B is an illustration of step 2 of a 7-step process for delivery of a co-axial prosthetic valve to the tricuspid annulus. FIG. 103B shows a 24-34 Fr delivery catheter 138 being advanced over the guidewire 311/310 to and through the native tricuspid annulus to the right ventricle.

FIG. 103C is an illustration of step 3 of a 7-step process for delivery of a co-axial prosthetic valve to the tricuspid annulus. FIG. 103C shows a capsule 301 having a compressed valve 143 therein where the capsule 301 is loaded into the proximal end of the delivery catheter 138 and the valve is withdrawn/delivered from the capsule 301 into the delivery catheter 138, with sheathed guidewire 311 threaded through the valve and providing a wire path to the RVOT, planned deployment location.

FIG. 103D is an illustration of step 4 of a 7-step process for delivery of a co-axial prosthetic valve to the tricuspid annulus. FIG. 103D shows the valve 143 advanced up the catheter and deployed into the native annulus by pushing on the outer hypotube sheath 310 of the guidewire 311 to pull the valve 143 up the catheter 138 and into position. Tension arm 266 is used to position the valve.

FIG. 103E is an illustration of step 5 of a 7-step process for delivery of a co-axial prosthetic valve to the tricuspid annulus. FIG. 103E shows a steerable balloon catheter 295 being used to push the proximal side of the valve 143 into position within the annulus.

FIG. 103F is an illustration of step 6 of a 7-step process for delivery of a co-axial prosthetic valve to the tricuspid annulus. FIG. 103F shows balloon expansion of the co-axial valve 143 in the native annulus and anchoring of the proximal side of the valve to the annular tissue.

FIG. 103G is an illustration of step 7 of a 7-step process for delivery of a co-axial prosthetic valve to the tricuspid annulus. FIG. 103G shows withdrawal of the delivery system and anchoring of the proximal side of the expanded valve 143 to the annular tissue.

FIG. 104A is an illustration of step 1 of a 6-step process for delivery of a co-axial prosthetic valve to the tricuspid annulus. FIG. 104A shows the delivery catheter deployed to the native annulus.

FIG. 104B is an illustration of step 2 of a 6-step process for delivery of a co-axial prosthetic valve to the tricuspid annulus. FIG. 104B shows a co-axial balloon-expandable valve 143 being loaded into the delivery catheter 138, with the hypotube 310 sheathed guidewire 311 threaded through the tension arm 269 and channel-type guidewire collar 291.

FIG. 104C is an illustration of step 3 of a 6-step process for delivery of a co-axial balloon-expandable prosthetic valve 143 to the tricuspid annulus. FIG. 104C shows a co-axial valve 143 being delivered to the proximal end of the delivery catheter 138, with the hypotube 310 sheathed guidewire 311 threaded through the tension arm and guidewire collar 291.

FIG. 104D is an illustration of step 4 of a 6-step process for delivery of a co-axial prosthetic valve to the tricuspid annulus. FIG. 104D shows a co-axial valve 143 partially expelled from the delivery catheter 138, with the tension arm and guidewire collar 291 being positioned into the RVOT. FIG. 104D shows balloon catheter 295 connected to the valve 143.

FIG. 104E is an illustration of step 5 of a 6-step process for delivery of a co-axial prosthetic valve to the tricuspid annulus. FIG. 104E shows that, once positioned and expanded by the balloon catheter 294, the balloon-expanded co-axial valve 143 can be completely deployed into the inner circumference of the native annulus to function as a prosthetic valve.

FIG. 104F is an illustration of step 6 of a 6-step process for delivery of a co-axial prosthetic valve 143 to the tricuspid annulus. FIG. 104F shows the deployed valve.

EXAMPLES

Example—One embodiment of an orthogonally delivered transcatheter prosthetic valve has a tubular frame with a flow control component mounted within the tubular frame and configured to permit blood flow in a first direction through an inflow end of the valve and block blood flow in a second direction, opposite the first direction, through an outflow end of the valve, wherein the valve is compressible to a compressed configuration for introduction into the body using a delivery catheter for implanting at a desired location in the body, said compressed configuration having a long-axis oriented at an intersecting angle of between 45-135 degrees to the first direction, and expandable to an expanded configuration having a long-axis oriented at an intersecting angle of between 45-135 degrees to the first direction, wherein the long-axis of the compressed configuration of the valve is substantially parallel to a lengthwise cylindrical axis of the delivery catheter, wherein the valve has a height of about 5-60 mm and a diameter of about 25-80 mm. Importantly, this heart valve substitute does not have a traditional valve configuration, can be delivered to the heart using the inferior vena cava (IVC/femoral transcatheter delivery pathway compressed within a catheter, and expelled from the catheter to be deployed without open heart surgery.

Example—In another embodiment of a transcatheter valve, comprises: a cylindrical tubular frame having a height of about 5-60 mm and an outer diameter of about 25-80 mm, said tubular frame comprised of a braid, wire, or laser-cut wire frame having a substantially circular central aperture, said tubular frame partially covered with a biocompatible material; a collapsible flow control component disposed within the central aperture, said sleeve having a height of about 5-60 mm and comprised of at least two opposing leaflets that provide a reciprocating closable channel from a heart atrium to a heart ventricle; an upper tension arm attached to a distal upper edge of the tubular frame, the upper tension arm comprised of stent, segment of tubular frame, wire loop or wire frame extending from about 10-30 mm away from the tubular frame; a lower tension arm extending from a distal side of the tubular frame, the lower tension arm comprised of stent, segment of tubular frame, wire loop or wire frame extending from about 10-40 mm away from the tubular frame; and at least one tissue anchor to connect the tubular frame to native tissue.

Example—In another embodiment of a transcatheter valve, there is provided a feature wherein the sleeve is shaped as a conic cylinder, said top end having a diameter of 30-35 mm and said bottom end having a diameter of 8-20 mm.

Example—In another embodiment of a transcatheter valve, there is provided a feature wherein the cover is comprised of polyester, polyethylene terephthalate, decellularized pericardium, or a layered combination thereof.

Example—In an embodiment, there is also provided a method for orthogonal delivery of implantable prosthetic valve to a desired location in the body, the method comprising the steps: (i) advancing a delivery catheter to the desired location in the body and delivering an expandable prosthetic valve to the desired location in the body by releasing the valve from the delivery catheter, wherein the valve comprises a tubular frame having a flow control component mounted within the tubular frame and configured to permit blood flow in a first direction through an inflow end of the valve and block blood flow in a second direction, opposite the first direction, through an outflow end of the valve, wherein the valve is compressible to a compressed configuration for introduction into the body using a delivery catheter for implanting at a desired location in the body, said compressed configuration having a long-axis oriented at an intersecting angle of between 45-135 degrees to the first direction, and expandable to an expanded configuration having a long-axis oriented at an intersecting angle of between 45-135 degrees to the first direction, wherein the long-axis of the compressed configuration of the valve is substantially parallel to a lengthwise cylindrical axis of the delivery catheter, wherein the valve has a height of about 5-60 mm and a diameter of about 25-80 mm.

Example—In an embodiment, there is also provided a method for orthogonally loading an implantable prosthetic valve into a delivery catheter, the method comprising the steps: loading an implantable prosthetic valve sideways into a tapering fixture or funnel attached to a delivery catheter, wherein the valve comprises a tubular frame having a flow control component mounted within the tubular frame and configured to permit blood flow in a first direction through an inflow end of the valve and block blood flow in a second direction, opposite the first direction, through an outflow end of the valve, wherein the valve is compressible to a compressed configuration for introduction into the body using a delivery catheter for implanting at a desired location in the body, said compressed configuration having a long-axis oriented at an intersecting angle of between 45-135 degrees to the first direction, and expandable to an expanded configuration having a long-axis oriented at an intersecting angle of between 45-135 degrees to the first direction, wherein the long-axis of the compressed configuration of the valve is substantially parallel to a lengthwise cylindrical axis of the delivery catheter, wherein the valve has a height of about 5-60 mm and a diameter of about 25-80 mm.

Example—In an embodiment, there is also provided a method for orthogonally loading an implantable prosthetic valve into a delivery catheter, the method comprising the steps: (i) loading an implantable prosthetic valve into a tapering fixture or funnel attached to a delivery catheter, wherein the valve comprises a tubular frame having a flow control component mounted within the tubular frame and configured to permit blood flow in a first direction through an inflow end of the valve and block blood flow in a second direction, opposite the first direction, through an outflow end of the valve, wherein said loading is perpendicular or substantially orthogonal to the first direction, wherein the valve is compressible to a compressed configuration for introduction into the body using a delivery catheter for implanting at a desired location in the body, said compressed configuration having a long-axis oriented at an intersecting angle of between 45-135 degrees to the first direction, and expandable to an expanded configuration having a long-axis oriented at an intersecting angle of between 45-135 degrees to the first direction, wherein the long-axis of the compressed configuration of the valve is substantially parallel to a lengthwise cylindrical axis of the delivery catheter, wherein the valve has a height of about 5-60 mm and a diameter of about 25-80 mm.

Example—The transcatheter prosthetic heart valve may be percutaneously delivered using a transcatheter process via the femoral through the IVC, carotid, sub-xyphoid, intercostal access across the chest wall, and trans-septal to the mitral annulus through the fossa ovalis. The device is delivered via catheter to the right or left atrium and is expanded from a compressed shape that fits with the internal diameter of the catheter lumen. The compressed valve is loaded external to the patient into the delivery catheter, and is then pushed out of the catheter when the capsule arrives to the atrium. The cardiac treatment technician visualizes this delivery using available imaging techniques such as fluoroscopy or ultrasound, and in an embodiment the valve self-expands upon release from the catheter since it is constructed in part from shape-memory material, such as Nitinol®, a nickel-titanium alloy used in biomedical implants.

In another embodiment, the valve may be constructed of materials that requires balloon-expansion after the capsule has been ejected from the catheter into the atrium.

The atrial collar/frame and the flow control component are expanded to their functional diameter, as they are deployed into the native annulus, providing a radial tensioning force to secure the valve. Once the frame is deployed about the tricuspid annulus, fasteners secure the device about the native annulus. Additional fastening of the device to native structures may be performed, and the deployment is complete. Further adjustments using hemodynamic imaging techniques are contemplated to ensure the device is secure, is located and oriented as planned, and is functioning as a substitute or successor to the native tricuspid valve.

Example—One embodiment of an orthogonally delivered transcatheter prosthetic valve frame has a tubular frame, wherein the valve frame is compressible to a compressed configuration for introduction into the body using a delivery catheter for implanting at a desired location in the body, said compressed configuration having a long-axis oriented at an intersecting angle of between 45-135 degrees to the central, cylindrical axis of the native annulus, and expandable to an expanded configuration having a long-axis oriented at an intersecting angle of between 45-135 degrees to the central, cylindrical axis of the native annulus, wherein the long-axis of the compressed configuration of the valve is substantially parallel to a lengthwise cylindrical axis of the delivery catheter, wherein the valve has a height of about 5-60 mm and a diameter of about 25-80 mm. This heart valve frame can be delivered to the heart using the inferior vena cava (IVC/femoral transcatheter delivery pathway compressed within a catheter, and expelled from the catheter to be deployed without open heart surgery.

Example—In another embodiment of a transcatheter valve frame, comprises: a cylindrical tubular frame having a height of about 5-60 mm and an outer diameter of about 25-80 mm, said tubular frame comprised of a braid, wire, or laser-cut wire frame having a substantially circular central aperture, said tubular frame partially covered with a biocompatible material; an upper tension arm attached to a distal upper edge of the tubular frame, the upper tension arm comprised of stent, segment of tubular frame, wire loop or wire frame extending from about 10-30 mm away from the tubular frame; a lower tension arm extending from a distal side of the tubular frame, the lower tension arm comprised of stent, segment of tubular frame, wire loop or wire frame extending from about 10-40 mm away from the tubular frame; and at least one tissue anchor to connect the tubular frame to native tissue.

Example—In an embodiment, there is also provided a method for orthogonal delivery of implantable prosthetic valve frame to a desired location in the body, the method comprising the steps: (i) advancing a delivery catheter to the desired location in the body and delivering an expandable prosthetic valve frame to the desired location in the body by releasing the valve frame from the delivery catheter, wherein the valve frame is compressible to a compressed configuration for introduction into the body using a delivery catheter for implanting at a desired location in the body, said compressed configuration having a long-axis oriented at an intersecting angle of between 45-135 degrees to the central, cylindrical axis of the native annulus, and expandable to an expanded configuration having a long-axis oriented at an intersecting angle of between 45-135 degrees to the central, cylindrical axis of the native annulus, wherein the long-axis of the compressed configuration of the valve frame is substantially parallel to a lengthwise cylindrical axis of the delivery catheter, wherein the valve frame has a height of about 5-60 mm and a diameter of about 25-80 mm.

Example—In an embodiment, there is also provided a method for orthogonally loading an implantable prosthetic valve frame into a delivery catheter, the method comprising the steps: loading an implantable prosthetic valve frame sideways into a tapering fixture or funnel attached to a delivery catheter, wherein the valve frame is compressible to a compressed configuration for introduction into the body using a delivery catheter for implanting at a desired location in the body, said compressed configuration having a long-axis oriented at an intersecting angle of between 45-135 degrees to the central, cylindrical axis of the native annulus, and expandable to an expanded configuration having a long-axis oriented at an intersecting angle of between 45-135 degrees to the central, cylindrical axis of the native annulus, wherein the long-axis of the compressed configuration of the valve frame is substantially parallel to a lengthwise cylindrical axis of the delivery catheter, wherein the valve frame has a height of about 5-60 mm and a diameter of about 25-80 mm.

Example—The transcatheter prosthetic heart valve may be percutaneously delivered using a transcatheter process via the femoral through the inferior vena cava (IVC), superior vena cava (SVC), jugular vein, brachial vein, sub-xyphoid, intercostal access across the chest wall, and trans-septal through the fossa ovalis. The device is delivered via catheter to the right or left atrium and is expanded from a compressed shape that fits with the internal diameter of the catheter lumen. The compressed valve is loaded external to the patient into the delivery catheter, and is then pushed out of the catheter when the capsule arrives to the atrium. The cardiac treatment technician visualizes this delivery using available imaging techniques such as fluoroscopy or ultrasound, and in an embodiment the valve frame self-expands upon release from the catheter since it is constructed in part from shape-memory material, such as Nitinol®, a nickel-titanium alloy used in biomedical implants.

In another embodiment, the valve frame may be constructed of materials that requires balloon-expansion after the capsule has been ejected from the catheter into the atrium. The atrial collar/frame is expanded to their functional diameter, and deployed into the native annulus, providing a radial tensioning force to secure the valve frame. Once the frame is deployed about the tricuspid annulus, fasteners secure the device about the native annulus. Additional fastening of the device to native structures may be performed, and the deployment is complete. Further adjustments using hemodynamic imaging techniques are contemplated in order to ensure the device is secure, is located and oriented as planned, and is functioning.

Example—Compression methods. In another embodiment, there is provided a method of compressing, wherein the implantable prosthetic heart valve is rolled or folded into a compressed configuration using a step selected from the group consisting of: (i) unilaterally rolling into a compressed configuration from one side of the annular support frame; (ii) bilaterally rolling into a compressed configuration from two opposing sides of the annular support frame; (iii) flattening the annular support frame into two parallel panels that are substantially parallel to the long-axis, and then rolling the flattened annular support frame into a compressed configuration; and (iv) flattening the annular support frame along a vertical axis to reduce a vertical dimension of the valve from top to bottom.

The embodiments herein and the various features and advantageous details thereof are explained more fully with reference to the non-limiting embodiments that are illustrated in the accompanying drawings and detailed in the following description. Descriptions of well-known components and processing techniques are omitted so as to not unnecessarily obscure the embodiments herein. The examples used herein are intended merely to facilitate an understanding of ways in which the embodiments herein may be practiced and to further enable those of skill in the art to practice the embodiments herein. Accordingly, the examples should not be construed as limiting the scope of the embodiments herein.

Rather, these embodiments are provided so that this disclosure will be thorough and complete, and will fully convey the scope of the inventive concepts to those skilled in the art. Like numbers refer to like elements throughout. As used herein the term "and/or" includes any and all combinations of one or more of the associated listed items.

The terminology used herein is for the purpose of describing particular embodiments only and is not intended to limit the full scope of the claims. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

Unless defined otherwise, all technical and scientific terms used herein have the same meanings as commonly understood by one of ordinary skill in the art. Nothing in this disclosure is to be construed as an admission that the embodiments described in this disclosure are not entitled to antedate such disclosure by virtue of prior invention. As used in this document, the term "comprising" means "including, but not limited to."

Many modifications and variations can be made without departing from its spirit and scope, as will be apparent to those skilled in the art. Functionally equivalent methods and apparatuses within the scope of the disclosure, in addition to those enumerated herein, will be apparent to those skilled in the art from the foregoing descriptions. Such modifications and variations are intended to fall within the scope of the appended claims. The present disclosure is to be limited only by the terms of the appended claims, along with the full scope of equivalents to which such claims are entitled. It is to be understood that this disclosure is not limited to particular methods, reagents, compounds, compositions or biological systems, which can, of course, vary. It is also to be understood that the terminology used herein is for the purpose of describing particular embodiments only, and is not intended to be limiting.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity.

It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

In addition, where features or aspects of the disclosure are described in terms of Markush groups, those skilled in the art will recognize that the disclosure is also thereby described in terms of any individual member or subgroup of members of the Markush group.

As will be understood by one skilled in the art, for any and all purposes, such as in terms of providing a written description, all ranges disclosed herein also encompass any and all possible subranges and combinations of subranges thereof. Any listed range can be easily recognized as sufficiently describing and enabling the same range being broken down into at least equal subparts. As will be understood by one skilled in the art, a range includes each individual member.

While various embodiments have been described above, it should be understood that they have been presented by way of example only, and not limitation. Where methods described above indicate certain events occurring in certain order, the ordering of certain events may be modified. Additionally, certain of the events may be performed concurrently in a parallel process when possible, as well as performed sequentially as described above.

Where schematics and/or embodiments described above indicate certain components arranged in certain orientations or positions, the arrangement of components may be modified. While the embodiments have been particularly shown and described, it will be understood that various changes in form and details may be made. Any portion of the apparatus and/or methods described herein may be combined in any combination, except mutually exclusive combinations. The embodiments described herein can include various combinations and/or sub-combinations of the functions, components, and/or features of the different embodiments described.

What is claimed is:

1. A method for delivering a valve, the method comprising the steps:
    advancing a guidewire to a desired location within a body, the guidewire having an outer sheath and an inner shaft;
    advancing a delivery catheter over the guidewire to the desired location;
    mounting a valve capsule onto a proximal end of the guidewire, the valve capsule containing a valve in a compressed configuration, the valve having a central axis and a distal tension arm extending laterally from the valve, the distal tension arm having a guidewire collar, the guidewire collar having an aperture sized to permit the inner shaft of the guidewire to extend through the aperture and to block the outer sheath of the guidewire from extending, through the aperture;
    loading the valve capsule into a proximal, end of the delivery catheter;
    advancing the valve in the compressed configuration from the valve capsule into a lumen of the delivery catheter such that the central axis of the valve is perpendicular to a lengthwise axis of the delivery catheter and the distal tension arm is distal to the central axis; and
    advancing the valve in the compressed configuration through the lumen of the delivery catheter to the desired, location by advancing the outer sheath of the guidewire over the inner shaft of the guidewire.

2. The method of claim 1, further comprising:
    compressing the valve in a first direction that is co-axial with the central axis and in a second direction that is co-axial with a lateral axis of the valve, the lateral axis being perpendicular to the central axis.

3. The method of claim 2, wherein the valve in an expanded configuration has a first height along the central axis and a first lateral width along the lateral axis, the valve in the compressed configuration has a second height along the central axis that is less than the first height, and a second lateral width along the lateral axis that is less than the first lateral width.

4. The method of claim 3, further comprising:
    deploying the valve in the expanded configuration in an annulus of a native valve between an atrium of a heart and a ventricle of the heart such that a portion of the valve including the distal tension arm is disposed below the annulus in the ventricle.

5. The method of claim 1, wherein the valve includes a self-expanding valve frame.

6. The method of claim 5, wherein the valve frame forms a plurality of compressible wire cells having an orientation and cell geometry substantially orthogonal to the central axis.

7. The method of claim 1, wherein the valve has a long-axis oriented perpendicular to the central axis, the advancing the valve in the compressed configuration from the valve capsule into the lumen of the delivery catheter is such that the long-axis of the valve in the compressed configuration is substantially parallel to the lengthwise axis of the delivery catheter.

* * * * *